United States Patent
Bunnage et al.

(10) Patent No.: US 6,251,904 B1
(45) Date of Patent: Jun. 26, 2001

(54) PYRAZOLOPYRIMIDINONE CGMP PDE5 INHIBITORS FOR THE TREATMENT OF SEXUAL DYSFUNCTION

(75) Inventors: Mark Edward Bunnage; John Paul Mathias; Stephen Derek Albert Street; Anthony Wood, all of Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/402,242

(22) PCT Filed: Mar. 25, 1999

(86) PCT No.: PCT/IB99/00519

§ 371 Date: Sep. 29, 1999

§ 102(e) Date: Sep. 29, 1999

(87) PCT Pub. No.: WO99/54333

PCT Pub. Date: Oct. 28, 1999

(30) Foreign Application Priority Data

Apr. 20, 1998 (GB) .................................................. 9808315
Jun. 30, 1998 (GB) .................................................. 9814187

(51) Int. Cl.[7] ...................... C07D 487/04; C07D 401/12; A61K 31/505

(52) U.S. Cl. ...................... 514/252.6; 514/258; 544/262

(58) Field of Search ................ 544/262; 514/258, 514/252.16

(56) References Cited

U.S. PATENT DOCUMENTS

| | | | |
|---|---|---|---|
| 4,663,326 | 5/1987 | Hamilton | 514/258 |
| 4,666,908 | 5/1987 | Hamilton | 514/229 |
| 4,871,843 | 10/1989 | Roger et al. | 540/575 |
| 5,250,534 | 10/1993 | Bell et al. | 514/258 |
| 5,272,147 | 12/1993 | Bell et al. | 514/234.2 |
| 5,294,612 | 3/1994 | Bacon et al. | 514/234.2 |
| 5,346,901 | 9/1994 | Bell et al. | 514/258 |
| 5,426,107 | 6/1995 | Bell et al. | 514/234.2 |
| 5,719,283 | 2/1998 | Bell et al. | 544/262 |
| 5,734,053 | 3/1998 | Terrett | 544/277 |
| 5,736,548 | 4/1998 | Bacon et al. | 514/258 |
| 5,955,611 | 9/1999 | Dunn et al. | 544/262 |

FOREIGN PATENT DOCUMENTS

| | | | |
|---|---|---|---|
| 0201188 | * 4/1986 | (EP) . | |
| 0201188 | 12/1986 | (EP) | C07D/487/04 |
| 0352960 | 1/1990 | (EP) | C07D/473/30 |
| 0463756 | 1/1992 | (EP) | C07D/487/04 |
| 0349239 | 1/1994 | (EP) | C07D/487/04 |
| 0636626 | 2/1995 | (EP) | C07D/487/04 |
| 0526004 | 10/1997 | (EP) | C07D/487/04 |
| WO9306104 | 4/1993 | (WO) | C07D/487/04 |
| WO9307149 | 4/1993 | (WO) | C07D/487/04 |
| WO9312095 | 6/1993 | (WO) | C07D/239/91 |
| WO9315062 | 8/1993 | (WO) | C07D/241/04 |
| WO9400453 | 1/1994 | (WO) | C07D/473/30 |
| WO9405661 | 3/1994 | (WO) | C07D/471/04 |
| WO9428902 | 12/1994 | (WO) | A61K/31/505 |
| WO9616644 | 6/1996 | (WO) | A61K/31/00 |
| WO9616657 | 6/1996 | (WO) | A61K/31/505 |
| WO9628429 | 9/1996 | (WO) | C07D/239/70 |
| WO9628448 | 9/1996 | (WO) | C07D/487/04 |
| WO9849166 | 11/1998 | (WO) | C07D/487/04 |
| WO9954333 | 10/1999 | (WO) | C07D/487/04 |
| WO9964004 | 12/1999 | (WO) | A61K/31/505 |

OTHER PUBLICATIONS

Henze et al., J. Amer. Chem. Soc., Feb., 1939, pp. 433–435.
Terfort, et al., J. Chem. Soc. Perkin Trans. 1.1996, pp. 1467–1479.
J. Med. Chem., 1996, 39, 1635.
Harriet W. Hamilton, J. Med. Chem., 1987, 30, pp. 91–96.
Czarmiecki et al in Annual Reports in Medicinal Chemistry, 31, 61–70 (PC9496).
Abstract 08253484.

* cited by examiner

*Primary Examiner*—Mukund J. Shah
*Assistant Examiner*—Hong Liu
(74) *Attorney, Agent, or Firm*—Peter C. Richardson; Gregg C. Benson; James T. Jones

(57) ABSTRACT

Compounds of the formulae (IA) and (IB):

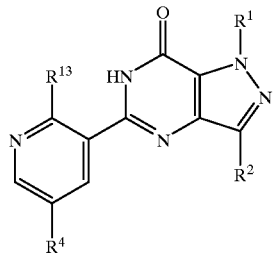

(IA)

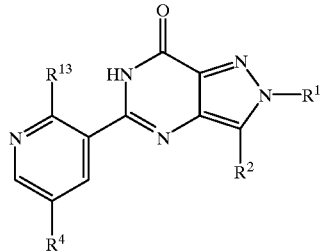

(IB)

wherein $R^1$ is $C_1$ to $C_3$ alkyl optionally substituted with phenyl, Het or a N-linked heterocyclic group selected from piperidinyl and morpholinyl; wherein said phenyl group is optionally substituted by one or more substitutents selected from $C_1$ to $C_4$ alkoxy; halo; CN; $CF_3$; $OCF_3$ or $C_1$ to $C_4$ alkyl wherein said $C_1$ to $C_4$ alkyl group is optionally substituted by $C_1$ to $C_4$ haloalkyl or haloalkoxy either of which is substituted by one or more halo atoms; $R^2$ is $C_1$ to $C_6$ alkyl and $R^{13}$ is $OR^3$ or $NR^5R^6$, or pharmaceutically or veterinarily acceptable salts thereof, or pharmaceutically or veterinarily acceptable solvates of either entity are potent and selective inhibitors of type 5 cyclic guanosine 3',5'-monophosphate phosphodiesterase (cGMP PDE5) and have utility in the treatment of, inter alia, male erectile dysfunction (MED) and female sexual dysfunction (FSD).

11 Claims, No Drawings

PYRAZOLOPYRIMIDINONE CGMP PDE5 INHIBITORS FOR THE TREATMENT OF SEXUAL DYSFUNCTION

This is a National Stage filing under 35 USC 371 based on PCT/IB99/00519 which was filed internationally on Mar. 25, 1999.

This invention relates to a series of pyrazolo[4,3-d]pyrimidin-7-ones, which inhibit cyclic guanosine 3',5'-monophosphate phosphodiesterases (cGMP PDEs). More notably, the compounds of the invention are potent and selective inhibitors of type 5 cyclic guanosine 3',5'-monophosphate phosphodiesterase (cGMP PDE5) and have utility therefore in a variety of therapeutic areas.

In particular, the compounds are of value in the treatment of male erectile dysfunction (MED) and female sexual dysfunction (FSD) but, clearly, will be useful also for treating other medical conditions for which a potent and selective cGMP PDE5 inhibitor is indicated. Such conditions include premature labour, dysmenorrhoea, benign prostatic hyperplasia (BPH), bladder outlet obstruction, incontinence, stable, unstable and variant (Prinzmetal) angina, hypertension, pulmonary hypertension, congestive heart failure, atherosclerosis, conditions of reduced blood vessel patency, e.g. post-percutaneous transluminal coronary angioplasty (post-PTCA), peripheral vascular disease, stroke, bronchitis, allergic asthma, chronic asthma, allergic rhinitis, glaucoma and diseases characterised by disorders of gut motility, e.g. irritable bowel syndrome (IBS).

Other conditions which may be mentioned include pre-eclampsia, Kawasaki's syndrome, nitrate tolerance, multiple sclerosis, peripheral diabetic neuropathy, stroke, Alzheimer's disease, acute respiratory failure, psoriasis, skin necrosis, cancer, metastasis, baldness, nutcracker oesophagus, anal fissure and hypoxic vasoconstriction.

Particularly preferred conditions include MED and FSD.

Thus the invention provides compounds of formulae (IA) and (IB):

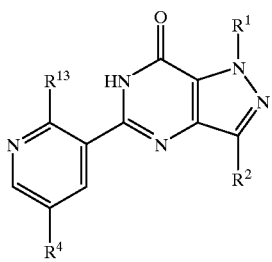

(IA)

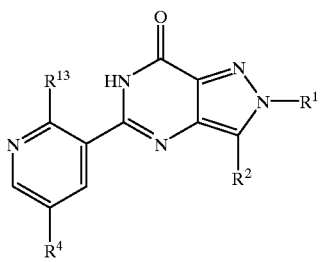

(IB)

or a pharmaceutically or veterinarily acceptable salt thereof, or a pharmaceutically or veterinarily acceptable solvate of either entity, wherein $R^1$ is $C_1$ to $C_3$ alkyl optionally substituted with phenyl, Het or a N-linked heterocyclic group selected from piperidinyl and morpholinyl; wherein said phenyl group is optionally substituted by one or more substituents selected from $C_1$ to $C_4$ alkoxy; halo; CN; $CF_3$, $OCF_3$ or $C_1$ to $C_4$ alkyl wherein said $C_1$ to $C_4$ alkyl group is optionally substituted by $C_1$ to $C_4$ haloalkyl or $C_1$ to $C_4$ haloalkoxy either of which is substituted by one or more halo atoms;

$R^2$ is $C_1$ to $C_6$ alkyl;

$R^{13}$ is $OR^3$ or $NR^5R^6$;

$R^3$ is $C_1$ to $C_6$ alkyl optionally substituted with one or two substituents selected from $C_3$ to $C_5$ cycloalkyl, OH, $C_1$ to $C_4$ alkoxy, benzyloxy, $NR^5R^6$, phenyl, furanyl and pyridinyl; $C_3$ to $C_6$ cycloalkyl; 1-($C_1$ to $C_4$ alkyl) piperdinyl; tetrahydrofuranyl or tetrahydropyranyl; and wherein the $C_1$ to $C_6$ alkyl and $C_1$ to $C_4$ alkoxy groups may optionally be terminated by a haloalkyl group such as $CF_3$;

$R^4$ is $SO_2NR^7R^8$;

$R^5$ and $R^6$ are each independently selected from H and $C_1$ to $C_4$ alkyl optionally substituted with $C_3$ to $C_5$ cycloalkyl or $C_1$ to $C_4$ alkoxy, or, together with the nitrogen atom to which they are attached, form an azetidinyl, pyrrolidinyl, piperidinyl or morpholinyl group;

$R^7$ and $R^8$, together with the nitrogen atom to which they are attached, form a 4-$R^{10}$-piperazinyl group optionally substituted with one or two $C_1$ to $C_4$ alkyl groups and optionally in the form of its 4-N-oxide;

$R^{10}$ is H; $C_1$ to $C_4$ alkyl optionally substituted with one or two substituents selected from OH, $NR^5R^6$, $CONR^5R^6$, phenyl optionally substituted with $C_1$ to $C_4$ alkoxy, benzodioxolyl and benzodioxanyl; $C_3$ to $C_6$ alkenyl; pyridinyl or pyrimidinyl; and Het is a C-linked 6-membered heterocyclic group containing one or two nitrogen atoms, optionally in the form of its mono-N-oxide, or a C-linked 5-membered heterocyclic group containing two or three nitrogen atoms, wherein either of said heterocyclic groups is optionally substituted with $C_1$ to $C_4$ alkyl, $C_1$ to $C_4$ alkoxy or $NHR^{15}$ wherein $R^{15}$ is H, $C_1$ to $C_4$ alkyl or $C_1$ to $C_4$ alkanoyl.

In the above definition, unless otherwise indicated, alkyl, alkoxy and alkenyl groups having three or more carbon atoms, and alkanoyl groups having four or more carbon atoms, may be straight chain or branched chain. The term halo atom includes, Cl, Br, F, and I. Haloalkyl and haloalkoxy are preferably $CF_3$ and O $CF_3$ respectively.

The compounds of formulae (IA) and (IB) may contain one or more chiral centres and therefore can exist as stereoisomers, i.e. as enantiomers or diastereosomers, as well as mixtures thereof. The invention includes both the individual stereoisomers of the compounds of formulae (IA) and (IB) and any mixture thereof. Separation of diastereoisomers may be achieved by conventional techniques, e.g. by fractional crystallisation or chromatography (including HPLC) of a diastereoesomeric mixture of a compound of formula (IA) or (IB) or a suitable salt or derivative thereof. An individual enantiomer of a compound of formula (IA) or (IB) may be prepared from a corresponding optically pure intermediate or by resolution, either by HPLC of the racemate using a suitable chiral support or, where appropriate, by fractional crystallisation of the diastereoisomeric salts formed by reaction of the racemate with a suitable optically active acid or base.

The compounds of formulae (IA) and (IB) may also exist in tautomeric forms and the invention includes both mixtures thereof and the individual tautomers.

Also included in the invention are radiolabelled derivatives of compounds of formulae (IA) and (IB) which are suitable for biological studies.

The pharmaceutically or veterinarily acceptable salts of the compounds of formulae (IA) and (IB) which contain a basic centre are, for example, non-toxic acid addition salts formed with inorganic acids such as hydrochloric, hydrobromic, sulphuric and phosphoric acid, with carboxylic acids or with organo-sulphonic acids. Compounds of formulae (IA) and (IB) can also provide pharmaceutically or veterinarily acceptable metal salts, in particular non-toxic alkali metal salts, with bases. Examples include the sodium and potassium salts.

A preferred group of compounds of formulae (IA) and (IB) is that wherein $R^1$ is $C_1$ to $C_2$ alkyl optionally substituted with Het; 2-(morpholin-4-yl)ethyl or benzyl; $R^2$ is $C_2$ to $C_4$ alkyl; $R^{13}$ is $OR^3$ or $NR^5R^6$; $R^3$ is $C_1$ to $C_4$ alkyl optionally substituted with one or two substituents selected from cyclopropyl, cyclobutyl, OH, methoxy, ethoxy, benzyloxy, $NR^5R^6$, phenyl, furan-3-yl, pyridin-2-yl and pyridin-3-yl; cyclobutyl; 1-methylpiperidin-4-yl; tetrahydrofuran-3-yl or tetrahydropyran-4-yl; $R^5$ and $R^6$ are each independently selected from H and $C_1$ to $C_2$ alkyl optionally substituted with cyclopropyl or methoxy, or, together with the nitrogen atom to which they are attached, form a azetidinyl, pyrrolidinyl or morpholinyl group; $R^7$ and $R^8$, together with the nitrogen atom to which they are attached, form a 4-$R^{10}$-piperazinyl group optionally substituted with one or two methyl groups and optionally in the form of its 4-N-oxide; $R^{10}$ is H, $C_1$ to $C_3$ alkyl optionally substituted with one or two substituents selected from OH, $NR^5R^6$, $CONR^5R^6$, phenyl optionally substituted with methoxy, benzodioxol-5-yl and benzodioxan-2-yl; allyl; pyridin-2-yl; pyridin-4-yl or pyrimidin-2-yl; and Het is selected from pyridin-2-yl; 1-oxidopyridin-2-yl; 6-methylpyridin-2-yl 6-methoxypyridin-2-yl; pyridazin-3-yl; pyrimidin-2-yl and 1-methylimidazol-2-yl.

A more preferred group of compounds of formulae (IA) and (IB) is that wherein $R^1$ is $C_1$ to $C_2$ alkyl optionally substituted with Het; 2-(morpholin-4-yl)ethyl or benzyl; $R^2$ is $C_2$ to $C_4$ alkyl; $R^{13}$ is $OR^3$; $R^3$ is $C_1$ to $C_4$ alkyl optionally monosubstituted with cyclopropyl, cyclobutyl, OH, methoxy, ethoxy, phenyl, furan-3-yl or pyridin-2-yl; cyclobutyl; tetrahydrofuran-3-yl or tetrahydropyran-4-yl; $R^7$ and $R^8$, together with the nitrogen atom to which they are attached, form a 4-$R^{10}$-piperazinyl group optionally in the form of its 4-N-oxide; $R^{10}$ is $C_1$ to $C_3$ alkyl optionally monosubstituted with OH; and Het is selected from pyridin-2-yl; 1-oxidopyridin-2-yl; 6-methylpyridin-2-yl; 6-methoxypyridin-2-yl; pyridazin-3-yl; pyrimidin-2-yl and 1-methylimidazol-2-yl.

Particularly preferred individual compounds of the invention include 3-ethyl-5-[2-(2-methoxyethoxy)-5-(4-methylpiperazin-1-ylsulphonyl)pyridin-3-yl]-2-(pyridin-2-yl)methyl-2,6-dihydro-7H-pyrazolo[4,3-d]pyrimidin-7-one;

3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one;

3-ethyl-5-[5-(4-ethyl-4-oxidopiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one;

5-[2-(2-methoxyethoxy)-5-(4-methylpiperazin-1-ylsulphonyl)pyridin-3-yl]-3-n-propyl-2-(pyridin-2-yl)methyl-2,6-dihydro-7H-pyrazolo[4,3-d]pyrimidin-7-one;

5-[5-(4-ethylpiperazin-1-ylsulphonyl)-2-(2-methoxyethoxy) pyridin-3-yl]-3-n-propyl-2-(pyridin-2-yl)methyl-2,6-dihydro-7H-pyrazolo[4,3-d]pyrimidin-7-one;

(+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one;

3-ethyl-5-[5-(4-ethylpiperazin-1-ylsulphonyl)-2-(2-methoxy-1(R)-methylethoxy)pyridin-3-yl]-2-(6-methylpyridin-2-yl)methyl-2,6-dihydro-7H-pyrazolo[4,3-d]pyrimidin-7-one;

5-[2-ethoxy-5-(4-ethylpiperazin-1-ylsulphonyl)pyridin-3-yl]-3-ethyl-2-(6-methoxypyridin-2-yl)methyl-2,6-dihydro-7H-pyrazolo[4,3-d]pyrimidin-7-one;

5-[2-i-butoxy-5-(4-ethylpiperazin-1-ylsulphonyl)pyridin-3-yl]-2,3-diethyl-2,6-dihydro-7H-pyrazolo[4,3-d]pyrimidin-7-one; and 5-[2-ethoxy-5-(4-ethylpiperazin-1-ylsulphonyl)pyridin-3-yl]-3-ethyl-2-[1-(pyridin-2-yl)ethyl]-2,6-dihydro-7H-pyrazolo[4,3-d]pyrimidin-7-one.

According to a further aspect of the present invention there are provided compounds of the formula (IA) and (IB) as defined hereinbefore but wherein $R^1$ is not unsubstituted $C_1$ alkyl; the optional substituent on the $C_1$ alkyl group of $R^1$ is not a substituted phenyl group or a N-linked heterocyclic group; the optional substituent on the $C_2$ or $C_3$ alkyl group of $R^1$ is not phenyl or Het; or wherein $R^{13}$ is not $NR^5R^6$; or wherein the alkyl group of $R^3$ is not $C_5$ or $C_6$; or wherein the optional substituent on $R^3$ is not $C_3$ to $C_5$ cycloalkyl; or wherein neither the alkyl or the optional alkoxy substituents on $R^3$ are terminated by a haloalkyl group; or wherein the $C_1$ to $C_4$ alkyl groups of $R^5$ and $R^6$ are not substituted by $C_3$ to $C_5$ cycloalkyl or $C_1$ to $C_4$ alkoxy; or wherein the $C_1$ to $C_4$ alkyl groups of $R^5$ and $R^6$ do not, together with the nitrogen group to which they are attached form an azetidinyl group; or wherein Het is not a $C_1$ to $C_4$ alkoxy or an $HNR^{15}$ group.

In a further aspect, the present invention provides processes for the preparation of compounds of formulae (IA) and (IB), their pharmaceutically and veterinarily acceptable salts, and pharmaceutically and veterinarily acceptable solvates of either entity, as illustrated below.

It will be appreciated by persons skilled in the art that, within certain of the processes described, the order of the synthetic steps employed may be varied and will depend inter alia on factors such as the nature of other functional groups present in a particular substrate, the availability of key intermediates and the protecting group strategy (if any) to be adopted. Clearly, such factors will also influence the choice of reagent for use in the said synthetic steps.

Illustrative of a protecting group strategy is the route to the 2'-(2-hydroxyethoxy) analogue (Example 33), the precursor to which (Example 32) contains benzyl as the alcohol-protecting group.

It will also be appreciated that various standard substituent or functional group interconversions and transformations within certain compounds of formulae (IA) and (IB) will provide other compounds of formulae (IA) and (IB). Examples include alkoxide exchange at the 2-position of the 5-(pyridin-3-yl) substituent (see conversions of Example 1 to Examples 4B, 9, 11, 13, 23, 24, 32 and 64, Example 2 to Example 14, Example 20 to Example 21, Example 26 to Examples 29, 65, 66, 67 and 68, Example 35 to Example 36, Example 38 to Examples 39 and 40, and Example 45 to Example 46), amine exchange at the 2-position of the 5-(pyridin-3-yl) substituent (see conversions of Example 78 to Examples 148 and 154) and piperazine and/or pyridine N-oxidation (see conversions of Example 1 to Example 70, Example 28 to Example 71, and Example 4 to Examples 72 and 73).

The following processes are illustrative of the general synthetic procedures which may be adopted in order to obtain the compounds of the invention.

1. A compound of formula (IA) or (IB) may be prepared from a compound of formula (IIA) or (IIB) respectively:

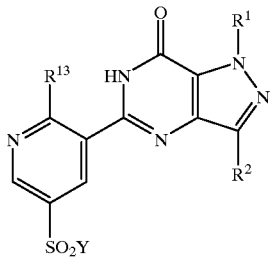

(IIA)

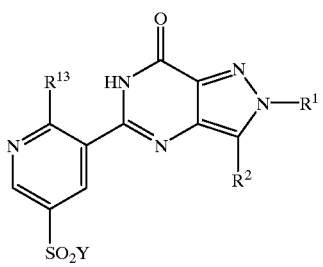

(IIB)

wherein Y is halo, preferably chloro, and R¹, R² and R¹³ are as previously defined for formulae (IA) and (IB), by reaction with a compound of formula (III):

(III)

wherein R⁷ and R⁸ are as previously defined for formulae (IA) and (IB).

The reaction is generally conducted at from about 0° C. to about room temperature, preferably in the presence of an appropriate solvent such as a $C_1$ to $C_3$ alkanol or dichloromethane, using an excess of (III) or other suitable base such as triethylamine to scavenge the acid by-product (HY).

Conveniently, this reaction lends itself to "high-speed analogue synthesis" (HSAS), as illustrated by Examples 203 to 212 in which a particular compound of formula (IIB) is coupled with a range of readily accessible amines of formula (III).

A compound of formula (IIA) or (IIB) may be prepared from a compound of formula (IVA) or (IVB) respectively:

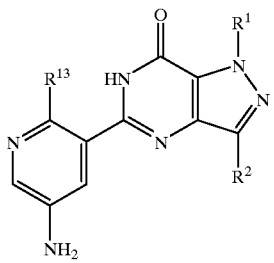

(IVA)

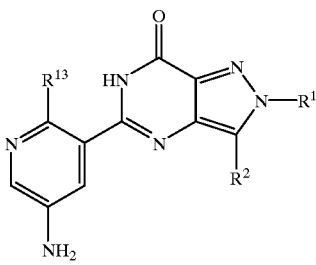

(IVB)

wherein R¹, R² and R¹³ are as previously defined for formulae (IIA) and (IIB), by the application of known methods for converting amino to a $SO_2Y$ group wherein Y is also as previously defined for formulae (IIA) and (IIB). For example, when Y is chloro, by the action of about a two-fold excess of sodium nitrite in a mixture of concentrated hydrochloric acid and glacial acetic acid at from about −25° C. to about 0° C., followed by treatment with excess liquid sulphur dioxide and a solution of about a three-fold excess of cupric chloride in aqueous acetic acid at from about −15° C. to about room temperature. When R¹³ contains a primary or secondary amino group, protection of the said amino group with an acid stable group such as acetyl or benzyl will generally be advantageous.

A compound of formula (IVA) or (IVB) may be prepared by cyclisation of a compound of formula (VA) or (VB) respectively:

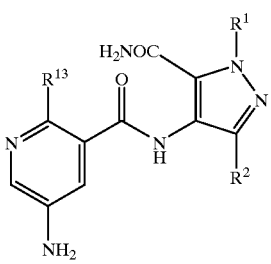

(VA)

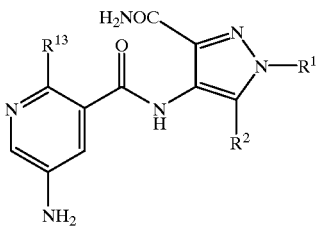

(VB)

wherein R¹, R² and R¹³ are as previously defined for formulae (IVA) and (IVB). Preferably, the cyclisation is base-mediated, using an alkali metal salt of a sterically hindered alcohol or amine. For example, the required cyclisation may be effected using about a 1.5 to 5, preferably a 3- to 5-fold excess of potassium t-butoxide or potassium bis(trimethylsilyl)amide, optionally in the presence of molecular sieves, in a suitable solvent at the reflux temperature of the reaction mixture, or, optionally in a sealed vessel at about 100° C. When R¹³ is OR³ and an alcohol is selected as solvent, the appropriate alcohol of formula R³OH should be employed in order to obviate potential problems associated with alkoxide exchange at the 2-position of the pyridine ring.

A compound of formula (VA) or (VB) may be prepared by reduction of a compound of formula (VIA) or (VIB) respectively:

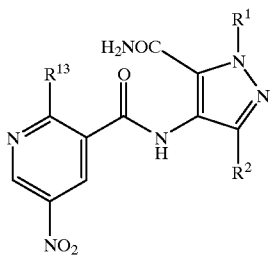
(VIA)

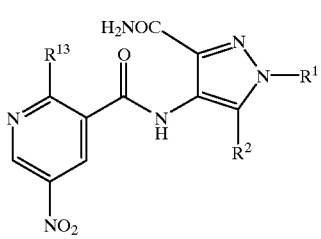
(VIB)

wherein $R^1$, $R^2$ and $R^{13}$ are as previously defined for formulae (VA) and (VB), by conventional catalytic or catalytic transfer hydrogenation procedures. Typically, the hydrogenation is achieved using a Raney nickel catalyst or a palladium catalyst such as 10% Pd on charcoal, in a suitable solvent such as ethanol at a hydrogen pressure of from about 345 kPa (50 psi) to about 414 kPa (60 psi) at from about room temperature to about 60° C., preferably from about 40° C. to about 50° C.

A compound of formula (VIA) or (VIB) may be prepared by reaction of a compound of formula (VIIA) or (VIIB) respectively:

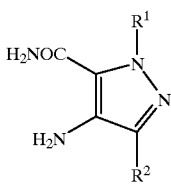
(VIIA)

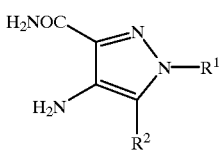
(VIIB)

wherein $R^1$ and $R^2$ are as previously defined for formulae (VIA) and (VIB), with a compound of formula (VIII):

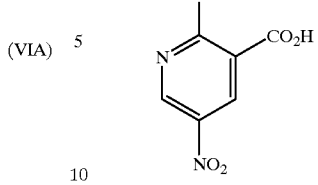
(VIII)

wherein $R^{13}$ is also as previously defined for formulae (VIA) and (VIB). Again, as for (IVA) and (IVB), a conventional amine protecting group strategy is preferred for (VII) when $R^{13}$ contains a primary or secondary amino group.

The coupling reaction may be achieved using conventional amide bond-forming techniques, e.g. via the acyl chloride derivative of (VIII) in the presence of up to about a five-fold excess of a tertiary amine such as triethylamine or pyridine to act as scavenger for the acid by-product (HY), optionally in the presence of a catalyst such as 4-dimethylaminopyridine, in a suitable solvent such as dichloromethane, at from about 0° C. to about room temperature. For convenience pyridine may also be used as the solvent.

In particular, any one of a host of amino acid coupling variations may be used. For example, the acid of formula (VIII) or a suitable salt (e.g. sodium salt) thereof may be activated using a carbodiimide such as 1,3-dicyclohexylcarbodiimide or 1-ethyl-3-(3-dimethylaminoprop-1-yl)carbodiimide optionally in the presence of 1-hydroxybenzotriazole hydrate and/or a catalyst such as 4-dimethylaminopyridine, or by using a halotrisaminophosphonium salt such as bromotris(pyrrolidino)phosphonium hexafluorophosphate or by using a suitable pyridinium salt such as 2-chloro-1-methylpyridinium iodide. Either type of coupling is conducted in a suitable solvent such as dichloromethane or tetrahydrofuran, optionally in the presence of a tertiary amine such as N-methylmorpholine or N-ethyldiisopropylamine (for example when either the compound of formula (VIIA) or (VIIB), or the activating reagent, is presented in the form of an acid addition salt), at from about 0° C. to about room temperature. Preferably, from 1 to 2 molecular equivalents of the activating reagent and from 1 to 3 molecular equivalents of any tertiary amine present are employed.

In a further variation, the carboxylic acid function of (VII) may first of all be activated using up to about a 5% excess of a reagent such as N,N'-carbonyldiimidazole in a suitable solvent, e.g. ethyl acetate or butan-2-one, at from about room temperature to about 80° C., followed by reaction of the intermediate imidazolide with either (VIIA) or (VIIB) at from about 20° C. to about 90° C.

2. An alternative, generally applicable, synthetic route to compounds of formulae (IA) and (IB) involves the incorporation of the $R^4$ substituent at an earlier stage of the synthesis.

Thus a compound of formula (IA) or (IB) may be prepared by cyclisation of a compound of formula (IXA) or (IXB) respectively:

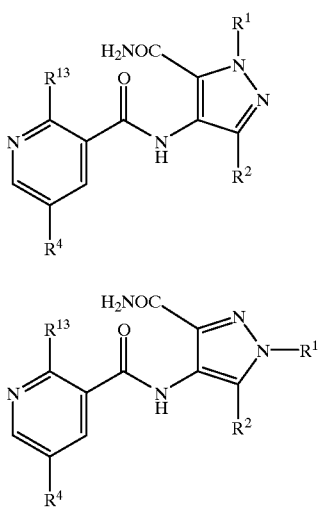

wherein $R^1$, $R^2$, $R^{13}$ and $R^4$ are as previously defined for formulae (IA) and (IB), by analogy with the previously described cyclisation of the compounds of formulae (VA) and (VB).

Alternative reaction conditions are to conduct the reaction with about 1.2 to 4 molecular equivalents of sterically hindered base in a sealed vessel at from about 100° C. to about 120° C. or, rather than an alcohol of formula $R^3OH$, to use a sterically hindered alcohol, e.g. 3-methylpentan-3-ol, as solvent with about 1.5 to 4.5 molecular equivalents of sterically hindered base, such as potassium t-butoxide or KHMDS, and optionally in a sealed vessel at from about 120° C. to about 150° C.

A compound of formula (IXA) or (IXB) may be prepared by reaction of a compound of formula (VIIA) or (VIIB) respectively, wherein $R^1$ and $R^2$ are as previously defined for formulae (IXA) and (IXB) with a compound of formula (X):

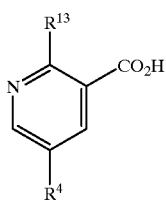

wherein $R^{13}$ and $R^4$ are also as previously defined for formulae (IXA) and (IXB), by analogy with the reactions of (VIIA) or (VIIB) with the nicotinic acid derivatives of formula (VIII) already described. Compounds having the general formula (X) may be prepared directly from compounds having the general formula (VIII) by reduction and subsequent conversion to $R^4$ as detailed previously herein.

3. As mentioned earlier, certain compounds of formulae (IA) and (IB) can be interconverted by inducing alkoxide exchange or displacement at the 2-position of the 5-(pyridin-3-yl) substituent.

(i) When $R^{13}$ is $OR^3$, this may be achieved, by treating the appropriate alcohol with an alkali metal salt of a sterically hindered alcohol or amine in order to generate the required alkoxide anion which then reacts with the substrate. Typically, in a two-step procedure, a mixture of from about 5 to about 8 molecular equivalents of potassium bis(trimethylsilyl)amide and the required alcohol as solvent is heated at from about 80° C. to about 100° C. for about 0.5 to 1 hour, followed by addition of the compound of formula (IA) or (IB) and heating of the reaction mixture at from about 100° C. to about 120° C. Alternatively, in a one-step procedure, the substrate may be treated directly, in the required alcohol as solvent, with from about 1.2 to about 6, preferably from about 4 to about 6 molecular equivalents of, for example, potassium bis(trimethylsilyl) amide or potassium t-butoxide at from about 80° C. to about 130° C. A further variation employs the required alcohol as solvent, saturated with ammonia, at about 100° C. in a sealed vessel.

(ii) When $R^{13}$ is $NR^5R^6$, the substrate may be treated with an excess of $R^5R^6NH$, or a suitable acid addition salt thereof, in the presence of an excess of a sterically hindered amine in a suitable solvent. Typically, $R^5R^6NH$ is used as the free base with about a 3-fold excess (over the substrate) of potassium bis (trimethylsilyl)amide (KHMDS) in dimethylformamide (DMF) as solvent at about 100° C. Alternatively, an excess of $R^5R^6NH$ may be used as the solvent and the reaction conducted in the presence of about a 50% excess of copper(II) sulphate at up to the reflux temperature of the reaction medium. Where the desired amino substituent on the compound of the formula (IA) or (IB) is $—NR^5R^6$ and one of either $R^5$ or $R^6$ is H, then the exchange reaction may be carried out by refluxing with the appropriate amine, and copper(II)sulphate penta- or hepta-hydrate or KHDMS in DMF. Typically, to exchange the $OR^3$ group for alternative amines of the formula $NHR^5R^6$, such as compounds wherein $R^5$ or $R^6$ are selected from aliphatic or cyclic amines, optionally including oxygen, then the reaction is preferably carried out by treating with the appropriate amine and about 3 equivalents of potassium bis(trimethylsilyl) amide in DMF for about 18 hours at 100° C.

4. Clearly, for certain compounds of formulae (IA) and (IB) wherein $R^{13}$ is $OR^3$, by exploiting the cyclisation and alkoxide exchange methodology described hereinbefore, it may be particularly advantageous to generate a compound of formula (IA) or (IB) from a compound of formula (IXA) or (IXB) respectively, wherein the 2-alkoxy group of the 5-(pyridin-3-yl) substituent in the former is different from that in the latter, directly in a "one-pot reaction".

When the alcohol which is to provide the new 2-alkoxy group is too scarce or expensive to be employed as the reaction solvent, then it will be expedient to use a suitable alternative such as 1,4-dioxan.

5. A further, generally applicable, synthetic route to compounds of formula (IA) and (IB) involves incorporation of the $R^1$ substituent in the final step of the synthesis.

Thus a compound of formula (IA) or (IB) may be prepared by alkylation of a compound of formula (IA) or (IB) wherein $R^1$ is hydrogen and $R^2$, $R^{13}$ and $R^4$ are as previously defined for formulae (IA) and (IB), using one or more of a plethora of well-known methods, such as:

(i) reaction with a compound of formula $R^1 X$, wherein $R^1$ is as previously defined for formulae (IA) and (IB), and X is a suitable leaving group, e.g. halo (preferably chloro, bromo or iodo), $C_1$–$C_4$ alkanesulphonyloxy, trifluoromethanesulphonyloxy or arylsulphonyloxy (such as benzenesulphonyloxy or p-toluenesulphonyloxy), in the presence of an appropriate base, optionally in the presence of sodium iodide or potassium iodide, at from about −70° C. to about 100° C. Preferably the alkylation is conducted at from about room temperature to about 80° C. Suitable base-solvent combinations may be selected from (a) sodium, potassium or caesium carbonate, sodium or potassium bicarbonate, or a tertiary amine such as triethylamine or pyridine, together with a $C_1$ to $C_4$ alkanol, 1,2-dimethoxyethane, tetrahydrofuran, 1,4-dioxan, acetonitrile, pyridine, dimethylformamide or N,N-dimethylacetamide;

(a) sodium or potassium hydroxide, or a sodium or potassium $C_1$ to $C_4$ alkoxide, together with a $C_1$ to $C_4$ alkanol, water or mixtures thereof;

(b) lithium, sodium or potassium hydride, lithium, sodium or potassium bis(trimethylsilyl)amide, lithium diisopropylamide or butyllithium, together with toluene, ether, 1,2-dimethoxyethane, tetrahydrofuran or 1,4-dioxan; or (d) under phase transfer catalysis conditions, a tetraalkylammonium halide or hydroxide, together with a mixture of an aqueous solution of sodium or potassium hydroxide and dichloromethane, 1,2-dichloroethane or chloroform:

(i) reaction with a compound of formula $R^1OH$, wherein $R^1$ is as previously defined for formulae (IA) and (IB), using classical Mitsunobu methodology. Typical reaction conditions involve treating the substrate with the alkanol in the presence of a triarylphosphine and a di($C_1$ to $C_4$)alkyl azodicarboxylate, in a suitable solvent such as tetrahydrofuran or 1,4-dioxan, at from about −5° C. to about room temperature.

Typically, about a 10% excess of sodium hydride is added to a solution of the substrate in a suitable solvent, e.g. anhydrous tetrahydrofuran, and the resulting anion treated with about a 10% excess of the required $R^1X$.

A compound of formula (IA) or (IB) wherein $R^1$ is hydrogen and $R^2$, $R^{13}$ and $R^4$ are as previously defined for formulae (IA) and (IB) may be obtained from a compound of formula (IXA) or (IXB) respectively wherein $R^1$ is hydrogen and $R^2$, $R^{13}$ and $R^4$ are as previously defined for formulae (IXA) and (IXB), under the same conditions as those used for the conversion of a compound of formula (IXA) or (IXB) to a compound of formula (IA) or (IB) respectively when $R^1$ is other than hydrogen, followed by acidification of the reaction mixture to a pH of about 6.

The amines of formula (III), the 4-aminopyrazole-5-carboxamides of formulae (VIIA) and (VIIB), the carboxylic acids of formulae (VII) and (X), the nitrites of formula (XIII) and the esters of formula (XVI), when neither commercially available nor subsequently described, can be obtained either by analogy with the processes described in the Preparations section or by conventional synthetic procedures, in accordance with standard textbooks on organic chemistry or literature precedent, from readily accessible starting materials using appropriate reagents and reaction conditions.

Moreover, persons skilled in the art will be aware of variations of, and alternatives to, those processes described hereinafter in the Examples and Preparations sections which allow the compounds defined by formulae (IA) and (IB) to be obtained.

The pharmaceutically acceptable acid addition salts of the compounds of formulae (IA) and (IB) which contain a basic centre may also be prepared in a conventional manner. For example a solution of the free base is treated with the appropriate acid, either neat or in a suitable solvent, and the resulting salt isolated either by filtration of by evaporation under vacuum of the reaction solvent. Pharmaceutically acceptable base addition salts can be obtained in an analogous manner by treating a solution of a compound of formula (IA) or (IB) with the appropriate base. Both types of salt may be formed or interconverted using ion-exchange resin techniques.

The biological activities of the compounds of the present invention were determined by the following test methods.

Phosphodiesterase (PDE) Inhibitory Activity

In vitro PDE inhibitory activities against cyclic guanosine 3',5'-monophosphate (cGMP) and cyclic adenosine 3',5'-monophosphate (cAMP) phosphodiesterases were determined by measurement of their $IC_{50}$ values (the concentration of compound required for 50% inhibition of enzyme activity).

The required PDE enzymes were isolated from a variety of sources, including human corpus cavernosum, human and rabbit platelets, human cardiac ventricle, human skeletal muscle and bovine retina, essentially by the method of W. J. Thompson and M. M. Appleman (Biochem., 1971, 10, 311). In particular, the cGMP-specific PDE (PDE5) and the cGMP-inhibited cAMP PDE (PDE3) were obtained from human corpus cavernosum tissue, human platelets or rabbit platelets; the cGMP-stimulated PDE (PDE2) was obtained from human corpus cavernosum; the calcium/calmodulin (Ca/CAM)-dependent PDE (PDE1) from human cardiac ventricle; the cAMP-specific PDE (PDE4) from human skeletal muscle; and the photoreceptor PDE (PDE6) from bovine retina.

Assays were performed using a modification of the "batch" method of W. J. Thompson et al. (Biochem., 1979, 18, 5228). Results from these tests show that the compounds of the present invention are potent and selective inhibitors of cGMP-specific PDE5.

Functional Activity

This was assessed in vitro by determining the capacity of a compound of the invention to enhance sodium nitroprusside-induced relaxation of pre-contracted rabbit corpus cavernosum tissue strips, as described by S. A. Ballard et al. (Brit. J. Pharmacol., 1996, 118 (suppl.), abstract 153P).

In vivo Activity

Compounds were screened in anaesthetised dogs to determine their capacity, after i.v. administration, to enhance the pressure rises in the corpora cavernosa of the penis induced by intracavemosal injection of sodium nitroprusside, using a method based on that described by Trigo-Rocha et al. (Neurourol. and Urodyn., 1994, 13, 71).

In human therapy, the compounds of formulae (IA) and (IB), their pharmaceutically acceptable salts, and pharmaceutically acceptable solvates of either entity, can be administered alone, but will generally be administered in admixture with a pharmaceutical carrier selected with regard to the intended route of administration and standard pharmaceutical practice. Preferably, they are administered orally in the form of tablets containing such excipients as starch or lactose, or in capsules or ovules either alone or in admixture with excipients, or in the form of elixirs, solutions or suspensions containing flavouring or colouring agents. They can also be injected parenterally, for example intracavernosally, intravenously, intramuscularly or subcutaneously. For parenteral administration, they are best used in the form of a sterile aqueous solution which may contain other substances, for example enough salts or monosaccharides to make the solution isotonic with blood. For buccal or sublingual administration they may be administered in the form of tablets or lozenges which can be formulated in a conventional manner. The compounds may also be administered intranasally or formulated for dermal application.

For oral, parenteral, buccal and sublingual administration to patients, the daily dosage level of the compounds of formulae (IA) and (IB) and their pharmaceutically acceptable salts and solvates may be from 10 to 500 mg (in single or divided doses). Thus, for example, tablets or capsules may contain from 5 to 250 mg of active compound for administration singly, or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited and such are within the scope of this invention. The skilled person will also appreciate that, in the treatment of certain conditions (including MED and FSD), compounds of the invention may be taken as a single dose on an "as required" basis (i.e. as needed or desired).

Generally, in humans, oral administration of the compounds of the invention is the preferred route, being the most convenient and, for example in MED, avoiding the well-known disadvantages associated with intracavernosal (i.c.) administration. A preferred oral dosing regimen in MED for a typical man is from 25 to 250 mg of compound when required. In circumstances where the recipient suffers from a swallowing disorder or from impairment of drug absorption after oral administration, the drug may be administered parenterally, sublingually or buccally.

For veterinary use, a compound of formula (IA) or (IB), or a veterinarily acceptable salt thereof, or a veterinarily acceptable solvate of either entity, is administered as a suitably acceptable formulation in accordance with normal veterinary practice and the veterinary surgeon will determine the dosing regimen and route of administration which will be most appropriate for a particular animal.

Thus the invention provides a pharmaceutical composition comprising a compound of formula (IA) or (IB), or a pharmaceutically acceptable salt thereof, or a pharmaceutically acceptable solvate of either entity, together with a pharmaceutically acceptable diluent or carrier.

It further provides a veterinary formulation comprising a compound of formula (IA) or (IB), or a veterinarily acceptable salt thereof, or a veterinarily acceptable solvate of either entity, together with a veterinarily acceptable diluent or carrier.

The invention also provides a compound of formula (IA) or (IB), or a pharmaceutically acceptable salt thereof, or a pharmaceutically acceptable solvate of either entity, or a pharmaceutical composition containing any of the foregoing, for use as a human medicament.

In addition, it provides a compound of formula (IA) or (IB), or a veterinarily acceptable salt thereof, or a veterinarily acceptable solvate of either entity, or a veterinary formulation containing any of the foregoing, for use as an animal medicament.

In yet another aspect, the invention provides the use of a compound of formula (IA) or (IB), or a pharmaceutically acceptable salt thereof, or a pharmaceutically acceptable solvate of either entity, for the manufacture of a human medicament for the curative or prophylactic treatment of a medical condition for which a cGMP PDE5 inhibitor is indicated. There is further provided the use of a compound of formula (IA) or (IB) or a suitable salt or solvate thereof, in the manufacture of a medicament for the treatment of a medical condition in which inhibition of a cGMP PDE5 is desirable.

It also provides the use of a compound of formula (IA) or (IB), or a veterinarily acceptable salt thereof, or a veterinarily acceptable solvate of either entity, for the manufacture of an animal medicament for the curative or prophylactic treatment of a medical condition for which a cGMP PDE5 inhibitor is indicated.

Moreover, the invention provides the use of a compound of formula (IA) or (IB), or a pharmaceutically acceptable salt thereof, or a pharmaceutically acceptable solvate containing either entity, for the manufacture of a human medicament for the curative or prophylactic treatment of male erectile dysfunction (MED), female sexual dysfunction (FSD), premature labour, dysmenorrhoea, benign prostatic hyperplasia (BPH), bladder outlet obstruction. incontinence, stable, unstable and variant (Prinzmetal) angina, hypertension. pulmonary hypertension, congestive heart failure, atherosclerosis, stroke, peripheral vascular disease, conditions of reduced blood vessel patency, (e.g. post transluminal coronary angioplasty (post-PTCA)), chronic asthma, bronchitis, allergic asthma, allergic rhinitis, glaucoma or diseases characterised by disorders of gut motility (e.g. irritable bowel syndrome (IBS)). Other conditions which may be mentioned include pre-eclampsia, Kawasaki's syndrome, nitrate tolerance, multiple sclerosis, peripheral diabetic neuropathy. stroke, Alzheimer's disease, acute respiratory failure, psoriasis, skin necrosis, cancer, metastasis, baldness, nutcracker oesophagus, anal fissure and hypoxic vasoconstriction. Particularly preferred conditions include MED and FSD.

It also provides the use of a compound of formula (IA) or (IB), or a veterinarily acceptable salt thereof, or a veterinarily acceptable solvate containing either entity, for the manufacture of an animal medicament for the curative or prophylactic treatment of male erectile dysfunction (MED), female sexual dysfunction (FSD), premature labour, dysmenorrhoea, benign prostatic hyperplasia (BPH), bladder outlet obstruction, incontinence, stable, unstable and variant (Prinzmetal) angina, hypertension, pulmonary hypertension, congestive heart failure, atherosclerosis, stroke, peripheral vascular disease, conditions of reduced blood vessel patency (e.g. post-PTCA), chronic asthma, bronchitis, allergic asthma, allergic rhinitis, glaucoma or diseases characterised by disorders of gut motility (e.g. IBS). Other conditions which may be mentioned include pre-eclampsia, Kawasaki's syndrome, nitrate tolerance, multiple sclerosis, peripheral diabetic neuropathy, stroke, Alzheimer's disease, acute respiratory failure, psoriasis, skin necrosis, cancer, metastasis, baldness, nutcracker oesophagus, anal fissure and hypoxic vasoconstriction. Particularly preferred conditions include MED and FSD.

Additionally, the invention provides a method of treating or preventing a medical condition for which a cGMP PDE5 inhibitor is indicated, in a mammal (including a human being), which comprises administering to said mammal a therapeutically effective amount of a compound of formula (IA) or (IB), or a pharmaceutically or veterinarily acceptable salt thereof, or a pharmaceutically or veterinarily acceptable solvate of either entity, or a pharmaceutical composition or veterinary formulation containing any of the foregoing.

Still further, the invention provides a method of treating or preventing male erectile dysfunction (MED), female sexual dysfunction (FSD), premature labour, dysmenorrhoea, benign prostatic hyperplasia (BPH), bladder outlet obstruction, incontinence, stable, unstable and variant (Prinzmetal) angina, hypertension, pulmonary hypertension, congestive heart failure, atherosclerosis, stroke, peripheral vascular disease, conditions of reduced blood vessel patency (e.g. post PTCA), chronic asthma, bronchitis, allergic asthma, allergic rhinitis, glaucoma or diseases characterised by disorders of gut motility in a mammal (including a human being), which comprises administering to said mammal a therapeutically effective amount of a compound of formula (IA) or (IB), or a pharmaceutically or veterinarily acceptable salt thereof, or a pharmaceutically or veterinarily acceptable solvate of either entity, or a pharmaceutical composition or veterinary formulation containing any of the foregoing.

The invention also includes any novel intermediates described herein, for example those of formulae (IIA), (IIB), (IVA), (IVB), (IXA), (IXB), (VA) and (VB).

The syntheses of the compounds of the invention and of the intermediates for use therein are illustrated by the following Examples and Preparations.

$^1$H Nuclear magnetic resonance (NMR) spectra were recorded using either a Varian Unity 300 or a Varian Inova 400 spectrometer and were in all cases consistent with the proposed structures. Characteristic chemical shifts ($\delta$) are given in parts-per-million downfield from tetramethylsilane using conventional abbreviations for designation of major peaks: e.g. s, singlet; d, doublet; t, triplet; q, quartet; m, multiplet; br, broad.

Mass spectra (m/z) were recorded using a Fisons Instruments Trio mass spectrometer in the thermospray ionisation mode.

Room temperature means 20 to 25° C.

EXAMPLE 1

5-[2-Ethoxy-5-(4-ethylpiperazin-1-ylsulphonyl)pyridin-3-yl]-3-ethyl-2-(pyridin-2-yl)methyl-2,6-dihydro-7H-pyrazolo[4,3-d]pyrimidin-7-one Alternative A 60% Sodium hydride dispersion in mineral oil (14.3 mg, 0.36 mmol) was added to a stirred suspension of the title compound of Preparation 44 (150 mg, 0.325 mmol) in anhydrous tetrahydrofuran (5 ml) under nitrogen. After 1 hour, a solution of 2-(chloromethyl)pyridine (45.5 mg, 0.36 mmol) in tetrahydrofuran (1 ml) was added and the reaction mixture heated at 40° C. for 16 hours, then allowed to cool. The resulting mixture was evaporated under reduced pressure and the residue partitioned between dichloromethane (15 ml) and water (5 ml). The organic phase was separated, combined with a dichloromethane extract (20 ml) of the aqueous phase, dried (MgSO$_4$) and evaporated under reduced pressure. The residual yellow foam was purified by column chromatography on silica gel, using dichloromethane: methanol (97:3) as eluant, followed by HPLC using a 5 μm Spherisorb silica column with water: acetonitrile: diethylamine (50:50:0.1) as eluant at a rate of 1 ml/min, to give the title compound (30 mg, 17%) as a white foam. $\delta$ (CDCl$_3$): 1.03 (3H,t), 1.30 (3H,t), 1.57 (3H,t), 2.40 (2H,q), 2.53 (4H,m), 3.05 (2H,q), 3.12 (4H,m), 4.75 (2H,q), 5.68 (2H,s), 7.10 (1H,d), 7.22 (1H,m), 7.64 (1H,m), 8.56 (1H,d), 8.64 (1H,s), 9.04 (1H,s), 10.65 (1H,s). LRMS: m/z 553 (M+1)$^+$.

Alternative B

A mixture of the title compound of Preparation 45B (17.4 g, 30.5 mmol) and potassium bis(trimethylsilyl)amide (7.28 g, 36.5 mmol) in ethanol (155 ml) was heated at 120° C. in a sealed vessel for 10 hours, allowed to cool and evaporated under reduced pressure. The residue was suspended in water (200 ml), the suspension extracted with dichloromethane (2×300 ml) and the combined extracts dried (MgSO$_4$) and evaporated under reduced pressure. The crude product was purified by column chromatography on silica gel, using dichloromethane: methanol (97:3) as eluant, to give a pale yellow foam (11.2 g, 66%) which was crystallised from diisopropyl ether-methanol to yield the title compound as a crystalline solid. Found: C, 55.58; H, 5.90; N, 19.58. C$_{26}$H$_{32}$N$_8$O$_4$S; 0.50 H$_2$O requires C, 55.60; H, 5.92; N, 19.95%.

EXAMPLE 2

5-[2-Ethoxy-5-(4-methylpiperazin-1-ylsulphonyl)pyridin-3-yl]-3-n-propyl-2-(pyridin-2-yl)methyl-2,6-dihydro-7H-pyrazolo[4,3-d]pyrimidin-7-one 1-Methylpiperazine (0.2 ml, 1.8 mmol) was added dropwise to a stirred suspension of the title compound of Preparation 63 (450 mg, 0.92 mmol) in ethanol (40 ml) and the reaction mixture stirred at room temperature for 18 hours, then evaporated under reduced pressure. The residue was partitioned between saturated aqueous sodium bicarbonate solution (30 ml) and ethyl acetate (90 ml), then the organic phase separated, washed with brine (2×20 ml), dried (Na$_2$SO$_4$) and evaporated under reduced pressure. The residual oil was purified by column chromatography on silica gel, using an elution gradient of dichloromethane: methanol (100:0 to 96:4), followed by crystallisation from hexane-ethyl acetate to provide the title compound (340 mg, 67%) as a white solid. Found: C, 55.90; H, 5.85; N, 20.04. C$_{26}$H$_{32}$N$_8$O$_4$S; 0.50 H$_2$O requires C, 55.60; H, 5.92; N, 19.95%. $\delta$ (CDCl$_3$): 0.94 (3H,t), 1.58 (3H,t), 1.74 (2H,m), 2.27 (3H,s), 2.40 (4H,m), 2.99 (2H,t), 3.14 (4H,m), 4.69 (2H,q), 5.68 (2H,s), 7.09 (1H,d), 7.23 (1H,m), 7.63 (1H,m), 8.58 (1H,d), 8.63 (1H,s), 9.03 (1H,s), 10.64 (1H,s). LRMS: m/z 552 (M)$^+$.

EXAMPLE 3

3-Ethyl-5-[2-(2-methoxyethoxy)-5-(4-methylpiperazin-1-ylsulphonyl)pyridin-3-yl]-2-(pyridin-2-yl)methyl-2,6dihydro-7H-pyrazolo[4.3-d]pyrimidin-7-one Triethylamine (83 μl, 0.59 mmol) and 1-methylpiperazine (36 mg, 0.356 mmol) were added to a stirred, ice-cooled suspension of the title compound of Preparation 64 (150 mg, 0.30 mmol) in dichloromethane (10 ml) and the reaction mixture stirred for 2 hours at room temperature. The resulting mixture was washed with water (5 ml), dried (MgSO$_4$) and evaporated under reduced pressure to give a beige solid, which was purified by column chromatography on silica gel, using an elution gradient of dichloromethane: methanol (98:2 to 95:5), followed by trituration with ether, to furnish the title compound (145 mg, 85%) as a white solid. Found: C, 54.53; H, 5.69; N, 19.38. C$_{26}$H$_{32}$N$_8$O$_5$S requires C, 54.92; H, 5.67; N, 19.71%. $\delta$ (CDCl$_3$): 1.30 (3H,t), 2.28 (3H,s), 2.50 (4H,m), 3.04 (2H,q), 3.14 (4H,m), 3.57 (3H,s), 3.86 (2H,t), 4.78 (2H,t), 5.68 (2H,s), 7.09 (1H,d), 7.22 (1H,m), 7.62 (1H,m), 8.58 (1H,d), 8.62 (1H,s), 8.97 (1H,s), 10.81 (1H,s). LRMS: m/z 569 (M+1)$^+$.

EXAMPLE 4

3-Ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one Alternative A Potassium t-butoxide (56 mg, 0.50 mmol) was added to a stirred solution of the title compound of Preparation 45A (200 mg, 0.35 mmol) in 2-methoxyethanol (10 ml) and the reaction mixture stirred under reflux for 2 hours, then allowed to cool. Saturated aqueous ammonium chloride solution (1 ml) was added, followed by water (5 ml), and the mixture extracted with ethyl acetate (2×10 ml). The combined extracts were dried (MgSO$_4$) and evaporated under reduced pressure, then the residue purified by column chromatography on silica gel, using an elution gradient of dichloromethane: methanol (100:0 to 95:5), to afford the title compound (11 mg, 5%) as a solid. δ (CDCl$_3$): 1.03 (3H,t), 1.30 (3H,t), 2.41 (2H,q), 2.54 (4H,m), 3.04 (2H,q), 3.14 (4H,m), 3.56 (3H,s), 3.87 (2H,t), 4.78 (2H,t), 5.69 (2H,s), 7.10 (1H,d), 7.21 (1H,m), 7.61 (1H,m), 8.56 (1H,d), 8.62 (1H,s), 8.95 (1H,s), 10.82 (1H,s). LRMS: m/z 583 (M+1)$^+$.

Alternative B

A mixture of potassium bis(trimethylsilyl)amide (16.58 g, 83 mol) and 2-methoxyethanol (250 ml) was stirred at 90° C. for 30 minutes, then allowed to cool. The title compound of Example 1 (9.21 g, 16.7 mmol) was then added and the reaction mixture stirred at 110° C. for 6 hours. The resulting mixture, when cool, was evaporated under reduced pressure, the residue dissolved in water (300 ml) and the solution neutralised to pH 7 with 2M hydrochloric acid and then extracted with ethyl acetate (3×200 ml). The combined extracts were washed with brine (3×200 ml), dried (Na$_2$SO$_4$) and evaporated under reduced pressure. The residual yellow solid was purified by column chromatography on silica gel, using dichloromethane: methanol (98:2) as eluant, followed by trituration with ether, crystallisation from ethyl acetate and recrystallisation from acetone, to afford a solvate (with acetone) of the title compound (7.7 g, 79%) as colourless crystals, m.p. 171.5–173° C. Found: C, 55.59; H, 5.94; N, 18.78. C$_{27}$H$_{34}$N$_8$O$_5$S; 0.125 C$_3$H$_6$O requires C, 55.72; H, 5.94; N, 19.00%.

The product was suspended in water (200 ml), sufficient 2M hydrochloric acid added to achieve dissolution and then the solution washed with ether (3×50 ml) and neutralised with saturated aqueous sodium bicarbonate solution. The resulting precipitate was collected, washed with water and dried at 80° C. to afford a hemihydrate of the title compound (5.99 g, 61.6%) as a white solid, m.p. 139–140° C. Found: C, 54.74; H, 5.92; N, 18.86. C$_{27}$H$_{34}$N$_8$O$_5$S; 0.50 H$_2$O requires C, 54.81; H, 5.96; N, 18.94%.

EXAMPLE 5

3-Ethyl-5-[2-(2-methoxyethoxy)-5-[4-(prop-1-yl)piperazin-1-ylsulphonyl]pyridin-3-yl]-2-(pyridin-2-yl)methyl-2,6-dihydro-7H-pyrazolo[4,3-d]pyrimidin-7-one Obtained as a yellow foam (88%) from the title compound of Preparation 64 and 1-(prop-1-yl)piperazine dihydrobromide, using the procedure of Example 3. Found: C, 56.12; H, 6.06; N, 18.62. C$_{28}$H$_{36}$N$_8$O$_5$S requires C, 56.36; H, 6.08; N, 18.78%. δ (CDCl$_3$): 0.86 (3H,t), 1.30 (3H,t), 1.43 (2H,m), 2.30 (2H,t), 2.53 (4H,m), 3.04 (2H,q), 3.12 (4H,m), 3.57 (3H,s), 3.88 (2H,t), 4.78 (2H,t), 5.68 (2H,s), 7.10 (1H,d), 7.23 (1H,m), 7.62 (1H,m), 8.58 (1H,d), 8.62 (1H,s), 8.97 (1H,s), 10.81 (1H,s). LRMS: m/z 597 (M+1)$^+$.

EXAMPLE 6

3-Ethyl-5-{2-(2-methoxyethoxy)-5-[4-(prop-2-yl)piperazin-1-ylsulphonyl]pyridin-3-yl}-2-(pyridin-2-yl)methyl-2,6dihydro-7H-pyrazolo[4,3-d]pyrimidin-7-one Obtained as a white powder (78%) from the title compound of Preparation 64 and 1-(prop-2-yl)piperazine, using the procedure of Example 3. Found: C, 55.95; H, 6.06; N, 18.46. C$_{28}$H$_{36}$N$_8$O$_5$S requires C, 56.36; H, 6.08; N, 18.78%. δ (CDCl$_3$): 1.00 (6H,2xd), 1.30 (3H,t), 2.61 (4H,m), 2.68 (1H,m), 3.02 (2H,q), 3.12 (4H,m), 3.57 (3H,s), 3.86 (2H,t), 4.79 (2H,t), 5.68 (2H,s), 7.10 (1H,d), 7.22 (1H,m), 7.62 (1H,m), 8.58 (1H,d), 8.62 (1H,s), 8.97 (1H,s), 10.71 (1H,s). LRMS: m/z 597 (M+1)$^+$.

EXAMPLE 7

5-{5-[4-(2-Aminoethyl)piperazin-1-ylsulphonyl]-2-(2-methoxyethoxy)pyridin-3-yl}-3-ethyl-2-(pyridin-2-yl)methyl-2,6dihydro-7H-pyrazolo[4,3-d]pyrimidin-7-one A solution of the title compound of Preparation 64 (100 mg, 0.198 mmol) in dichloromethane (10 ml) was added dropwise over 1 hour to a stirred solution of 1-(2-aminoethyl)piperazine (102 mg, 0.79 mmol) in dichloromethane (10 ml) and the reaction mixture stirred for a further 1 hour at room temperature. The resulting mixture was washed with water (10 ml), dried (MgSO$_4$) and evaporated under reduced pressure to give a beige solid, which was purified by column chromatography on silica gel, using an elution gradient of dichloromethane: methanol:0.88 ammonia (90:10:0 to 90:10:1), to yield the title compound (104 mg, 88%) as a white foam. δ (CDCl$_3$): 1.29 (3H,t), 2.43 (2H,t), 2.54 (4H,m), 2.74 (2H,t), 3.04 (2H,q), 3.12 (4H,m), 3.56 (3H,s), 3.88 (2H,t), 4.79 (2H,t), 5.68 (2H,s), 7.10 (1H,d), 7.22 (1H,m), 7.63 (1H,m), 8.56 (1H,d), 8.62 (1H,s), 8.99 (1H,s). LRMS: m/z 598 (M+1)$^+$.

EXAMPLE 8

5-[5-(4-Ethylpiperazin-1-ylsulphonyl)-2-(2-methoxyethoxy)pyridin-3-yl]-3-n-propyl-2-(pyridin-2-yl)methyl-2,6-dihydro-7H-pyrazolo[4,3-d]pyrimidin-7-one Potassium t-butoxide (104 mg, 0.97 mmol) was added to a stirred suspension of the title compound of Preparation 53 (380 mg, 0.618 mmol) in 3-methylpentan-3-ol (30 ml) and the reaction mixture heated under reflux for 1 hour, then allowed to cool. The resulting mixture was evaporated under reduced pressure and the residual yellow gum partitioned between dichloromethane (20 ml) and saturated aqueous sodium bicarbonate solution (10 ml). The phases were separated, the aqueous phase extracted with dichloromethane (2×10 ml) and the combined extracts dried (MgSO$_4$) and evaporated under reduced pressure. The crude product was purified by column chromatography on silica gel, using an elution gradient of dichloromethane: methanol (98:2 to 95:5) to provide the title compound (75 mg, 13%) as a white foam. δ (CDCl$_3$): 0.93 (3H,t), 1.04 (3H,t), 1.73 (2H,m), 2.41 (2H,q), 2.54 (4H,m), 2.97 (2H,t), 3.13 (4H,m), 3.56 (3H,s), 3.86 (2H,t), 4.78 (2H,t), 5.68 (2H,s), 7.08 (1H,d), 7.21 (1H,m), 7.61 (1H,m), 8.54 (1H,d), 8.62 (1H,s), 8.97 (1H,s), 10.80 (1H,s). LRMS: m/z 597 (M+1)$^+$.

EXAMPLE 9

5-[2-(2-Ethoxyethoxy)-5-(4-ethylpiperazin-1-ylsulphonyl)pyridin-3-yl]-3-ethyl-2-(pyridin-2-yl)methyl-2,6-dihydro-7H-pyrazolo[4,3-d]pyrimidin-7-one A stirred mixture of potassium bis(trimethylsilyl)amide (434 mg, 2.2 mmol) and 2-ethoxyethanol (2 ml) was heated at 90° C. for 30 minutes, then allowed to cool. A solution of the title compound of Example 1 (153 mg, 0.27 mmol) in 2-ethoxyethanol (2 ml) was added and the reaction mixture stirred at 110° C. for 18 hours, then allowed to cool. The resulting mixture was evaporated under reduced pressure and the residual brown oil purified by column chromatography on silica gel, using dichloromethane: methanol (95:5) as eluant, to furnish the title compound (110 mg, 68%) as a yellow foam. δ (CDCl$_3$): 1.04 (3H,t), 1.31 (6H,m), 2.41 (2H,q), 2.54 (4H,m), 3.04 (2H,q), 3.14 (4H,m), 3.72 (2H,q), 3.90 (2H,t), 4.78 (2H,t), 5.67 (2H,s), 7.10 (1H,d), 7.22 (1H,m), 7.63 (1H,m), 8.57 (1H,d), 8.62 (1H,s), 8.99 (1H,s), 10.78 (1H,s). LRMS: m/z 597 (M+1)$^+$.

EXAMPLE 10

5-[2-(2-Ethoxyethoxy)-5-(4-ethylpiperazin-1-ylsulphonyl)pyridin-3-yl]-3-n-propyl-2-(pyridin-2-yl)methyl-2,6-dihydro-7H-pyrazolo[4,3d]pyrimidin-7-one A mixture of potassium t-butoxide (110 mg, 0.98 mmol), the title compound of Preparation 54 (400 mg, 0.63 mmol) and 3-methylpentan-3-ol (5 ml) was stirred at 150° C. for 3 hours, then allowed to cool. The resulting mixture was evaporated under reduced pressure and the residue partitioned between water (5 ml) and ethyl acetate (5 ml). The phases were separated, the aqueous phase extracted with ethyl acetate (2×10 ml) and the combined organic solutions dried ($MgSO_4$) and evaporated under reduced pressure. The residue was purified by column chromatography on silica gel, using an elution gradient of dichloromethane:methanol:0.88 aqueous ammonia (99:1:0.5 to 98:2:0.5), to afford the title compound (74 mg, 12%) as a white foam. Found: C, 56.92; H, 6.33; N, 17.80. $C_{29}H_{36}N_8O_5S$ requires C, 57.21; H, 5.96; N, 18.41%. δ ($CDCl_3$): 0.94 (3H,t), 1.03 (3H,t), 1.30 (3H,t), 1.72 (2H,m), 2.41 (2H,q), 2.54 (4H,m), 3.14 (4H,m), 3.72 (2H,q), 3.90 (2H,t), 4.78 (2H,t), 5.67 (2H,s), 7.09 (1H,d), 7.22 (1H,m), 7.62 (1H,m), 8.57 (1H,d), 8.62 (1H,s), 8.98 (1H,s), 10.77 (1H,s).

EXAMPLE 11

3-Ethyl-5-[5-(4-ethylpiperazin-1-ylsulphonyl)-2-(3-methoxyprop-1-oxy)pyridin-3-yl]-2-(pyridin-2-yl)methyl-2,6-dihydro-7H-pyrazolo[4,3-d]pyrimidin-7-one A mixture of the title compound of Example 1 (200 mg, 0.36 mmol), potassium bis(trimethylsilyl)amide (361 mg, 1.81 mmol) and 3-methoxypropan-1-ol (1.5 ml) was stirred at 90° C. for 18 hours, then allowed to cool. The resulting mixture was evaporated under reduced pressure and the residue purified by column chromatography on silica gel, using an elution gradient of dichloromethane: methanol (97:3 to 95:5), to give the title compound (81 mg, 38%) as a foam. Found: C, 55.36; H, 6.11; N, 18.18. $C_{28}H_{36}N_8O_5S$; 0.50 $H_2O$ requires C, 55.52; H, 6.16; N, 18.50%. δ ($CDCl_3$): 1.01 (3H,t), 1.29 (3H,t), 2.19 (2H,m), 2.40 (2H,q), 2.54 (4H,m), 3.02 (2H,q), 3.12 (4H,m), 3.39 (3H,s), 3.65 (2H,t), 4.76 (2H,t), 5.68 (2H,s), 7.09 (1H,d), 7.21 (1H,m), 7.62 (1H,m), 8.56 (1H,d), 8.62 (1H,s), 8.93 (1H,s), 10.84 (1H,s). LRMS: m/z 597 $(M+1)^+$.

EXAMPLE 12

5-[5-(4-Ethylpiperazin-1-ylsulphonyl)-2-(3-methoxyprop-1-oxy)pyridin-3-yl]-3-n-propyl-2-(pyridin-2-yl)methyl-2,6-dihydro-7H-pyrazolo[4,3-d]pyrimidin-7-one Obtained as a foam (26%) from the title compound of Preparation 55, using the procedure of Example 10. Found: C, 56.86; H, 6.47; N, 17.78. $C_{29}H_{38}N_8O_5S$ requires C, 57.04; H, 6.27; N, 18.35%. δ ($CDCl_3$): 0.93 (3H,t), 1.02 (3H,t), 1.72 (2H,m), 2.20 (2H,m), 2.40 (2H,q), 2.54 (4H,m), 2.97 (2H,t), 3.12 (4H,m), 3.40 (3H,s), 3.65 (2H,t), 4.77 (2H,t), 5.67 (2H,s), 7.08 (1H,d), 7.21 (1H,m), 7.61 (1H,m), 8.58 (1H,d), 8.62 (1H,s), 8.94 (1H,s), 10.83 (1H,s). LRMS: m/z 611 $(M+1)^+$.

EXAMPLE 13

3-Ethyl-5-[5-(4-ethylpiperazin-1-ylsulphonyl)-2-(1-methoxyprop-2(S)-oxy)pyridin-3-yl]-2-(pyridin-2-yl) methyl-2,6-dihydro-7H-pyrazolo[4,3-d]pyrimidin-7-one Obtained as a foam (33%) from the title compound of Example 1 and 1-methoxypropan-2(S)-ol (J.Chem.Soc., Perkin Trans. I, 1996, 1467), using the procedure of Example 9, but with ether:methanol:0.88 aqueous ammonia (97:3:1) as chromatographic eluant. Found: C, 55.91; H, 6.17; N, 18.10. $C_{28}H_{36}N_8O_5S$; 0.50 $H_2O$ requires C, 55.52; H, 6.16; N, 18.50%. δ ($CDCl_3$): 1.04 (3H,t), 1.30 (3H,t), 1.52 (3H,d), 2.42 (2H,q), 2.56 (4H,m), 3.04 (2H,q), 3.14 (4H,m), 3.55 (3H,s), 3.66 (1H,dd), 3.74 (1H,dd), 5.60 (1H,m), 5.68 (2H,s), 7.08 (1H,d), 7.21 (1H,m), 7.62 (1H,m), 8.57 (1H,d), 8.61 (1H,s), 8.89 (1H,s), 10.85 (1H,s). LRMS: m/z 597 $(M+1)^+$.

EXAMPLE 14

5-[2-(2-Methoxyethoxy)-5-(4-methylpiperazin-1-ylsulphonyl)pyridin-3-yl]3-n-propyl-2-(pyridin-2-yl)methyl-2,6-dihydro-7H-pyrazolo[4,3-d]pyrimidin-7-one A mixture of potassium bis(trimethylsilyl)amide (460 mg, 2.3 mmol) and 2-methoxyethanol (40 ml) was stirred at 90° C. for 30 minutes, then allowed to cool. The title compound of Example 2 (270 mg, 0.46 mmol) was added and the reaction mixture stirred at 110° C. for 5 hours, allowed to cool and evaporated under reduced pressure. The residue was suspended in water (20 ml), the pH adjusted to 7 with hydrochloric acid and the resulting solution extracted with ethyl acetate (3×30 ml). The combined extracts were washed with brine (3×20 mm), dried ($Na_2SO_4$) and evaporated under reduced pressure. The residual oil was purified by column chromatography on silica gel, using an elution gradient of dichloromethane: methanol (100:0 to 96:4), followed by crystallisation from hexane-ethyl acetate, to yield the title compound (200 mg, 75%) as a white solid. Found: C, 54.83; H, 5.83; N, 18.90. $C_{27}H_{34}N_8O_5S$; 0.50 $H_2O$ requires C, 54.81; H, 5.96; N, 18.94%. δ ($CDCl_3$): 0.94 (3H,t), 1.74 (2H,m), 2.28 (3H,s), 2.50 (4H,m), 2.98 (2H,t), 3.15 (4H,m), 3.57 (3H,s), 3.87 (2H,t), 4.80 (2H,t), 5.68 (2H,s), 7.08 (1H,d), 7.22 (1H,m), 7.62 (1H,m), 8.57 (1H,d), 8.64 (1H,s), 8.96 (1H,s), 10.80 (1H,s). LRMS: m/z 583 $(M+1)^+$.

EXAMPLE 15

5-[2-(1,3-Dimethoxyprop-2-oxy)-5-(4-ethylpiperazin-1-ylsulphonyl)pyridin-3-yl]-3-n-propyl-2-(pyridin-2-yl) methyl-2,6-dihydro-7H-pyrazolo[4,3-d]-pyrimidin-7-one A mixture of the title compound of Preparation 72 (70 mg, 0.10 mmol), potassium t-butoxide (23 mg, 0.20 mmol) and 3-methylpentan-3-ol (3 ml) was stirred under reflux for 4 hours, then allowed to cool and evaporated under reduced pressure. The residue was purified by column chromatography on silica gel, using dichloromethane: methanol (98:2) as eluant, to provide the title compound (6 mg, 9%) as an off-white solid. δ ($CDCl_3$): 0.93 (3H,t), 1.03 (3H,t), 1.72 (2H,m), 2.42 (2H,q), 2.55 (4H,m), 2.98 (2H,t), 3.16 (4H,m), 3.50 (6H,s), 3.77 (2H,m), 3.86 (2H,m), 5.68 (3H,m), 7.08 (1H,d), 7.21 (1H,m), 7.62 (1H,m), 8.57 (1H,d), 8.61 (1H,s), 8.84 (1H,s), 10.87 (1H,s). LRMS: m/z 641 $(M+1)^+$.

EXAMPLE 16

3-Ethyl-5-[5-(4-ethylpiperazin-1-ylsulphonyl)-2-(2-methoxyethoxy)pyridin-3-yl]-1-(pyridin-2-yl)methyl-1,6-dihydro-7H-pyrazolo[4,3-d]pyrimidin-7-one Obtained as a white solid (50%) from the title compound of Preparation 65, using the procedure of Example 10. Found: C, 55.45; H, 5.91; N, 18.94. $C_{27}H_{34}N_8O_5S$ requires C, 55.66; H, 5.88; N, 19.23%. δ ($CDCl_3$): 1.02 (3H,t), 1.40 (3H,t), 2.42 (2H,q), 2.56 (4H,m), 3.00 (2H,q), 3.16 (4H,m), 3.55 (3H,s), 3.86 (2H,t), 4.78 (2H,t), 5.95 (2H,s), 7.01 (1H,d), 7.17 (1H,m), 7.60 (1H,m), 8.57 (1H,d), 8.62 (1H,s), 9.02 (1H,s), 11.04 (1H,s). LRMS: m/z 583 $(M+1)^+$.

EXAMPLE 17

3-Ethyl-5-[5-(4-ethylpiperazin-1-ylsulphonyl)-2-(tetrahydrofuran-3(S)-yloxy)pyridin-3-yl]-2-(pyridin-2-yl) methyl-2,6-dihydro-7H-pyrazolo[4,3-d]pyrimidin-7-one Obtained as a solid (29%) from the title compound of Preparation 56, using the procedure of Example 10. Found: C, 55.85; H, 5.98; N, 17.86. $C_{28}H_{34}N_8O_5S$; 0.20 $H_2O$; 0.10 $CH_2Cl_2$ requires C, 55.24; H, 5.73; N, 18.41%. δ ($CDCl_3$): 1.02 (3H,t), 1.28 (3H,t), 2.40 (4H,m), 2.55 (4H,m), 3.02 (2H,q), 3.13 (4H,m), 4.00 (2H,m) 4.16 (2H,m), 5.68 (2H,s), 5.86 (1H,m), 7.10 (1H,d), 7.22 (1H,m), 7.63 (1H,m), 8.56 (1H,d), 8.63 (1H,s), 8.98 (1H,s), 10.42 (1H,s). LRMS: m/z 594 $(M)^+$. $[\alpha]_D^{25}$ −13.8° (c=0.10, $CH_3OH$).

EXAMPLE 18

3-Ethyl-5-[5-(4-ethylpiperazin-1-ylsulphonyl)-2-(tetrahydrofuran-3(R)-yloxy)pyridin-3-yl]-2-(pyridin-2-yl) methyl-2,6-dihydro-7H-pyrazolo[4,3-d]pyrimidin-7-one Obtained as a solid (24%) from the title compound of Preparation 75, using the procedure of Example 10. Found: C, 55.32; H, 5.82; N, 17.70. $C_{28}H_{34}N_8O_5S$; $H_2O$ requires C, 54.88; H, 5.92; N, 18.29%. δ ($CDCl_3$): 1.02 (3H,t), 1.28 (3H,t), 2.40 (4H,m), 2.55 (4H,m), 3.02 (2H,q), 3.13 (4H,m), 4.00 (2H,m), 4.16 (2H,m), 5.68 (2H,s), 5.86 (1H,m), 7.10 (1H,d), 7.22 (1H,m), 7.63 (1H,m), 8.56 (1H,d), 8.63 (1H,s), 8.98 (1H,s), 10.42 (1H,s). LRMS: m/z 595 $(M+1)^+$. $[\alpha]_D^{25}$+ 14.0° (c=0.14, $CH_3OH$).

EXAMPLE 19
5-[5-(4-Ethylpiperazin-1-ylsulphonyl)-2-(tetrahydropyran-4-yloxy)pyridin-3-yl]-3-n-propyl-2-(pyridin-2-yl)methyl-2,6-dihydro-7H-pyrazolo[4,3-d]pyrimidin-7-one Obtained as a white solid (30%) from the title compound of Preparation 76, using the procedure of Example 10. δ ($CDCl_3$): 0.94 (3H,t), 1.03 (3H,t), 1.73 (2H,m), 2.01 (2H,m), 2.22 (2H,m), 2.40 (2H,q), 2.55 (4H,m), 2.98 (2H,t), 3.12 (4H,m), 3.66 (2H,m), 4.06 (2H,m), 5.60 (1H,m), 5.69 (2H,s), 7.10 (1H,d), 7.22 (1H,m), 7.63 (1H,m), 8.57 (1H,d), 8.61 (1H,s), 9.01 (1H,s), 10.55 (1H,s). LRMS: m/z 623 $(M+1)^+$.

EXAMPLE 20
3-Ethyl-5-[5-(4-methylpiperazin-1-ylsulphonyl)-2-n-propoxypyridin-3-yl]-2-(pyridin-2-yl)methyl-2,6-dihydro-7H-pyrazolo[4,3-d]pyrimidin-7-one Potassium t-butoxide (540 mg, 4.8 mmol) was added to a stirred solution of the title compound of Preparation 52 (683 mg, 1.2 mmol) in n-propanol (10 ml) and the reaction mixture stirred under reflux for 18 hours, then allowed to cool. The resulting mixture was evaporated under reduced pressure and the residual oil purified by column chromatography on silica gel, using an elution gradient of dichloromethane: methanol (100:0 to 95:5) to furnish the title compound (290 mg, 44%) as a foam. Found: C, 56.32; H, 6.04; N, 19.36. $C_{26}H_{32}N_8O_4S$ requires C, 56.50; H, 5.83; N, 20.27%. δ ($CDCl_3$): 1.02 (3H,t), 1.30 (3H,t), 1.98 (2H,m), 2.38 (3H,s), 2.50 (4H,m), 3.04 (2H,q), 3.13 (4H,m), 4.64 (2H,t), 5.69 (2H,s), 7.10 (1H,d), 7.22 (1H,m), 7.30 (1H,m), 8.58 (1H,d), 8.63 (1H,s), 9.04 (1H,s), 10.66 (1H,s). LRMS: m/z 553 $(M+1)^+$.

EXAMPLE 21
3-Ethyl-5-[5-(4-methylpiperazin-1-ylsulphonyl)-2-(prop-2-oxy)pyridin-3-yl]-2-(pyridin-2-yl)methyl-2,6-dihydro-7H-pyrazolo[4,3-d]pyrimidin-7-one Potassium t-butoxide (290 mg, 2.60 mmol) was added to a stirred solution of the title compound of Example 20 (239 mg, 0.43 mmol) in propan-2-ol (7 ml) under nitrogen and the reaction mixture heated under reflux for 48 hours, then allowed to cool. The resulting mixture was evaporated under reduced pressure and the residue partitioned between water (20 ml) and ethyl acetate (20 ml).

The phases were separated, the aqueous phase extracted with ethyl acetate and the combined organic solutions dried ($MgSO_4$) and evaporated under reduced pressure. The residue was purified by column chromatography on silica gel, using an elution gradient of dichloromethane: methanol (100:0 to 95:5), to afford the title compound (84 mg,35%) as a foam. δ ($CDCl_3$): 1.28 (3H,t), 1.56 (6H,2xd), 2.28 (3H,s), 2.50 (4H,m), 3.04 (2H,q), 3.14 (4H,m), 5.68 (3H,m), 7.09 (1H,d), 7.22 (1H,m), 7.62 (1H,m), 8.57 (1H,d), 8.62 (1H,s), 9.02 (1H,s), 10.68 (1H,s). LRMS: m/z 553 $(M+1)^+$.

EXAMPLE 22
3-Ethyl-5-[5-(4-ethylpiperazin-1-ylsulphonyl)-2-(prop-2-oxy)pyridin-3-yl]-2-(pyridin-2-yl)methyl-2,6-dihydro-7H-pyrazolo[4,3-d]pyrimidin-7-one A mixture of the title compound of Preparation 45A (200 mg, 0.35 mmol), 60% sodium hydride dispersion in mineral oil (400 mg, 1 mmol) and propan-2-ol (20 ml) was stirred under reflux for 18 hours, then allowed to cool. Saturated aqueous ammonium chloride solution (20 ml) was added, the resulting mixture extracted with ethyl acetate (3×50 ml), then the combined extracts washed with aqueous sodium bicarbonate solution (150 ml), dried ($MgSO_4$) and evaporated under reduced pressure. The residue was purified by column chromatography on silica gel, using an elution gradient of dichloromethane: methanol (100:0 to 95:5), to give the title compound (11 mg, 6%) as a foam. δ ($CDCl_3$): 1.04 (3H,t), 1.30 (3H,t), 1.56 (6H,2xd), 2.1 (2H,q), 2.55 (4H,m), 3.04 (2H,q), 3.13 (4H,m), 5.68 (3H,m), 7.10 (1H,d), 7.22 (1H,m), 7.62 (1H,m), 8.57 (1H,d), 8.62 (1H,s), 9.02 (1H,s), 10.68 (1H,s). LRMS: m/z 567 $(M+1)^+$.

EXAMPLE 23
5-[2-n-Butoxy-5-(4-ethylpiperazin-1-ylsulphonyl)pyridin-3-yl]-3-ethyl-2-(pyridin-2-yl)methyl-2,6-dihydro-7H-pyrazolo[4,3-d]pyrimidin-7-one A mixture of the title compound of Example 1 (200 mg, 0.36 mmol), potassium bis(trimethylsilyl)amide (360 mg, 1.81 mmol) and n-butanol (5 ml) was stirred at 100° C. for 18 hours, then allowed to cool. The resulting mixture was evaporated under reduced pressure and the residue partitioned between water (5 ml) and dichloromethane (5 ml). The phases were separated and the aqueous layer extracted with dichloromethane (2×10 ml), then the combined organic solutions dried ($MgSO_4$) and evaporated under reduced pressure. The residual yellow solid was purified by column chromatography on silica gel, using dichloromethane: methanol (97.5:2.5) as eluant, to yield the title compound (145 mg, 69%) as a white solid. Found: C, 57.43; H, 6.29; N, 18.82. $C_{28}H_{36}N_8O_4S$; 0.20 $H_2O$ requires C, 57.56; H, 6.28; N, 19.18%. δ ($CDCl_3$): 1.03 (6H,2xt), 1.30 (3H,t), 1.55 (2H,m), 1.94 (2H,m), 2.40 (2H,q), 2.55 (4H,m), 3.03 (2H,q), 3.13 (4H,m), 4.67 (2H,t), 5.68 (2H,s), 7.10 (1H,d), 7.22 (1H,m), 7.62 (1H,m), 8.56 (1H,d), 8.62 (1H,s), 9.01 (1H,s), 10.64 (1H,s). LRMS: m/z 581 $(M+1)^+$.

EXAMPLE 24
5-[2-i-Butoxy-5-(4-ethylpiperazin-1-ylsulphonyl)pyridin-3-yl]-3-ethyl-2-(pyridin-2-yl)methyl-2,6-dihydro-7H-pyrazolo[4,3-d]pyrimidin-7-one Obtained as a white solid (67%) from the title compound of Example 1 and i-butanol, using the procedure of Example 23. Found: C, 57.25; H, 6.24; N, 18.84. $C_{28}H_{36}N_8O_4S$; 0.20 $H_2O$ requires C, 57.56; H, 6.28; N, 19.18%. δ ($CDCl_3$): 1.03 (3H,t), 1.12 (6H,d), 1.30 (3H,t), 2.30 (1H,m), 2.40 (2H,q), 2.55 (4H,m), 3.04 (2H,q), 3.13 (4H,m), 4.45 (2H,d), 5.68 (2H,s), 7.10 (1H,d), 7.22 (1H,m), 7.63 (1H,m), 8.58 (1H,d), 8.62 (1H,s), 9.02 (1H,s), 10.63 (1H,s). LRMS: m/z 581 $(M+1)^+$.

EXAMPLE 25
5-[2-Cyclobutoxy-5-(4-ethylpiperazin-1-ylsulphonyl)pyridin-3-yl]-3-ethyl-2-(pyridin-2-yl)methyl-2,6-dihydro-7H-pyrazolo[4,3-d]pyrimidin-7-one A stirred mixture of the title compound of Preparation 45A (200 mg, 0.35 mmol), cyclobutanol (144 mg, 2 mmol), potassium t-butoxide (80 mg, 0.70 mmol) and 1,4-dioxan (5 ml) was heated under reflux for 24 hours, then allowed to cool. The resulting mixture was poured into stirred aqueous sodium bicarbonate solution (20 ml) and this mixture extracted with ethyl acetate (3×20 ml). The combined extracts were dried ($MgSO_4$) and evaporated under reduced pressure, then the residue purified by column chromatography on silica gel, using an elution gradient of dichloromethane: methanol (100:0 to 96:4), to provide the title compound (9 mg, 4%) as a solid. δ (CDCl$_3$): 1.03 (3H,t), 1.29 (3H,t), 1.78 (2H,m), 1.98 (2H,m), 2.35 (2H,m), 2.55 (6H,m), 3.04 (2H,q), 3.12 (4H,m), 5.48 (1H,m), 5.68 (2H,s), 7.10 (1H,d), 7.23 (1H,m), 7.63 (1H,m), 8.56 (1H,d), 8.60 (1H,s), 9.01 (1H,s), 10.67 (1H,s). LRMS: m/z 579 (M+1)$^+$.

EXAMPLE 26
5-[2-Ethoxy-5-(4-ethylpiperazin-1-ylsulphonyl)pyridin-3-yl]-3-n-propyl-2-(pyridin-2-yl)methyl-2,6-dihydro-7H-pyrazolo[4,3-d]pyrimidin-7-one Potassium t-butoxide (2.38 g, 21.2 mmol) was added to a solution of the title compound of Preparation 77 (3.1 g, 5.3 mmol) in absolute ethanol (95 ml) and the reaction mixture heated at 100° C. in a sealed vessel for 40 hours, then allowed to cool. The resulting mixture was evaporated under reduced pressure, the residue dissolved in water (20 ml) and the aqueous solution acidified to pH 5 with 2M hydrochloric acid. The aqueous suspension thus obtained was extracted with dichloromethane (3×30 ml) and the combined extracts dried (MgSO$_4$) and evaporated under reduced pressure. The residual brown foam was purified by column chromatography on silica gel, using an elution gradient of dichloromethane: methanol (99:1 to 97:3), to furnish the title compound (1.39 g, 46%) as a foam. δ (CDCl$_3$): 0.93 (3H,t), 1.02 (3H,t), 1.58 (3H,t), 1.74 (2H,m), 2.40 (2H,q), 2.54 (4H,m), 2.98 (2H,t), 3.13 (4H,m), 4.75 (2H,q), 5.68 (2H,s), 7.09 (1H,d), 7.23 (1H,m), 7.63 (1H,m), 8.58 (1H,d), 8.63 (1H,s), 9.02 (1H,s), 10.64 (1H,s).

EXAMPLE 27
5-{5-[4-(3-Dimethylaminoprop-1-yl)piperazin-1-ylsulphonyl]-2-ethoxypyridin-3-yl}-3-n-propyl-2-(pyridin-2-yl)methyl-2,6-dihydro-7H-pyrazolo[4,3-d]pyrimidin-7-one Trihydrochloride A solution of freshly distilled 1-(3-dimethylaminoprop-1-yl)piperazine (J.Chem.Soc. (C), 1971, 132; 160 mg, 0.93 mmol) in ethanol (2 ml) was added to a stirred solution of the title compound of Preparation 63 (230 mg, 0.467 mmol) in ethanol (10 ml) and the reaction mixture stirred at room temperature for 18 hours, then evaporated under reduced pressure. The residue was suspended in aqueous sodium bicarbonate solution (30 ml), the suspension extracted with ethyl acetate (3×30 ml) and the combined extracts washed with brine (2×30 ml), dried (Na$_2$SO$_4$), and evaporated under reduced pressure. The residual oil was purified by column chromatography on silica gel, using an elution gradient of dichloromethane: methanol (100:0 to 90:10), then the product dissolved in the minimum volume of ethyl acetate. Saturated ethereal hydrogen chloride solution was added and the resulting white precipitate collected, triturated with ether and dried under suction to afford the title compound (140 mg, 37%) as a white solid. Found: C, 44.45; H, 6.34; N, 15.38. C$_{30}$H$_{41}$N$_9$O$_4$S; 3HCl; 4H$_2$O requires C, 44.75; H, 6.51; N, 15.66%. δ (DMSOd$_6$): 0.86 (3H,t), 1.34 (3H,t), 1.64 (2H,m), 2.12 (2H,m), 2.72 (6H,2xs), 2.95 (2H,t), 3.00 (2H,m), 3.12 (2H,t), 3.18 (2H,m), 3.56 (2H,m), 3.84 (2H,m), 4.50 (2H,q), 5.75 (2H,s), 7.27 (1H,d), 7.42 (1H,m), 7.90 (1H,m), 8.28 (1H,s), 8.57 (1H,d), 8.73 (1H,s), 10.63 (1H,s), 11.47 (1H,s), 11.96 (1H,s). LRMS: m/z 624 (M+1)$^+$.

EXAMPLE 28
5-[5-(4-Ethylpiperazin-1-ylsulphonyl)-2-n-propoxypyridin-3-yl]-3-n-propyl-2-(pyridin-2-yl)methyl-2,6-dihydro-7H-pyrazolo[4,3-d]pyrimidin-7-one Obtained as a colourless solid (40%) from the title compound of Preparation 80, using the procedure of Example 20. Found: C, 57.16; H, 6.15; N, 18.85. C$_{28}$H$_{36}$N$_8$O$_4$S; 0.50 H$_2$O requires C, 57.03; H, 6.32; N, 19.00%. δ (CDCl$_3$): 0.94 (3H,t), 1.02 (3H,t), 1.13 (3H,t), 1.74 (2H,m), 1.98 (2H,m), 2.40 (2H,q), 2.54 (4H,m), 2.98 (2H,t), 3.12 (4H,m), 4.62 (2H,t), 5.66 (2H,s), 7.09 (1H,d), 7.21 (1H,m), 7.62 (1H,m), 8.57 (1H,d), 8.62 (1H,s), 9.02 (1H,s), 10.63 (1H,s). LRMS: m/z 582 (M+2)$^+$.

EXAMPLE 29
5-[5-(4-Ethylpiperazin-1-ylsulphonyl)-2-(prop-2-oxy)pyridin-3-yl]-3-n-propyl-2-(pyridin-2-yl)methyl-2,6-dihydro-7H-pyrazolo[4,3-d]pyrimidin-7-one Obtained as a solid (48%) from the title compound of Example 26 and propan-2-ol, using the procedure of Example 21. δ (CDCl$_3$): 0.94 (3H,t), 1.03 (3H,t), 1.57 (6H,d), 1.74 (2H,m), 2.41 (2H,q), 2.56 (4H,m), 2.98 (2H,t), 3.12 (4H,m), 5.68 (3H,m), 7.08 (1H,d), 7.22 (1H,m), 7.63 (1H,m), 8.57 (1H,d), 8.63 (1H,s), 9.02 (1H,s), 10.67 (1H,s). LRMS: m/z 581 (M+1)$^+$.

EXAMPLE 30
5-{2-Ethoxy-5-[4-(2-hydroxyethyl)piperazin-1-ylsulphonyl]pyridin-3-yl}-3-n-propyl-2-(pyridin-2-yl)methyl-2,6-dihydro-7H-pyrazolo[4,3-d]pyrimidin-7-one Obtained as a white solid (49%) from the title compound of Preparation 63 and 1-(2-hydroxyethyl)piperazine, using the procedure of Example 2. Found: C, 55.48; H, 5.93; N, 18.85. C$_{27}$H$_{34}$N$_8$O$_5$S; 0.10 C$_4$H$_8$O$_2$ requires C, 55.64; H, 5.93; N, 18.94%. δ (CDCl$_3$): 0.95 (3H,t), 1.59 (3H,t), 1.75 (2H,m), 2.28 (1H,s), 2.58 (2H,m), 2.65 (4H,m), 3.00 (2H,t), 3.16 (4H,m), 3.60 (2H,t), 4.76 (2H,q), 5.68 (2H,s), 7.10 (1H,d), 7.22 (1H,m), 7.62 (1H,m), 8.58 (1H,d), 8.64 (1H,s), 9.04 (1H,s), 10.66 (1H,s). LRMS: m/z 583 (M+1)$^+$.

EXAMPLE 31
5-{2-Ethoxy-5-[4-(3-hydroxyprop-1-yl)piperazin-1-ylsulphonyl]pyridin-3-yl}-3-n-propyl-2-(pyridin-2-yl)methyl-2,6-dihydro-7H-pyrazolo[4,3-d]pyrimidin-7-one Obtained as a white solid (52%) from the title compound of Preparation 63 and 1-(3-hydroxyprop-1-yl)piperazine, using the procedure of Example 2. Found: C, 56.27; H, 6.13; N, 18.38. C$_{28}$H$_{36}$N$_8$O$_5$S requires C, 56.36; H, 6.08; N, 18.78%. δ (CDCl$_3$): 0.94 (3H,t), 1.60 (3H,t), 1.72 (4H,m), 2.63 (6H,m), 2.98 (2H,t), 3.12 (4H,m), 3.72 (2H,t), 4.15 (1H,s), 4.77 (2H,q), 5.69 (2H,s), 7.08 (1H,d), 7.23 (1H,m), 7.63 (1H,m), 8.58 (1H,d), 8.61 (1H,s), 9.01 (1H,s), 10.67 (1H,s). LRMS: m/z 596 (M)$^+$.

EXAMPLE 32
5-[2-(2-Benzyloxyethoxy)-5-(4-ethylpiperazin-1-ylsulphonyl)pyridin-3-yl]-3-ethyl-2-(pyridin-2-yl)methyl-2,6-dihydro-7H-pyrazolo[4,3-d]pyrimidin-7-one Obtained as a yellow oil (57%) from the title compound of Example 1 and 2-benzyloxyethanol, using the procedure of Example 11. δ (CDCl$_3$): 1.02 (3H,t), 1.32 (3H,t), 2.40 (2H,q), 2.54 (4H,m), 3.04 (2H,q), 3.13 (4H,m), 3.94 (2H,t), 4.76 (2H,s), 4.80 (2H,t), 5.69 (2H,s), 7.11 (1H,d), 7.20–7.37 (4H,m), 7.41 (2H,m), 7.64 (1H,m), 8.60 (2H,m), 8.98 (1H,s), 10.80 (1H,s). LRMS: m/z 659 (M+1)$^+$.

EXAMPLE 33
3-Ethyl-5-[5-(4-ethylpiperazin-1-ylsulphonyl)-2-(2-hydroxyethoxy)pyridin-3-yl]-2-(pyridin-2-yl)methyl-2,6-dihydro-7H-pyrazolo[4,3-d]pyrimidin-7-one Ammonium formate (62 mg, 0.99 mmol) was added to a mixture of the title compound of Example 32 (130 mg, 0.197 mmol), 10% palladium on charcoal (15 mg) and acetone (9 ml) and the reaction mixture stirred under reflux for 14 hours, then allowed to cool. The resulting mixture was evaporated under reduced pressure and the residue purified by column chromatography on silica gel, using an elution gradient of dichloromethane: methanol (100:0 to 90:10), to give the title compound (18 mg, 16%) as a solid. δ (CD$_3$OD): 1.06 (3H,t), 1.28 (3H,t), 2.44 (2H,q), 2.58 (4H, m), 3.06 (2H,q), 3.14 (4H,m), 3.97 (2H,t), 4.68 (2H,t), 5.75 (2H,s), 7.20 (1H,d), 7.36 (1H,m), 7.80 (1H,m), 8.54 (2H,m), 8.68 (1H,s). LRMS: m/z 569 (M+1)$^+$.

EXAMPLE 34

5-[2-(2-Benzyloxyethoxy)-5-(4-ethylpiperazin-1-ylsulphonyl)pyridin-3-yl]-3-n-propyl-2-(pyridin-2-yl) methyl-2,6-dihydro-7H-pyrazolo[4,3-d]pyrimidin-7-one A stirred mixture of the title compound of Preparation 84 (500 mg, 0.72 mmol), potassium bis(trimethylsilyl)amide (347 mg, 3.09 mmol) and 3-methylpentan-3-ol (8 ml) was heated under reflux for 36 hours, then allowed to cool. The resulting mixture was evaporated under reduced pressure and the residue partitioned between water (10 ml) and dichloromethane (10 ml). The phases were separated, the aqueous phase extracted with dichloromethane (2×10 ml) and the combined organic solutions dried (MgSO$_4$) and evaporated under reduced pressure. The crude product was purified by two column chromatography operations on silica gel, using firstly dichloromethane: methanol:0.88 aqueous ammonia (90:10:1) and then a gradient of ethyl acetate: methanol (100:0 to 80:20) as eluants, to yield the title compound as an oil. δ (CDCl$_3$): 0.92 (3H,t), 1.02 (3H,t), 1.73 (2H,m), 2.40 (2H,q), 2.54 (4H,m), 2.99 (2H,t), 3.10 (4H,m), 3.84 (2H,t), 4.58 (2H,s), 4.78 (2H,t), 5.68 (2H,s), 7.09 (1H,d), 7.18–7.42 (6H,m), 7.62 (1H,m), 8.55 (1H,d), 8.61 (1H,s), 8.97 (1H,s), 10.81 (1H,s). LRMS: m/z 673 (M+1)$^+$.

EXAMPLE 35

2-Benzyl-5-[2-ethoxy-5-(4-ethylpiperazin-1-ylsulphonyl) pyridin-3-yl]-3-ethyl-2,6-dihydro-7H-pyrazolo[4,3-d] pyrimidin-7-one Obtained as a white foam (27%) from the title compound of Preparation 87, using the procedure of Example 10. δ (CDCl$_3$): 0.90 (3H,t): 1.03 (3H,t), 1.28 (3H,t), 2.40 (2H,q), 2.54 (4H,m), 2.94 (2H,q), 3.12 (4H,m), 4.75 (2H,q), 5.58 (2H,s), 7.22 (2H,m), 7.31 (3H,m), 8.62 (1H,s), 9.01 (1H,s), 10.65 (1H,s). LRMS: m/z 552 (M+1)$^+$.

EXAMPLE 36

2-Benzyl-3-ethyl-5-[5-(4-ethylpiperazin-1-ylsulphonyl)-2-(2-methoxyethoxy)pyridin-3-yl]-2,6-dihydro-7H-pyrazolo [4,3-d]pyrimidin-7-one Obtained as a cream foam (80%) from the title compound of Example 35 and 2-methoxyethanol, using the procedure of Example 9. Found: C, 57.05; H, 6.19; N, 16.15. C$_{28}$H$_{35}$N$_7$O$_5$S; 0.10 CH$_2$Cl$_2$ requires C, 57.19; H, 6.01; N, 16.61%. δ (CDCl$_3$): 1.02 (3H,t), 1.27 (3H,t), 2.40 (2H,q), 2.55 (4H,m), 2.94 (2H,q), 3.13 (4H,m), 3.57 (3H,s), 3.86 (2H,t), 4.78 (2H,t), 5.56 (2H,s), 7.22 (2H,m), 7.32 (3H,m), 8.61 (1H,s), 8.96 (1H,s), 10.80 (1H,s).

EXAMPLE 37

3-Ethyl-5-[5-(4-ethylpiperazin-1-ylsulphonyl)-2-(2-methoxyethoxy)pyridin-3-yl]-2-(1-methylimidazol-2-yl) methyl-2,6-dihydro-7H-pyrazolo[4,3-d]pyrimidin-7-one Obtained as a foam (33%) from the title compound of Preparation 90, using the procedure of Example 10. δ (CDCl$_3$): 1.05 (3H,t), 1.34 (3H,t), 2.41 (2H,q), 2.54 (4H,m), 3.13 (4H,m), 3.19 (2H,q), 3.57 (3H,s), 3.79 (3H,s), 3.86 (2H,t), 4.78 (2H,t), 5.65 (2H,s), 6.84 (1H,s), 7.00 (1H,s), 8.62 (1H,s), 8.94 (1H,s), 10.83 (1H,s). LRMS: m/z 586 (M+1)$^+$.

EXAMPLE 38

5-[2-Ethoxy-5-(4-ethylpiperazin-1-ylsulphonyl)pyridin-3-yl]-2-(1-methylimidazol-2-yl)methyl-3-n-propyl-2,6-dihydro-7H-pyrazolo[4,3-d]pyrimidin-7-one A mixture of the title compounds of Preparation 28 (232 mg, 0.58 mmol) and Preparation 92 (152 mg, 0.58 mmol), triethylamine (403 μl, 2.9 mmol) and dichloromethane (8 ml) was stirred at room temperature for 18 hours. Brine (20 ml) was added and the resulting mixture extracted with dichloromethane (2×20 ml), then the combined extracts were dried (MgSO$_4$) and evaporated under reduced pressure.

A stirred solution of this intermediate and potassium bis(trimethylsilyl)amide (305 mg, 1.53 mmol) in ethanol (10 ml) was heated at 100° C. for 14 hours, then allowed to cool. The resulting mixture was evaporated under reduced pressure and the residue purified by column chromatography on silica gel, using dichloromethane: methanol (95:5) as eluant, to provide the title compound (163 mg, 49%) as a yellow oil. δ (CDCl$_3$): 0.96 (3H,t), 1.01 (3H,t), 1.57 (3H,t), 1.72 (2H, m), 2.40 (2H,q), 2.55 (4H,m), 3.13 (6H,m), 3.77 (3H,s), 4.75 (2H,q), 5.67 (2H,s), 6.85 (1H,s), 7.00 (1H,s), 8.63 (1H,s), 9.00 (1H,s), 10.65 (1H,s). LRMS: m/z 570 (M+1)$^+$.

EXAMPLE 39

5-[5-(4-Ethylpiperazin-1-ylsulphonyl)-2-(2-methoxyethoxy)pyridin-3-yl]-2-(1-methylimidazol-2-yl) methyl-3-n-propyl-2,6-dihydro-7H-pyrazolo[4,3-d] pyrimidin-7-one Obtained as a solid (61%) from the title compound of Example 38 and 2-methoxyethanol, using the procedure of Example 9. δ (CDCl$_3$): 0.97 (3H,t), 1.02 (3H,t), 1.74 (2H, m), 2.41 (2H,q), 2.55 (4H,m), 3.14 (6H,m), 3.57 (3H,s), 3.76 (3H,s), 3.86 (2H,t), 4.78 (2H,t), 5.66 (2H,s), 6.86 (1H,s), 7.00 (1H,s), 8.62 (1H,s), 8.94 (1H,s), 10.82 (1H,s). LRMS: m/z 600 (M+1)$^+$.

EXAMPLE 40

5-[2-n-Butoxy-5-(4-ethylpiperazin-1-ylsulphonyl)pyridin-3-yl]-2-(1-methylimidazol-2-yl)methyl-3-n-propyl-2,6-dihydro-7H-pyrazolo[4,3-d]pyrimidin-7-one Obtained as a cream coloured foam (76%) from the title compound of Example 38 and n-butanol, using the procedure of Example 9. Found: C, 54.83; H, 6.74; N, 20.08. C$_{28}$H$_{39}$N$_9$O$_4$S; H$_2$O requires C, 54.62; H, 6.71; N, 20.47%. δ (CDCl$_3$): 0.93 (3H,t), 1.00 (6H,m), 1.54 (2H,m), 1.77 (2H,m), 1.92 (2H,m), 2.40 (2H,q), 2.53 (4H,m), 3.12 (6H, m), 3.76 (3H,s), 4.66 (2H,t,), 5.67 (2H,s), 6.85 (1H,s), 6.98 (1H,s), 8.62 (1H,s), 8.97 (1H,s), 10.64 (1H,s). LRMS: m/z 599 (M+2)$^+$.

EXAMPLE 41

5-[5-(4-Ethylpiperazin-1-ylsulphonyl)-2-(prop-2-oxy) pyridin-3-yl]-3-n-propyl-2-(pyridazin-3-yl)methyl-2,6-dihydro-7H-pyrazolo[4,3-d]pyrimidin-7-one A mixture of the title compound of Preparation 98 (230 mg, 0.38 mmol), potassium t-butoxide (258 mg, 2.3 mmol) and propan-2-ol (10 ml) was heated in a sealed vessel at 100° C. for 24 hours, then allowed to cool. The resulting mixture was evaporated under reduced pressure, then the residue purified by two column chromatography operations on silica gel, using firstly an elution gradient of dichloromethane: methanol (100:0 to 95:5) and then an elution gradient of ethyl acetate: methanol (90:10 to 80:20), to furnish the title compound (42 mg, 19%) as an orange gum. δ (CDCl$_3$): 0.93 (3H,t), 1.01 (3H,t), 1.55 (6H,d), 1.75 (2H,m), 2.40 (2H,q), 2.54 (4H,m), 3.02 (2H,t), 3.12 (4H,m), 5.67 (1H,m), 5.88 (2H,s), 7.47 (2H,m), 8.60 (1H,s), 8.98 (1H,s), 9.16 (1H,d), 10.70 (1H,s). LRMS: m/z 582 (M+1)$^+$.

EXAMPLE 42

5-[5-(4-Ethylpiperazin-1-ylsulphonyl)-2-(2-methoxyethoxy)pyridin-3-yl]-3-n-propyl-2-(pyrimidin-2-yl)methyl-2,6-dihydro-7H-pyrazolo[4,3-d]pyrimidin-7-one Obtained as a yellow foam (14%) from the title compound of Preparation 102b, using the procedure of Example 10. δ (CDCl$_3$): 0.99 (3H,t), 1.03 (3H,t), 1.81 (2H,m), 2.42 (2H,q), 2.55 (4H,m), 2.97 (2H,t), 3.14 (4H,m), 3.54 (3H,s), 3.86 (2H,t), 4.78 (2H,t), 5.80 (2H,s), 7.22 (1H,m), 8.62 (1H,s), 8.70 (2H,d), 8.99 (1H,s), 10.72 (1H,s). LRMS: m/z 597 (M)$^+$.

EXAMPLE 43a

5-[2-Ethoxy-5-(4-ethylpiperazin-1-ylsulphonyl)pyridin-3-yl]-3-n-propyl-1-(pyrimidin-2-yl)methyl-1,6-dihydro-7H-pyrazolo[4,3-d]pyrimidin-7-one
and

EXAMPLE 43b

5-[2-Ethoxy-5-(4-ethylpiperazin-1-ylsulphonyl)pyridin-3-yl]-3-n-propyl-2-(pyrimidin-2-yl)methyl-2,6-dihydro-7H-pyrazolo[4,3-d]pyrimidin-7-one A stirred mixture of the title compounds of Preparation 103a and Preparation 103b (390 mg, 0.66 mmol), potassium t-butoxide (224 mg, 2.0 mmol), 4 Å molecular sieves and ethanol (10 ml) was heated in a sealed vessel for 18 hours at 100° C., then allowed to cool and filtered. The filtrate was evaporated under reduced pressure and the residual brown oil suspended in dichloromethane (25 ml). This mixture was washed with water (5 ml), dried (MgSO$_4$) and evaporated under reduced pressure, then the residue purified by column chromatography on silica gel, using an elution gradient of dichloromethane: methanol (99:1 to 95:5) to give an orange foam. This product was further purified by HPLC using a C$_{18}$ Magellan column and methanol: water:diethylamine (50:50:0.1) as eluant, at a rate of 20 ml/min, to afford the first title compound (1-isomer; 20 mg) as a white solid. δ (CDCl$_3$): 1.04 (6H,m), 1.58 (3H,t), 1.88 (2H,m), 2.42 (2H,q), 2.57 (4H,m), 2.98 (2H,t), 3.14 (4H,m), 4.75 (2H,q), 6.07 (2H,s), 7.18 (1H,m), 8.64 (3H,m), 9.10 (1H,s), 10.75 (1H,s). LRMS: m/z 568 (M+1)$^+$; followed by the second title compound (2-isomer; 20 mg) as a white solid. δ (CDCl$_3$): 1.02 (6H,m), 1.58 (3H,t), 1.82 (2H,m), 2.42 (2H,q), 2.55 (4H,m), 2.98 (2H,t), 3.15 (4H,m), 4.74 (2H,q), 5.80 (2H,s), 7.23 (1H,m), 8.63 (1H,s), 8.70 (2H,m), 9.03 (1H,s), 10.56 (1H,s). LRMS: m/z 568 (M+1)$^+$.

EXAMPLE 44

5-[2-Ethoxy-5-(4-ethylpiperazin-1-ylsulphonyl)pyridin-3-yl]-3-n-propyl-1-(pyridin-2-yl)methyl-1,6-dihydro-7H-pyrazolo[4,3-d]pyrimidin-7-one A stirred mixture of the title compound of Preparation 105 (304 mg, 0.52 mmol), potassium t-butoxide (175 mg, 1.56 mmol) and ethanol (10 ml) was heated in a sealed vessel at 100° C. for 18 hours, then allowed to cool. The resulting mixture was evaporated under reduced pressure and the residual brown oil partitioned between dichloromethane (15 ml) and water (5 ml). The phases were separated, then the organic phase dried (MgSO$_4$) and evaporated under reduced pressure to give a brown foam, which was purified by column chromatography on silica gel, using dichloromethane: methanol (97:3) as eluant, to provide the title compound (230 mg, 78%) as a white foam. Found: C, 56.93; H, 6.03; N, 19.42. C$_{27}$H$_{34}$N$_8$O$_4$S requires C, 57.22; H, 6.04; N, 19.77%. δ (CDCl$_3$) 1.01 (3H,t), 1.59 (6H,m), 1.86 (2H,m), 2.42 (2H,q), 2.57 (4H,m), 2.97 (2H,t), 3.16 (4H,m), 4.74 (2H,q), 5.94 (2H,s), 7.02 (1H,d), 7.18 (1H,m), 7.60 (1H,m), 8.57 (1H,d), 8.63 (1H,s), 9.10 (1H,s), 10.85 (1H,s). LRMS: m/z 567 (M+1)$^+$.

EXAMPLE 45

5-[2-Ethoxy-5-(4-ethylpiperazin-1-ylsulphonyl)pyridin-3-yl]-3-ethyl-1-(1-methylimidazol-2-yl)methyl-1,6-dihydro-7H-pyrazolo[4,3-d]pyrimidin-7-one Obtained as a pale yellow solid (60%) from the title compound of Preparation 107, using the procedure of Example 44. δ (CDCl$_3$): 1.02 (3H,t), 1.38 (3H,t), 1.59 (3H,t), 2.41 (2H,q), 2.56 (4H,m), 2.97 (2H,q), 3.15 (4H,m), 3.78 (3H,s), 4.75 (2H,q), 5.89 (2H,s), 6.85 (1H,s), 7.00 (1H,s), 8.64 (1H,s), 9.07 (1H,s), 10.87 (1H,s). LRMS: m/z 556 (M+1)$^+$.

EXAMPLE 46

3-Ethyl-5-[5-(4-ethylpiperazin-1-ylsulphonyl)-2-(2-methoxyethoxy)pyridin-3-yl]-1-(1-methylimidazol-2-yl)methyl-1,6-dihydro-7H-pyrazolo[4,3-d]pyrimidin-7-one A stirred mixture of the title compound of Example 45 (1 50 mg, 0.27 mmol), potassium t-butoxide (126 mg, 1.1 mmol) and 2-methoxyethanol (6 ml) was heated under reflux for 48 hours, then allowed to cool. The resulting mixture was evaporated under reduced pressure and the residue purified by column chromatography on silica gel, using dichloromethane:methanol:0.88 aqueous ammonia (90:10:1) as eluant. The product was triturated with diisopropyl ether, the mixture filtered and the filtrate evaporated under reduced pressure to yield the title compound (43 mg, 27%) as a foam. δ (CDCl$_3$): 1.10 (3H,t), 1.36 (3H,t), 2.52 (2H,q), 2.65 (4H,m), 2.96 (2H,q), 3.22 (4H,m), 3.56 (3H,s), 3.75 (3H,s), 3.86 (2H,t), 4.78 (2H,t), 5.92 (2H,s), 6.85 (1H,s), 7.01 (1H,s), 8.63 (1H,s), 8.99 (1H,s), 11.10 (1H,s). LRMS: m/z 585 (M)$^+$.

EXAMPLE 47

5-[5-(4-Ethylpiperazin-1-ylsulphonyl)-2-(2-methoxyethoxy)pyridin-3-yl]-1-(1-methylimidazol-2-yl)methyl-3-n-propyl-1,6-dihydro-7H-pyrazolo[4,3-d]pyrimidin-7-one Obtained as a solid (11%) from the title compound of Preparation 109, using the procedure of Example 10. Found: C, 52.43; H, 6.11; N. 20.12. C$_{27}$H$_{37}$N$_9$O$_5$S; H$_2$O requires C, 52.50; H, 6.36; N, 20.41%. δ (CDCl$_3$): 0.98 (3H,t), 1.03 (3H,t), 1.81 (2H,m), 2.41 (2H,q), 2.55 (4H,m), 2.90 (2H,t), 3.15 (4H,m), 3.58 (3H,s), 3.75 (3H,s), 3.86 (2H,t), 4.78 (2H,t), 5.92 (2H,s), 6.85 (1H,s), 7.00 (1H,s), 8.63 (1H,s), 9.00 (1H,s), 11.07 (1H,s). LRMS: m/z 600 (M+1)$^+$.

EXAMPLE 48

5-[5-(4-Ethylpiperazin-1-ylsulphonyl)-2-(2-methoxyethoxy)pyridin-3-yl]-3-n-propyl-1-(pyrimidin-2-yl)methyl-1,6-dihydro-7H-pyrazolo[4,3-d]pyrimidin-7-one Obtained as a yellow foam (5%) from the title compound of Preparation 102a, using the procedure of Example 10. δ (CDCl$_3$): 1.02 (6H,m), 1.86 (2H,m), 2.42 (2H,q), 2.56 (4H,m), 2.97 (2H,t), 3.17 (4H,m), 3.54 (3H,s), 3.83 (2H,t), 4.77 (2H,t), 6.09 (2H,s), 7.16 (1H,m), 8.65 (3H,m), 9.03 (1H,s), 11.00 (1H,s). LRMS: m/z 598 (M+1)$^+$.

EXAMPLE 49

5-{2-Ethoxy-5-[4-(pyrrolidin-1-ylcarbonymethyl)piperazin-1-ylsulphonyl]pyridin-3-yl}-3-n-propyl-2-(pyridin-2-yl)methyl-2,6dihydro-7H-pyrazolo[4,3-d]pyrimidin-7-one A mixture of the title compound of Preparation 63 (350 mg, 0.715 mmol), 1-(pyrrolidin-1-ylcarbonylmethyl)piperazine (150 mg, 0.715 mmol) and ethanol (40 ml) was stirred at room temperature for 18 hours, then evaporated under reduced pressure. The residue was suspended in aqueous sodium bicarbonate solution (30 ml) and the suspension extracted with ethyl acetate (3×30 ml). The combined extracts were washed with brine (3×20 ml), dried (Na$_2$SO$_4$) and evaporated under reduced pressure. The resulting residue was purified by column chromatography on silica gel, using an elution gradient of dichloromethane: methanol (100:0 to 96:4) to give an oil, which was triturated with ether to furnish the title compound (240 mg, 52%) as a colourless foam. Found: C, 56.79; H, 6.30; N, 18.49. C$_{31}$H$_{39}$N$_9$O$_5$S; 0.50 H$_2$O; 0.25 C$_2$H$_{10}$O requires C, 56.75; H, 6.32; N, 18.61%. δ (CDCl$_3$): 0.94 (3H,t), 1.60 (3H,t), 1.66–1.86 (4H,m), 1.92 (2H,m), 2.68 (4H,m), 2.98 (2H,t), 3.14 (2H,s), 3.18 (4H,m), 3.32–3.46 (4H,m), 4.75 (2H,q), 5.70 (2H,s), 7.18 (1H,d), 7.22 (1H,m), 7.62 (1H,m), 8.58 (1H,d), 8.63 (1H,s), 9.00 (1H,s), 10.66 (1H,s). LRMS: m/z 650 (M+1)$^+$.

EXAMPLE 50

5-[2-Ethoxy-5-(4-allyl-2(S),5(R)-dimethylpiperazin-1-ylsulphonyl)pyridin-3-yl]-3-n-propyl-2-(pyridin-2-yl)methyl-2,6-dihydro-7H-pyrazolo[4,3-d]pyrimidin-7-one A solution of (–)-1-allyl-2(R),5(S)-dimethylpiperazine (WO 93/15062; 502 mg, 3.2 mmol) in ethanol (4 ml) was added dropwise to a stirred suspension of the title compound of Preparation 63 (800 mg, 1.6 mmol) in ethanol and the reaction mixture stirred at room temperature for 18 hours, then evaporated under reduced pressure. The residue was partitioned between aqueous sodium carbonate solution (20 ml) and ethyl acetate (20 ml), the phases separated and the aqueous phase extracted with ethyl acetate (2×20 ml). The combined organic solutions were washed with brine (20 ml), dried (Na$_2$SO$_4$) and evaporated under reduced pressure. The residual orange oil was purified by column chromatography on silica gel, using an elution gradient of dichloromethane: methanol (100:0 to 98:2), followed by trituration with ether, to afford the title compound (550 mg, 57%) as a colourless foam. Found: C, 59.07; H, 6.37; N, 18.18. C$_{30}$H$_{38}$N$_8$O$_4$S requires C, 59.39; H, 6.31; N, 18.47%. δ (CDCl$_3$): 0.95 (3H,t), 0.99 (3H,d), 1.24 (3H,d), 1.58 (3H,t), 1.72 (2H,m), 2.27 (1H,dd), 2.73 (1H,dd), 2.92 (1H,m), 3.00 (4H,m), 3.20 (1H,dd), 3.48 (1H,dd), 3.85 (1H,m), 4.75 (2H,q), 5.22 (2H,m), 5.68 (2H,s), 5.74 (1H,m), 7.09 (1H,d), 7.22 (1H,m), 7.62 (1H,m), 8.58 (1H,d), 8.67 (1H,s), 9.08 (1H,s), 10.69 (1H,s). LRMS: m/z 607 (M–1)$^+$.

Example 50a

3-Ethyl-5-[5-(4-ethylpiperazine-1-ylsulphonyl)-2-(2-methoxy-1(R)-methylethoxy)pyridin-3-yl]-2-(1-methylimidazol-2-yl)methyl-2,6-dihydro-7H-pyrazolo[4,3-d]pyrimidin-7-one Obtained as a white foam (82%), from the title compounds of Preparations 165 and 170, following a similar procedure to that described in Example 11. Found: C, 52.14; H, 6.15; N, 19.73. C$_{27}$H$_{37}$N$_9$O$_5$S;1.5H$_2$O requires C, 51.74; H, 6.43; N, 20.11%. δ (CDCl$_3$): 1.02 (3H, t), 1.32 (3H, t), 1.50 (3H, d), 2.40 (2H, q), 2.56 (4H, m), 3.04–3.22 (6H, m), 3.54 (3H, s), 3.62–3.80 (5H, m), 5.59 (1H, m) 5.66 (2H, s), 6.83 (1H, s), 6.99 (1H, s), 8.60 (1H, s), 8.84 (1H, s), 10.87 (1H, s). LRMS: m/z 600 (M+1)$^+$.

EXAMPLE 51 TO 60

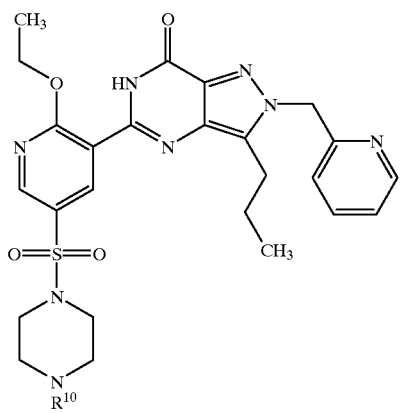

A group of analogues based on the structural formula identified above, in which the R$^{10}$ substituent is varied, was obtained by the technique of high-speed analogue synthesis (HSAS) as described hereinafter.

A 0.4 M solution of triethylamine in dichloromethane (100 μl, 40 μmol) was added to each well of a 96-well plate containing the required range of 1-substituted piperazines (10 μmol). A 0.1M solution of the title compound of Preparation 63 in dichloromethane (100 μl, 10 μmol) was added to each well, then the plate covered and shaken at room temperature for 18 hours. The reaction mixtures were filtered through a 96-well filtration block, which was washed with dichloromethane (1 ml), then the filtrates evaporated under reduced pressure. The residues were dissolved in dimethylsulphoxide (1 ml) and purified by HPLC using a 5μHypersil C18 column (10×0.46 cm) with a flow rate of 4 ml/min and an elution gradient of 0.1% trifluoroacetic acid in water: acetonitrile.

The following compounds were thus obtained:

| Example | R$^{10}$ | LRMS (m/z) | Retention time (min) |
|---|---|---|---|
| 51 | *∼∕∖ | 581 (M + 1)$^+$ | 5.25 |
| 52 | *—CH(CH$_3$)$_2$ | 581 (M + 1)$^+$ | 5.10 |
| 53 | *—CH$_2$—Ph | 629 (M + 1)$^+$ | 5.70 |
| 54 | *—CH$_2$—(2-MeO-C$_6$H$_4$) | 659 (M + 1)$^+$ | 6.02 |
| 55 | *—CH$_2$—(3,4-methylenedioxyphenyl) | 672 (M)$^+$ | 5.36 |

-continued

| Example | R¹⁰ | LRMS (m/z) | Retention time (min) |
|---|---|---|---|
| 56 | diphenylmethyl | 706 (M + 2)⁺ | 8.24 |
| 57 | (2,3-dihydro-1,4-benzodioxin-2-yl)methyl | 687 (M + 1)⁺ | 6.64 |
| 58 | pyridin-2-yl | 617 (M + 2)⁺ | 5.45 |
| 59 | pyridin-4-yl | 616 (M + 1)⁺ | 5.57 |
| 60 | pyrimidin-2-yl | 617 (M + 1)⁺ | 7.38 |

* = point of attachment of R¹⁰

EXAMPLE 61
3-Ethyl-5-[2-(2-methoxyethoxy)-5-(3,4,5-trimethylpiperazin-1-ylsulphonyl)pyridin-3-yl]-2-(pyridin-2-yl)methyl-2,6-dihydro-7H-pyrazolo[4,3-d]pyrimidin-7-one Obtained as a white solid (170 mg, 47%) from the title compound of Preparation 64 and 1,2,6-trimethylpiperazine (J.Med.Chem., 1968, 11, 592), using the procedure of Example 50. Found: C, 55.78; H, 6.02; N, 18.42. $C_{28}H_{36}N_8O_5S$; 0.50 $H_2O$ requires C, 55.22; H, 6.16; N, 18.58%. δ (CDCl₃): 1.09 (6H,d), 1.31 (3H,t), 2.01 (5H,m), 2.36 (2H,m), 3.04 (2H,q), 3.60 (5H,m), 3.88 (2H,t), 4.79 (2H,t), 5.68 (2H,s), 7.12 (1H,d), 7.22 (1H,m), 7.64 (1H,m), 8.58 (1H,d), 8.62 (1H,s), 8.95 (1H,s), 10.79 (1H,s). LRMS: m/z 597 (M+1)⁺.

EXAMPLE 62
3-Ethyl-5-[2-(2-methoxyethoxy)-5-piperazin-1-ylsulphonyl)pyridin-3-yl]-2-(pyridin-2-yl)methyl-2,6-dihydro-7H-pyrazolo[4,3-d]pyrimidin-7-one A solution of the title compound of Preparation 64 (200 mg, 0.40 mmol) in dichloromethane (10 ml) was added dropwise to a stirred solution of piperazine (136 mg, 1.58 mmol) and triethylamine (110 μl, 0.79 mmol) in dichloromethane (10 ml) and the reaction mixture stirred at room temperature for 1 hour, then washed with water (10 ml), dried (MgSO₄) and evaporated under reduced pressure. The residual yellow solid was purified by column chromatography on silica gel, using an elution gradient of dichloromethane: methanol (98:2 to 92:8), followed by trituration with dichloromethane, to give the title compound (189 mg, 86%) as a white foam. Found: C, 52.75; H, 5.43; N, 19.18. $C_{25}H_{30}N_8O_5S$; 0.75 $H_2O$ requires C, 52.85; H. 5.59; N, 19.72%. δ (CDCl₃): 1.30 (3H,t), 2.94–3.13 (10H,m), 3.58 (3H,s), 3.88 (2H,t), 4.79 (2H,t), 5.68 (2H,s), 7.10 (1H,d), 7.22 (1H,m), 7.62 (1H,m), 8.58 (1H,d), 8.62 (1H,s), 8.98 (1H,s), 10.82 (1H,s). LRMS: m/z 555 (M+1)⁺.

EXAMPLE 63
3-Ethyl-5-[5-(4-ethylpiperazin-1-ylsulphonyl]-2-methoxypyridin-3-yl]-2-(pyridin-2-yl)methyl-2,6-dihydro-7H-pyrazolo[4,3-d]pyrimidin-7-one A stirred mixture of the title compound of Example 1 (350 mg, 0.63 mmol), potassium bis(trimethylsilyl)amide (630 mg, 3.15 mmol) and n-propanethiol (5 ml) was heated in a sealed vessel at 110° C. for 48 hours, then allowed to cool and evaporated under reduced pressure. The residue was azeotroped with dichloromethane: methanol (95:5), then partitioned between water (10 ml) and dichloromethane (15 ml). The phases were separated, the aqueous phase extracted with dichloromethane (2×15 ml) and the combined organic solutions dried (MgSO₄) and evaporated under reduced pressure. This residue was purified by column chromatography on silica gel, using dichloromethane: methanol (97:3) as eluant, to yield the title compound (170 mg, 50%) as a yellow solid. Found: C, 54.50; H, 5.64; N, 19.93. $C_{25}H_{30}N_8O_4S$; 0.75 $H_2O$ requires C, 54.38; H, 5.75; N, 20.29%. δ (CDCl₃): 1.02 (3H,t), 1.32 (3H,t,) 2.40 (2H,q), 2.55 (4H,m), 3.06 (2H,q), 3.14 (4H,m), 4.26 (3H,s), 5.68 (2H,s), 7.14 (1H,d), 7.22 (1H,m), 7.64 (1H,m), 8.58 (1H,d), 8.66 (1H,s), 9.05 (1H,s), 10.59 (1H,s). LRMS: m/z 540 (M+2)⁺.

EXAMPLE 64
5-[2-Benzyloxy-5-(4-ethylpiperazin-1-ylsulphonyl)pyridin-3-yl]-3-ethyl-2-(pyridin-2-yl)methyl-2,6-dihydro-7H-pyrazolo[4,3-d]pyrimidin-7-one Potassium bis(trimethylsilyl)amide (360 mg, 1.81 mmol) was added to a stirred solution of the title compound of Example 1 (200 mg, 0.36 mmol) in benzyl alcohol (5 ml) at 100° C. and the reaction mixture stirred for 14 hours, then allowed to cool. The resulting mixture was partitioned between dichloromethane (10 ml) and brine (10 ml), the phases separated, the aqueous phase extracted with dichloromethane (2×10 ml) and the combined organic solutions dried (Na₂SO₄) and evaporated under reduced pressure. The residual benzyl alcohol was removed by Kugelrohr distillation, then the crude product purified by column chromatography on silica gel, using dichloromethane: methanol (97.5:2.5) as eluant, to provide the title compound (86 mg, 39%) as a white solid. Found: C, 59.92; H, 5.64; N, 17.60. $C_{31}H_{34}N_8O_4S$; 0.40 $H_2O$ requires C, 59.87; H, 5.64; N, 18.02%. δ (CDCl₃): 1.05 (3H,t), 1.29 (3H,t), 2.41 (2H,q), 2.56 (4H,m), 3.05 (2H,q), 3.15 (4H,m), 5.68 (2H,s) 5.75 (2H,s), 7.10 (1H,d), 7.24 (1H,m), 7.42 (3H,m), 7.52 (2H,m), 7.64 (1H,m), 8.58 (1H,d), 8.65 (1H,s), 9.02 (1H,s), 10.58 (1H,s). LRMS: m/z 615 (M+1)⁺.

EXAMPLE 65
5-[5-(4-Ethylpiperazin-1-ylsulphonyl)-2-(furan-3-ylmethoxy)pyridin-3-yl]-3-n-propyl-2-(pyridin-2-yl)methyl-2,6-dihydro-7H-pyrazolo[4,3-d]pyrimidin-7-one Potassium bis(trimethylsilyl)amide (176 mg, 0.88 mmol) was added to a stirred suspension of the title compound of Example 26 (100 mg, 0.17 mmol) in 3-hydroxymethylfuran (4 ml) and the reaction mixture heated under reflux for 24 hours then allowed to cool. The resulting mixture was evaporated under reduced pressure and the residue purified by column chromatography on silica gel, using dichloromethane: methanol (95:5) as eluant, to furnish the title compound (33 mg, 31%) as a pale yellow foam. δ (CDCl₃):

0.93 (3H,t), 1.04 (3H,t), 1.72 (2H,m), 2.41 (2H,q), 2.55 (4H,m), 2.99 (2H,t), 3.14 (4H,m), 5.63 (2H,s), 5.68 (2H,s), 6.60 (1H,s), 7.09 (1H,d), 7.22 (1H,m), 7.44 (1H,s), 7.64 (2H,m), 8.57 (1H,d), 8.68 (1H,s), 9.02 (1H,s), 10.53 (1H,s). LRMS: m/z 619 (M+1)$^+$.

EXAMPLE 66
5-[5-(4-Ethylpiperazin-1-ylsulphonyl)-2-(pyridin-2-ylmethoxy)pyridin-3-yl]-3-n-propyl-2-(pyridin-2-yl)methyl-2,6dihydro-7H-pyrazolo[4,3-d]pyrimidin-7-one A stirred mixture of potassium bis(trimethylsilyl)amide (260 mg, 1.32 mmol) and 2-hydroxymethylpyridine (5 ml) was heated at 100° C. for 1 hour, then the title compound of Example 26 (150 mg, 0.26 mmol) added and the reaction mixture stirred at 100° C. for 14 hours. The resulting cool mixture was partitioned between dichloromethane (10 ml) and brine (10 ml), the phases separated and the aqueous phase extracted with dichloromethane (2×10 ml). The combined organic solutions were dried (MgSO$_4$) and evaporated under reduced pressure, then the residual yellow oil purified by column chromatography on silica gel, using dichloromethane: ethyl acetate: methanol (47.5:47.5:5) as eluant, to afford the title compound (35 mg, 21%) as a white solid. δ (CDCl$_3$): 0.94 (3H,t), 1.03 (3H,t), 1.73 (2H,m), 2.40 (2H,q), 2.55 (4H,m), 2.98 (2H,t), 3.14 (4H,m), 5.69 (2H,s), 5.92 (2H,s), 7.07 (1H,d), 7.21 (1H,m), 7.33 (2H,m), 7.62 (1H,m), 7.76 (1H,m), 8.58 (2H,m), 8.81 (1H,s), 8.85 (1H,d), 12.80 (1H,s). LRMS: m/z 630 (M+1)$^+$.

EXAMPLE 67
5-[2-(2-Dimethylaminoethoxy)-5-(4-ethylpiperazin-1-ylsulphonyl)pyridin-3-yl]-3-n-propyl-2-(pyridin-2-yl)methyl-2,6dihydro-7H-pyrazolo[4,3-d]pyrimidin-7-one A mixture of the title compound of Example 26 (200 mg, 0.35 mmol), potassium bis(trimethylsilyl)amide (352 mg, 1.76 mmol) and 2-dimethylaminoethanol (1.5 ml) was stirred at 90° C. for 18 hours, then allowed to cool. Water (5 ml) was added, the mixture extracted with ethyl acetate (3×5 ml) and the combined extracts dried (MgSO$_4$) and evaporated under reduced pressure. The residue was purified by column chromatography on silica gel, using an elution gradient of dichloromethane: methanol (95:5 to 90:10), to give the title compound (147 mg, 68%) as an off-white foam. Found: C, 56.35; H, 6.37; N, 20.12. C$_{29}$H$_{39}$N$_9$O$_4$S; 0.50 H$_2$O requires C, 56.29; H, 6.52; N, 20.37%. δ (CDCl$_3$): 0.94 (3H,t), 1.04 (3H,t), 1.72 (2H,m), 2.43 (8H,m), 2.56 (4H,m), 2.74 (2H,t), 2.95 (2H,t), 3.15 (4H,m), 4.80 (2H,t), 5.67 (2H,s), 7.07 (1H,d), 7.21 (1H,m), 7.61 (1H,m), 8.56 (1H,d), 8.62 (1H,s), 8.75 (1H,s), 12.23 (1H,s). LRMS: m/z 610 (M+1)$^+$.

EXAMPLE 68
5-{-(4-Ethylpiperazin-1-ylsulphonyl)-2-[2-(morpholin-4-yl)ethoxy]pyridin-3-yl}-3-n-propyl-2-(pyridin-2-yl)methyl-2,6-dihydro-7H-pyrazolo[4,3-d]pyrimidin-7-one A mixture of potassium bis(trimethylsilyl)amide (180 mg, 0.88 mmol) and 4-(2-hydroxyethyl)morpholine (4 ml) was stirred at 100° C. for 1 hour, then the title compound of Example 26 (100 mg, 0.17 mmol) added and the reaction mixture stirred at 110° C. for 18 hours. The resulting, cool mixture was partitioned between water (10 ml) and dichloromethane (20 ml), the phases separated and the organic phase washed with water (10 ml), dried (MgSO$_4$) and evaporated under reduced pressure. The residual yellow oil was purified by column chromatography on silica gel, using an elution gradient of ethyl acetate: methanol (90:10 to 80:20), to yield the title compound (33 mg, 30%) as a white solid. δ (CDCl$_3$): 0.95 (3H,t), 1.04 (3H,t), 1.74 (2H,m), 2.42 (2H,q), 2.56 (4H,m), 2.64 (4H,m), 2.90 (2H,t), 2.99 (2H,t), 3.15 (4H,m), 3.80 (4H,m), 4.75 (2H,t), 5.68 (2H,s), 7.12 (1H,d), 7.25 (1H,m), 7.63 (1H,m), 8.58 (1H,d), 8.62 (1H,s), 8.92 (1H,s), 11.16 (1H,s). LRMS: m/z 652 (M+1)$^+$.

EXAMPLE 69
5-[5-(4-Ethylpiperazin-1-ylsulphonyl)-2-(1-methylpiperidin-4-yloxy)pyridin-3-yl]-3-n-propyl-2-(pyridin-2-yl)methyl-2,6dihydro-7H-pyrazolo[4,3-d]pyrimidin-7-one Caesium t-butoxide (76 mg, 0.37 mmol) was added to a stirred solution of the title compound of Preparation 119 (160 mg, 0.24 mmol) in 3-methylpentan-3-ol (5 ml) and the reaction mixture stirred at 120° C. for 3 hours, then allowed to cool. The resulting mixture was evaporated under reduced pressure and the residue partitioned between dichloromethane (10 ml) and water (10 ml). The phases were separated, the aqueous phase extracted with dichloromethane (2×10 ml) and the combined organic solutions dried (MgSO$_4$) and evaporated under reduced pressure. The residual yellow oil was purified by column chromatography on silica gel, using an elution gradient of dichloromethane: methanol (95:5 to 92.5:7.5), to provide the title compound as a yellow foam. δ (CDCl$_3$): 0.94 (3H,t), 1.03 (3H,t), 1.74 (2H,m), 2.10 (2H,m), 2.22 (2H,m), 2.42 (5H,m), 2.58 (6H,m), 2.78 (2H,m), 2.99 (2H,t), 3.13 (4H,m), 5.59 (1H,m), 5.67 (2H,s), 7.10 (1H,d), 7.22 (1H,m), 7.63 (1H,m), 8.57 (1H,d), 8.61 (1H,s), 9.00 (1H,s), 10.63 (1H,s). LRMS: m/z 636 (M+1)$^+$.

EXAMPLE 70
5-[2-Ethoxy-5-(4-ethyl-4-oxidopiperazin-1-ylsulphonyl)pyridin-3-yl]-3-ethyl-2-(pyridin-2-yl)methyl-2,6-dihydro-7H-pyrazolo[4,3-d]pyrimidin-7-one A mixture of the title compound of Example 1 (180 mg, 0.32 mmol), 3-chlorobenzoic acid (13 mg, 0.08 mmol) and dichloromethane (10 ml) was stirred at room temperature for 20 minutes, 3-chloroperoxybenzoic acid (112 mg, 0.32 mmol) added and the reaction mixture stirred for a further 18 hours, then partitioned between dichloromethane (20 ml) and aqueous sodium bicarbonate solution (10 ml). The phases were separated, the aqueous phase extracted with dichloromethane (2×20 ml) and the combined organic solutions dried (MgSO$_4$) and evaporated under reduced pressure. The residue was purified by column chromatography on silica gel, using dichloromethane: methanol (80:20) as eluant, to furnish the title compound (82 mg, 45%) as a white powder. Found: C, 52.73; H, 5.67; N, 17.69. C$_{26}$H$_{32}$N$_8$O$_5$S; 0.50 CH$_2$Cl$_2$ requires C, 52.08; H, 5.44; N, 18.34%. δ (CDCl$_3$): 1.30 (3H,t), 1.40 (3H,t), 1.58 (3H,t), 3.02 (2H,q), 3.20 (2H,m), 3.32 (4H,m), 3.48 (2H,m), 3.72 (2H,m), 4.76 (2H,q), 5.68 (2H,s), 7.08 (1H,d), 7.22 (1H,m), 7.63 (1H,m), 8.58 (1H,d), 8.65 (1H,s), 9.03 (1H,s), 10.70 (1H,s).

EXAMPLE 71
5-[5-(4-Ethyl-4-oxidopiperazin-1-ylsulphonyl)-2-n-propoxypyridin-3-yl]-3-n-propyl-2-(pyridin-2-yl)methyl-2,6-dihydro-7H-pyrazolo[4,3-d]pyrimidin-7-one 3-Chloroperoxybenzoic acid (93 mg, 0.27 mmol) was added to a stirred solution of the title compound of Example 28 (155 mg, 0.27 mmol) in dichloromethane (2 ml) and the reaction mixture stirred at room temperature for 2 hours, then evaporated under reduced pressure. The residue was purified by column chromatography on silica gel, using dichloromethane:methanol:0.88 aqueous ammonia (90:10:1) as eluant, to afford the title compound (40 mg, 25%) as a solid. δ (CDCl$_3$): 0.93 (3H,t), 1.14 (3H,t), 1.41

(3H;t), 1.72 (2H,m), 2.00 (2H,m), 2.97 (2H,t), 3.15 (2H,m), 3.31 (4H,m), 3.50 (2H,m), 3.70 (2H,m), 4.65 (2H,t), 5.68 (2H,s), 7.06 (1H,d), 7.24 (1H,m), 7.64 (1H,m), 8.58 (1H,d), 8.66 (1H,s), 9.06 (1H,s), 10.67 (1H,s). LRMS: m/z 598 $(M+1)^+$.

EXAMPLE 72
3-Ethyl-5-[5-(4-ethyl-4-oxidopiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one
and

EXAMPLE 73
3-Ethyl-5-[5-(4-ethyl-4-oxidopiperazin-1-ylsulphonyl)-2-(2-methoxyethoxy)pyridin-3-yl]-2-(1-oxidopyridin-2-yl)methyl-2,6-dihydro-7H-pyrazolo[4,3-d]pyrimidin-7-one 3-Chlorobenzoic acid (15 mg, 0.096 mmol) was added to a stirred solution of the title compound of Example 4 (223 mg, 0.38 mmol) in dichloromethane (3 ml) and the mixture stirred at room temperature for 30 minutes. 3-Chloroperoxybenzoic acid (132 mg, 0.38 mmol) was then added and the reaction mixture stirred at room temperature for 14 hours, then partitioned between dichloromethane (5 ml) and aqueous sodium bicarbonate solution (5 ml). The phases were separated, the aqueous phase extracted with dichloromethane (3×10 ml) and the combined organic solutions dried ($MgSO_4$) and evaporated under reduced pressure. The residue was purified by column chromatography on silica gel, using an elution gradient of dichloromethane:methanol (90:10 to 80:20), to give the first title compound (78 mg, 34%) as a solid. Found: C, 51.77; H, 5.82; N, 17.33. $C_{27}H_{34}N_8O_6S$; 1.75 $H_2O$ requires C, 51.46; H, 6.00; N, 17.78%. δ ($CDCl_3$): 1.28 (3H,t), 1.42 (3H,t), 3.02 (2H,q), 3.18 (2H,m), 3.30 (4H,m), 3.50 (2H,m), 3.56 (3H,s), 3.72 (2H,m), 3.88 (2H,t), 4.80 (2H,t), 5.68 (2H,s), 7.08 (1H,d), 7.22 (1H,m), 7.64 (1H,m), 8.58 (1H,d), 8.68 (1H,s), 8.99 (1H,s), 10.84 (1H,s); followed by the second title compound (50 mg, 22%) as a solid. Found: C, 50.15; H, 5.81; N, 16.85. $C_{27}H_{34}N_8O_6S$; 2.0 $H_2O$ requires C, 49.84; H, 5.89; N, 17.22%. δ ($CDCl_3$): 1.32 (3H,t), 1.42 (3H,t), 3.05 (2H,q), 3.18 (2H,m), 3.32 (4H,m), 3.53 (5H,m), 3.72 (2H,m), 3.86 (2H,t), 4.80 (2H,t), 5.81 (2H,s), 6.78 (1H,d), 7.22 (2H,m), 8.29 (1H,d), 8.66 (1H,s), 8.99 (1H,s), 10.90 (1H,s).

EXAMPLE 74
5-[2-Ethoxy-5-(4-ethylpiperazin-1-ylsulphonyl)pyridin-3-yl]-2-(2-morpholin-4-yl)ethyl-3-n-propyl-2,6-dihydro-7H-pyrazolo[4,3-d]pyrimidin-7-one Potassium t-butoxide (110 mg, 0.99 mmol) was added to a stirred solution of the title compound of Preparation 120 (400 mg, 0.66 mmol) in 3-methylpentan-3-ol (20 ml) and the reaction mixture heated under reflux for 3 hours, then allowed to cool. The resulting mixture was evaporated under reduced pressure, the residue suspended in water (10 ml) and the suspension extracted with dichloromethane (3×10 ml). The combined extracts were dried ($MgSO_4$) and evaporated under reduced pressure, then the residual yellow oil purified by column chromatography on silica gel, using dichloromethane: methanol (97.5:2.5) as eluant, to yield the title compound (65 mg, 17%) as a white foam. Found: C, 54.51; H, 6.95; N, 18.18. $C_{27}H_{40}N_8O_5S$; 0.15 $CH_2Cl_2$ requires C, 54.51; H, 6.92; N, 18.14%. δ ($CDCl_3$): 1.04 (6H,m), 1.58 (3H,t), 1.88 (2H,m), 2.41 (2H,q), 2.54 (8H,m), 2.99 (4H,m), 3.15 (4H,m), 3.68 (4H,m), 4.40 (2H,t), 4.75 (2H,q), 8.62 (1H,s), 9.04 (1H,s), 10.61 (1H,s). LRMS: m/z 589 $(M+1)^+$.

EXAMPLE 75
5-[5-(4-Ethylpiperazin-1-ylsulphonyl)-2-(2-methoxyethoxy)pyridin-3-yl]-2-(2-morpholin-4-yl)ethyl-3-n-propyl-2,6-dihydro-7H-pyrazolo[4,3-d]pyrimidin-7-one Obtained as a white solid (24%) from the title compound of Example 74 and 2-methoxyethanol, using the procedure of Example 66. Found: C, 53.81; H, 6.93; N, 16.89. $C_{28}H_{42}N_8O_6S$; 0.30 $C_4H_8O_2$; 0.20 $H_2O$ requires C, 54.06; H, 6.96; N, 17.27%. δ ($CDCl_3$): 1.04 (6H,m), 1.87 (2H,m), 2.42 (2H,q), 2.55 (8H,m), 2.99 (4H,m), 3.16 (4H,m), 3.56 (3H,s), 3.69 (4H,m), 3.88 (2H,t), 4.40 (2H,t), 4.79 (2H,t), 8.63 (1H,s), 8.98 (1H,s), 10.78 (1H,s). LRMS: m/z 619 $(M+1)^+$.

EXAMPLE 76
3-t-Butyl-5-[2-ethoxy-5-(4-ethylpiperazin-1-ylsulphonyl)pyridin-3-yl-]-1-(pyridin-2-yl)methyl-1,6-dihydro-7H-pyrazolo[4,3-d]pyrimidin-7-one A stirred mixture of the title compound of Preparation 121 (150 mg, 0.25 mmol), potassium t-butoxide (71 mg, 0.625 mmol) and ethanol (10 ml) was heated at 100° C. for 18 hours in a sealed vessel, then allowed to cool. The resulting mixture was evaporated under reduced pressure and the residue partitioned between water (10 ml) and ethyl acetate (15 ml). The phases were separated, the aqueous phase extracted with ethyl acetate (2×15 ml) and the combined organic solutions dried ($MgSO_4$) and evaporated under reduced pressure. The crude product was purified by column chromatography on silica gel, using dichloromethane:methanol (100:0 to 95:5) as eluant, to provide the title compound (140 mg, 97%) as a white solid. Found: C, 56.30; H, 6.39; N, 18.43. $C_{28}H_{36}N_6O_4S$; $H_2O$ requires C, 56.17; H, 6.40; N, 18.72%. δ ($CDCl_3$): 1.04 (3H,t), 1.56 (12H,m), 2.42 (2H,q), 2.56 (4H,m), 3.16 (4H,m), 4.76 (2H,q), 5.95 (2H,s), 6.94 (1H,d), 7.18 (1H,m), 7.60 (1H,m), 8.58 (1H,d), 8.64 (1H,s), 9.08 (1H,s), 10.82 (1H,s). LRMS: m/z 581 $(M+1)^+$.

EXAMPLE 77
5-[2-Ethoxy-5-(4-ethylpiperazin-1-ylsulphonyl)pyridin-3-yl]-1-(2-morpholin-4-yl)ethyl-3-n-propyl-1,6-dihydro-7H-pyrazolo[4,3-d]pyrimidin-7-one Obtained as a white solid (68%) from the title compound of Preparation 122, using the procedure of Example 74. Found: C, 54.59; H, 6.91; N, 18.08. $C_{27}H_{40}N_8O_5S$; 0.15 $CH_2Cl_2$ requires C, 54.59; H, 6.89; N, 18.08%. δ ($CDCl_3$): 1.01 (6H,m), 1.60 (3H,t), 1.84 (2H,m), 2.42 (2H,q), 2.53 (8H,m), 2.86 (2H,t), 2.94 (2H,t), 3.15 (4H,m), 3.62 (4H,m), 4.72 (4H,m), 8.63 (1H,s), 9.09 (1H,s), 10.81 (1H,s). LRMS: m/z 589 $(M+1)^+$.

EXAMPLE 78
5-[2-Ethoxy-5-(4-ethylpiperazin-1-ylsulphonyl)pyridin-3-yl]-3-ethyl-2-methyl-2,6-dihydro-7H-pyrazolo[4,3-d]pyrimidin-7-one

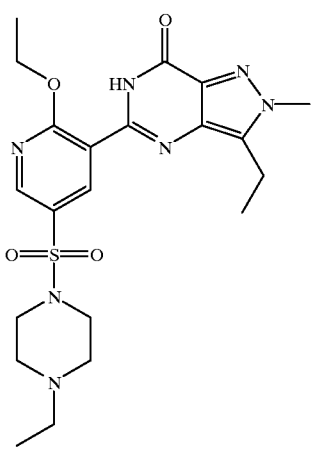

A mixture of the title compound of Preparation 152 (25.9 g, 52.5 mmol), and potassium bis(trimethylsilyl)amide (22.0 g, 110.0 mmol) in ethanol (1 500 ml) was heated at 120° C. for 18 hours in a sealed vessel. The cooled solution was concentrated under reduced pressure, and pre-adsorbed onto silica gel. The crude product was purified by column chromatography on silica gel, using an elution gradient of ethyl acetate: diethylamine (97:3 to 95:5) and triturated with ether to afford the title compound (11.0 g, 44%) as a white solid. δ (CDCl$_3$): 1.03 (3H, t), 1.40 (3H, t), 1.59 (3H, t), 2.41 (2H, q), 2.57 (4H, m), 3.04 (2H, q), 3.14 (4H, m), 4.09 (3H, s), 4.75 (2H, q), 8.62 (1H, s), 9.04 (1H, s), 10.64 (1H, s). LRMS: m/z 476 (M+1)$^+$

EXAMPLE 79
5-[2-Ethoxy-5-(4-methylipiperazin-1-ylsulphonyl)pyridin-3-yl]-2-methyl-3-n-propyl-2,6-dihydro-7H-pyrazolo[4,3-d]pyrimidin-7-one

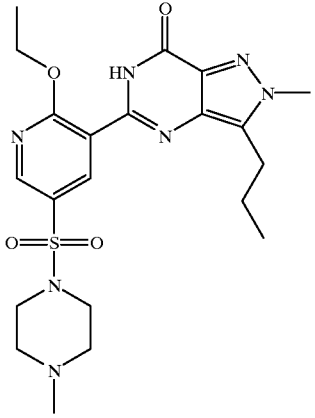

The title compound of Preparation 151 (500 mg, 1.0 mmol) was added to a solution of potassium bis(trimethylsilyl)amide (610 mg, 3.06 mmol) in ethanol (20 ml), and the reaction heated at 110° C. in a sealed vessel for 18 hours. The cooled mixture was evaporated under reduced pressure and the residue dissolved in water and neutralised using hydrochloric acid. This aqueous suspension was extracted with dichloromethane (3×30 ml), the combined organic extracts washed with brine (3×30 ml), dried (Na$_2$SO$_4$) and evaporated under reduced pressure. The residual oil was purified by column chromatography on silica gel using an elution gradient of dichloromethane: methanol (100:0 to 97.5:2.5), and triturated with ether, to afford the title compound (207 mg, 44%) as an off-white solid. δ (CDCl$_3$): 1.03 (3H, t), 1.59 (3H, t), 1.83 (2H, m), 2.29 (3H, s), 2.53 (4H, m), 3.00 (2H, t), 3.16 (4H, m), 4.10 (3H, s), 4.75 (2H, q), 8.63 (1H, s), 9.06 (1H, s), 10.65 (1H, s). LRMS: m/z 476 (M+1)$^+$

EXAMPLES 80 TO 84

The compounds of the general formula:

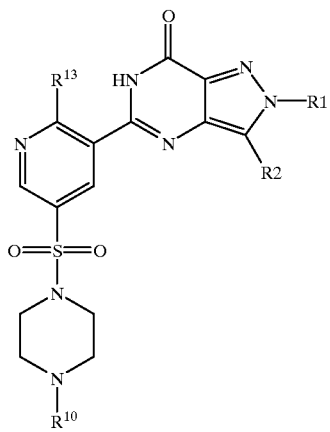

were prepared from the appropriate pyrazole-5-carboxamides, i.e. Preparations 153, 154, 156, 157 and 155 respectively, following procedures similar to that described in Example 79. In Examples 80 to 84, R$^1$ is methyl and R$^{13}$ is —OR$^3$.

| Ex | R1 | R2 | R3 | R10 | Data |
|---|---|---|---|---|---|
| 80 | CH$_3$ | (CH$_2$)$_2$CH$_3$ | CH$_2$CH$_3$ | CH$_2$CH$_3$ | Found: C, 53.97; H, 6.38; N, 19.75. C$_{22}$H$_{31}$N$_7$O$_4$S requires C, 53.97; H, 6.38; N, 20.03% δ (CDCl$_3$): 1.03 (6H, t), 1.58 (3H, t), 1.82 (2H, m), 2.41 (2H, q), 2.56 |

-continued

| Ex | R1 | R2 | R3 | R10 | Data |
|---|---|---|---|---|---|
| 81 | CH₂CH₃ | CH₂CH₃ | CH₂CH₃ | CH₂CH₃ | (4H, m), 2.99 (2H, t), 3.14 (4H, m), 4.09 (3H, s), 4.76 (2H, q), 8.63 (1H, s), 9.05 (1H, s), 10.64 (1H, s). LRMS: m/z 490 (M + 1)⁺ δ (CDCl₃): 1.02 (3H, t), 1.40 (3H, t), 1.58 (6H, m), 2.41 (2H, q), 2.55 (4H, m), 3.00–3.18 (6H, m), 4.38 (2H, q), 4.75 (2H, q), 8.63 (1H, s), 9.04 (1H, s), 10.63 (1H, s). LRMS: m/z 490 (M + 1)⁺ |
| 82 [1,2] | ![2-methyl-6-pyridylmethyl] | CH₂CH₃ | CH₂CH₃ | CH₂CH₃ | Found: C, 56.66; H, 6.03; N, 19.57 $C_{27}H_{34}N_8O_4S$;0.25 $H_2O$ requires C, 56.78; H, 6.09; N, 19.62%. δ (CDCl₃): 1.02 (3H, t), 1.30 (3H, t), 1.58 (3H, t), 2.41 (2H, q), 2.57 (7H, m), 3.04 (2H, q), 3.15 (4H, m), 4.77 (2H, q), 5.64 (2H, s), 6.80 (1H, d), 7.08 (1H, d), 7.50 (1H, m), 8.62 (1H, s), 9.02 (1H, s), 10.66 (1H, s). LRMS: m/z 567 (M + 1)⁺ |
| 83 | ![6-methoxy-2-pyridylmethyl] | CH₂CH₃ | CH₂CH₃ | CH₂CH₃ | δ (CDCl₃): 1.04 (3H, t), 1.40 (3H, t), 1.58 (3H, t), 2.42 (2H, q), 2.58 (4H, m), 3.01 (2H, q), 3.16 (4H, m), 3.80 (3H, s), 4.75 (2H,q ), 5.82 (2H, s), 6.54 (1H, d), 6.60 (1H, d), 7.46 (1H, m), 8.64 (1H, s), 9.10 (1H, s), 10.85 (1H, s). LRMS: m/z 583 (M + 1)⁺ |
| 84 [1] | ![1-(2-pyridyl)ethyl] | CH₂CH₃ | CH₂CH₃ | CH₂CH₃ | δ (CDCl₃): 1.03 (3H, t), 1.25 (3H, t), 1.58 (3H, t), 2.13 (3H, d), 2.40 (2H, q), 2.55 (4H, m), 3.01 (2H, q), 3.14 (4H, m), 4.77 (2H, q), 5.84 (1H, q), 7.19 (2H, m), 7.61 (1H, m), 8.56 (1H, d), 8.62 (1H, s), 9.00 (1H, s), 10.60 (1H, s). LRMS: m/z 567 (M + 1)⁺ |

1 = 1.5 equivalents of potassium bis(trimethylsilyl)amide were used
2 = dichloromethane:methanal:0.88 ammonia (96:4:0.4) was used as the chromatographic eluant

EXAMPLE 85

3-Ethyl-5-[5-(4-ethylpiperazin-1-ylsulphonyl)-2-methoxypyridin-3-yl]-2-methyl-2,6-dihydro-7H-pyrazolo[4,3-d]pyrimidin-7-one

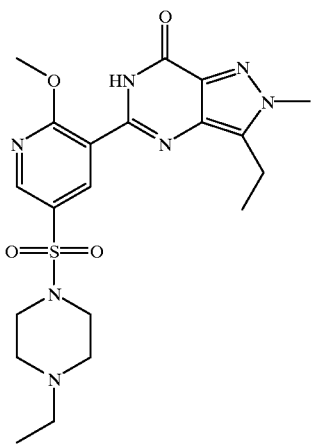

A mixture of the title compound of Example 78 (100 mg, 0.21 mmol), and copper (II) sulphate heptahydrate (75 mg, 0.3 mmol) in saturated methanolic ammonia (20 ml) was heated at 100° C. for 4 hours in a sealed vessel. The cooled mixture was evaporated under reduced pressure and the residue suspended in aqueous sodium carbonate solution (20 ml) and extracted with dichloromethane (3×20 ml). The combined organic extracts were washed with brine (3×20 ml), dried (Na₂SO₄) and evaporated under reduced pressure to give a green solid. The crude product was purified by column chromatography on silica gel, using an elution gradient of dichloromethane: methanol (100:0 to 97:3) and recrystallised from hexane/ethyl acetate/methanol to afford the title compound (23 mg, 24%) as a white solid. Found: C, 51.22; H, 5.81; N, 20.61. $C_{20}H_{27}N_7O_4S$:0.5$H_2O$ requires C, 51.05; H, 6.00; N, 20.84% δ (CDCl₃): 1.07 (3H, t), 1.40 (3H, t), 2.40–2.65 (6H, m), 3.04 (2H, q), 3.19 (4H, m), 4.09 (3H, s), 4.24 (3H, s), 8.65 (1H, s), 9.05 (1H, s), 10.58 (1H, s). LRMS: m/z 462 (M+1)⁺

EXAMPLE 86

3-Ethyl-5-[5-(4-ethylpiperazin-1-ylsulphonyl)-2-(1(R)-methyl-n-propoxy)pyridin-3-yl]-2-methyl-2,6-dihydro-7H-pyrazolo[4,3-d]pyrimidin-7-one

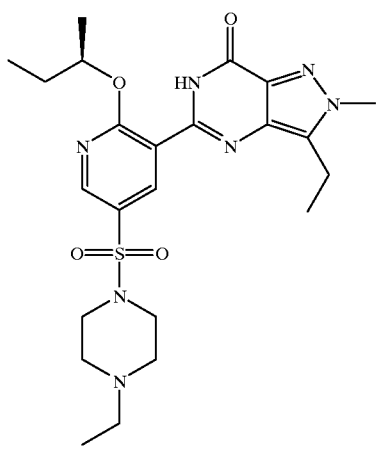

The title compound of Example 78 (400 mg, 0.84 mmol) was added to a mixture of potassium bis(trimethylsilyl) amide (840 mg, 4.2 mmol) in (R)-2-butanol (4 ml) and the mixture stirred at 110° C. for 18 hours. The cooled mixture was concentrated under reduced pressure and the residue suspended in water (10 ml) and neutralised using 2N hydrochloric acid. This aqueous suspension was extracted with ethyl acetate (3×30 ml), the combined organic extracts washed with sodium hydroxide solution (20 ml), brine (2×30 ml), dried ($Na_2SO_4$) and evaporated under reduced pressure. The crude product was purified by is column chromatography on silica gel, using an elution gradient of dichloromethane: methanol (100:0 to 97.5:2.5) and the product suspended in ether and evaporated under reduced pressure. This solid was recrystallised from hexane/ethyl acetate to afford the title compound (72 mg, 17%) as a white solid.

$[\alpha]_D = -20.88°$ (c=0.083, dichloromethane) Found: C, 54.65; H, 6.63; N, 19.25. $C_{23}H_{33}N_7O_4S;0.5H_2O$ requires C, 53.89; H, 6.69; N, 19.13% δ ($CDCl_3$): 1.06 (6H, m), 1.40 (3H, t), 1.50 (3H, d), 1.86 (1H, m), 1.99 (1H, m), 2.42 (2H, q), 2.58 (4H, m), 3.04 (2H, q), 3.16 (4H, m), 4.09 (3H, s), 5.56 (1H, m), 8.62 (1H, s), 9.05 (1H, s), 10.70 (1H, s). LRMS: m/z 504 $(M+1)^+$

EXAMPLES 87 TO 97

The compounds of the general formula wherein $R^1$ is methyl and $R^{13}$ is $—OR^3$:

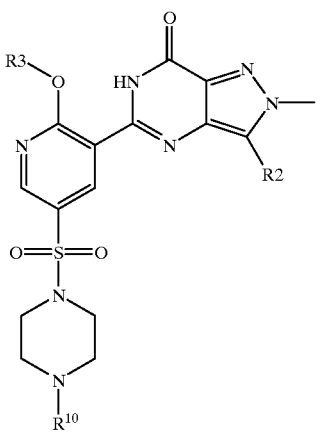

were prepared from the appropriate alcohols and pyrazolo [4,3-d]pyrimidin-7-ones, following procedures similar to that described in Example 86.

| Ex | R2 | R3 | R10 | Data |
|---|---|---|---|---|
| 87 | $CH_2CH_3$ | ![isobutyl] | $CH_2CH_3$ | Found: C, 54.02; H, 6.59; N, 18.87 $C_{23}H_{33}N_7O_4S;0.5H_2O$ requires C, 53.89; H, 6.69; N, 19.13% δ ($CDCl_3$): 1.02 (3H, t), 1.14 (6H, d), 1.40 (3H, t), 2.30 (1H, m), 2.42 (2H, q), 2.58 (4H, m), 3.03 (2H, q), 3.15 (4H, m), 4.09 (3H, s), 4.44 (2H, d), 8.62 (1H, s), 9.03 (1H, s), 10.62 (1H, s). |
| 88 | $(CH_2)_2CH_3$ | ![isobutyl] | $CH_2CH_3$ | δ ($CDCl_3$): 1.02 (6H, m), 1.14 (6H, d), 1.82 (2H, m), 2.30 (1H, m), 2.42 (2H, q), 2.56 (4H, m), 2.99 (2H, t), 3.16 (4H, m), 4.08 (3H, s), 4.45 (2H, d), 8.62 (1H, s), 9.03 (1H, s), 10.62 (1H, s). LRMS: m/z 518 $(M + 1)^+$ |
| 89 | $CH_2CH_3$ | ![cyclobutyl] | $CH_2CH_3$ | Found: C, 55.11; H, 6.25; N, 1945. $C_{23}H_{31}N_7O_4S$ requires C, 55.07; H, 6.23; N, 19.55%. δ ($CDCl_3$): 1.04 (3H, t), 1.40 (3H, t), 1.90 (1H, m), 1.98 (1H, m), 2.30–2.44 (4H, m), 2.57 (6H, m), 3.02 (2H, q), 3.14 (4H, m), 4.09 (3H, s), 5.50 (1H, m), 8.60 (1H, s), 9.04 (1H, s), 10.68 (1H, s). LRMS: m/z 502 $(M+ 1)^+$ |

-continued

| Ex | R2 | R3 | R10 | Data |
|---|---|---|---|---|
| 90[1] | (CH$_2$)$_2$CH$_3$ | *—CH$_2$—cyclopropyl | CH$_2$CH$_3$ | Found: C, 56.08; H, 6.45; N, 18.72. C$_{24}$H$_{33}$N$_7$O$_4$S requires C, 55.90; H, 6.45; N, 19.01% δ (CDCl$_3$): 0.47 (2H, m), 0.77 (2H, m), 1.02 (6H, m), 1.47 (1H, m), 1.83 (2H, m), 2.41 (2H, q), 2.56 (4H, m), 2.99 (2H, t), 3.15 (4H, m) 4.09 (3H, s), 4.50 (2H, d), 8.60 (1H, s), 9.05 (1H, s), 10.76 (1H, s). LRMS: m/z 516 (M + 1)$^+$ |
| 91[2] | (CH$_2$)$_2$CH$_3$ | *—CH$_2$—cyclobutyl | CH$_2$CH$_3$ | Found: C, 56.53; H, 6.68; N, 18.43. C$_{25}$H$_{35}$N$_7$O$_4$S requires C, 56.69; H, 6.66; N, 18.51% δ (CDCl$_3$): 1.02 (6H, m), 1.82 (2H, m), 1.91–2.10 (4H, m), 2.26 (2H, m), 2.41 (2H, q), 2.57 (4H, m), 2.98 (3H, m), 3.14 (4H, m), 4.08 (3H, s), 4.62 (2H, d), 8.61 (1H, s), 9.02 (1H, s), 10.60 (1H, s). LRMS: m/z 530 (M + 1)$^+$ |
| 92 | CH$_2$CH$_3$ | CH$_3$O—CH$_2$CH$_2$—* | CH$_2$CH$_3$ | Found: C, 52.20; H, 6.16; N, 19.26. C$_{22}$H$_{31}$N$_7$O$_5$S requires C, 52.26; H, 6.18; N, 19.39% δ (CDCl$_3$): 1.04 (3H, t), 1.40 (3H, t), 2.42 (2H, q), 2.56 (4H, m), 3.03 (2H, q), 3.15 (4H, m), 3.58 (3H, s), 3.86 (2H, t), 4.09 (3H, s), 4.79 (2H, t), 8.62 (1H, s), 9.00 (1H, s), 10.78 (1H, s). LRMS: m/z 506 (M + 1)$^+$ |
| 93[3] | (CH$_2$)$_2$CH$_3$ | CH$_3$O—CH$_2$CH$_2$—* | CH$_2$CH$_3$ | Found: C, 52.86; H, 6.39; N, 18.67. C$_{23}$H$_{33}$N$_7$O$_5$S requires C, 53.16; H, 6.40; N, 18.62% δ (CDCl$_3$): 1.04 (6H, m), 1.82 (2H, m), 2.40 (2H, q), 2.55 (4H, m), 2.98 (2H, t), 3.14 (4H, m), 3.57 (3H, s), 3.85 (2H, t), 4.07 (3H, s), 4.78 (2H, t), 8.61 (1H, s), 8.99 (1H, s), 10.76 (1H, s). LRMS: m/z 520 (M + 1)$^+$ |
| 94[3] | CH$_2$CH$_3$ | *—CH(iPr)—CH(OH)CH$_3$ | CH$_2$CH$_3$ | Found: C, 53.16; H, 6.48; N, 18.32. C$_{23}$H$_{33}$N$_7$O$_5$S;0.5H$_2$O requires C, 52.26; H. 6.48; N, 18.55% δ (CDCl$_3$): 1.04 (3H, t), 1.38 (6H, m), 1.50 (3H, d), 2.41 (2H, q), 2.57 (4H, m), 2.96 (1H, s), 3.01 (2H, m), 3.15 (4H, m), 4.08 (3H, s). 4.18 (1H, m), 5.22 (1H, m), 8.60 (1H, s), 8.82 (1H, s), 11.27 (1H, s). [α]$_D$ = +35.46° (c = 0.073, dichloromethane |
| 95[2] | (CH$_2$)$_2$CH$_3$ | *—CH$_2$—(2-pyridyl) | CH$_2$CH$_3$ | δ (CDCl$_3$): 1.04 (6H, m), 1.84 (2H, m), 2.41 (2H, q), 2.56 (4H m), 2.99 (2H, t), 3.15 (4H, m), 4.08 (3H, s), 5.91 (2H, s), 7.24–7.37 (2H, m), 7.76 (1H, m), 8.59 (1H, s), 8.83 (2H, m), 12.70 (1H, s). LRMS: m/z 553 (M + 1)$^+$ |
| 96[1] | (CH$_2$)$_2$CH$_3$ | *—CH$_2$—(3-pyridyl) | CH$_2$CH$_3$ | Found: C, 55.22; H, 5.76; N, 19.42, C$_{26}$H$_{32}$N$_8$O$_4$S;0.2CH$_2$Cl$_2$ requires C, 55.24; H, 5.73; N, 19.67% δ (CDCl$_3$): 1.01 (6H, m), 1.82 (2H, m), 2.41 (2H, q), 2.56 (4H, m), 2.98 (2H, t), 3.15 (4H, m), 4.09 (3H, s), 5.78 (2H, s), 7.38 (1H, m), 7.88 (1H, d), 8.61 (2H, m), 8.79 (1H, s), 9.02 (1H, s), 10.45 (1H, s). LRMS: m/z 553 (M + 1)$^+$ |
| 97[1] | (CH$_2$)$_2$CH$_3$ | *—CH$_2$—(3-furyl) | CH$_2$CH$_3$ | δ (CDCl$_3$): 1.02 (6H, m), 1.82 (2H, m), 2.41 (2H, q), 2.56 (4H, m), 2.98 (2H, t), 3.16 (4H, m), 4.06 (3H, s), 5.62 (2H, s), 6.60 (1H, s), 7.43 (1H, s), 7.62 (1H, s), 8.66 (1H, s), 9.02 (1H, s), 10.51 (1H, s). LRMS: m/z 542(M + 1)$^+$ |

[1] = dichloromethane:methanol:0.88 ammonia (100:0:0.5 to 99.5:1:0.5) used as chromatographic eluant, and the compound was isolated without crystallisation.
[2] = dichloromethane:methanol:0.88 ammonia (100:0:0.5 to 99.5:1:0.5) used as chromatographic eluant, and the compound was triturated with ether.
[3] = isolated without crystallisation

EXAMPLE 98

3-Ethyl-5-[5-(4-ethylpiperazin-1-ylsulphonyl)-2-(2-(R)-methoxy-1-(R)-methylpropoxy)pyridin-3-yl]-2-methyl-2,6-dihydro-7H-pyrazolo[4,3-d]pyrimidin-7-one

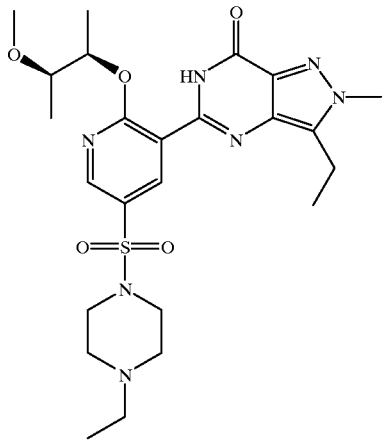

(R,R)-2,3 butanediol (7.78 ml, 85 mmol) was added dropwise to an ice-cold solution of sodium hydride (3.74 g, 60% dispersion in mineral oil, 93.5 mmol) in ether (800 ml), and the solution stirred at room temperature for 30 minutes. Methyl iodide (5.6 ml, 89.3 mmol) was added dropwise and the reaction stirred under reflux for 48 hours. 1,3-Dimethyl-3,4,5,6tetrahydro-2(1H)-pyrimidinone (10.24 ml, 85 mmol) was added and stirring continued for a further 90 minutes under reflux. The cooled reaction was washed with aqueous ammonium chloride solution (500 ml), dried ($MgSO_4$) and evaporated under reduced pressure. The residual oil was purified by column chromatography on silica gel using an elution gradient of ether: pentane (10:90 to 50:50) to give a pale yellow oil. The title compound of Example 78 (100 mg, 0.2 mmol) and potassium bis(trimethylsilyl)amide (121 mg, 0.61 mmol) in the intermediate alcohol (1 ml), was heated at 110° C. for 30 hours, then the reaction cooled and concentrated under reduced pressure. The residual brown solid was purified by column chromatography on silica gel using diethylamine: ethyl acetate (5:95) as eluant, and repeated using methanol: ethyl acetate (5:95) as eluant. The product was triturated with ether to afford the title compound (7 mg, 60%) as a white solid. δ ($CDCl_3$): 1.03 (3H, t), 1.25 (3H, d), 1.40 (3H, t), 1.48 (3H, d), 2.41 (2H, q), 2.55 (4H, m), 3.03 (2H, q), 3.15 (4H, m), 3.52 (3H, s), 3.70 (1H. m), 4.09 (3H, s), 5.39 (1H, m), 8.60 (1H, s), 8.97 (1H, s). LRMS: m/z 534 $(M+1)^+$

EXAMPLE 99

3-Ethyl-5-[5-(4-ethylpiperazin-1-ylsulphonyl)-2-(pyridin-2-yl)methoxypyridin-3-yl]-2-methyl-2,6-dihydro-7H-pyrazolo[4,3-d]pryimidin-7-one

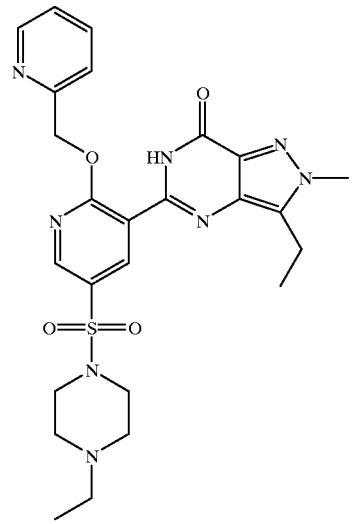

A mixture of the title compound of Example 78 (100 mg, 0.2 mmol), potassium bis(trimethylsilyl)amide (210 mg, 1.1 mmol) in pyridine-2-methanol (1 ml) was heated to 110° C. for 18 hours. The cooled mixture was partitioned between ethyl acetate (10 ml) and water (10 ml), and the phases separated. The aqueous layer was extracted with ethyl acetate (2×5 ml) and dichloromethane (10 ml), the combined organic solutions dried ($Na_2SO_4$) and evaporated under reduced pressure. The residue was purified by column chromatography on silica gel, using methanol:ethyl acetate (10:90) as eluant, and triturated with ether, to afford the title compound (49 mg, 43%) as a solid.

δ ($CDCl_3$): 1.02 (3H, t), 1.40 (3H, t), 2.40 (2H, q), 2.55 (4H, m), 3.04 (2H, q), 3.14 (4H, m), 4.10 (3H, s), 5.90 (2H, s), 7.32 (2H, m), 7.76 (1H, m), 8.58 (1H, s), 8.82 (2H, m), 12.72 (1H, s). LRMS: m/z 539 $(M+1)^+$.

EXAMPLE 100

5-[2-Cyclobutylmethoxy-5-(4-ethylpiperazin-1-ylsulphonyl)pyridin-3-yl]-3-ethyl-2-methyl-2,6-dihydro-7H-pyrazolo[4,3-d]pyrimidin-7-one

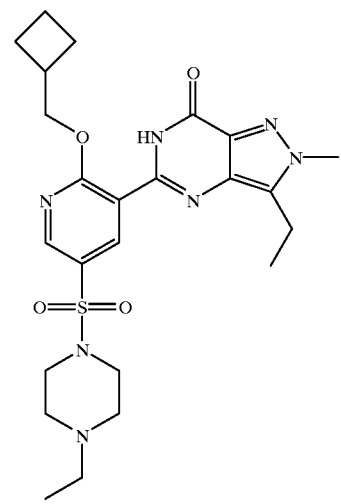

Obtained (69%) from the title compound of Example 78 and cyclobutanemethanol, following a procedure similar to that described in Example 99. Found: C, 55.71; H, 6.44; N, 18.83. $C_{24}H_{33}N_7O_4S$ requires C, 55.90; H, 6.45; N, 19.01%. δ (CDCl$_3$): 1.03 (3H, t), 1.40 (3H, t), 1.98 (4H, m), 2.26 (2H, m), 2.42 (2H, q), 2.57 (4H, m), 3.02 (3H, m), 3.15 (4H, m), 4.10 (3H, s), 4.62 (2H, d), 8.62 (1H, s), 9.04 (1H, s), 10.61 (1H, s). LRMS: m/z 516 (M+1)$^+$

EXAMPLE 101

5-[2-n-Butoxy-5-(4-ethylpiperazin-1-ylsulphonyl)pyridin-3-yl]-2-methyl-3-n-propyl-2,6-dihydro-7H-pyrazolo[4,3-d]pyrimidin-7-one

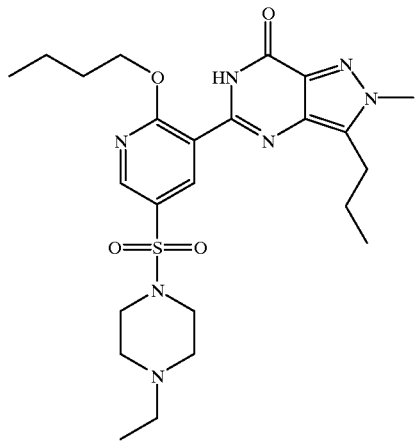

A mixture of the title compound of Example 90 (104 mg, 0.2 mmol) and potassium bis(trimethylsilyl)amide (200 mg, 1.0 mmol) in n-butanol (5 ml) was stirred under reflux for 5 days. The cooled mixture was concentrated under reduced pressure, the residue suspended in ethyl acetate (20 ml) and the mixture neutralised using 1M hydrochloric acid. The layers were separated, the organic phase washed with brine (10 ml), dried (MgSO$_4$) and evaporated under reduced pressure. The crude product was triturated with ether, and the resulting solid, filtered and further purified by column chromatography on silica gel using an elution gradient of dichloromethane:methanol:0.88 ammonia (100:0:0.5 to 99:1:0.5) to afford the title compound, (86 mg, 82%) as a solid.

δ (CDCl$_3$):1.02 (9H, m), 1.57 (2H, m), 1.82 (2H, m), 1.95 (2H, m), 2.42 (2H, q), 2.58 (4H, m), 2.99 (2H, t), 3.15 (4H, m). 4.08 (3H, s), 4.68 (2H, t), 8.62 (1H, s), 9.02 (1H, s), 10.62 (1H, s). LRMS: m/z 518 (M+1)$^+$

EXAMPLE 102

3-Ethyl-5-[2-(2-methoxy-1-methylethoxy)-5-(4-n-propylpiperazin-1-ylsulphonyl)pyridin-3-yl]-2-methyl-2,6-dihydro-7H-pyrazolo[4,3-d]pyrimidin-7-one (Isomer 1)

and

EXAMPLE 103

3-Ethyl-5-[2-(2-methoxy-1-methylethoxy)-5-(4-n-propylpiperazin-1-ylsulphonyl)pyridin-3-yl]-2-methyl-2,6-dihydro-7H-pyrazolo[4,3-d]pyrimidin-7-one (Isomer 2)

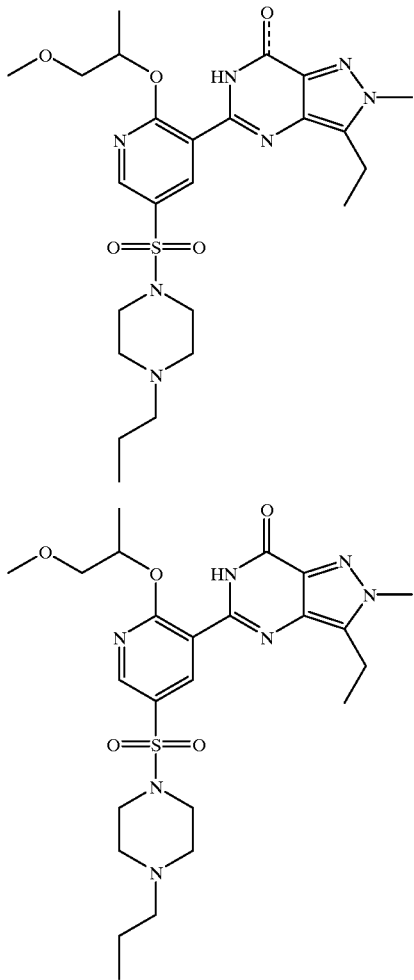

Potassium bis(trimethylsilyl)amide (325 mg, 1.63 mmol) was added to a solution of the title compound of Example 119 (200 mg, 0.41 mmol) in 1-methoxy-2-propanol (6 ml) and the reaction stirred under reflux for 18 hours. The cooled mixture was evaporated under reduced pressure and the residue purified by column chromatography on silica gel, using dichloromethane:methanol (95:5) as eluant to give 193 mg of a colourless oil. This product was further purified by HPLC using an AD250 column, using hexane:isopropanol:diethylamine (70:30:0.3) as eluant to afford, the title compound of Example 102 (58 mg, 26%, 99.5% ee). δ (CDCl$_3$): 0.86 (3H, t), 1.40 (5H, m), 1.50 (3H, d), 2.32 (2H, t), 2.56 (4H, m), 3.03 (2H, q) 3.15 (4H, m), 3.55 (3H, s), 3.66 (1H, m), 3.76 (1H, m), 4.08 (3H, s), 5.61 (1H, m), 8.61 (1H, s), 8.92 (1H, s), 10.82 (1H, s). LRMS: m/z 534 (M+1)$^+$, and the title compound of Example 103 (47 mg, 21%, 98.7% ee). δ (CDCl$_3$): 0.86 (3H, t), 1.41 (5H, m), 1.50 (3H, d), 2.32 (2H, t) 2.56 (4H, m), 3.04 (2H, q), 3.14 (4H, m), 3.55 (3H, s), 3.66 (1H, m), 3.76 (1H, m), 4.08 (3H, s), 5.61 (1H, m), 8.60 (1H, s), 8.92 (1H, s), 10.82 (1H, s). LRMS: m/z 534 (m+1)$^+$

EXAMPLE 104

(+)-5-[2-(2-Methoxy-1-methylethoxy)-5-(4-methylpiperazin-1-ylsulphonyl)pyridin-3-yl]-2-methyl-3-n-propyl-2,6-dihydro-7H-pyrazolo[4,3-d]pyrimidin-7-one (Isomer 1)

and

EXAMPLE 105

(−)-5-[2-(2-Methoxy-1-methylethoxy)-5-(4-methylpiperazin-1-ylsulphonyl)pyridin-3-yl]-2-methyl-3-n-propyl-2,6-dihydro-7H-pyrazolo[4,3-d]pyrimidin-7-one (Isomer 2)

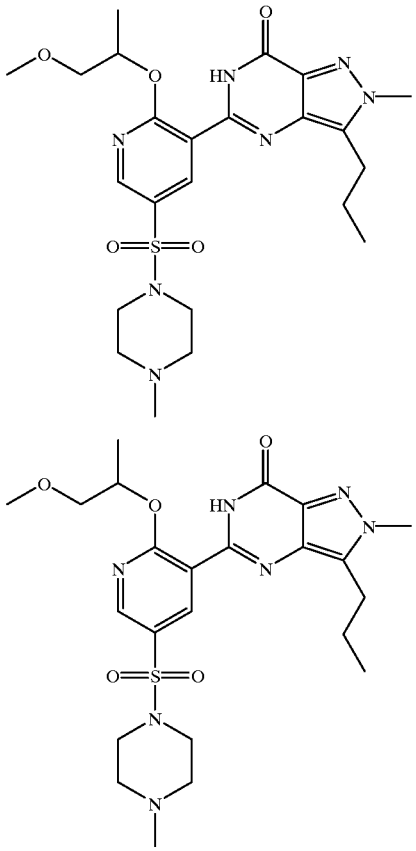

The title compound of Example 79 (198 mg, 0.42 mmol) was added to a solution of potassium bis(trimethylsilyl)amide (415 mg, 2.1 mmol) in 1-methoxy-2-propanol (5 ml), and the reaction heated at 110° C. for 72 hours. The cooled mixture was evaporated under reduced pressure, the residue dissolved in water and neutralised using 2M hydrochloric acid. This aqueous solution was extracted with ethyl acetate (3×30 ml), the combined organic extracts washed with brine (2×20 ml), dried ($Na_2SO_4$) and evaporated under reduced pressure.

The residual yellow oil was purified by column chromatography on silica gel using an elution gradient of dichloromethane:methanol (100:0 to 97:3), and evaporated from ether to give a white solid.

The racemic product was purified by chiral HPLC using an AD250 column, and hexane:isopropanol:trifluoroacetic acid (80:20:0.5) as eluant. The first enantiomer was redissolved in water, basified using aqueous sodium carbonate solution, and this mixture extracted with ethyl acetate (3×20 ml). The combined organic extracts were washed with brine (2×20 ml) dried ($Na_2SO_4$) and evaporated under reduced pressure. This product was then further purified by column chromatography on silica gel, using an elution gradient of dichloromethane:methanol (100:0 to 97:3), and evaporated from ether, to afford the title compound of Example 104 (39 mg, 18%, 98.1% ee) as a colourless solid.

$[\alpha]_D$=+30.31° (c=0.067, dichloromethane) Found: C, 53.32; H, 6.49; N, 18.48. $C_{23}H_{33}N_7O_5S$ requires C, 53.16; H, 6.40; N, 18.87%. δ ($CDCl_3$): 1.02 (3H, t), 1.50 (3H, d), 1.82 (2H, m), 2.28 (3H, s), 2.53 (4H, m), 2.98 (2H, t), 3.16 (4H, m), 3.55 (3H, s), 3.66 (1H, m), 3.76 (1H, m), 4.07 (3H, s), 5.61 (1H, m), 8.61 (1H, s), 8.92 (1H, s), 10.82 (1H, s). LRMS: m/z 520 (M+1)$^+$ The title compound of Example 105 was isolated using the same procedure as for Example 104, (26 mg, 12%, 94.0% ee).

$[\alpha]_D$=−30.31° (c=0.067, dichloromethane) δ ($CDCl_3$): 1.02 (3H, t), 1.51 (3H, d), 1.82 (2H, m), 2.29 (3H, s), 2.53 (4H, m), 2.98 (2H, t), 3.14 (4H, m), 3.55 (3H, s), 3.65 (1H, m), 3.77 (1H, m), 4.08 (3H, s), 5.61 (1H, m), 8.61 (1H, s), 8.92 (1H, s), 10.82 (1H, s). LRMS: m/z 520 (M+1)$^+$

EXAMPLE 106

(+)-5-[5-(4-Ethylpiperazin-1-ylsulphonyl)-2-(2-methoxy-1-methylethoxy)pyridin-3-yl]-2-methyl-3-n-propyl-2,6-dihydro-7H-pyrazolo[4,3-d]pyrimidin-7-one and

EXAMPLE 107

(−)-5-[5-(4-Ethylpiperazin-1-ylsulphonyl)-2-(2-methoxy-1-methylethoxy)pyridin-3-yl]-2-methyl-3-n-propyl-2,6-dihydro-7H-pyrazolo[4,3-d]pyrimidin-7-one (Isomers 1 and 2)

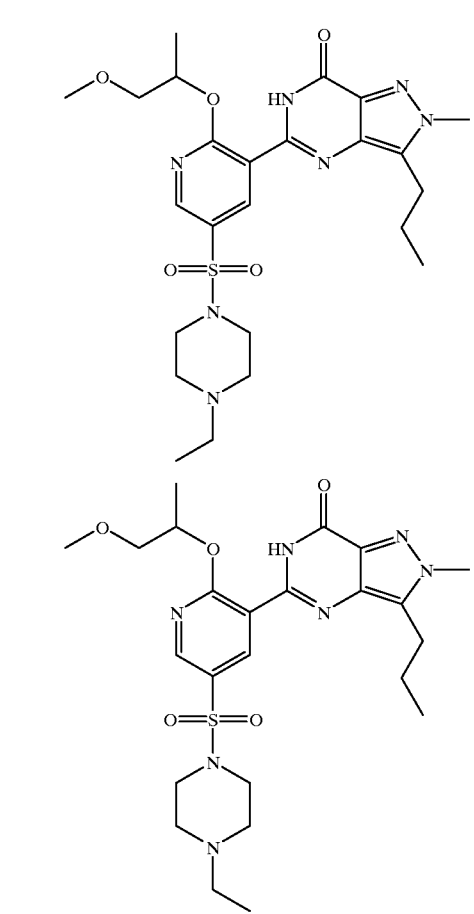

Potassium bis(trimethylsilyl)amide (1.47 g, 7.4 mmol) was added to a solution of the title compound of Example 80 (720 mg, 1.5 mmol) in 1-methoxy-2-propanol (10 ml) and the reaction stirred under reflux for 72 hours. The cooled mixture was evaporated under reduced pressure and the residual brown gum purified by column chromatography on silica gel, using ethyl acetate:diethylamine (97:3) as eluant. This racemic mixture was purified by chiral HPLC using an AD 250 column, and hexane:isopropanol:diethylamine (70:30:0.3) as eluant, to give each enantiomer. The first enantiomer was partitioned between dichloromethane (20 ml) and aqueous sodium carbonate solution (10 ml), the phases separated, and the organic layer dried ($Na_2SO_4$), and evaporated under reduced pressure. The product was further purified by column chromatography on silica gel, using ethyl acetate:methanol (95:5) as eluant, to afford the title compound of Example 106 (130 mg, 16%, 99.76% ee) as a white foam. $[\alpha]_D$=+15.55° (c=0.093, methanol). Found: C, 53.47; H, 6.66; N, 17.92. $C_{24}H_{35}N_7O_5S;0.3H_2O$ requires C, 53.48; H, 6.66; N, 18.19% δ ($CDCl_3$): 1.02 (6H, m), 1.52 (3H, t), 1.82 (2H, m), 2.42 (2H, q), 2.57 (4H, m), 2.98 (2H, t), 3.14 (4H, m), 3.55 (3H, s), 3.65 (1H, m), 3.76 (1H, m), 4.08 (3H, s), 5.60 (1H, s), 8.61 (1H, s), 8.90 (1H, s) 10.81 (1H, s. LRMS: m/z 534 (M+1)$^+$ The title compound of Example 107 was obtained (94 mg, 12%, 97.2% ee) as a white foam, using the same procedure as in Example 106.

$[\alpha]_D$=−14.52° (c=0.10, methanol) Found: C, 53.66; H, 6.73; N, 17.89. $C_{24}H_{35}N_7O_5S;0.25H_2O$ requires C, 53.57; H, 6.65; N, 18.22% δ ($CDCl_3$): 1.03 (6H, m), 1.50 (3H, d), 1.82 (2H, m), 2.42 (2H, q), 2.57 (4H, m), 2.98 (2H, m), 3.17 (4H, m), 3.55 (3H, s), 3.65 (1H, m), 3.75 (1H, m), 4.08 (3H, s), 5.60 (1H, m), 8.60 (1H, s), 8.91 (1H, s), 10.81 (1H, s). LRMS: m/z 534 (M+1)$^+$

EXAMPLE 108

3-Ethyl-5-[5-(4-ethylpiperazin-1-ylsulphonyl)-2-(2-methoxy-n-propoxy)pyridin-3-yl]-2-methyl-2,6-dihydro-7H-pyrazolo[4,3-d]pyrimidin-7-one (Isomer 1)

and

EXAMPLE 109

3-Ethyl-5-[5-(4-ethylpiperazin-1-ylsulphonyl)-2-(2-methoxy-n-propoxy)pyridin-3-yl]-2-methyl-2,6-dihydro-7H-pyrazolo[4,3-d]pyrimidin-7-one (Isomer 2)

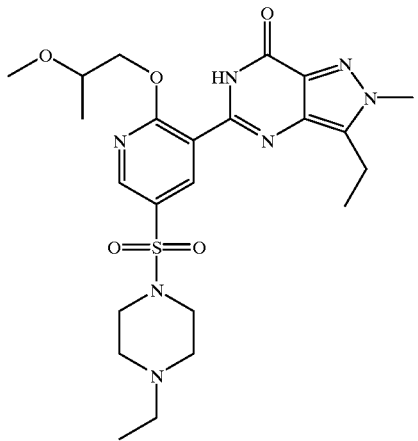

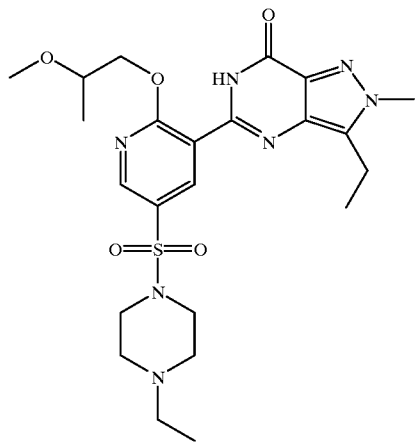

The title compounds were prepared from the title compound of Example 78, and 2-methoxy-1-propanol following a similar procedure to that described for Examples 104 and 105.

The racemate was further purified by HPLC using an AD250 column and hexane:ethanol:diethylamine (60:40:1) as eluant, to give isomer 1. This product was re-purified by column chromatography on silica gel using an elution gradient of dichloromethane:methanol (100:0 to 97:3) and triturated with ether to afford the title compound of Example 108 (8 mg, 2%, 82% ee) as a white solid.

δ ($CDCl_3$): 1.19–1.36 (6H, m), 1.40 (3H, t), 2.68–3.10 (8H, m), 3.32–3.59 (7H, m), 3.92 (1H, m), 4.09 (3H, s), 4.47 (1H, m), 4.72 (1H, m), 8.62 (1H, s), 8.97 (1H, s), 10.90 (1H, s). LRMS: m/z 520 (M+1)$^+$

The title compound of Example 109 was isolated (5 mg, 1%, 93% ee) as a white solid, using the same procedure as described for Example 108.

δ ($CDCl_3$): 1.26 (3H, t), 1.32 (3H, d), 1.40 (3H, t), 2.80–3.10 (8H, m), 3.38–3.60 (7H, m), 3.92 (1H, m), 4.09 (3H, s), 4.48 (1H, m), 4.72 (1H, m), 8.61 (1H, s), 8.98 (1H, s), 10.89 (1H, s). LRMS: m/z 520 (M+1)$^+$

EXAMPLE 110

3-Ethyl-5-[5-(4-ethylpiperazin-1-ylsulphonyl)-2-(3-methoxy-1-methyl-n-propoxy)pyridin-3-yl]-2-methyl-2,6-dihydro-7H-pyrazolo[4,3-d]pyrimidin-7-one and

EXAMPLE 111

3-Ethyl-5-[5-(4-ethylpiperazin-1-ylsulphonyl)-2-(3-methoxy-1-methyl-n-propoxy)pyridin-3-yl]-2-methyl-2,6-dihydro-7H-pyrazolo[4,3-d]pyrimidin-7-one (Isomers 1 and 2)

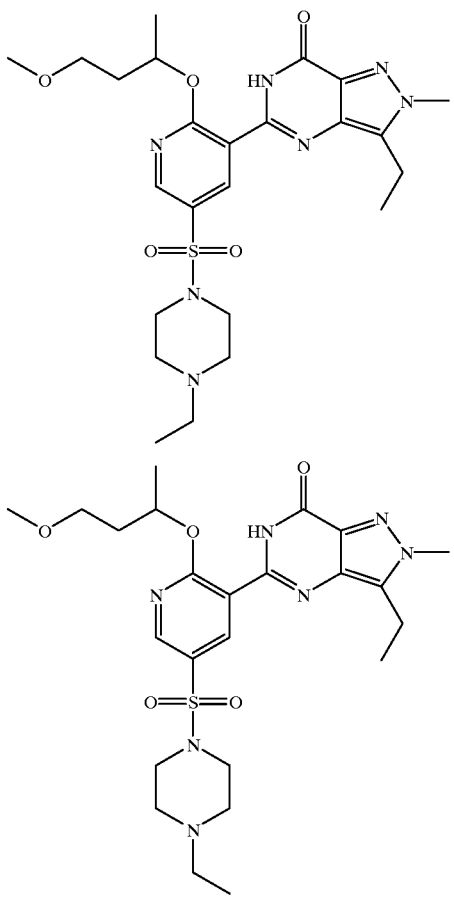

A mixture of the title compound of Example 78 (330 mg, 0.70 mmol) and potassium bis(trimethylsilyl)amide (693 mg, 3.47 mmol) in the title compound of preparation 166 (2.5 ml) was heated at 110° C. for 16 hours. The cooled reaction was suspended in ethyl acetate (25 ml), and washed with saturated ammonium chloride solution (5 ml), then saturated sodium bicarbonate solution (10 ml), dried (MgSO$_4$) and evaporated under reduced pressure. The residue was purified by column chromatography on silica gel using methanol:dichloromethane (5:95) as eluant, and repeated using diethylamine:ethyl acetate (10:90) as eluant to give a gum.

This racemate was purified by HPLC using an AD250 column, and hexane:ethanol:diethylamine (85:15:1) as eluant to afford the title compound of Example 110 (25 mg, 6.7%, 98.9% ee)

δ (CDCl$_3$): 1.04 (3H, t), 1.39 (3H, t), 1.49 (3H, d), 2.04 (1H, m), 2.24 (1H, m), 2.42 (2H, q), 2.56 (4H, m), 3.01 (2H, m), 3.16 (4H, m), 3.33 (3H, s), 3.57 (1H, m), 3.68 (1H, m), 4.06 (3H, s), 5.75 (1H, m), 8.61 (1H, s), 8.88 (1H, s), 10.99 (1H, s). LRMS: m/z 534 (M+1)$^+$ and the title compound of Example 111 (29 mg, 7.8%, 99.7% ee).

δ (CDCl$_3$): 1.03 (3H, t), 1.40 (3H, t), 1.48 (3H, d), 2.04 (1H, m), 2.24 (1H, m), 2.42 (2H, q), 2.58 (4H, m), 3.02 (2H, q), 3.16 (4H, m), 3.34 (3H, s), 3.57 (1H, m), 3.66 (1H, m), 4.08 (3H, s), 5.74 (1H, m), 8.60 (1H, s), 8.98 (1H, s), 10.98 (1H, s). LRMS: m/z 534 (M+1)$^+$

EXAMPLE 112

(+)-3-Ethyl-5-[5-(4-ethylpiperazin-1-ylsulphonyl)-2-(2-ethoxy-1-methylethoxy)pyridin-3-yl]-2-methyl-2,6-dihydro-7H-pyrazolo[4,3-d]pyrimidin-7-one (Isomer 1) and

EXAMPLE 113

(−)-3-Ethyl-5-[5-(4-Ethylpiperazin-1-ylsulphonyl)-2-(2-ethoxy-1-methylethoxy)pyridin-3-yl]-2-methyl-2,6-dihydro-7H-pyrazolo[4,3-d]pyrimidin-7-one (Isomer 2)

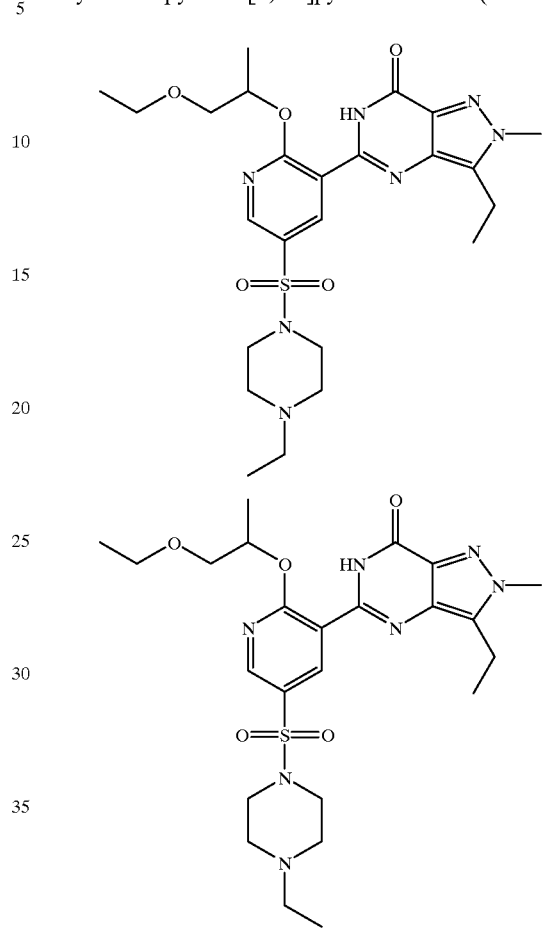

The racemate was prepared (70%) from the title compound of Example 78 and 1-ethoxy-2-propanol, following the procedure described for Examples 104 and 105.

This racemate was purified by chiral HPLC using an AD 250 column, and hexane:isopropanol:diethylamine (70:30:0.3) as eluant, to give enantiomer 1. This product was further purified by column chromatography on silica gel, using dichloromethane:methanol (97:3) as eluant, and evaporated from ether, to afford the title compound of Example 112 (52 mg, 15%, 99.5% ee) as a foam.

[α]$_D$=+18.60° (c=0.067, dichloromethane) Found: C, 53.20; H, 6.70; N, 17.78. C$_{24}$H$_{35}$N$_7$O$_5$S;0.5H$_2$O requires C, 53.12; H, 6.69; N, 18.07% δ (CDCl$_3$): 1.04 (3H, t), 1.25 (3H, t), 1.40 (3H, t), 1.52 (3H, d), 2.42 (2H, q), 2.57 (4H, m), 3.02 (2H, q), 3.15 (4H, m), 3.60–3.82 (4H, m), 4.08 (3H, s), 5.60 (1H, m), 8.61 (1H, s), 8.94 (1H, s), 10.81 (1H, s). LRMS: m/z 534 (M+1)$^+$ The title compound of Example 113 was isolated (11 mg, 3%, 99.5% ee) following the same procedure to that described for Example 112.

[α]$_D$=−19.43° (c=0.070, dichloromethane) Found: C, 53.34; H, 6.66; N, 17.86. C$_{24}$H$_{35}$N$_7$O$_5$S;0.5H$_2$O requires C, 53.12; H, 6.69; N, 18.07% δ (CDCl$_3$): 1.04 (3H, t), 1.25 (3H, t), 1.40 (3H, t), 1.52 (3H, d), 2.42 (2H, q), 2.57 (4H, m), 3.03 (2H, q), 3.16 (4H, m), 3.60–3.82 (4H, m), 4.09 (3H, s), 5.60

(1H, m), 8.62 (1H, s), 8.92 (1H, s), 10.82 (1H, s). LRMS: m/z 534 (M+1)+

EXAMPLE 114
(+)-3-Ethyl-5-[5-(4-ethylpiperazin-1-ylsulphonyl)-2-(1-methoxymethyl-n-propoxy)pyridin-3-yl]-2-methyl-2,6-dihydro-7H-pyrazolo[4,3-d]pyrimidin-7-one
and

EXAMPLE 115
(−)-3-Ethyl-5-[5-(4-ethylpiperazin-1-ylsulphonyl)-2-(1-methoxymethyl-n-propoxy)pyridin-3-yl]-2-methyl-2,6-dihydro-7H-pyrazolo[4,3-d]pyrimidin-7-one (Isomers 1 and 2)

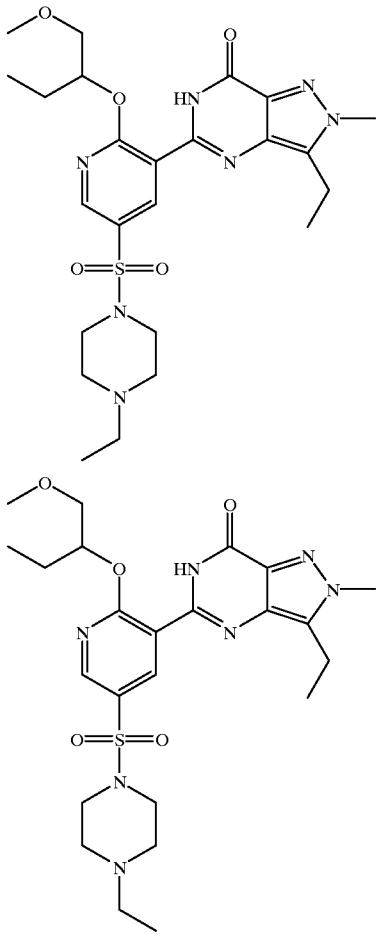

The title compounds of Examples 114 and 115 were obtained (11%, 93% ee) and (6.7%, 97% ee) respectively from the title compound of Example 78 and 1-methoxy-2-butanol, using the procedure described in Examples 108 and 109.

[α]$_D$=+37.04° (c=0.097, dichloromethane) Found : C, 53.36; H, 6.73; N, 17.84. $C_{24}H_{35}N_7O_5S;0.5H_2O$ requires C, 53.12; H, 6.69; N, 18.07%

δ (CDCl$_3$): 1.03 (6H, m), 1.39 (3H, t), 1.92 (2H, m), 2.42 (2H, q), 2.57 (4H, m), 3.02 (2H, q), 3.16 (4H, m), 3.51 (3H, s), 3.66 (1H, m), 3.77 (1H, m), 4.08 (3H, s), 5.57 (1H, m), 8.60 (1H, s), 8.88 (1H, s), 10.84 (1H, s). LRMS: m/z 534 (M+1)+; and α$_D$=−40.08° (c=0.093, dichloromethane) Found: C, 53.44; H, 6.75; N, 17.76. $C_{24}H_{35}N_7O_5S;0.5H_2O$ requires C, 53.12; H, 6.69; N, 18.07% δ (CDCl$_3$): 1.03 (6H, m), 1.40 (3H, t), 1.92 (2H, m), 2.42 (2H, q), 2.57 (4H, m), 3.02 (2H, q), 3.16 (4H, m), 3.51 (3H, s), 3.68 (1H, m), 3.78 (1H, m), 4.10 (3H, s), 5.57 (1H, m), 8.61 (1H, m), 8.89 (1H, s), 10.83 (1H, s).

EXAMPLE 116
(−)-3-Ethyl-5-{5-(4-ethylpiperazin-1-ylsulphonyl)-2-[1-(pyridin-2-yl)ethoxy]pyridin-3-yl}-2-methyl-2,6-dihydro-7H-pyrazolo[4,3-d]pyrimidin-7-one (Isomer 1)
and

EXAMPLE 117
(+)-3-Ethyl-5-{5-(4-ethylpiperazin-1-ylsulphonyl)-2-[1-(pyridin-2-yl)ethoxy]pyridin-3-yl}-2-methyl-2,6-dihydro-7H-pyrazolo[4,3-d]pyrimidin-7-one (Isomer 2)

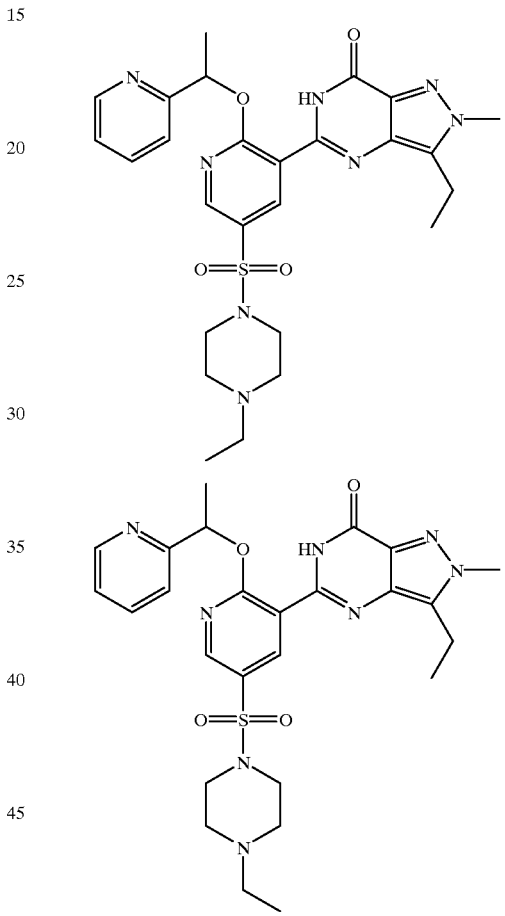

The title compounds of Example 116 and 117 were obtained as solids, (4%, 99.0% ee) and (2%, 99.0% ee) respectively, from the title compound of Example 78 and 1-(pyridin-2-yl) ethanol (Helv.Chim.Acta., 1955, 38, 1114), following a similar procedure to that described for Examples 112 and 113, except that hexane:isopropanol:diethylamine (70:30:1) was used as the HPLC eluant.

[α]$_D$=−90.11° (c=0.033, dichloromethane) δ (CDCl$_3$): 1.02 (3H, t), 1.40 (3H, t), 1.80 (3H, d), 2.41 (2H, q), 2.54 (4H, m), 3.00–3.17 (6H, m), 4.10 (3H, s), 6.69 (1H, q), 7.32 (2H, m), 7.75 (1H, m), 8.54 (1H, s), 8.75 (1H, s), 8.80 (1H, d), 13.14 (1H, s). LRMS: m/z 553 (M+1)+

[α]$_D$=+82.02° (c=0.040, dichloromethane) δ (CDCl$_3$): 1.04 (3H, t), 1.40 (3H, m), 1.80 (3H, d), 2.41 (2H, q), 2.55 (4H, m), 3.00–3.18 (6H, m), 4.10 (3H, s), 6.69 (1H, q), 7.34 (2H, m), 7.75 (1H, m), 8.52 (1H, s), 8.76 (1H, s), 8.80 (1H, d), 13.16 (1H, s). LRMS: m/z 553 (M+1)+

EXAMPLE 118

(+)-3-Ethyl-5-[5-(4-ethylpiperazin-1-ylsulphonyl)-2-(2-methoxy-1(R)-methyl ethoxy)pyridin-3-yl]-2-methyl-2,6-dihydro-7H-pyrazolo[4,3-d]pyrimidin-7-one

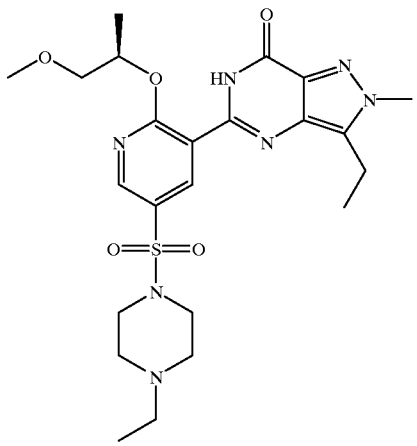

A mixture of the title compound of example 78 (2.0 g, 4.2 mmol) and potassium bis(trimethylsilyl)amide (4.2 g, 21.0 mmol) in the title compound of Preparation 165 (16 ml), was heated at 110° C. for 18 hours. The cooled mixture was concentrated under reduced pressure and the residue purified by column chromatography on silica gel using an elution gradient of diethylamine:methanol:ethyl acetate (2.5:0:97.5 to 0:10:90). The product was purified further by column chromatography on silica gel using methanol:ethyl acetate (2.5:97.5) as eluant to afford the title compound (640 mg, 29%) as a solid. Found : C, 53.16; H, 6.54; N, 18.37. $C_{23}H_{33}N_7O_5S;0.2CH_3CO_2C_2H_5$ requires C, 53.21; H, 6.49; N, 18.25%

$[\alpha]_D$=+16.6° (c=0.10 methanol) δ (CDCl$_3$): 1.04 (3H, t), 1.40 (3H, t), 1.52 (3H, d), 2.42 (2H, q), 2.57 (4H, m), 3.03 (2H, q), 3.15 (4H, m), 3.56 (3H, s), 3.66 (1H, m), 3.77 (1H, m), 4.09 (3H, s), 5.61 (1H, m), 8.62 (1H, s), 8.93 (1H, s), 10.82 (1H, s). LRMS: m/z 520 (M+1)$^+$

EXAMPLE 119

5-[2-Ethoxy-5-(4-n-propylpiperazin-1-ylsulphonyl)pyridin-3-yl]-3-ethyl-2-methyl-2,6-dihydro-7H-pyrazolo[4,3-d]pyrimidin-7-one

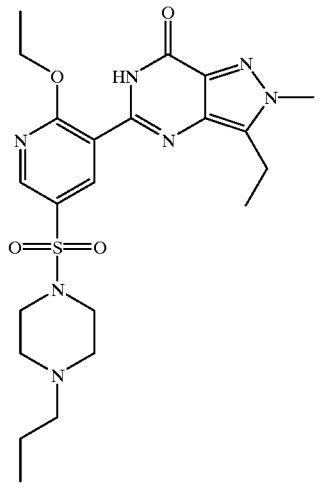

1-n-propylpiperazine (308 mg, 1.01 mmol) and triethylamine (440 ml, 3.2 mmol) were added to a solution of the title compound of Preparation 164 (211 mg, 0.53 mmol) in dichloromethane (6 ml), and the reaction mixture stirred at room temperature for 2 hours. The mixture was purified directly by column chromatography on silica gel, using dichloromethane: methanol (95:5) as eluant to afford the title compound (210 mg, 85%) as a white foam. δ (CDCl$_3$): 0.86 (3H, t), 1.42 (5H, m), 1.58 (3H, t), 2.29 (2H, t), 2.56 (4H, m), 3.03 (2H, q), 3.14 (4H, m), 4.10 (3H, s), 4.76 (2H, q), 8.62 (1H, s), 9.04 (1H, s), 10.67 (1H, s). LRMS: m/z 490 (M+1)$^+$

EXAMPLE 120

5-{2-Ethoxy-5-[4-(prop-2-yl)piperazin-1-ylsulphonyl]pyridin-3-yl}-3-ethyl-2-methyl-2,6-dihydro-7H-pyrazolo[4,3-d]pyrimidin-7-one

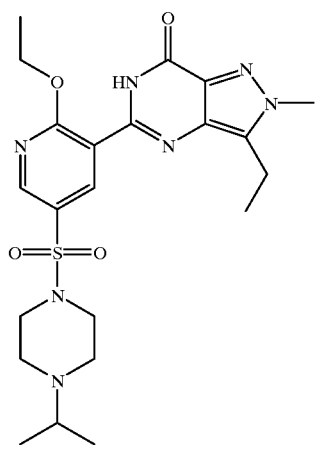

Obtained as a white solid (71%), from the title compound of Preparation 164 and 1-(prop-2-yl)-piperazine, following the procedure described in Example 119.

δ (CDCl$_3$): 0.99 (6H, d), 1.40 (3H, t), 1.57 (3H, t), 2.62 (4H, m), 2.70 (1H, m), 3.02 (2H, q), 3.13 (4H, m), 4.08 (3H, s), 4.74 (2H, q), 8.62 (1H, s), 9.03 (1H, s), 10.64 (1H, s). LRMS: m/z 490 (M+1)$^+$

EXAMPLE 121

5-{2-Ethoxy-5-[4-(pyridin-2-yl)piperazin-1-ylsulphonyl]pyridin-3-yl-3}-3-ethyl-2-methyl-2,6-dihydro-7H-pyrazolo[4,3-d]pyrimidin-7-one

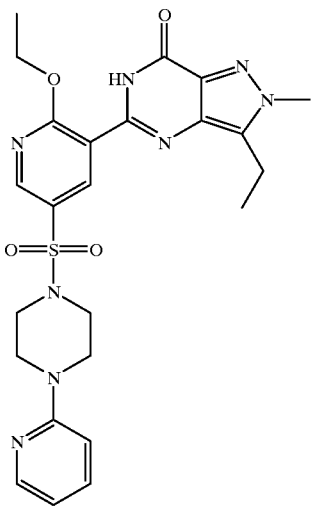

Obtained as a white solid (58%), from the title compound of Preparation 164 and 1-(pyridin-2-yl-piperazine, following the procedure described in Example 119.

δ (CDCl$_3$): 1.41 (3H, t), 1.59 (3H, t), 3.05 (2H, q), 3.22 (4H, m), 3.70 (4H, m), 4.10 (3H, s), 4.75 (2H, q), 6.62 (2H, m), 7.47 (1H, m), 8.16 (1H, d), 8.64 (1H, s), 9.07 (1H, s), 10.65 (1H, s). LRMS: m/z 525 (M+1)$^+$

EXAMPLE 122

3-Ethyl-5-{2-(2-methoxy-1-methylethoxy)-5-[4-pyridin-2-yl)piperazin-1-ylsulphonyl]pyridin-3-yl}-2-methyl-2,6-dihydro7H-pyrazolo[4,3-d]pyrimidin-7-one

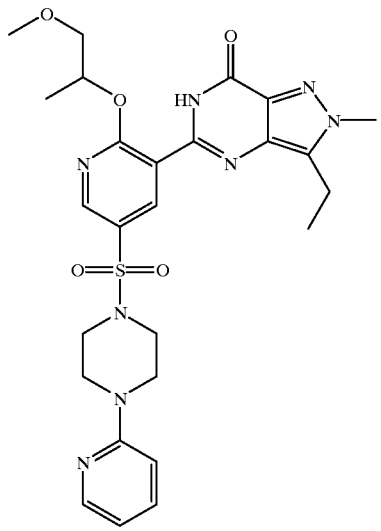

Potassium bis(trimethylsilyl)amide (76 mg, 0.38 mmol) was added to a solution of the title compound of Example 121 (50 mg, 0.095 mmol) in 1-methoxy-2-propanol (5 ml) and the reaction heated under reflux for 18 hours. The cooled mixture was purified directly by column chromatography on silica gel, using dichloromethane:methanol (95:5) as eluant to afford the title compound (32 mg, 59% as a yellow oil.

δ (CDCl$_3$): 1.40 (3H, t), 1.50 (3H, d), 3.04 (2H, q), 3.22 (4H, m), 3.54 (3H, s), 3.69 (6H, m), 4.09 (3H, s), 5.60 (1H, m), 6.63 (2H, m), 7.47 (1H, m), 8.16 (1H, d), 8.63 (1H, s), 8.94 (1H, s), 10.81 (1H, s). LRMS: m/z 569 (M+1)$^+$

EXAMPLE 123

5-[2-Ethoxy-5-(4-ethylpiperazin-1-ylsulphonyl)pyridin-3-yl]-3-ethyl-1-methyl-1,6-dihydro-7H-pyrazolo[4,3-d]pyrimidin-7-one

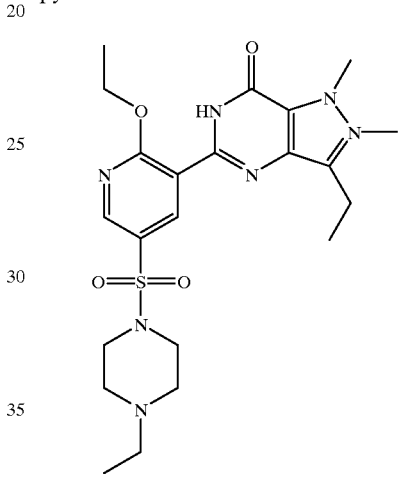

A mixture of the title compound of Preparation 158 (596 mg, 1.21 mmol) and potassium bis(trimethylsilyl)amide (723 mg, 3.62 mmol) in ethanol (20 ml) was heated at 120° C. for 18 hours in a sealed vessel. The cooled mixture was evaporated under reduced pressure and the residue purified by column chromatography on silica gel twice, using dichloromethane:methanol (95:5) as eluant. The product was triturated with ether to afford the title compound (3.58 mg, 62%) as an off-white solid.

Found: C, 52.71; H, 6.00; N, 20.48. $C_{21}H_{29}N_7O_4S$ requires C, 53.04; H, 6.15; N, 20.62%

δ (CDCl$_3$): 1.04 (3H, t), 1.40 (3H, t), 1.60 (3H, t), 2.42 (2H q), 2.58 (4H, m), 2.99 (2H, q), 3.16 (4H, m), 4.28 (3H, s), 4.78 (2H, q), 8.64 (1H, s), 9.08 (1H, s), 10.80 (1H, s). LRMS: 476 (M+1)$^+$

EXAMPLE 124

5-[2-Ethoxy-5-(4-ethylpiperazin-1-ylsulphonyl)pyridin-3-yl]1-1-methyl-3-n-propyl-1,6-dihydro-7H-pyrazolo[4,3-d]pyrimidin-7-one

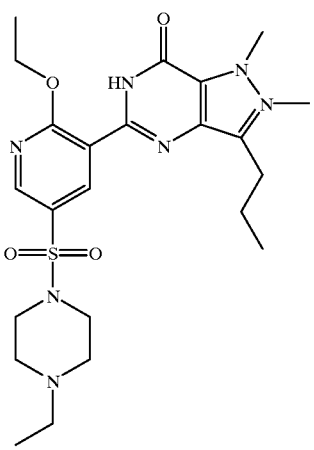

Obtained (42%) from the title compound of Preparation 159, following a similar procedure to that described in Example 123. Found: C, 53.68; H, 6.34; N, 19.97. $C_{22}H_{31}N_7O_4S$ requires C, 53.97; H, 6.38; N, 20.03%

δ ($CDCl_3$): 1.02 (6H, m), 1.60 (3H, t), 1.85 (2H, m), 2.42 (2H, q), 2.58 (4H, m), 2.95 (2H, t), 3.16 (4H, m), 4.29 (3H, s), 4.78 (2H, q), 8.63 (1H, s), 9.08 (1H, s), 10.78 (1H, s). LRMS: m/z491 (M+1)+

EXAMPLE 125
3-Ethyl-5-[5-(4-ethylpiperazin-1-ylsulphonyl)-2-(2-methoxy-1 (R)-methylethoxy)pyridin-3-yl]-1-methyl-1,6-dihydro7H-pyrazolo[4,3-d]pyrimidin-7-one

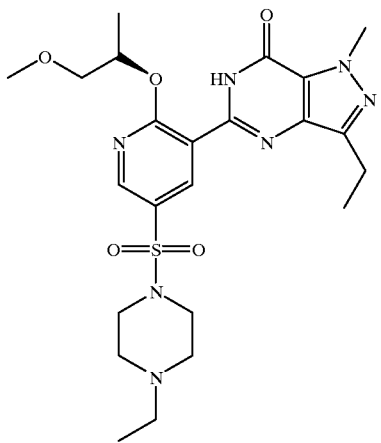

A mixture of the title compound of Example 123 (70 mg, 0.15 mmol) and potassium bis(trimethylsilyl)amide (150 mg, 0.74 mmol) in the title compound of Preparation 165 (1 ml), was stirred at 110° C. for 18 hours. The cooled mixture was concentrated under reduced pressure and the residue partitioned between water (5 ml) and dichloromethane (5 ml), and the mixture neutralised by the addition of solid carbon dioxide. The layers were separated, the aqueous phase extracted with dichloromethane (2×5 ml), the combined organic solutions dried ($Na_2SO_4$), and evaporated under reduced pressure. The crude product was purified by column chromatography on silica gel, using ethyl acetate-:diethylamine (97:3) as eluant to afford the title compound (62 mg, 80%).

δ ($CDCl_3$): 1.04 (3H, t), 1.39 (3H, t), 1.50 (3H, d), 2.42 (2H, q), 2.58 (4H, m), 2.98 (2H, q), 3.15 (4H, m), 3.58 (3H, s), 3.70 (2H, m), 4.28 (3H, s), 5.58 (1H, m), 8.62 (1H, s), 8.90 (1H, s), 11.07 (1H, s). LRMS: m/z 520 (M+1)+

EXAMPLE 126
5-[5-(4-Ethylpiperazin-1-ylsulphonyl)-2-(2-methoxyethoxy)pyridin-3-yl]-1-methyl-3-n-propyl-1,6-dihydro-7H-pyrazolo[4,3-d]pyrimidin-7-one

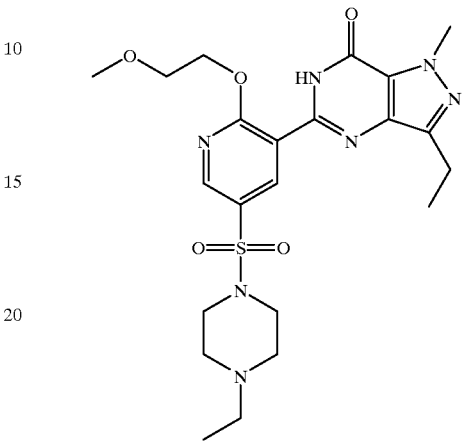

A mixture of the title compound of Example 124 (111 mg, 0.23 mmol) and potassium bis(trimethylsilyl)amide (226 mg, 1.13 mmol) in 2-methoxyethanol (5 ml) was stirred under reflux for 18 hours. The cooled mixture was evaporated under reduced pressure and the residue purified by column chromatography on silica gel, using dichloromethane: methanol (96:4) as eluant, and triturated with ether to afford the title compound (75 mg, 64%) as a white crystalline solid. Found: C, 52.87; H. 6.35; N, 18.68. $C_{23}H_{33}N_7O_5S$ requires C, 53.16; H, 6.40; N, 18.87% δ ($CDCl_3$): 1.02 (6H, m), 1.85 (2H, m), 2.42 (2H, q), 2.57 (4H, m), 2.94 (2H, t), 3.16 (4H, m), 3.60 (3H, s), 3.86 (2H, t), 4.27 (3H, s), 4.78 (2H, t), 8.62 (1H, s), 9.00 (1H, s), 10.51 (1H, s). LRMS: m/z 521 (M+2)+

EXAMPLE 127
5-{5-(4-Ethylpiperazin-1-ylsulphonyl)-2-[pyridin-2-yl)methoxy]pyridin-3-yl}-1-methyl-3-n-propyl-1,6-dihydro-7H-pyrazolo[4,3-d]pyrimidin-7-one

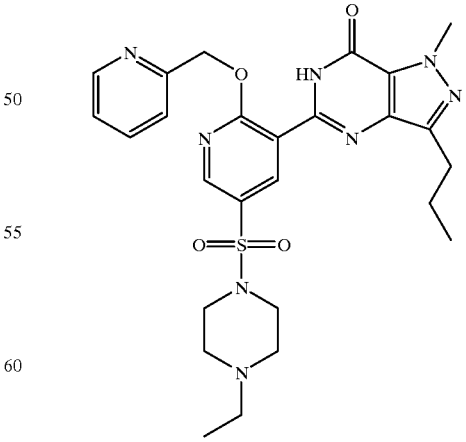

A mixture of the title compound of Example 124 (100 mg, 0.20 mmol) and potassium bis(trimethylsilyl)amide (204 mg, 1.02 mmol) in pyridine-2-methanol (2 ml) was stirred at 110° C. for 18 hours, then cooled. The solvent was removed by Kugelrohr distillation, and the residue was purified by column chromatography on silica gel, using dichloromethane:methanol (95:5) as eluant. This product was triturated with ether to afford the title compound (8 mg, 7%) as a solid. δ (CDCl$_3$): 1.03 (6H, m), 1.87 (2H, m), 2.42 (2H, q), 2.56 (4H, m), 2.95 (2H, t), 3.16 (4H, m), 4.30 (3H, s), 5.94 (2H, s), 7.36 (2H, m), 7.68 (1H, m), 8.60 (1H, s), 8.86 (2H, d), 13.34 (1H, s). LRMS: m/z 554 (M+1)$^+$

EXAMPLE 128

(+)-5-[5-(4-Ethylpiperazin-1-ylsulphonyl)-2-(2-methoxy-1-methylethoxy)pyridin-3-yl]-1-methyl 3-n-propyl-1,6-dihydro-7H-pyrazolo[4,3-d]pyrimidin-7-one
and

EXAMPLE 129

(+)-5-[5-(4-Ethylpiperazin-1-ylsulphonyl)-2-(2-methoxy-1-methylethoxy)pyridin-3-yl]-1-methyl 3-n-propyl-1,6-dihydro-7H-pyrazolo[4,3-d]pyrimidin-7-one (Isomer 1 and Isomer 2)

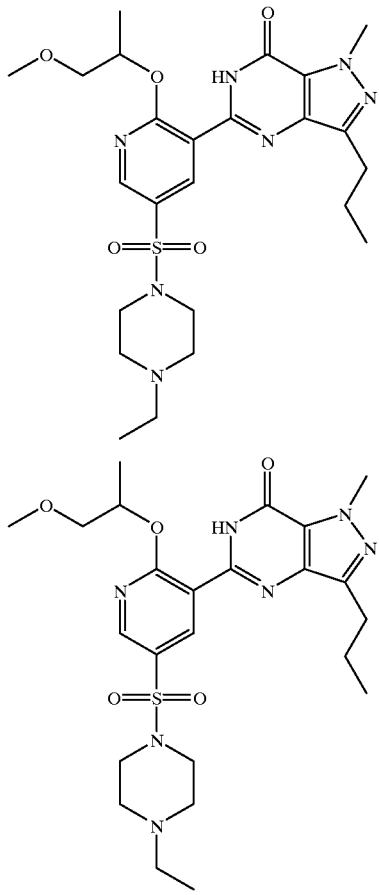

The title compounds of Examples 128 and 129 were prepared from Example 124 (17%, 99.5% ee) and (15%, 98.6% ee) respectively, following a procedure similar to that described in Examples 106 and 107, except that hexane:isopropanol:diethylamine:trifluoroacetic acid (85:15:0.2:0.3) was used as the HPLC eluant. [α]$_D$=+31.21° (c=0.067 dichloromethane) Found: C. 53.77; H, 6.71; N, 17.89. C$_{24}$H$_{35}$N$_7$O$_5$S;0.5H$_2$O requires C, 53.12; H, 6.69; N, 18.07% δ (CDCl$_3$): 1.02 (6H, m), 1.50 (3H, d), 1.84 (2H, m), 2.42 (2H, q), 2.58 (4H, m), 2.94 (2H, t), 3.17 (4H, m), 3.58 (3H, s), 3.72 (2H, m), 4.28 (3H, s), 5.58 (1H, m), 8.62 (1H, s), 8.90 (1H, s), 11.08 (1H, s); and [α]$_D$=−34.10° (c=0.072 dichloromethane) Found: C, 53.75; H, 6.67; N, 18.04. C$_{24}$H$_{35}$N$_7$O$_5$S requires C, 54.02; H, 6.61; N, 18.37% δ (CDCl$_3$): 1.02 (6H, m), 1.50 (3H, d), 1.84 (2H, m), 2.42 (2H, q), 2.58 (4H, m), 2.94 (2H, t), 3.15 (4H, m), 3.59 (3H, s), 3.70 (2H, m), 4.28 (3H, s), 5.59 (1H, m), 8.62 (1H, s), 8.92 (1H, s), 11.17 (1H, s), respectively.

EXAMPLE 130

5-[5-(4-Ethyl-4-oxidopiperazin-1-ylsulphonyl)-2-(2-methoxyethoxy)pyridin-3-yl]-2-methyl-3-n-propyl-2,6-dihydro-7H-pyrazolo[4,3-d]pyrimidin-7-one

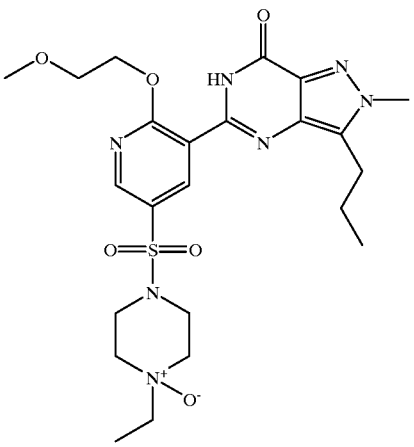

A mixture of the title compound of Example 93 (130 mg, 0.25 mmol) and 3-chloroperbenzoic acid (95 mg, 0.275 mmol) in dichloromethane (6 ml) was stirred at room temperature for 2½ hours. The reaction mixture was washed with aqueous sodium bicarbonate solution (5 ml), dried (MgSO$_4$), and evaporated under reduced pressure. The residual foam was purified by column chromatography on silica gel, using an elution gradient of dichloromethane:methanol:0.88 ammonia (93:7:0 to 93:7:1) to afford the title compound (110 mg, 82%) as a white solid. Found: C, 50.71; H, 6.27; N, 17.82. C$_{23}$H$_{33}$N$_7$O$_6$S requires C, 50.72; H, 6.30; N, 18.00% δ (CDCl$_3$): 1.00 (3H, t), 1.40 (3H, t), 1.81 (2H, m), 2.98 (2H, t), 3.19 (2H, m), 3.33 (4H, m), 3.54 (5H, m), 3.70 (2H, m), 3.86 (2H, t), 4.06 (3H, s), 4.78 (2H, t), 8.63 (1H, s), 8.97 (1H, s), 10.87 (1H, s). LRMS: m/z 536 (M+1)$^+$

EXAMPLE 131

5-[2-Ethoxy-5-(4-ethyl-4-oxidopiperazin-1-ylsulphonyl) pyridin-3-yl]-2-methyl-3-n-propyl-2,6-dihydro-7H-pyrazolo[4,3-d]pyrimidin-7-one

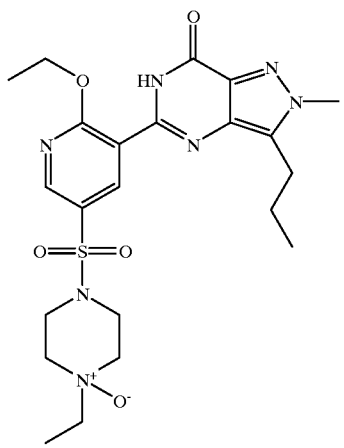

Obtained as a white foam (81%), from the title compound of Example 80 following the procedure described in Example 130. δ (CDCl$_3$): 1.00 (3H, t), 1.40 (2H, t), 1.38 (3H, t), 1.81 (2H, m), 2.97 (2H, t), 3.16 (2H, m), 3.30 (4H, m), 3.50 (2H, m), 3.70 (2H, m), 4.08 (3H, s), 4.74 (2H, q), 8.64 (1H, s), 9.00 (1H, s), 10.75 (1H, s). LRMS: m/z 506 (M+1)$^+$

EXAMPLE 132
3-Ethyl-5-[5-(4-ethyl-4-oxidopiperazin-1-ylsulphonyl)-2-(2-methoxy-1(R)-methyl ethoxy)pyridin-3-yl]-2-methyl-2,6-dihydro-7H-pyrazolo[4,3-d]pyrimidin-7-one

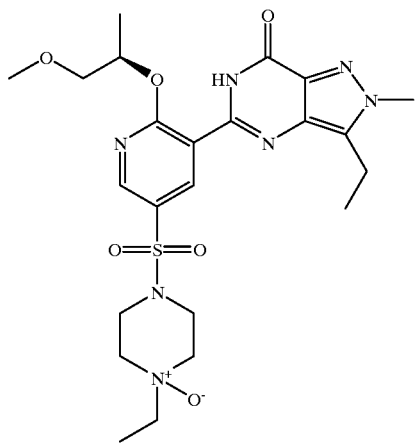

3-Chloroperbenzoic acid (95 mg, 0.28 mmol) was added to a solution of the title compound of Example 118 (130 mg, 0.25 mmol) in dichloromethane (2 ml), and the reaction stirred at room temperature for 3 hours. The mixture was concentrated under reduced pressure and the residue was purified by column chromatography on silica gel, using an elution gradient of dichloromethane:methanol:0.88 ammonia (95:5:0 to 90:10:1) to afford the title compound (130 mg, 87%).

δ (CDCl$_3$): 1.40 (6H, m), 1.52 (3H, d), 3.01 (2H, q), 3.22 (2H, m), 3.34 (4H, m), 3.54 (5H, m), 3.73 (4H, m), 4.08 (3H, s), 5.62 (1H, m), 8.64 (1H, s), 8.94 (1H, s). LRMS: m/z 536 (M+1)$^+$

EXAMPLE 133
5-[5-(4-Ethyl-4-oxidopiperazin-1-ylsulphonyl)-2-(2-methoxyethoxy)pyridin-3-yl]-1-methyl-3-n-propyl-1,6-dihydro-7H-pyrazolo[4,3-d]pyrimidin-7-one

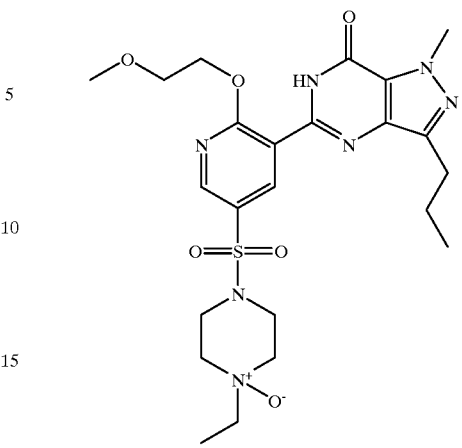

Obtained as a white solid (51%) from the title compound of Example 126, using a similar procedure to that described in Example 130.

δ (CDCl$_3$): 1.02 (3H, t), 1.41 (3H, t), 1.84 (2H, q), 2.92 (2H, t), 3.32 (2H, d), 3.36 (4H, m), 3.46–3.60 (5H, m), 3.74 (2H, m), 3.86 (2H, t), 4.29 (3H, s), 4.78 (2H, t), 8.64 (1H, s), 9.01 (1H, s), 11.05 (1H, s). LRMS : m/z 535 (M)$^+$

EXAMPLE 134
2,3-Diethyl-5-[5-(4-ethylpiperazin-1-ylsulphonyl)-2-n-propoxypyridin-3-yl]-2,6-dihydro-7H-pyrazolo[4,3-d]pyrimidin-7-one

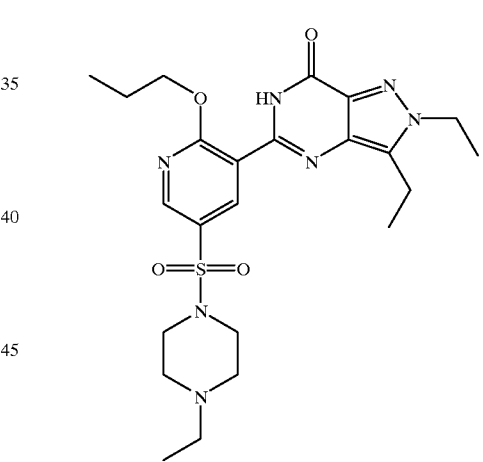

A mixture of the title compound of Example 81 (200 mg, 0.41 mmol), and potassium bis(trimethylsilyl)amide (407 mg, 2.04 mmol) in n-propanol (5 ml) was stirred at 110° C. for 18 hours and the cooled reaction, evaporated under reduced pressure. The residue was purified by column chromatography on silica gel, using an elution gradient of ethyl acetate:diethylamine (100:0 to 95:5) and triturated with ether to afford the title compound (1 60 mg, 68%) as a solid. (CDCl$_3$): 1.02 (3H, t), 1.10 (3H, t), 1.42 (3H, t), 1.59 (3H, t), 2.00 (4H, m), 2.42 (2H, q), 2.58 (4H, m), 3.02 (2H, q), 3.14 (4H, m), 4.38 (2H, q), 4.63 (2H, t), 8.63 (1H, s), 9.04 (1H, s). LRMS: m/z 504 (M+1)$^+$

EXAMPLE 135
5-[2-i-Butoxy-5-(4-ethylpiperazin-1-ylsulphonyl)pyridin-3-yl]-2,3-diethyl-2,6-dihydro-7H-pyrazolo[4,3d]pyrimidin-7-one

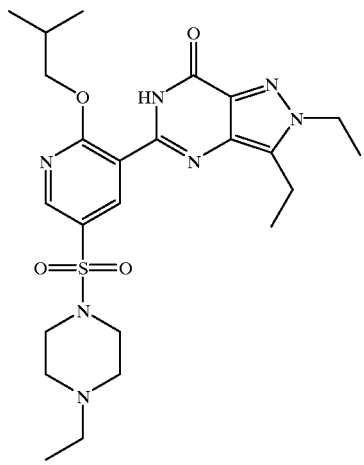

Obtained as a solid (65%) from the title compound of Example 81 and i-butanol, using the procedure described in Example 134. δ (CDCl₃): 1.02 (3H, t), 1.15 (6H, d), 1.42 (3H, t), 1.58 (3H, t), 2.30 (1H, m), 2.42 (2H, q), 2.57 (4H, m), 3.06 (2H, q), 3.16 (4H, m), 4.38 (2H, q), 4.45 (2H, d), 8.62 (1H, s), 9.03 (1H, s). LRMS: mz 518 (M+1)⁺

EXAMPLE 136

2,3-Diethyl-5-[5-(4-ethylpiperazin-1-ylsulphonyl)-2-(2-methoxyethoxy)pyridin-3-yl]-2,6-dihydro-7H-pyrazolo[4,3-d]pyrimidin-7-one

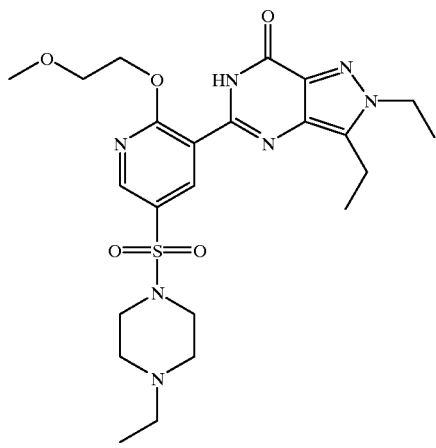

Obtained as a solid (33%) from the title compound of Example 81 and 2-methoxyethanol, using the procedure described in Example 134. Found: C, 53.29; H, 6.20; N, 18.19. C₂₃H₃₃N₇O₅S requires C, 53.16; H, 6.40; N, 18.87% δ (CDCl₃): 1.02 (3H, t), 1.42 (3H, t), 1.59 (3H, t), 2.44 (2H, q), 2.57 (4H, m), 3.05 (2H, q), 3.16 (4H, m), 3.58 (3H, s), 3.86 (2H, t), 4.28 (2H, q), 4.79 (2H, t), 8.62 (1H, s), 8.99 (1H, s). LRMS: m/z 520 (M+1)⁺

EXAMPLE 137

2,3-Diethyl-5-[5-(4-ethylpiperazin-1-ylsulphonyl)-2-(3-hydroxy-n-propoxy)pyridin-3-yl]-2,6-dihydro-7H-pyrazolo[4,3-d]pyrimidin-7-one

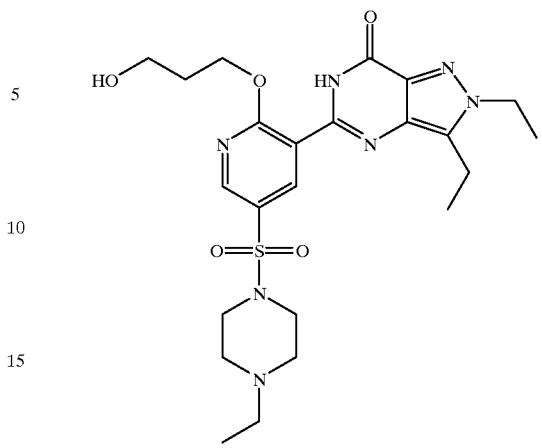

A mixture of the title compound of Example 81 (200 mg, 0.41 mmol) and potassium bis(trimethylsilyl)amide (407 mg, 2.04 mmol) in 1,3-propanediol (3 ml) was stirred at 110° C. for 18 hours, then cooled and evaporated under reduced pressure. The residue was purified by column chromatography on silica gel, using an elution gradient of ethyl acetate: diethylamine (100:0 to 95:5). The product was partitioned between water (5 ml) and dichloromethane (10 ml), and the phases separated. The organic layer was washed with water (2×5 ml), dried (MgSO₄), evaporated under reduced pressure and triturated with ether, to afford the title compound (90 mg, 42%) as a solid. δ (CDCl₃): 1.02 (3H, t), 1.40 (3H, t), 1.57 (3H, t), 2.16 (2H, m), 2.42 (2H, q), 2.55 (4H, m), 3.02 (2H, q), 3.15 (4H, m), 4.00 (2H, t), 4.37 (2H, q), 4.80 (2H, t), 8.62 (1H, s), 8.96 (1H, s). LRMS: m/z 520 (M+1)⁺

EXAMPLE 138

2,3-Diethyl-5-[5-(4-ethylpiperazin-1-ylsulphonyl)-2-(1-methyl-n-propoxy)pyridin-3-yl]-2,6-dihydro-7H-pyrazolo[4,3-d]pyrimidin-7-one (Isomer 1)
and

EXAMPLE 139

2,3-Diethyl-5-[5-(4-ethylpiperazin-1-ylsulphonyl)-2-(1-methyl-n-propoxy)pyridin-3-yl]-2,6-dihydro-7H-pyrazolo[4,3-d]pyrimidin-7-one (Isomer 2)

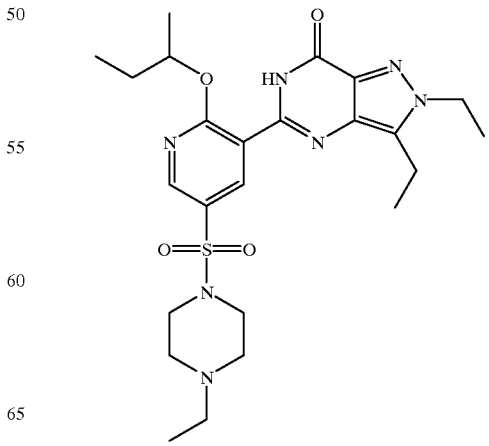

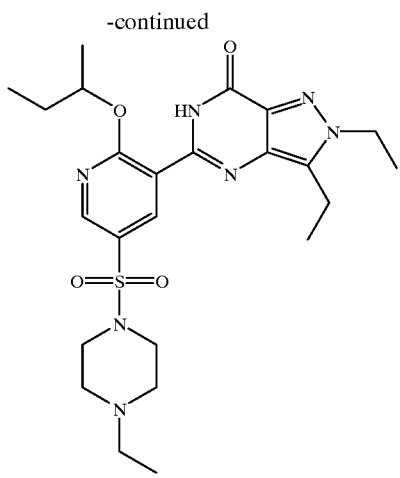
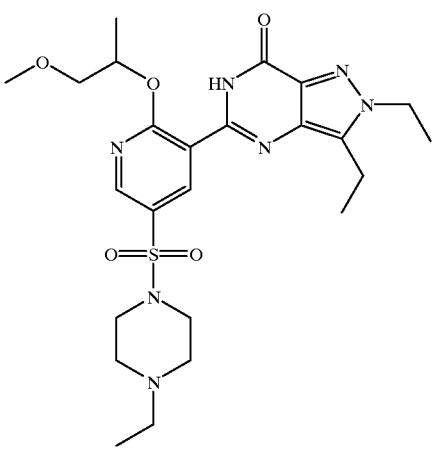

A mixture of the title compound of Example 81 (500 mg, 1.02 mmol) and potassium bis(trimethylsilyl)amide (1.01 g, 5.11 mmol) in 1-methyl-n-propanol (5 ml) was stirred at 110° C. for 18 hours, then cooled and evaporated under reduced pressure. The residue was purified by column chromatography on silica gel, using an elution gradient of ethyl acetate: diethylamine (100:0 to 95:5) and triturated with ether to give a solid. This racemate was further purified by chiral HPLC using an AD 250 column using hexane:isopropanol:diethylamine (90:10:1) as eluant, to afford the title compound of Example 138 (40 mg, 8%, 95% ee) as a solid. Found: C, 54.41; H, 6.71; N, 18.17; $C_{24}H_{35}N_7O_4S;0.2CH_2Cl_2$ requires C, 54.37; H, 6.67; N, 18.34% δ (CDCl$_3$): 1.04 (6H, m), 1.41 (3H, t), 1.50 (3H, d), 1.58 (3H, t0, 1.86 (1H, m), 1.98 (1H, m), 2.41 (2H, q), 2.58 (4H, m), 3.02 (2H, q), 3.15 (4H, m), 4.38 (2H, q), 5.55 (1H, m), 8.61 (1H, s), 9.02 (1H, s). 10.66 (1H, s); and the title compound of Example 139 (70 mg, 13%, 86% ee) as a solid. Found: C, 55.91; H, 7.11; N, 18.55 $C_{24}H_{35}N_7O_4S$ requires C, 55.69; H, 6.82; N, 18.95% δ (CDCl$_3$): 1.05 (6H, m), 1.40 (3H, t), 1.50 (3H, d), 1.57 (3H, t), 1.84 (1H, m), 1.98 (1H, m), 2.42 (2H, q), 2.58 (4H, m), 3.04 (2H, q), 3.15 (4H, m), 4.38 (2H, q), 5.54 (1H, m), 8.61 (1H, s), 9.03 (1H, s), 10.67 (1H, s).

EXAMPLE 140

2,3-Diethyl-5-[5-(4-ethylpiperazin-1-ylsulphonyl)-2-(2-methoxy-1-methylethoxy)pyridin-3-yl]-2,6-dihydro-7H-pyrazolo[4,3-d]pyrimidin-7-one (Isomer 1)

and

EXAMPLE 141

2,3-Diethyl-5-[5-(4-ethylpiperazin-1-ylsulphonyl)-2-(2-methoxy-1-methylethoxy)pyridin-3-yl]-2,6-dihydro-7H-pyrazolo[4,3-d]pyrimidin-7-one (Isomer 2)

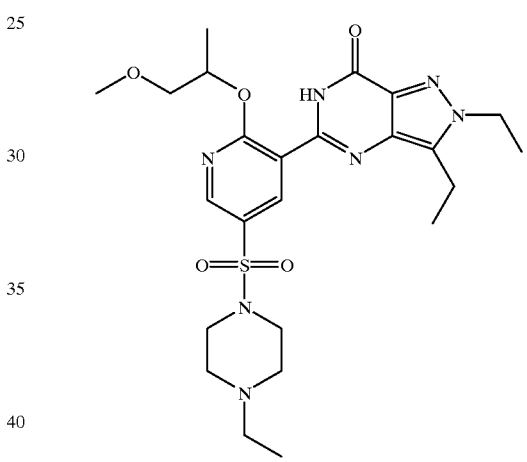

Obtained as solids (10%, 99.5%ee) and (10%, 99.1% ee) respectively, from the title compound of Example 81 and 1-methoxy-2-propanol (5 ml), following a similar procedure to that described above, except, that hexane:isopropanol:diethylamine (70:30:1) was used as the HPLC eluant. δ (CDCl$_3$): 1.03 (3H, t), 1.40 (3H, t), 1.50 (3H, d), 1.58 (3H, t), 2.42 (2H, q), 2.58 (4H, m), 3.03 (2H, q), 3.15 (4H, m), 3.55 (3H, s), 3.64 (1H, m), 3.76 (1H, m), 4.37 (2H, q), 5.60 (1H, m), 8.60 (1H, s), 8.90 (1H, s). LRMS: m/z 535 (M+2)$^+$ Found: C, 54.09; H, 6.91; N, 17.03. $C_{24}H_{35}N_7O_5S$ requires C, 54.02; H, 6.61; N, 18.38% δ (CDCl$_3$): 1.04 (3H, t), 1.40 (3H, t), 1.50 (3H, d), 1.58 (3H, t), 2.42 (2H, q), 2.58 (4H, m), 3.02 (2H, q), 3.12 (4H, m), 3.56 (4H, m), 3.65 (1H, m), 3.74 (1H, m), 4.37 (2H, q), 5.60 (1H, m), 8.60 (1H, s), 8.90 (1H, s). LRMS: m/z 535 (M+2)$^+$, respectively.

EXAMPLE 142

3-Ethyl-5-[5-(4-ethylpiperazin-1-ylsulphonyl)-2-(2-methoxyethoxy)pyridin-3-yl]-2-(6-methyl-pyridin-2-yl)methyl-2,6-dihydro-7H-pyrazolo[4,3-d]pyrimidin-7-one

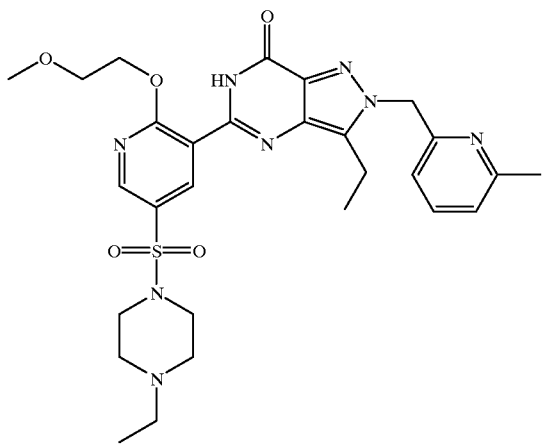

A mixture of the title compound of Example 82 (100 mg, 0.176 mmol), and potassium bis(trimethylsilyl)amide (175 mg, 0.88 mmol) in 2-methoxyethanol (1 ml) was heated under reflux for 18 hours, then cooled. The solution was concentrated under reduced pressure and the residue partitioned between water (5 ml) and dichloromethane (100 ml), and the mixture neutralised using (2N) hydrochloric acid. The phases were separated, the aqueous layer extracted with dichloromethane (10 ml), and the combined organic solutions dried (MgSO$_4$), and evaporated under reduced pressure. The crude product was purified by column chromatography on silica gel, using dichloromethane:methanol:0.88 ammonia (96:4:0.4) as eluant, and triturated with pentane, to afford the title compound (27 mg, 26%) as an off-white solid. Found: C, 56.14; H, 6.09; N, 18.53. C$_{28}$H$_{36}$N$_8$O$_5$S requires C, 56.36; H, 6.08; N, 18.78% δ (CDCl$_3$): 1.02 (3H, t), 1.30 (3H, t), 2.42 (2H, q), 2.57 (7H, m), 3.04 (2H, q), 3.16 (4H, m), 3.58 (3H, s), 3.86 (2H, t), 4.79 (2H, t), 5.63 (2H, s), 6.78 (1H, d), 7.08 (1H, d), 7.48 (1H, m), 8.61 (1H, s), 8.98 (1H, s), 10.82 (1H, s).

EXAMPLE 143

3-Ethyl-5-[5-(4-ethylpiperazin-1-ylsulphonyl)-2-(2-methoxy-1(R)-methylethoxy)pyridin-3-yl]-2-(6-methylpyridin-2-yl)methyl-2,6-dihydro-7H-pyrazolo[4,3-d]pyrimidin-7-one

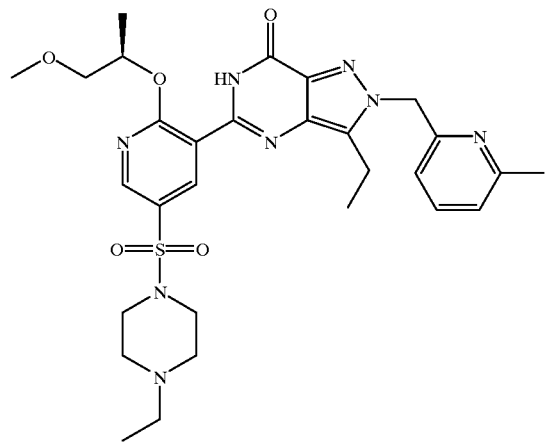

Obtained as a white solid (12%) from the title compounds of Examples 82 and 165, using a similar procedure to that described in Example 142, except the product was additionally purified by column chromatography on silica gel, using an elution gradient of ethyl acetate:methanol:0.88 ammonia (100:0:0 to 90:10:1), and then triturated with pentane. δ (CDCl$_3$):1.03 (3H, t), 1.30 (3H, t), 1.50 (3H, d), 2.42 (2H, q), 2.55 (6H, m), 3.02 (2H, q), 3.15 (4H, m), 3.56 (4H, m), 3.66 (1H, m), 3.76 (1H, m), 5.62 (3H, m), 6.78 (1H, d), 7.06 (1H, d), 7.49 (1H, m), 8.61 (1H, s), 8.90 (1H, s), 10.84 (1H, s). LRMS: m/z 611 (M+1)$^+$

EXAMPLE 144

3-Ethyl-5-[5-(4-ethylpiperazin-1-ylsulphonyl)-2-(2-methoxyethoxy)pyridin-3-yl]-2-[1-(pyridin-2-yl)ethyl]-2,6-dihydro-7H-pyrazolo[4,3-d]pyrimidin-7-one (Isomer 1)

and

EXAMPLE 145

3-Ethyl-5-[5-(4-ethylpiperazin-1-ylsulphonyl)-2-(2-methoxyethoxy)pyridin-3-yl]-2-[1-(pyridin-2-yl)ethyl]-2,6-dihydro-7H-pyrazolo[4,3-d]pyrimidin-7-one (Isomer2)

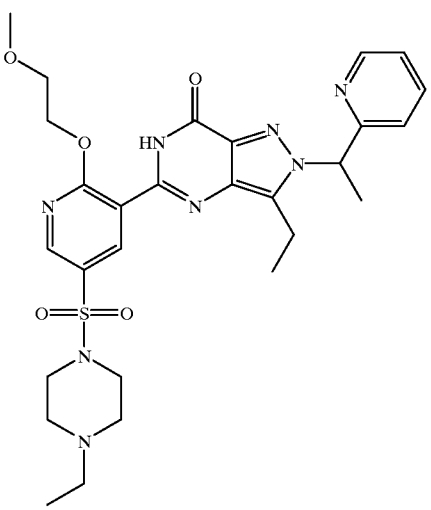

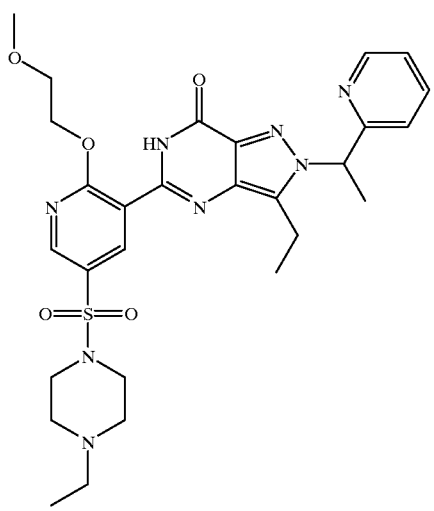

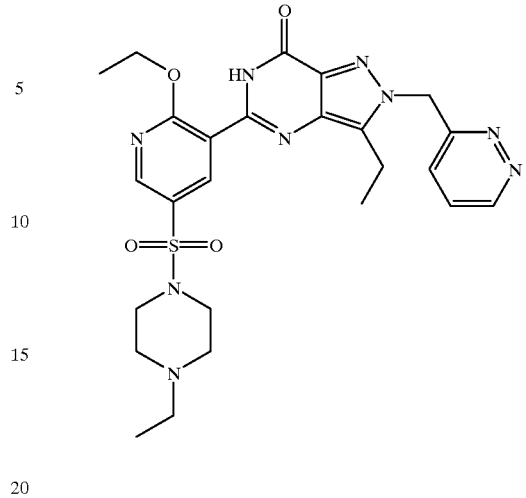

A mixture of the title compound of Example 84 (200 mg, 0.35 mmol) and potassium bis(trimethylsilyl)amide (350 mg, 1.76 mmol) in 2-methoxyethanol (5 ml) was stirred at 120° C. for 18 hours. The cooled mixture was concentrated under reduced pressure and the residue partitioned between aqueous saturated sodium bicarbonate solution (20 ml) and ethyl acetate (20 ml). The phases were separated, the aqueous layer extracted with ethyl acetate (2×10 ml), and the combined organic solutions dried (MgSO$_4$), and evaporated under reduced pressure. The crude product was purified by column chromatography on silica gel, using an elution gradient of dichloromethane:methanol (100:0 to 95:5) to give a foam. This racemate was further purified by HPLC using an AD 250 column and hexane:isopropanol:diethylamine (50:50:1) as eluant to afford the title compound of Example 144 (24 mg, 11%, 100.0% ee) δ (CDCl$_3$): 1.02 (3H, t), 1.25 (3H, t), 2.10 (3H, d), 2.40 (2H, q), 2.56 (4H, m), 3.00 (2H, q), 3.13 (4H, m), 3.58 (3H, s), 3.86 (2H, t), 4.77 (2H, t), 5.83 (1H, q), 7.18 (2H, m), 7.60 (1H, m), 8.55 (1H, d), 8.60 (1H, s). 8.96 (1H, s), 10.82 (1H, s). LRMS: m/z 598 (M+1)$^+$ and the title compound of Example 145 (28 mg. 13%, 99.8% ee). δ(CDCl$_3$): 1.00 (3H, t), 1.24 (3H, t), 2.10 (3H, d), 2.40 (2H, q), 2.55 (4H, m), 3.00 (2H, q), 3.14 (4H, m), 3 57 (3H, s), 3.84 (2H, t), 4.78 (2H, t), 5.82 (1H, q), 7.18 (2H, m), 7.60 (1H, m), 8.54 (1H, d), 8.60 (1H, s). 8.94 (1H, s), 10.82 (1H, s). LRMS: m/z 598 (M+1)$^+$

EXAMPLE 146

5-[2-Ethoxy-5-(4-ethylpiperazin-1-ylsulphonyl)pyridin-3-yl]-3-ethyl-2-(pyridazin-3-yl)methyl-2,6-dihydro-7H-pyrazolo[4,3-d]pyrimidin-7-one A suspension of the title compound of Preparation 142 (1.12 g, 4.55 mmol) and triethylamine (1.5 g, 13.7 mmol) was added to an ice-cold suspension of the title compound of Preparation 28 (2.0 g, 5.0 mmol) in dichloromethane (25 ml), and the reaction stirred at room temperature for 2 hours. The reaction mixture was washed with brine (15 ml), saturated aqueous sodium bicarbonate solution (2×10 ml), more brine (15 ml), dried (MgSO$_4$) and evaporated under reduced pressure. The residue was purified by column chromatography on silica gel using an elution gradient of dichloromethane:methanol:0.88 ammonia (99:0:1 to 96:3:1) to give a solid (1.73 g).

A mixture of this intermediate (829 mg, 1.45 mmol) and potassium bis(trimethylsilyl)amide (347 mg, 1.74 mmol) in 3-methyl-3-pentanol (3 ml) was heated under reflux for 6 hours, and then stirred for 72 hours at room temperature. Additional potassium bis(trimethylsilyl)amide (87 mg, 0.43 mmol) was added, the reaction heated under reflux for a further 5 hours, then cooled, 2M hydrochloric acid (2 ml) added and the mixture concentrated under reduced pressure. The residue was partitioned between dichloromethane (20 ml) and water (10 ml), the layers separated, the organic phase washed consecutively with water (10 ml), saturated sodium bicarbonate solution (10 ml), brine (10 ml), dried (MgSO$_4$) and evaporated under reduced pressure. The crude product was purified by column chromatography on silica gel using an elution gradient of dichloromethane:methanol (100:0 to 98:2) to afford the title compound (1.24 g, 49%) as a light brown foam. δ(CDCl$_3$): 1.02 (3H, t), 1.36 (3H, t), 1.59 (3H, t), 2.40 (2H, q), 2.55 (4H, m), 3.14 (6H, m), 4.76 (2H, q), 5.90 (2H, s), 7.46 (1H, m), 7.56 (1H, m), 8.63 (1H, s), 9.01 (1H, s), 9.18 (1H, d), 10.70 (1H, s). LRMS: m/z 554 (M+1)$^+$

EXAMPLE 147

5-[2-n-Butoxy-5-(4-ethylpiperazin-1-ylsulphonyl)pyridin-3-yl]-3-ethyl-2-(pyridazin-3-yl)methyl-2,6-dihydro-7H-pyrazolo[4,3-d]pyrimidin-7-one

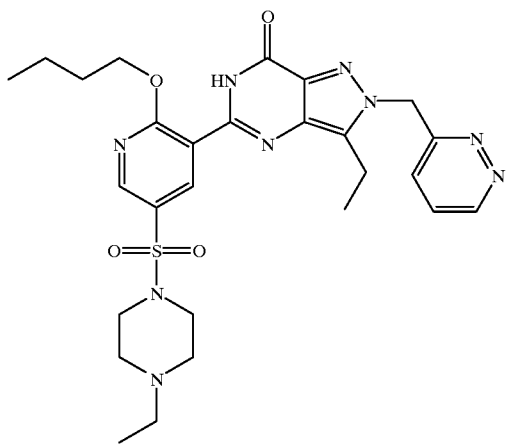

Potassium bis(trimethylsilyl)amide (35 mg, 0.176 mmol) was added to a solution of the title compound of Example 146 (80 mg, 0.145 mmol) in n-butanol (2 ml), and the reaction stirred at 110° C. for 6½ hours. The cooled mixture was concentrated under reduced pressure and the residue partitioned between ethyl acetate (20 ml) and sodium bicarbonate solution (10 ml). The phases were separated, the organic layer washed with additional sodium bicarbonate solution (10 ml), brine (10 ml), dried (MgSO$_4$) and evaporated under reduced pressure. The crude product was purified by column chromatography on silica gel using an elution gradient of dichloromethane:methanol:0.88 ammonia (100:0:0 to 99.6:0.4:0.5) to afford the title compound (50 mg, 59%) as a white foam. δ (CDCl$_3$): 1.04 (6H, m), 1.35 (3H, t), 1.58 (2H, m), 1.95 (2H, m), 2.41 (2H, q,) 2.57 (4H, m), 3.10 (6H, m), 4.66 (2H, t), 5.90 (2H, s), 7.46 (1H, m), 7.56 (1H, m), 8.62 (1H, s), 9.01 (1H, s), 9.17 (1H, d), 10.79 (1H, s). LRMS: m/z 582 (M+1)$^+$

EXAMPLE 148
3-Ethyl-5-[5-(4-ethylpiperazin-1-ylsulphonyl)-2-(2-methoxyethylamino)pyridin-3-yl]-2-methyl-2,6-dihydro-7H-pyrazolo[4,3-d]pyrimidin-7-one

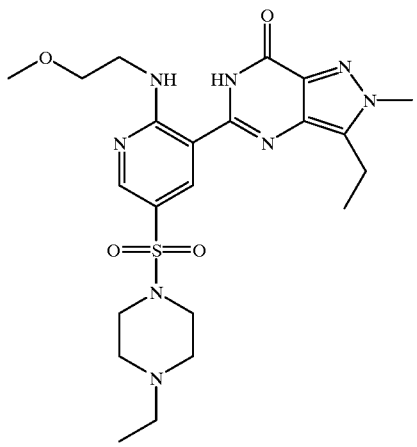

A mixture of the title compound of Example 78 (200 mg, 0.42 mmol), and copper (II) sulphate pentahydrate (150 mg, 0.60 mmol) in 2-methoxyethylamine (2 ml) was heated under reflux for 2 hours, then cooled. The reaction was partitioned between dichloromethane (20 ml) and aqueous sodium carbonate solution (5 ml), and the layers separated. The organic phase was dried (Na$_2$SO$_4$) and evaporated under reduced pressure. The residue was purified by column chromatography on silica gel using an elution gradient of dichloromethane: methanol (98:2 to 95:5) to afford the title compound (150 mg, 69%). δ (CDCl$_3$): 1.04 (3H, t), 1.40 (3H, t), 2.42 (2H, q), 2.55 (4H, m), 2.92 (3H, s), 3.01 (2H, q), 3.13 (4H, m), 3.50 (4H, m), 3.48 (3H, s), 3.68 (2H, t), 3.88 (2H, t), 4.07 (3H, s), 8.34 (1H, s), 8.58 (1H, s). LRMS: m/z 519 (M+1)$^+$

EXAMPLES 149 TO 153

The compounds of the general formula:

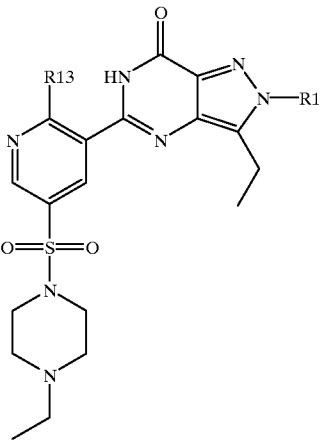

were prepared from the appropriate pyrazolo[4,3-d] pyrimidin-7-ones and amines, using procedures similar to that described in Example 148.

| Example | R1 | R13 | Data |
|---|---|---|---|
| 149 | CH₃ | N*-cyclobutyl | δ (CDCl₃): 1.02 (3H, t), 1.37 (3H, t), 2.26–2.42 (4H, m), 2.54 (4H, m), 3.01 (2H, q), 3.10 (4H, m), 4.05 (7H, m), 8.00 (1H, s), 8.57 (1H, s). LRMS: m/z 487 (M + 1)⁺ |
| 150 | CH₃ | N*-cyclopentyl | δ (CDCl₃): 1.02 (3H, t), 1.35 (3H, t), 1.89 (4H, m), 2.39 (2H, q), 2.55 (4H, m), 3.00 (2H, q), 3.11 (4H, m), 3.40 (4H, m), 4.08 (3H, s), 8.00 (1H, s), 8.57 (1H, s). LRMS: m/z 501 (M + 1)⁺ |
| 151 | CH₂CH₃ | N*-cyclopentyl | Found: C, 55.53; H, 6.70; N, 21.52. $C_{24}H_{34}N_8O_3S$ requires C, 56.01; H, 6.66; N, 21.77% δ (CDCl₃): 1.03 (3H, t), 1.38 (3H, t), 1.60 (3H, t), 1.88 (4H, m), 2.41 (2H, q), 2.57 (4H, m), 3.01 (2H,q), 3.10 (4H, m), 3.42 (4H, m), 4.38 (2H, q), 8.00 (1H. s), 8.58 (1H, s), 9.20 (1H, s). LRMS: m/z 515 (M + 1)⁺ |
| 152 | *-CH₂-(2-pyridyl) | NH*-CH₂CH₂-O-CH₃ | Found: C, 54.63; H, 6.15; N, 20.97. $C_{27}H_{35}N_9O_4S$ requires C, 54.89; H, 6.14: N, 21.34% δ (CDCl₃): 1.01 (3H, t), 1.33 (3H, t), 2.38 (2H, q), 2.54 (4H, m), 3.07 (2H, q), 3.16 (4H, m), 3.41 (3H, s), 3.65 (2H, t), 3.85 (2H, q), 5.67 (2H, s), 7.19 (1H, d), 7.25 (1H, m), 7.68 (1H, m), 8.14 (1H, s), 8.56 (1H, s), 8.58 (1H, d), 9.92 (1H, s), 10.07 (1H, m). LRMS: m/z 582 (M + 1)⁺ |
| 153 | *-CH₂-(2-pyridyl) | N*-cyclopentyl | δ (CDCl₃): 1.03 (3H, t), 1.26 (3H, t), 1.92 (4H, m), 2.41 (2H, q), 2.56 (4H, m), 3.02 (2H, q), 3.10 (4H, m), 3.42 (4H, m), 5.68 (2H, s), 7.19 (1H, d), 7.26 (1H, m), 7.67 (1H, m), 8.01 (1H, s), 8.58 (2H, m), 9.24 (1H, s). LRMS: m/z 578 (M + 1)⁺ |

EXAMPLE 154

5-[2-(N-Cyclopropylmethyl-N-methylamino)-5-(4-ethylpiperazin-1-ylsulphonyl)pyridin-3-yl]-3-ethyl-2-methyl-2,6-dihydro-7H-pyrazolo[4,3-d]pyrimidin-7-one

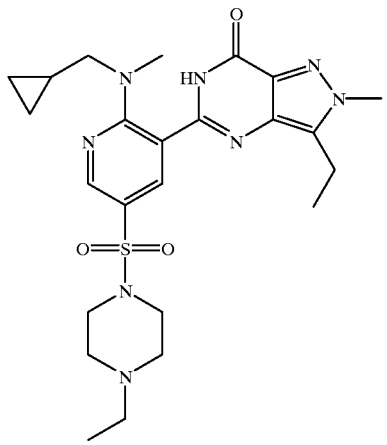

A mixture of the title compound of Example 78 (200 mg, 0.42 mmol), and N-cyclopropylmethyl-N-methylamine (600 mg, 7.05 mmol; obtained from the title compound of Preparation 168) and potassium bis(trimethylsilyl)amide (250 mg, 1.26 mmol) in N,N-dimethylformamide (2 ml), was stirred at 100° C. for 18 hours. The cooled mixture was partitioned between ethyl acetate (20 ml) and aqueous sodium bicarbonate solution (10 ml), and the phases separated. The organic layer was dried (MgSO₄), and evaporated under reduced pressure. The residue was purified by column chromatography on silica gel using an elution gradient of dichloromethane: methanol (100:0 to 95:5) to afford the title compound (100 mg, 46%) as a solid. δ (CDCl₃): 0.54 (2H, m), 0.71 (2H, m), 1.02 (3H, t), 1.37 (4H, m), 2.40 (2H, q), 2.56 (4H, m), 2.78–3.13 (11H, m), 4.08 (3H, s), 8.32 (1H, s), 8.60 (1H, s). LRMS: m/z 515 (M+1)⁺

EXAMPLES 155 TO 156

The compounds of the general formula:

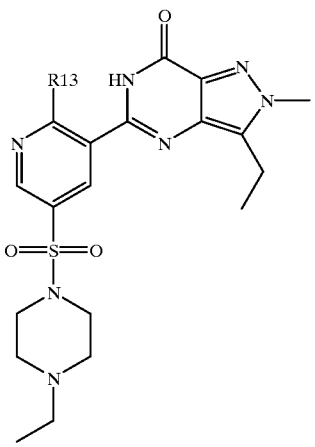

were prepared from the title compound of Example 78 and the appropriate amines, using procedures similar to that described in Example 154.

| Example | R13 | Data |
|---|---|---|
| 155 | piperidin-1-yl (N*) | δ (CDCl$_3$): 1.01 (3H, t), 1.40 (3H, t), 1.58 (2H, m), 1.64 (2H, m), 1.77 (4H, m), 2.41 (2H, q), 2.55 (4H, m), 3.02 (2H, q), 3.12 (4H, m), 3.26 (2H, m), 4.10 (3H, s), 8.55 (1H, s), 8.63 (1H, s), 10.63 (1H, s). LRMS: m/z 515 (M + 1)$^+$ |
| 156 | morpholin-4-yl (N*) | δ (CDCl$_3$): 1.04 (3H, t), 1.40 (3H, t), 2.42 (2H, q), 2.58 (4H, m), 3.03 (2H, q), 3.16 (4H, m), 3.35 (4H, m), 3.86 (4H, m), 4.10 (3H, s), 8.55 (1H, s), 8.68 (1H, s), 10.40 (1H, s). LRMS: m/z 517 (M + 1)$^+$ |

EXAMPLE 157

3-Ethyl-5-[5-(4-ethylpiperazin-1-ylsulphonyl)-2-n-propylaminopyridin-3-yl]-2-(pyridin-2-yl)methyl-2,6-dihydro-7H-pyrazolo[4,3-d]pyrimidin-7-one

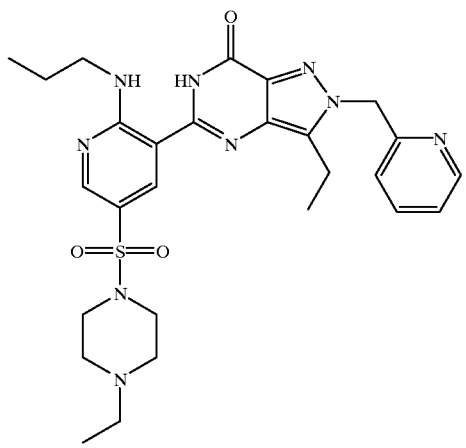

A mixture of the title compound of Preparation 160 (226 mg, 0.39 mmol) and potassium t-butoxide (112 mg, 1.0 mmol) in n-propanol (20 ml), was stirred under reflux for 5 days, then cooled. Saturated ammonium chloride solution (5 ml) was added, this solution poured into ethyl acetate (50 ml), and the layers separated. The organic phase was washed with sodium bicarbonate solution (20 ml), then brine (20 ml), dried (MgSO$_4$) and evaporated under reduced pressure. The residue was purified by column chromatography on silica gel, using an elution gradient of dichloromethane: methanol (100:0 to 94:6) to give an oil. This was crystallised from ether to afford the title compound (9 mg, 4%) as a white solid. δ (CDCl$_3$): 1.00 (3H, t), 1.18 (3H, t), 1.28 (3H, t), 1.70 (2H, m), 2.38 (2H, q), 2.50 (4H, m), 3.00 (2H, q), 3.07 (4H, m), 3.57 (2H, q), 5.62 (2H, s), 7.19 (1H, m), 7.63 (1H, m), 8.02 (1H, s), 8.55 (2H, m), 9.60 (1H, s), 9.80 (1H, s). LRMS: m/z 566 (M+1)$^+$

PREPARATION 1

2-Ethoxypyridine-3-carboxylic Acid

A solution of potassium t-butoxide (44.9 g, 0.40 mol) in absolute ethanol (300 ml) was added slowly to a solution of 2-chloronicotinic acid (30 g, 0.19 mol) in absolute ethanol (100 ml) and the reaction mixture heated in a sealed vessel at 170° C. for 20 hours, then allowed to cool. The resulting mixture was evaporated under reduced pressure, the residue dissolved in water (200 ml) and the solution acidified to pH 3 with hydrochloric acid and extracted with dichloromethane (4×200 ml). The combined extracts were dried (Na$_2$SO$_4$) and evaporated under reduced pressure to give the title compound (27.4 g, 41%) as a white solid. δ (CDCl$_3$): 1.53 (3H,t), 4.69 (2H,q), 7.13 (1H,m), 8.37 (1H,d), 8.48 (1H,d).

PREPARATION 2

2-(2-Methoxyethoxy)pyridine-3-carboxylic Acid

Obtained as a brown solid (92%) from 2-chloronicotinic acid and 2-methoxyethanol, using the procedure of Preparation 1. Found: C, 54.89; H, 5.61; N, 7.03. C$_9$H$_{11}$NO$_4$ requires C, 54.82; H, 5.62; N, 7.10%. δ (CDCl$_3$): 3.45 (3H,s), 3.79 (2H,t), 4.74 (2H,t), 7.14 (1H,m), 8.36 (lH,d), 8.46 (1H,d). LRMS: m/z 198 (M+1)$^+$.

PREPARATION 3

2-Ethoxypyridine-3-carboxylic Acid Ethyl Ester

A suspension of the title compound of Preparation 1 (16.4 g, 98 mmol) and caesium carbonate (32 g, 98 mmol) in dimethylformamide (240 ml) was stirred at room temperature for 2 hours. Ethyl iodide (7.85 ml, 98 mmol) was added and the reaction mixture stirred for 24 hours, then evaporated under reduced pressure. The residue was partitioned between aqueous sodium carbonate solution (100 ml) and ethyl acetate (100 ml), the phases separated and the aqueous phase extracted with ethyl acetate (2×100 ml). The com-

PREPARATION 4
2-(2-Methoxyethoxy)pyridine-3-carboxylic Acid Ethyl Ester

Obtained as a brown oil (98%) from the title compound of Preparation 2, using the procedure of Preparation 3. Found: C, 58.36; H, 6.74; N, 6.04. $C_{11}H_{15}NO_4$ requires C, 58.66; H, 6.71; N, 6.23%. δ ($CDCl_3$): 1.37 (3H,t), 3.44 (3H,s), 3.78 (2H,t), 4.34 (2H,q), 4.56 (2H,t), 6.92 (1H,m), 8.13 (1H,d), 8.26 (1H,d). LRMS: m/z 226 $(M+1)^+$.

PREPARATION 5
2-Ethoxy-5-nitropyridine-3-carboxylic Acid Ethyl Ester

Ammonium nitrate (5.36 g, 66 mmol) was added portionwise to a stirred, ice-cooled solution of the title compound of Preparation 3 (4.66 g, 22.3 mmol) in trifluoroacetic anhydride (50 ml) and the reaction mixture stirred for 18 hours at room temperature, then carefully poured into stirred ice-water (200 g). The resulting suspension was stirred for 1 hour, then the precipitate collected, washed with water and dried under suction to provide the title compound (3.29g, 61%). δ ($CDCl_3$): 1.41 (3H,t), 1.48 (3H,t), 4.41 (2H,q), 4.62 (8.89 (1H,s), 9.16 (1H,s).

PREPARATION 6
2-(2-Methoxyethoxy)-5-nitropyridine-3-carboxylic Acid Ethyl Ester Ammonium nitrate (10.57 g, 131 mmol) was added portionwise to a stirred, ice-cooled solution of the title compound of Preparation 4 (14.80 g, 65.7 mmol) in trifluoroacetic anhydride (150 ml) and the reaction mixture stirred for 3 hours at room temperature, then carefully poured onto stirred ice (120 g). The resulting solution was extracted with dichloromethane (3×150 ml), then the combined extracts dried ($MgSO_4$) and evaporated under reduced pressure. The residual orange oil was purified by column chromatography on silica gel, using an elution gradient of dichloromethane:methanol (100:0 to 97:3), to furnish the title compound (11.49 g, 65%) as a white solid. Found: C, 48.78; H, 5.13; N, 10.29. $C_{11}H_{14}N_2O_6$ requires C, 48.89; H, 5.22; N, 10.37%. δ ($CDCl_3$): 1.42 (3H,t), 3.46 (3H,s), 3.83 (2H,t), 4.41 (2H,q), 4.70 (2H,t), 8.92 (1H,s), 9.16 (1H,s). LRMS: m/z 271 $(M+1)^+$.

PREPARATION 7
5-Amino-2-ethoxypyridine-3-carboxylic Acid Ethyl Ester

A stirred mixture of the title compound of Preparation 5 (5.3 g, 22 mmol), Raney nickel (2.50 g) and ethanol (150 ml) was hydrogenated at 345 kPa (50 psi) and 50° C. for 18 hours, then allowed to cool and filtered. The filtrate was combined with an ethanol wash (150 ml) of the filter pad and then evaporated under reduced pressure. The residue was triturated with dichloromethane and the resulting solid collected and dried to afford the title compound (4.56 g, 98%) as a tan-coloured solid. Found: C. 57.12; H, 6.79; N, 12.98. $C_{10}H_{14}N_2O_3$ requires C, 57.13; H, 6.71; N, 13.33%. δ ($CDCl_3$): 1.39 (6H, 2xd), 3.41 (2H,s), 4.35 (4H,m), 7.55 (1H,s), 7.78 (1H,s). LRMS: m/z 211 $(M+1)^+$.

PREPARATION 8
2-Ethoxy-5-nitropyridine-3-carboxylic Acid

5M Aqueous sodium hydroxide solution (4 ml, 20 mmol) was added dropwise to a stirred solution of the title compound of Preparation 5 (5.1 g, 20 mmol) in ethanol (100 ml) and the reaction mixture stirred at room temperature for 18 hours, then evaporated under reduced pressure. The residue was suspended in water (50 ml) and the stirred suspension acidified to pH 3 with hydrochloric acid. The resulting aqueous solution was extracted with ethyl acetate (3×100 ml), then combined extracts washed with brine (100 ml), dried ($Na_2SO_4$) and evaporated under reduced pressure to afford a beige solid. The crude product was crystallised from hexane-ethyl acetate to give the title compound (3.32 g, 78%) as beige crystals. δ ($CDCl_3$): 1.55 (3H,t), 4.78 (2H,q), 9.17 (1H,s), 9.23 (1H,s).

PREPARATION 9
2-(2-Methoxyethoxy)-5-nitropyridine-3-carboxylic Acid

1M Aqueous sodium hydroxide solution (40 ml, 40 mmol) was added to a stirred, ice-cooled solution of the title compound of Preparation 6 (4.0 g, 14.8 mmol) in 1,4-dioxan (40 ml) and the reaction mixture stirred for 1.5 hours, then concentrated under reduced pressure to half its volume and acidified with hydrochloric acid to pH 3. The resulting suspension was extracted with dichloromethane (3×50 ml), then the combined extracts dried ($MgSO_4$) and evaporated under reduced pressure to yield the title compound (2.61 g, 73%) as a buff-coloured solid. Found: C, 44.11; H, 4.04; N, 11.46. $C_9H_{10}N_2O_6$ requires C, 44.63; H, 4.16; N, 11.57%. δ ($CDCl_3$): 3.47 (3H,s), 3.83 (2H,t), 4.82 (2H,t), 9.15 (1H,s), 9.21 (1H,s). LRMS: m/z 243 $(M+1)^+$.

PREPARATION 10
2-Aminopyridine-5-sulphonic Acid

2-Aminopyridine (80 g, 0.85 mol) was added portionwise over 30 minutes to stirred oleum (320 g) and the resulting solution heated at 140° C. for 4 hours, then allowed to cool. The reaction mixture was poured onto stirred ice (200 g) and this mixture stirred at ice-salt bath temperature for a further 2 hours. The resulting suspension was filtered, then the collected solid washed successively with ice-water (200 ml) and cold industrial methylated spirit (IMS) (200 ml) and, finally, dried under suction to provide the title compound (111.3 g, 75%) as a solid. LRMS: m/z 175 $(M+1)^+$.

PREPARATION 11
2-Amino-3-bromopyridine-5-sulphonic Acid

Bromine (99 g, 0.62 mol) was added dropwise, over 1 hour, to a stirred, hot solution of the title compound of Preparation 10 (108 g, 0.62 mol) in water (600 ml), at such a rate as to maintain steady reflux. When the addition was complete, the reaction mixture was allowed to cool and then filtered. The resulting solid was washed with water and dried under suction to furnish the title compound (53.4 g, 34%). δ ($DMSOd_6$): 8.08 (1H,s), 8.14 (1H,s). LRMS: m/z 253 $(M)^+$.

PREPARATION 12
3-Bromo-2-chloropyridine-5-sulphonyl Chloride

A solution of sodium nitrite (7.6 g, 110 mmol) in water (30 ml) was added dropwise to a stirred, ice-cooled solution of the title compound of Preparation 11 (25.3 g, 100 mmol) in 20% hydrochloric acid (115 ml), at such a rate as to maintain the temperature below 6° C. The reaction mixture was stirred for 30 minutes at 0° C. for a further 1 hour at room temperature, then evaporated under reduced pressure. The residue was dried under vacuum at 70° C. for 72 hours, then a mixture of the resulting solid, phosphorus pentachloride (30 g, 144 mmol) and phosphorus oxychloride (1 ml) was heated at 125° C. for 3 hours and then allowed to cool. The reaction mixture was poured onto stirred ice (100 g) and the resulting solid collected and washed with water. The crude product was dissolved in dichloromethane, then the solution dried (MgSO$_4$) and evaporated under reduced pressure to afford the title compound (26.58 g, 91%) as a yellow solid. δ (CDCl$_3$): 8.46 (1H,s), 8.92 (1H,s).

PREPARATION 13
3-Bromo-2-chloro-5-(4-ethylpiperazin-1-ylsulphonyl) pryridine A solution of 1-ethylpiperazine (11.3 ml, 89 mmol) and triethylamine (12.5 ml, 89 mmol) in dichloromethane (150 ml) was added dropwise to a stirred, ice-cooled solution of the title compound of Preparation 12 (23 g, 79 mmol) in dichloromethane (150 ml) and the reaction mixture stirred at 0° C. for 1 hour, then evaporated under reduced pressure. The residual brown oil was purified by column chromatography on silica gel, using an elution gradient of dichloromethane: methanol (99:1 to 97:3), to give the title compound (14.5 g, 50%) as an orange solid. δ (CDCl$_3$): 1.05 (3H,t), 2.42 (2H,q), 2.55 (4H,m), 3.12 (4H,m), 8.24 (1H,s), 8.67 (1H,s).

PREPARATION 14
3-Bromo-5-(4-ethylpiperazin-1-ylsulphonyl)-2-(2-methoxyethoxy)pyridine A 0.5M solution of potassium bis(trimethylsilyl)amide in toluene (8.1 ml, 4.07 mmol) was added to a stirred, ice-cooled solution of 2-methoxyethanol (416 μl, 5.4 mmol) in anhydrous tetrahydrofuran (30 ml) and the resulting solution stirred at 0° C. for 1 hour. Next, the title compound of Preparation 13 (1.0 g, 2.71 mmol) was added portionwise and the reaction mixture stirred at room temperature for 2 hours, then diluted with ethyl acetate (40 ml). The resulting mixture was washed with water (10 ml), dried (MgSO$_4$) and evaporated under reduced pressure to yield a yellow oil which was purified by column chromatography on silica gel, using dichloromethane: methanol (97:3) as eluant, to provide the title compound (1.02 g, 92%) as a colourless oil. Found: C, 40.83; H, 5.32; N, 9.99. C$_{14}$H$_{22}$BrN$_3$O$_4$S requires C, 41.18; H, 5.43; N, 10.29%. δ (CDCl$_3$): 1.04 (3H,t), 2.42 (2H,q), 2.53 (4H,m), 3.07 (4H,m), 3.46 (3H,s), 3.78 (2H,t), 4.60 (2H,t), 8.10 (1H,s), 8.44 (1H,s). LRMS: m/z 408 (M)$^+$.

PREPARATION 15
3-Bromo-2-(2-ethoxyethoxy)-5-(4-ethylpiperazin-1-ylsulphonyl)pyridine Sodium metal (93 mg, 4 mmol) was added to a stirred solution of 2-ethoxyethanol (537 μl, 5.5 mmol) in anhydrous tetrahydrofuran (5 ml). When the sodium had dissolved, the title compound of Preparation 13 (1.0 g, 2.7 mmol) was added portionwise and the reaction mixture stirred for 18 hours at room temperature, then concentrated under reduced pressure. The residue was partitioned between ethyl acetate (10 ml) and brine (10 ml), the phases separated and the aqueous phase extracted with ethyl acetate (2×10 ml). The combined organic solutions w ere washed with brine, dried (MgSO$_4$) and evaporated under reduced pressure, then the residue purified by column chromatography on silica gel, using an elution gradient of hexane: dichloromethane: methanol (50:50:0 to 0:98:2), to furnish the title compound (985 mg, 86%) as a yellow oil. δ (CDCl$_3$): 1.03 (3H,t), 1.22 (3H,t), 2.40 (2H,q), 2.54 (4H,m), 3.07 (4H,m), 3.61 (2H,q), 3.82 (2H,t), 4.59 (2H,t), 8.10 (1H,s), 8.43 (1H,s). LRMS: m/z 423 (M+1)$^+$.

PREPARATION 16
3-Bromo-5-(4-ethylpiperazin-1-ylsulphonyl)-2-(3-methoxyprop-1-oxy)pyridine Obtained as an oil (95%) from the title compound of Preparation 13 and 3-methoxypropan-1-ol, using the procedure of Preparation 15. δ (CDCl$_3$): 1.04 (3H,t), 2.09 (2H,m), 2.42 (2H,q), 2.52 (4H,m), 3.08 (4H,m), 3.37 (3H,s), 3H,s), 3.57 (2H,t), 4.54 (2H,t), 8.09 (1H,s), 8.45 (1H,s). LRMS: m/z 423 (M+1)$^+$.

PREPARATION 17
3-Bromo-5-(4-ethylpiperazin-1-ylsulphonyl)-2-(tetrahydrofuran-3(S)-yloxy)pyridine A mixture of a 2M solution of sodium bis(trimethylsilyl) amide in tetrahydrofuran (1.83 ml 3.66 mmol), (S)-(+)-3-hydroxytetrahydrofuran (272 μl, 6 mmol) and tetrahydrofuran (40 ml) was stirred for 30 minutes at room temperature. Next, the title compound of Preparation 13 (750 mg, 2 mmol) was added and the reaction mixture stirred for 18 hours, then evaporated under reduced pressure. The residue was purified by column chromatography on silica gel, using an elution gradient of hexane: ethyl acetate (25:75 to 0:100), to afford the title compound (430 mg, 51%) as an oil. δ (CDCl$_3$): 1.06 (3H,t), 2.20 (1H,m), 2.30 (1H,m), 2.42 (2H, q), 2.56 (4H,m), 3.08 (4H,m), 3.94 (2H,m), 4.02 (1H,m), 4.11 (1H,m), 5.62 (1H,m), 8.12 (1H,s), 8.44 (1H,s). LRMS: m/z 420 (M)$^+$.

PREPARATION 18
2-Ethoxy-5-(4-ethylpiperazin-1-ylsulphonyl)pyridine-3-carboxylic Acid Ethyl Ester Sodium nitrite (2.22 g, 32.1 mmol) was added to a stirred solution of the title compound of Preparation 7 (4.5 g, 21.4 mmol) in a mixture of concentrated hydrochloric acid (90 ml) and glacial acetic acid (90 ml) at −20° C. and the resulting mixture stirred for 2 hours, whilst allowing the temperature to rise to 0° C. The mixture was cooled again to −20° C., liquid sulphur dioxide (50 ml) and a solution of copper(II) chloride (8.4 g, 62.5 mmol) in a mixture of water (9 ml) and acetic acid (80 ml) added, then the reaction mixture stirred for 30 minutes at 0° C., followed by a further 2 hours at room temperature. The resulting mixture was poured onto stirred ice (80 g) and the aqueous solution thus obtained was extracted with dichloromethane (3×50 ml). The combined extracts were dried (MgSO$_4$) and evaporated under reduced pressure to give the crude sulphonyl chloride as a brown oil. 1-Ethylpiperazine (10.9 ml, 85.6 mmol) was added to a stirred solution of the sulphonyl chloride in ethanol (60 ml) and the reaction mixture stirred for 18 hours at room temperature, then evaporated under reduced pressure. The residue was partitioned between water (20 ml) and dichloromethane (30 ml), the separated aqueous phase extracted with dichloromethane (2×30 ml), then the combined organic solutions dried (MgSO$_4$) and evaporated under reduced pressure. The residual brown oil was purified by column chromatography on silica gel, using an elution gradient of dichloromethane: methanol (100:0 to 98:2), to yield the title compound (5.0 g, 63%) as a pale brown oil. Found: C, 51.40; H, 6.77; N, 11.15. C$_{16}$H$_{25}$N$_3$O$_5$S requires C, 51.74; H, 6.78; N, 11.31%. δ (CDCl$_3$): 1.02 (3H,t), 1.39 (3H,t), 1.45 (3H,t), 2.40 (2H,q), 2.54 (4H,m), 3.08 (4H,m), 4.38 (2H,q), 4.55 (2H,q), 8.37 (1H,s), 8.62 (1H,s). LRMS: m/z 372 (M+1)$^+$.

PREPARATION 19
5-(4-Ethylpiperazin-1-ylsulphonyl)-2-(2-methoxyethoxy) pyridine-3-carboxylic Acid Ethyl Ester Triethylamine (3 ml, 19 mmol) and tetrakis (triphenylphosphine) palladium (0) (260 mg, 0.22 mmol) were added to a solution of the title compound of Preparation 14 (1.30 g, 3 mmol) in ethanol (15 ml) and the mixture heated under carbon monoxide at 100° C. and 1034 kPa (150 psi) in a sealed vessel for 18 hours, then allowed to cool. The reaction mixture was filtered and the filtrate evaporated under reduced pressure to provide a yellow solid. The crude product was purified by column chromatography on silica gel, using an elution gradient of dichloromethane: methanol (100:0 to 97.3), to furnish the title compound (1.10 g, 92%) as a yellow oil. δ (CDCl$_3$): 1.02 (3H,t), 1.38 (3H,t), 2.40 (2H,q), 2.53 (4H,m), 3.08 (4H,m), 3.43 (3H,s), 3.80 (2H,t), 4.38 (2H,q), 4.63 (2H,t), 8.40 (1H,s), 8.61 (1H,s). LRMS: m/z 402 (M+1)$^+$.

PREPARATION 20

2-(2-Ethoxyethoxy)-5-(4-ethylpiperazin-1-ylsulphonyl)pyridine-3-carboxylic Acid Ethyl Ester Obtained as a gum (96%) from the title compound of Preparation 15, using the procedure of Preparation 19. δ (CDCl$_3$): 1.03 (3H,t), 1.22 (3H,t), 1.38 (3H,t), 2.40 (2H,q), 2.52 (4H,m), 3.08 (4H,m), 3.60 (2H,q), 3.83 (2H,t), 4.38 (2H,q), 4.62 (2H,t), 8.40 (1H,s), 8.62 (1H,s). LRMS: m/z 416 (M+1)$^+$.

PREPARATION 21

5-(4-Ethylpiperazin-1-ylsulphonyl)-2-(3-methoxyorop-1-oxy)-pyridine-3-carboxylic Acid Ethyl Ester A mixture of triethylamine (5 ml, 35.9 mmol), tetrakis(triphenylphosphine) palladium (0) (200 mg, 0.17 mmol), the title compound of Preparation 16 (1.08 g, 2.54 mmol) and ethanol (25 ml) was heated under carbon monoxide at 100° C. and 1034 kPa (150 psi) in a sealed vessel for 18 hours, then allowed to cool. The mixture was filtered and the filtrate evaporated under reduced pressure. The residue was dissolved in ethyl acetate (40 ml) and the solution washed consecutively with saturated aqueous sodium bicarbonate solution (20 ml), brine (20 ml) and 2M hydrochloric acid (5×10 ml). The combined acidic extracts were basified using solid sodium bicarbonate and the solution extracted with ethyl acetate (2×25 ml). The combined organic extracts were dried (MgSO$_4$) and evaporated under reduced pressure to afford the title compound (640 mg, 68%) as an oil. δ (CDCl$_3$): 1.05 (3H,t), 1.39 (3H,t), 2.09 (2H,m), 2.41 (2H,q), 2.54 (4H,m), 3.08 (4H,m), 3.36 (3H,s), 3.58 (2H,t), 4.39 (2H,q), 4.57 (2H,t), 8.40 (1H,s), 8.64 (1H,s). LRMS: m/z 416 (M+1)$^+$.

PREPARATION 22

5-(4-Ethylpiperazin-1-ylsulphonyl)-2-(tetrahydrofuran-3(S)-yloxy)pyridine-3-carboxylic Acid Ethyl Ester Obtained as a yellow oil (78%) from the title compound of Preparation 17, using the procedure of Preparation 19. δ (CDCl$_3$): 1.05 (3H,t), 1.39 (3H,t), 2.20 (1H,m), 2.30 (1H,m), 2.42 (2H,q), 2.55 (4H,m), 3.09 (4H,m), 3.97 (3H,m), 4.14 (1H,m), 4.38 (2H,q), 5.70 (1H,m), 8.41 (1H,s), 8.62 (1H,s). LRMS: m/z 414 (M+1)$^+$.

PREPARATION 23

2-Ethoxy-5-(4-ethylpiperazin-1-ylsulphonyl)pyridine-3-carboxylic Acid

A mixture of the title compound of Preparation 18 (4.96 g, 13.35 mmol), 2M aqueous sodium hydroxide solution (25 ml, 50 mmol) and ethanol (25 ml) was stirred at room temperature for 2 hours. The resulting mixture was concentrated under reduced pressure to half its volume, washed with ether and acidified to pH 5 using 4M hydrochloric acid. This aqueous solution was extracted with dichloromethane (3×30 ml), then the combined extracts dried (MgSO$_4$) and evaporated under reduced pressure to give the title compound (4.02 g, 88%) as a tan-coloured solid. δ (DMSOd$_6$): 1.18 (3H,t), 1.37 (3H,t), 3.08 (2H,q), 3.17–3.35 (8H,m), 4.52 (2H,q), 8.30 (1H,s), 8.70 (1H,s).

PREPARATION 24

2-Ethoxy-5-(4-ethylpiperazin-1-ylsulphonyl)pyridine-3-carboxylic Acid Sodium Salt 1M Aqueous sodium hydroxide solution (85 ml, 85 mmol) was added slowly to a stirred, ice-cooled solution of the title compound of Preparation 18 (30.2 g, 85 mmol) in ethanol (300 ml) and the reaction mixture stirred at room temperature for 18 hours. The resulting mixture was evaporated under reduced pressure and the residue partitioned between water (225 ml) and ethyl acetate (250 ml). The phases were separated, then the aqueous phase washed with ethyl acetate (2×200 ml) and evaporated under reduced pressure to yield the title compound (29.6 g, 81%) as a white solid. δ (DMSOd$_6$): 0.90 (3H,t), 1.25 (3H,t), 2.24 (2H,q), 2.40 (4H,m), 2.82 (4H,m), 4.39 (2H,q), 7.76 (1H,s), 8.28 (1H,s).

PREPARATION 25

4-(4-Ethylpiperazin-1-ylsulphonyl)-2-(2-methoxyethoxy)pyridine-3-carboxylic Acid Hydrochloride A solution of the title compound of Preparation 19 (1.18 g, 2.94 mmol) in a mixture of ethanol (10 ml) and 1M aqueous sodium hydroxide solution (10 ml, 10 mmol) was stirred for 1 hour at room temperature. The resulting mixture was concentrated under reduced pressure to half its volume and the residual aqueous solution washed with ethyl acetate (10 ml), then acidified to pH 3 with dilute hydrochloric acid. The acidic solution was extracted with dichloromethane: methanol (95:5) (6×20 ml), then the combined extracts dried (MgSO$_4$) and evaporated under reduced pressure to provide the title compound (995 mg, 82%) as a white foam. δ (DMSOd$_6$): 1.06 (3H,t), 2.28 (2H,q), 2.75–3.20 (8H,m), 3.28 (3H,s), 3.69 (2H,t), 4.56 (2H,t), 8.29 (1H,s), 8.68 (1H,s). LRMS: m/z 374 (M+1)$^+$.

PREPARATION 26

2-(2-Ethoxyethoxy)-5-4-(ethylpiperazin-1-ylsulphonyl)pyridine-3-carboxylic Acid Hydrochloride A mixture of the title compound of Preparation 20 (859 mg, 2.07 mmol), 1M aqueous sodium hydroxide solution (4.6 ml, 4.6 mmol) and 1,4-dioxan (5 ml) was stirred at room temperature for 2 hours. The 1,4-dioxan was removed by evaporation under reduced pressure and the pH of the remaining aqueous solution was adjusted to 3 with hydrochloric acid. The resulting solution was evaporated under reduced pressure, the residue triturated with hot ethanol and the mixture filtered. The filtrate was then evaporated under reduced pressure to furnish the title compound (760 mg, 87%) as a tan-coloured solid. δ (DMSOd$_6$): 1.08 (3H,t), 1.18 (3H,t), 2.98 (2H,m), 3.07 (4H,m), 3.37 (2H,m), 3.48 (2H,q), 3.72 (4H,m), 4.55 (2H,t), 8.30 (1H,s), 8.72 (1H,s). LRMS: m/z 387 (M)$^+$.

PREPARATION 27

5-(4-Ethylpiperazin-1-ylsulphonyl)-2-(3-methoxyprop1-oxy)pyridine-3-carboxylic Acid Hydrochloride Obtained as a solid (87%) from the title compound of Preparation 21, using the procedure of Preparation 26. δ (DMSOd$_6$): 1.17 (3H,t), 1.96 (2H,m), 3.08 (2H,q), 3.22 (3H,s), 3.33 (8H,m), 3.48 (2H,t), 4.48 (2H,t), 8.30 (1H,s), 8.73 (1H,s). LRMS: m/z 388 (M+1)$^+$.

PREPARATION 28

2-Ethoxy-5-(4-ethylpiperazin-1-ylsulphonyl)pyridine-3-carboxylic Acid Chloride Hydrochloride Oxalyl chloride (0.77 ml, 8.85 mmol) was added dropwise to a stirred, ice-cooled solution of the title compound of Preparation 23 (1.52 g, 4.42 mmol) and dimethylformamide (2 drops) in dichloromethane (30 ml) and the reaction mixture stirred for 18 hours at room temperature, then evaporated under reduced pressure. The residue was triturated with ethyl acetate and the resulting solid collected, washed with ether and dried under suction to afford the title compound (1.68 g, 95%). Found: C, 41.51; H, 5.27; N, 10.32. $C_{14}H_{21}Cl_2N_3O_4S$; 0.10 $CH_2Cl_2$ requires C, 41.73; H, 5.02; N, 10.36%. δ ($CDCl_3$): 1.46 (6H,m), 2.95 (2H,q), 3.11 (2H,m), 3.48 (2H,m), 3.55 (2H,m), 3.92 (2H,m), 4.60 (2H, q), 8.58 (1H,s), 8.66 (1H,s), 13.16 (1 H,s).

PREPARATION 29
5-(4-Ethylpiperazin-1-ylsulphonyl)-2-(2-methoxyethoxy) pyridine-3-carboxylic Acid Chloride Hydrochloride Oxalyl chloride (270 μl, 3.13 mmol) was added dropwise to a stirred, ice-cooled suspension of the title compound of Preparation 25 (390 mg, 1.04 mmol), dimethylformamide (100 μl) and dry dichloromethane (20 ml), then the reaction mixture stirred for 3 hours at room temperature. The resulting mixture was evaporated under reduced pressure and the residue azeotroped with toluene (2×20 ml) to give the title compound (390 mg, 95%) as a white solid. δ ($DMSOd_6$): 1.20 (3H,t), 2.92 (2H,q), 3.08 (4H,m), 3.30 (3H,s), 3.49 (2H,m), 3.70 (2H,t), 3.76 (2H,m), 4.58 (2H,t), 8.32 (1H,s), 8.72 (1H,s), 14.20 (1H,s).

PREPARATION 30
Ethyl 3-ethyl-1H-pyrazole-5-carboxylate

Ethanolic sodium ethoxide solution (21% w/w; 143 ml, 0.39 mol) was added dropwise to a stirred, ice-cooled solution of diethyl oxalate (59.8 ml, 0.44 mol) in absolute ethanol (200 ml) under nitrogen and the resulting solution stirred for 15 minutes. Butan-2-one (39 ml, 0.44 mol) was then added dropwise, the cooling bath removed, the reaction mixture stirred for 18 hours at room temperature and then for 6 hours at 40° C., then the cooling bath reintroduced. Next, glacial acetic acid (25 ml, 0.44 mol) was added dropwise, the resulting solution stirred for 30 minutes at 0° C., hydrazine hydrate (20 ml, 0.44 mol) added dropwise, then the reaction mixture allowed to warm to room temperature and maintained there over a period of 18 hours, before being evaporated under reduced pressure. The residue was partitioned between dichloromethane (300 ml) and water (100 ml), then the organic phase separated, washed with water (2×100 ml), dried ($Na_2SO_4$) and concentrated under reduced pressure to give the title compound (66.0 g). δ ($CDCl_3$): 1.04 (3H,t), 1.16 (3H,t), 2.70 (2H,q), 4.36 (2H,q), 6.60 (1H,s). LRMS: m/z 169 $(M+1)^+$.

PREPARATION 31
3-Ethyl-1H-pyrazole-5-carboxylic Acid

Aqueous sodium hydroxide solution (10M; 100 ml, 1.0 mol) was added dropwise to a stirred suspension of the title compound of Preparation 30 (66.0g, 0.39 mol) in methanol (400 ml) and the resulting solution heated under reflux for 4 hours. The cool reaction mixture was concentrated under reduced pressure to ca. 200 ml, diluted with water (200 ml) and this mixture washed with toluene (3×100 ml). The resulting aqueous phase was acidified with concentrated hydrochloric acid to pH 4 and the white precipitate collected and dried by suction to provide the title compound (34.1 g). δ ($DMSOd_6$): 1.13 (3H,t), 2.56 (2H,q), 6.42 (1H,s).

PREPARATION 32
4-Nitro-3-n-propyl-1H-pyrazole-5-carboxylic Acid

Fuming sulphuric acid (17.8 ml) was added dropwise to stirred, ice-cooled fuming nitric acid (16.0 ml), the resulting solution heated to 50° C., then 3-n-propyl-1H-pyrazole-5-carboxylic acid (Chem. Pharm. Bull., 1984, 32, 1568; 16.4 g, 0.106 mol) added portionwise over 30 minutes whilst maintaining the reaction temperature below 60° C. The resulting solution was heated for 18 hours at 60° C., allowed to cool, then poured onto ice. The white precipitate was collected, washed with water and dried by suction to yield the title compound (15.4 g), m.p. 170–172° C. Found: C, 42.35; H, 4.56; N, 21.07. $C_7H_9N_3O_4$ requires C, 42.21; H, 4.55; N, 21.10%. δ ($DMSOd_6$): 0.90 (3H,t), 1.64 (2H,m), 2.83 (2H,m), 14.00 (1H,s).

PREPARATION 33
3-Ethyl-4-nitro-1H-pyrazole-5-carboxylic Acid

Obtained from the title compound of Preparation 31, by analogy with Preparation 32, as a brown solid (64%). δ ($DMSOd_6$): 1.18 (3H,t), 2.84 (2H,m), 13.72 (1H,s).

PREPARATION 34
4-Nitro3-n-propyl-1H-pyrazole-5-carboxamide

A solution of the title compound of Preparation 32 (15.4 g, 0.077 mol) in thionyl chloride (75 ml) was heated under reflux for 3 hours and then the cool reaction mixture evaporated under reduced pressure. The residue was azeotroped with tetrahydrofuran (2×50 ml) and subsequently suspended in tetrahydrofuran (50 ml), then the stirred suspension ice-cooled and treated with gaseous ammonia for 1 hour. Water (50 ml) was added and the resulting mixture evaporated under reduced pressure to give a solid which, after trituration with water and drying by suction, furnished the title compound (14.3 g), m.p. 197–199° C. Found: C, 42.35; H, 5.07; N, 28.38. $C_7H_{10}N_4O_3$ requires C, 42.42; H, 5.09; N, 28.27%. δ (DMSOd6): 0.90 (3H,t), 1.68 (2H,m), 2.86 (2H,t), 7.68 (1H,s), 8.00 (1H,s).

PREPARATION 35
3-Ethyl-4-nitro-1H-pyrazole-5-carboxamide

Obtained from the title compound of Preparation 33, by analogy with Preparation 34, as a white solid (90%). δ ($DMSOd_6$): 1.17 (3H,t), 2.87 (2H,m), 7.40 (1H,s), 7.60 (1H,s), 7.90 (1H,s). LRMS: mnz 185 $(M+1)^+$.

PREPARATION 36
4-Amino-3-n-propyl-1H-pyrazole-5-carboxamide

A stirred mixture of the title compound of Preparation 34 (10.0 g, 0.050 mol), 10% palladium on charcoal (1.5 g) and ethanol (400 ml) was hydrogenated for 18 hours at 345 kPa (50 psi) and 50° C., then filtered. The filtrate was combined with an ethanol wash (200 ml) of the filter pad and then evaporated under reduced pressure to give an orange solid which, on crystallisation from ethyl acetate-methanol, afforded the title compound (6.8 g) as a white solid, m.p. 196–201° C. Found: C, 48.96; H, 6.98; N, 32.08. $C_7H_{12}N_4O$; 0.25 $H_2O$ requires C, 48.68; H, 7.30; N, 32.44%. δ ($DMSOd_6$): 0.88 (3H,t), 1.55 (2H,m), 2.46 (2H,t), 4.40 (2H,s), 7.00 (1H,s), 7.12 (1H,s), 12.20 (1H,s).

PREPARATION 37
4-Amino-3-ethyl-1H-pyrazole-5-carboxamide

Obtained from the title compound of Preparation 35, by analogy with Preparation 36, as a brown solid (80%). δ ($DMSOd_6$): 1.08 (3H,t), 2.45 (2H,q), 4.50 (1H,s), 6.88 (1H,s), 7.10 (1H,s), 7.26 (2H,s). LRMS: m/z 155 $(M+1)^+$.

PREPARATION 38a
3-Ethyl-4-nitro-1-(pyridin-2-yl)methylpyrazole-5-carboxamide
and

PREPARATION 38b
3-Ethyl-4-nitro-2-(pyridin-2-yl)methylpyrazole-5-carboxamide A mixture of the title compound of Preparation 35 (20.0 g, 109 mmol), 2-(chloromethyl)pyridine hydrochloride (17.9 g, 109 mmol), caesium carbonate (74.7 g, 222 mmol) and dimethylformamide (120 ml) was stirred for 18 hours at room temperature, then evaporated under reduced pressure. The residue was partitioned between water (100 ml) and dichloromethane (100 ml) and the phases separated. The aqueous layer was extracted with dichloromethane (3×100 ml) and the combined extracts dried ($MgSO_4$) and evaporated under reduced pressure. The residue was crystallised from dichloromethane-methanol to yield the first title compound (1-isomer; 6.5 g, 21%). δ ($CDCl_3$): 1.24 (3H,t), 2.90 (2H,q), 5.54 (2H,s), 6.03 (1H,s), 7.27 (1H,m), 7.36 (1H,d), 7.76 (1H,m), 8.52 (1H,d), 8.58 (1H,s).

The mother liquor was evaporated under reduced pressure and the residue purified by column chromatography on silica gel, using an elution gradient of dichloromethane: methanol (100:0 to 95:5), to provide the second title compound (2-isomer; 17.36 g, 58%) as a white solid. δ ($CDCl_3$): 1.16 (3H,t), 3.06 (2H,q), 5.48 (2H,s), 5.88 (1H,s), 7.19 (1H,d), 7.27 (1H,m), 7.70 (1H,m), 8.57 (1H,d).

PREPARATION 39a
4-Nitro-3-n-propyl-1-(pyridin-2-yl)methylpyrazole-5-carboxamide
and

PREPARATION 39b
4-Nitro-3-n-propyl-2-(pyridin-2-yl)methylpyrazole-5-carboxamide 2-(Chloromethyl)pyridine hydrochloride (24.6 g, 150 mmol) was added portionwise to a stirred solution of the title compound of Preparation 34 (30.0 g, 150 mmol) and caesium carbonate (123.5 g, 380 mmol) in dimethylformamide (300 ml) and the reaction mixture stirred at room temperature for 18 hours, then evaporated under reduced pressure. The residue was suspended in water and the resulting solid collected and dried under suction. The crude product was purified by two column chromatographic operations on silica gel, respectively using dichloromethane: methanol (98:2) and ethyl acetate: pentane (20:80) as eluants, to furnish the first title compound (1-isomer; 424 mg, 1%) as a white solid. Found: C, 53.74; H, 5.20; N, 23.91. $C_{13}H_{15}N_5O_3$ requires C, 53.97; H, 5.23; N, 24.21%. δ ($CDCl_3$): 0.94 (3H,t), 1.68 (2H,m), 2.86 (2H,t), 5.55 (2H,s) 6.07 (1H,s), 7.35 (1H,d), 7.75 (1H,m), 8.51 (1H,d), 8.56 (1H,s). LRMS: m/z 290 $(M+1)^+$; and the second title compound (2-isomer; 16.7 g, 38%) as a white solid. δ ($DMSOd_6$): 0.84 (3H,t), 1.46 (2H,m), 2.95 (2H,t), 5.49 (2H,s), 7.31 (2H,m), 7.60 (1H,s), 7.79 (1H,m), 7.90 (1H,s), 8.49 (1H,d).

PREPARATION 40
4-Amino-3-ethyl-2-(pyridin-2-yl)methylpyrazole-5-carboxamide

A stirred mixture of the title compound of Preparation 38b (16.36 g, 59 mmol), 10% palladium on charcoal (4 g) and ethanol (150 ml) was hydrogenated at 345 kPa (50 psi) for 4 hours, then filtered. The filtrate was combined with an ethyl acetate wash (150 ml) of the filter pad and then concentrated under reduced pressure to a volume of ca. 70 ml. The resulting precipitate was collected and dried under suction to afford the title compound (12.6 g, 87%) as a white solid. δ ($CDCl_3$): 1.03 (3H,t), 2.53 (2H,q), 4.00 (2H,s), 5.22 (1H,s), 5.36 (2H,s), 6.60 (1H,s), 6.81 (1H,d), 7.20 (1H,m), 7.62 (1H,m), 8.57 (1H,d). LRMS: m/z 246 $(M+1)^+$.

PREPARATION 41
4-Amino-3-n-propyl-2-(pyridin-2-yl)methylpyrazole-5-carboxamide A stirred mixture of the title compound of Preparation 39b (1.0 g, 3.46 mmol), Raney nickel (1 g) and ethanol (50 ml) was hydrogenated at 345 kPa (50 psi) and 50° C. for 18 hours, then allowed to cool and filtered. The filtrate was combined with an ethanol wash (50 ml) of the filter pad and then evaporated under reduced pressure to give the title compound (830 mg, 93%) as a crystalline solid. δ ($DMSOd_6$): 0.79 (3H,t), 1.33 (2H,m), 3.28 (2H,t), 4.60 (2H,s), 5.30 (2H,s), 6.88 (1H,d), 6.98 (1H,s), 7.13 (1H,s), 7.30 (1H,m), 7.74 (1H,m), 8.50 (1H,d). LRMS: m/z 274 $(M)^+$.

PREPARATION 42
4-Amino-3-ethyl-1-(pyridin-2-yl)methylpyrazole-5-carboxamide

Obtained as a solid (94%) from the title compound of Preparation 38a, using the procedure of Preparation 40. δ ($CDCl_3$): 1.20 (3H,t), 2.52 (2H,q), 3.72 (2H,s), 5.50 (2H,s), 7.21 (1H,m), 7.34 (1H,d), 7.68 (1H,m), 8.49 (1H,d). LRMS: m/z 246 $(M+1)^+$.

PREPARATION 43
4-[2-Ethoxy-5-(4-ethylpiperazin-1-ylsulphonyl)pyridin-3-ylcarboxamido]-3-ethyl-1H-pyrazole-5-carboxamide Hydrochloride A mixture of the title compound of Preparation 28 (1.0 g, 2.51 mmol), Preparation 37 (387 mg, 2.51 mmol) and pyridine (15 ml) was stirred at room temperature for 18 hours. The resulting mixture was evaporated under reduced pressure and the residue triturated with ether to yield the title compound (1.05 g, 87%) as a purple solid. Found: C, 44.82; H, 5.72; N, 18.62. $C_{20}H_{29}N_7O_5S$; HCl; $H_2O$ requires C, 44.98; H, 6.04; N, 18.36%. δ ($DMSOd_6$): 1.17 (6H,m), 1.46 (3H,t), 2.77 (2H,q), 3.09 (2H,q), 3.49 (4H,m), 3.78 (4H,m), 4.68 (2H,q), 7.30 (1H,s), 7.49 (1H,s), 8.52 (1H,s), 8.76 (1H,s), 10.54 (1H,s). LRMS: m/z 480 $(M+1)^+$.

PREPARATION 44
5-[2-Ethoxy-5-(4-ethylpiperazin-1-ylsulphonyl)pyridin-3-yl]-3-ethyl-1,6-dihydro-7H-pyrazolo[4,3-d]pyrimidin-7-one Potassium t-butoxide (943 g, 8.41 mmol) was added to a stirred suspension of the title compound of Preparation 43 (1.10 g, 2.1 mmol) in absolute ethanol (50 ml) and the reaction mixture heated in a sealed vessel at 100° C. for 18 hours, then allowed to cool. The resulting mixture was evaporated under reduced pressure and the residue dissolved in water (15 ml). The aqueous solution was acidified to pH 6 using hydrochloric acid and the resulting solid collected, washed with water and dried under suction. The crude product was purified by column chromatography on silica gel, using dichloromethane: methanol (97:3) as eluant, to provide the title compound (445 mg, 46%) as a yellow solid. Found: C, 51.95; H, 5.89; N, 20.87. $C_{20}H_{27}N_7O_4S$ requires C, 52.05; H, 5.90; N, 21.24%. δ ($DMSOd_6$): 0.92 (3H,t), 1.30 (6H,m), 2.30 (2H,q), 2.42 (4H,m), 2.86 (2H,q), 2.95 (4H,m), 4.49 (2H,q), 8.20 (1H,s), 8.64 (1H,s), 12.19 (1H,s), 13.80 (1H,s). LRMS: m/z 462 $(M+1)^+$.

PREPARATION 45
4-[2-Ethoxy-5-(4-ethylpiperazin-1-ylsulphonyl)pyridin-3-ylcarboxamido]-3-ethyl-2-(pyridin-2-yl)methylpyrazole-5-carboxamide Alternative A A mixture of the title compounds of Preparation 28 (1.0 g, 2.5 mmol), Preparation 40 (620 mg, 2.5 mmol), triethylamine (1.35 ml, 10 mmol) and dichloromethane (50 ml) was stirred at room temperature for 18 hours. The resulting mixture was poured into stirred water (50 ml), the phases separated and the aqueous phase extracted with dichloromethane (2×50 ml). The combined organic solutions were dried ($MgSO_4$) and evaporated under reduced pressure, then the residue purified by column chromatography on silica gel, using an elution gradient of dichloromethane: methanol (100:0 to 95:5), to furnish the title compound (1.29 g, 90%) as a foam. δ ($CDCl_3$): 1.00 (6H,m), 1.55 (3H,t), 2.37 (2H,q), 2.50 (4H,m), 2.87 (2H,q), 3.08 (4H,m), 4.77 (2H,q), 5.28 (1H,s), 5.45 (2H,s), 6.68 (1H,s), 6.90 (1H,d), 7.18 (1H,m), 7.61 (1H,m), 8.57 (1H,d), 8.62 (1H,s), 8.80 (1H,s), 10.57 (1H,s).

Alternative B 1-(3-Dimethylaminopropyl)-3-ethylcarbodiimide hydrochloride (17.6 g, 91.8 mmol) was added portionwise over 5 minutes to a stirred, ice-cooled suspension of 1-hydroxybenzotriazole hydrate (12 g, 88.9 mmol) and the title compound of Preparation 24 (24 g, 65.7 mmol) in tetrahydrofuran (300 ml), then the mixture stirred for 1 hour. N-Ethyidiisopropylamine (12.7 g, 98.3 mmol) and the title compound of Preparation 40 (12.9 g, 52.6 mmol) were added and the reaction mixture stirred at room temperature for 14 hours, then evaporated under reduced pressure. The residue was partitioned between water (100 ml) and ethyl acetate (200 ml), the phases separated and the organic phase washed consecutively with water (50 ml), saturated aqueous sodium bicarbonate solution (50 ml) and brine (50 ml), then dried ($MgSO_4$) and concentrated under reduced pressure to a low volume. The resulting suspension was cooled in ice for 1 hour, then the precipitate collected and dried under suction to afford the title compound (14.1 g, 47%) as a white crystalline solid, m.p. 185–187° C. Found: C, 54.59; H, 6.05; N, 19.32. $C_{26}H_{34}N_8O_3S$ requires C, 54.72; H, 6.00; N, 19.63%.

PREPARATION 46
2-n-Propoxypyridine-3-carboxylic Acid

Obtained as a pale brown oil (50%) from 2-chloronicotinic acid and n-propanol, using the procedure of Preparation 1. δ ($CDCl_3$): 1.08 (3H,t), 1.92 (2H,m), 4.56 (2H,t), 7.10 (1H,m), 8.35 (1H,d), 8.45 (1H,d).

PREPARATION 47
2-n-Propoxypridine-3-carboxylic Acid Methyl Ester

Diethyl azodicarboxylate (2.2 ml, 14 mmol) was added dropwise to a stirred solution of the title compound of Preparation 46 (2.30 g, 12.7 mmol), triphenylphosphine (3.67 g, 14 mmol) and methanol (0.60 ml, 15 mmol) in tetrahydrofuran (20 ml) and the reaction mixture stirred for 18 hours at room temperature, then evaporated under reduced pressure. The residue was triturated with pentane: ether (80:20) and the mixture filtered. The filtrate was evaporated under reduced pressure and the residue purified by column chromatography on silica gel, using pentane: ether (50:50) as eluant, to give the title compound (2.2 g, 89%) as a pale yellow oil. δ ($CDCl_3$): 1.07 (3H,t), 1.86 (2H,m), 3.92 (3H,s), 4.38 (2H,t), 6.93 (1H,m), 8.15 (1H,d), 8.30 (1H,d).

PREPARATION 48
5-Nitro-2-n-propoxypyridine-3-carboxylic Acid Methyl Ester

Obtained as pale yellow needles (32%), after crystallisation from methanol, from the title compound of Preparation 47, using the procedure of Preparation 5. δ ($CDCl_3$): 1.04 (3H,t), 1.84 (2H,m), 3.92 (3H,s), 4.48 (2H,t), 8.88 (1H,s), 9.14 (1H,s).

PREPARATION 49
5-Amino-2-n-propoxypyridine-3-carboxylic Acid Methyl Ester

A mixture of the title compound of Preparation 48 (1.8 g, 7.46 mmol), Raney nickel (500 mg) and methanol (50 ml) was hydrogenated at 345 kPa (50 psi) and 50° C. for 3 hours, then allowed to cool and filtered. The filtrate was combined with a methanol wash (100 ml) of the filter pad and then evaporated under reduced pressure to yield the title compound (1.5 g, 95%) as a brown oil. δ ($CDCl_3$): 1.04 (3H,t), 1.80 (2H,m), 3.40 (2H,s), 3.89 (3H,s), 4.28 (2H,t), 7.57 (1H,s), 7.80 (1H,s). LRMS: m/z 211 $(M+1)^+$.

PREPARATION 50
5-(4-Methylpiperazin-1-ylsulphonyl)-2-n-propoxypyridine-3-carboxylic Acid Methyl Ester Obtained as an oil (56%) from the title compound of Preparation 49 and 1-methylpiperazine, using the procedure of Preparation 18.

PREPARATION 51
5-(4-Methylpiperazin-1-ylsulphonyl)-2-n-propoxypyridine-3-carboxylic Acid Obtained as a white solid (82%) from the title compound of Preparation 50, using the procedure of Preparation 23. δ ($DMSOd_6$): 0.97 (3H,t), 1.74 (2H,m), 2.15 (3H,s), 2.38 (4H,m), 2.93 (4H,m), 4.37 (2H,t), 8.15 (1H,s), 8.56 (1H,s).

PREPARATION 52
3-Ethyl-4-[5-(4-methylpiperazin-1-ylsulphonyl)-2-n-propoxypyridin-3-ylcarboxamido1]-2-(pyridin-2-yl)methylpyrazole-5-carboxamide Oxalyl chloride (550 μl, 6.37 mmol), followed by dimethylformamide (2 drops), were added carefully to a stirred, ice-cooled suspension of the title compound of Preparation 51 (605 mg, 1.59 mmol) in dichloromethane (10 ml) and the reaction mixture stirred at room temperature for 2 hours, then evaporated under reduced pressure. The residue was azeotroped with toluene to produce a powder.

A solution of crude acid chloride in dichloromethane (10 ml) was added dropwise to a stirred, ice-cooled suspension of the title compound of Preparation 40 (430 mg, 1.76 mmol), triethylamine (558 μl, 4 mmol) and dichloromethane (10 ml) and the reaction mixture stirred at room temperature for 1.5 hours. The resulting mixture was washed successively with saturated aqueous sodium bicarbonate solution and brine, then the organic phase dried ($MgSO_4$) and evaporated under reduced pressure. The crude product was purified by column chromatography on silica gel, using an elution gradient of hexane: ethyl acetate: methanol (70:30:0 to 0:90:10), to provide the title compound (695 mg, 76%) as a solid. Found: C, 53.96; H, 6.09; N, 19.00. $C_{26}H_{34}N_8O_5S$ requires C, 54.22; H. 6.00; N, 19.64%. δ ($CDCl_3$): 1.07 (6H,m), 2.01 (2H,m), 2.26 (3H,s), 2.48 (4H,m), 2.88 (2H,q), 3.10 (4H,m), 4.67 (2H,t), 5.34 (1H,s), 5.48 (2H,s), 6.70 (1H,s), 6.94 (lH,d), 7.22 (1H,m), 7.66 (1H,m), 8.59 (1H,d), 8.65 (1H,s), 8.82 (1H,s), 10.48 (1H,s). LRMS: m/z 572 $(M+2)^+$.

PREPARATION 53
4-[5-(4-Ethylpiperazin-1-ylsulphonyl)-2-(2-methoxyethoxy)pyridin-3-ylcaarbozamido1]-3-n-propyl-2-(pyridin-2-yl)methylpyrazole-5-carboxamide Obtained as a white foam (70%) from the title compounds of Preparation 29 and Preparation 41, using the procedure of Preparation 45A. δ (CDCl₃): 0.81 (3H,t), 1.02 (3H,t), 1.46 (2H,m), 2.39 (2H,q), 2.51 (4H,m), 2.82 (2H,t), 3.10 (4H,m), 3.39 (3H,s), 3.94 (2H,t), 4.85 (2H,t), 5.30 (1H,s), 5.46 (2H,s), 6.69 (1H,s), 6.90 (1H,d), 7.21 (1H,m), 7.65 (1H,m), 8.60 (1H,d), 8.65 (1H,s), 8.82 (1H,s), 10.46 (1H,s). LRMS: m/z 615 (M+1)⁺.

PREPARATION 54
4-[2-(2-Ethoxyethoxy)-5-(4-ethylpiperazin-1-ylsulphonyl)pyridin-3-ylcarboxamido]-3-n-propyl-2-(pyridin-2-yl)methylpyrazole-5-carboxamide Obtained as a foam (69%) from the title compounds of Preparation 26 and Preparation 41, using the procedure of Preparation 52. Found: C, 55.13; H, 6.45; N, 17.27. $C_{29}H_{40}N_8O_6S$ requires C, 55.39; H, 6.41, N, 17.82%. δ (CDCl₃): 0.80 (3H,t), 1.02 (3H,t), 1.10 (3H,t), 1.45 (2H,m), 2.40 (2H,q), 2.50 (4H,m), 2.81 (2H,t), 3.09 (4H,m), 3.54 (2H,q), 3.98 (2H,t), 4.80 (2H,t), 5.30 (1H,s), 5.47 (2H,s), 6.70 (1H,s), 6.89 (1H,d), 7.22 (1H,m), 7.63 (1H,m), 8.59 (1H,d), 8.65 (1H,s), 8.82 (1H,s), 10.45 (1H,s). LRMS: m/z 629 (M+1)⁺.

PREPARATION 55
4-[5-(4-Ethylpiperazin-1-ylsulphonyl)-2-(3-methoxyprop-1-oxy)pyridin-3-ylcarboxamido]-3-n-propyl-2-(pyridin-2-yl)methylpyrazole-5-carboxamide Obtained as a foam (52%) from the title compounds of Preparation 27 and Preparation 41, using the procedure of Preparation 52. δ (CDCl₃): 0.82 (3H,t), 1.02 (3H,t), 1.44 (2H,m), 2.25 (2H,m), 2.40 (2H,q), 2.53 (4H,m), 2.84 (2H,t), 3.10 (4H,m), 3.29 (3H,s), 3.57 (2H,t), 4.79 (2H,t), 5.34 (1H,s), 5.47 (2H,s), 6.70 (1H,s), 6.92 (1H,d), 7.22 (1H,m), 7.66 (1H,m), 8.59 (1H,d) 8.65 (1H,s), 8.81 (1H,s), 10.45 (1H,s). LRMS: m/z 629 (M+1)⁺.

PREPARATION 56
3-Ethyl-4-[5-(4-ethylpiperazin-1-ylsulphonyl)-2-(tetrahydrofuran-3(S)-yloxy)pyridin-3-ylcarboxamido]-2-(pyridin-2-yl)methylpyrazole-5-carboxamide A solution of the title compound of Preparation 22 (330 mg, 0.80 mmol) and 1M aqueous sodium hydroxide solution (800 μl, 0.80 mmol) in ethanol (3 ml) was stirred for 3 hours at room temperature, then evaporated under reduced pressure.

A mixture of the resulting solid, the title compound of Preparation 40 (196 mg, 0.80 mmol), 1-hydroxybenzotriazole hydrate (135 mg, 0.88 mmol), N-ethyldiisopropylamine (307 μl, 1.76 mmol), 1-(3-dimethylaminopropyl)-3-ethylcarbodiimide hydrochloride (169 mg, 0.88 mmol) and tetrahydrofuran (15 ml) was stirred for 72 hours at room temperature, then evaporated under reduced pressure. The residue was partitioned between ethyl acetate (50 ml) and water (15 ml), the phases separated and the organic phase dried (Na₂SO₄) and evaporated under reduced pressure. The crude product was purified by column chromatography on silica gel, using an elution gradient of dichloromethane: methanol (95:5 to 90:10), to furnish the title compound (382 mg, 78%) as a foam. δ (CDCl₃): 1.05 (6H,m), 2.40 (3H,m), 2.54 (5H,m), 2.85 (2H,q), 3.11 (4H,m), 3.54 (1H,m), 4.15 (3H,m), 5.31 (1H,s), 5.48 (2H,s), 5.90 (1H,m), 6.69 (1H,s), 6.94 (1H,d), 7.24 (1H,m), 7.67 (1H,m), 8.60 (1H,m), 8.66 (1H,s), 8.87 (1H,s), 10.27 (1H,s). LRMS: m/z 613 (M+1)⁺.

PREPARATION 57
4-(2-Ethoxy-5-nitropyridin-3-ylcarboxamido)-3-n-propyl-2-(pyridin-2-yl)methylpyrazole-5-carboxamide Oxalyl chloride (2.73 ml, 31 mmol) was added dropwise to a stirred suspension of the title compound of Preparation 8 (3.31 g, 15.7 mmol) in dichloromethane (50 ml), followed by dimethylformamide (2 drops), and the reaction mixture stirred at room temperature for 3 hours. The resulting mixture was evaporated under reduced pressure and the residue azeotroped with hexane to give a white solid.

A solution of the crude acid chloride in dichloromethane (20 ml) was added dropwise to a stirred suspension of the title compound of Preparation 41 (4.06 g, 15.7 mmol), triethylamine (4.37 ml, 31 mmol) and dichloromethane (80 ml) and the reaction mixture stirred at room temperature for 20 hours. The resulting mixture was evaporated under reduced pressure and the residue partitioned between saturated aqueous sodium bicarbonate solution (200 ml) and dichloromethane (300 ml). The phases were separated, and the aqueous phase extracted with dichloromethane (2×300 ml). The combined organic solutions were washed with brine, dried (Na₂SO₄) and evaporated under reduced pressure to give a purple solid. The crude product was triturated with ether and the resulting solid collected and dried under suction to afford the title compound (6.26 g, 88%) as an off-white solid. Found: C, 55.42; H. 5.05; N, 21.49. $C_{21}H_{23}N_7O_5$ requires C, 55.62; H, 5.11; N, 21.62%. δ (CDCl₃): 0.83 (3H,t), 1.46 (2H,m), 1.60 (3H,t), 2.89 (2H,t), 4.85 (2H,q), 5.32 (1H,s), 5.48 (2H,s), 6.72 (1H,s), 6.95 (1H,d), 7.24 (1H,m), 7.67 (1H,m), 8.60 (1H,d), 9.16 (1H,s), 9.30 (1H,s), 10.59 (1H,s). LRMS: m/z 454 (M+1)⁺.

PREPARATION 58
3-Ethyl-4-[2-(2-methoxyethoxy)-5-nitropyridin-3-ylcarboxamido]-2-(pyridin-2-yl)methylpyrazole-5-carboxamide 1-Hydroxybenzotriazole hydrate (1.87 g, 12.2 mmol), N-ethyl diisopropyl amine (2.13 ml, 12.2 mmol), 1-(3-dimethylaminopropyl)-3-ethylcarbodiimide hydrochloride (2.34 g, 12.2 mmol) and the title compound of Preparation 40 (3.0 g, 12.2 mmol) were added, in turn, to a stirred, ice-cooled suspension of the title compound of Preparation 9 (2.96 g, 12.2 mmol) in dichloromethane (80 ml) and the reaction mixture stirred for 18 hours at room temperature. The resulting mixture was washed consecutively with water (25 ml), 2M hydrochloric acid (2×25 ml), saturated aqueous sodium bicarbonate solution (25 ml) and brine (25 ml), then dried (MgSO₄) and evaporated under reduced pressure. The residual solid was purified by column chromatography on silica gel; using an elution gradient of dichloromethane: methanol (99:1 to 97:3) to give the title compound (3.36, 58%) as a white solid. Found: C, 53.41; H, 4.90; N, 20.65. $C_{21}H_{23}N_7O_6$ requires C, 53.72; H, 4.94; N, 20.89%. δ (CDCl₃): 1.08 (3H,t), 2.88 (2H,q), 3.40 (3H,s), 3.98 (2H,t), 4.90 (2H,t), 5.28 (1H,s). 5.48 (2H,s), 6.70 (1H,s), 6.92 (1H,d), 7.23 (1H,m), 7.66 (1H,m), 8.60 (1H,d), 9.15 (lH,s), 9.31 (1H,s), 10.50 (1H,s). LRMS: m/z 470 (M+1)⁺.

PREPARATION 59
4-(5-Amino-2-ethoxypyridin-3-ylcarboxamido)-3-n-propyl-2-(pyridin-2-yl)methylpyrazole-5-carboxamide A stirred mixture of the title compound of Preparation 57 (5 g, 11 mmol), Raney nickel (2.5 g) and ethanol (150 ml) was hydrogenated at 345 kPa (50 psi) and 40° C. for 3 hours, then for a further 72 hours at room temperature. The resulting mixture was filtered and the filtrate evaporated under reduced pressure to give a pale yellow solid. The crude product was purified by column chromatography on silica gel, using an elution gradient of dichloromethane: methanol (99:1 to 95:5), followed by trituration with ether, to yield the title compound (4.4 g, 94%) as a beige solid. Found: C, 59.42; H, 5.96; N, 22.98. $C_{21}H_{25}N_7O_3$ requires C, 59.56: H, 5.95; N, 23.15%. δ (CDCl₃): 0.78 (3H,t) 1.43

(2H,m), 1.52 (3H,t), 2.82 (2H,t), 3.49 (2H,s), 4.59 (2H,q), 5.30 (1H,s), 5.46 (2H,s), 6.70 (1H,s), 6.93 (1H,d), 7.22 (1H,m), 7.65 (1H,m), 7.78 (1H,s), 7.94 (1H,s), 8.58 (1H,d), 10.53 (1H,s).

PREPARATION 60
4-[5-Amino2-(2-methoxyethoxy)pyridin-3-ylcarboxamido]-3-ethyl-2-(pyridin-2-yl)methylpyrazole-5-carboxamide A stirred mixture of the title compound of Preparation 58 (3.3 g, 7.0 mmol), Raney nickel (2 g) and ethanol (120 ml) was hydrogenated at 345 kPa (50 psi) and 50° C. for 18 hours. The resulting mixture was filtered and the filtrate evaporated under reduced pressure to provide the title compound (3.01 g, 98%) as a pale grey foam. Found: C, 56.47, H, 5.82; N, 21.40. $C_{21}H_{25}N_7O_4$; $0.40H_2O$ requires C, 56.47; H, 5.82; N, 21.95%. δ ($CDCl_3$): 1.06 (3H,t), 2.81 (2H,q), 3.38 (3H,s), 3.50 (2H,s), 3.92 (2H,t), 4.65 (2H,t), 5.33 (1H,s), 5.46 (2H,s), 6.70 (1H,s), 6.92 (1H,d), 7.22 (1H,m), 7.64 (1H,m), 7.76 (1H,s), 7.94 (1H,s), 8.60 (1H,d), 10.47 (1H,s). LRMS: m/z 440 $(M+1)^+$.

PREPARATION 61
5-(5-Amino-2-ethoxypyridin-3-yl)-3-n-propyl-2-(pyridin-2-yl)methyl-2,6-dihydro-7H-pyrazolo[4,3-d]pyrimidin-7-one Potassium t-butoxide (2.32 g, 20 mmol) was added carefully to a stirred suspension of the title compound of Preparation 59 (2.11 g, 5 mmol) and 4 Å molecular sieves in ethanol (50 ml) and the reaction mixture heated under reflux for 18 hours, allowed to cool and filtered. The filtrate was evaporated under reduced pressure and the residue partitioned between 1M hydrochloric acid (30 ml) and ethyl acetate (30 ml). The phases were separated, the aqueous phase extracted with ethyl acetate (2×30 ml) and the combined organic solutions washed with brine, dried ($Na_2SO_4$) and evaporated under reduced pressure. The residual brown oil was purified by column chromatography on silica gel, using an elution gradient of dichloromethane: methanol (100:0 to 96:4), to furnish the title compound (1.22 g, 60%) as a pale yellow solid. Found: C, 61.92; H, 5.69; N. 23.95. $C_{21}H_{23}N_7O_2$ requires C, 62.21; H, 5.72; N, 24.18%. δ ($CDCl_3$): 0.94 (3H,t), 1.51 (3H,t), 1.62 (2H,m), 2.95 (2H,t), 3.57 (2H,s), 4.50 (2H,q), 5.68 (2H,s), 7.06 (1H,d), 7.21 (1H,m), 7.60 (1H,m), 7.78 (1H,s) 8.16 (1H,d), 8.57 (1H,s), 11.07 (1H,s).

PREPARATION 62
5-[5-Amino-2-(2-methoxyethoxy)pyridin-3-yl]-3-ethyl-2-(pyridin-2-yl)methyl-2,6-dihydro-7H-pyrazolo[4,3-d]pyrimidin-7-one Potassium bis(trimethylsilyl)amide (6.58 g, 33.0 mmol) was added to a stirred suspension of the title compound of Preparation 60 (2.90 g, 6.60 mmol) in 2-methoxyethanol (70 ml) and the reaction mixture stirred under reflux for 18 hours. The resulting mixture was allowed to cool and then evaporated under reduced pressure to give a beige solid. The crude product was purified by column chromatography on silica gel, using an elution gradient of dichloromethane: methanol (98:2 to 95:5), to afford the title compound (2.21 g, 79%) as a white solid. Found: C, 59.10; H, 5.44; N, 22.86. $C_{21}H_{23}N_7O_3$ requires C, 59.85, H, 5.50; N, 23.26%. δ ($CDCl_3$): 1.28 (3H,t), 3.01 (2H,q), 3.53 (3H,s), 3.58 (2H,s), 3.82 (2H,t), 4.62 (2H,t,), 5.66 (2H,s), 7.08 (1H,d), 7.20 (1H,m), 7.61 (1H,m), 7.75 (1H,s), 8.09 (1H,s), 8.57 (1H,d), 11.14 (1H,s). LRMS: m/z 422 $(M+1)^+$.

PREPARATION 63
5-(5-Chlorosulphonyl-2-ethoxypyridin-3-yl)-3-n-propyl-2-(pyrdin-2-yl)methyl-2,6-dihydro-7H-pyrazolo[4,3,d]pyrimidin-7-one Sodium nitrite (295 mg, 4.4 mmol) was added portionwise to a stirred, ice-cooled solution of the title compound of Preparation 61 (900 mg, 2.2 mmol) in a mixture of glacial acetic acid (20 ml) and concentrated hydrochloric acid (20 ml) at such a rate as to maintain the temperature below –20° C. When the addition was complete, the mixture was allowed to warm slowly to 0° C. over 2 hours and then re-cooled to –15° C. Liquid sulphur dioxide (22 ml) and a solution of copper(II) chloride (860 mg, 6.6 mmol) in a mixture of water (2 ml) and glacial acetic acid (14 ml) were then added and the reaction mixture stirred at 0° C. for 30 minutes, followed by a further 2 hours at room temperature. The resulting mixture was carefully poured into stirred ice-water (300 ml) and the suspension thus obtained was extracted with dichloromethane (3×100 ml). The combined extracts were washed with brine, dried ($MgSO_4$) and evaporated under reduced pressure, then the residual oil triturated with ether to afford the title compound (720 mg, 67%) as an off-white solid. δ ($CDCl_3$): 0.97 (3H,t), 1.60 (3H,t), 1.73 (2H,m), 3.01 (2H,t), 4.82 (2H,q), 5.70 (2H,s), 7.10 (1H,d), 7.22 (1H,m), 7.64 (1H,m), 8.58 (1H,d), 8.90 (1H,s), 9.29 (1H,s), 10.55 (1H,s).

PREPARATION 64
5-[5-Chlorosulphonyl-2-(2-methoxyethoxy)pyridin-3-yl]-3-ethyl-2-(pyridin-2-yl)methyl-2,6-dihydro-7H-pyrazolo[4,3-d]pyrimidin-7-one Obtained as a cream solid (84%) from the title compound of Preparation 62, using the procedure of Preparation 63. δ ($CDCl_3$): 1.32 (3H,t), 3.08 (2H,q), 3.58 (3H,s), 3.89 (2H,t), 4.85 (2H,t), 5.69 (2H,s), 7.12 (1H,d), 7.22 (1H,m), 7.64 (1H,m), 8.57 (1H,d), 8.89 (1H,s), 9.26 (1H,s), 10.75 (1H,s). LRMS: m/z 505 $(M+1)^+$.

PREPARATION 65
3-Ethyl-4-[5-(4-ethylpiperazin-1-ylsulphonyl)-2-(2-methoxyethoxy)pyridin-3-ylcarboxamido]-1-(pyridin-2-yl)methylpyrazolo-5-carboxamide Obtained as a white crystalline solid (44%) from the title compounds of Preparation 19 and Preparation 42, using the procedure of Preparation 56. δ ($CDCl_3$): 1.02 (3H,t), 1.20 (3H,t), 2.40 (2H,q), 2.52 (4H,m), 2.66 (2H,q), 3.10 (4H,m), 3.39 (3H,s), 3.90 (2H,t), 4.81 (2H,t), 5.62 (2H,s), 5.70 (1H,s), 7.26 (2H,m), 7.71 (1H,m), 8.53 (1H,d), 8.66 (1H,s), 8.82 (1H,s), 9.04 (1H,s). LRMS m/z 601 $(M+1)^+$.

PREPARATION 66
3-Bromo-2-(1,3-dimethoxyprop-2-oxy)-5-(4-ethylpiperazin-1-ylsulphonyl)pyridine 60% Sodium hydride dispersion in mineral oil (133 mg, 3.33 mmol) was added to a stirred, ice-cooled solution of 1,3-dimethoxypropan-2-ol (J. Amer. Chem. Soc., 1939, 61, 433; 400 mg, 3.33 mmol) in tetrahydrofuran (30 ml) and the mixture stirred for 30 minutes. The title compound of Preparation 13 (500 mg, 1.35 mmol) was added and the reaction mixture stirred under reflux for 1 hour, then allowed to cool. The resulting mixture was evaporated under reduced pressure and the residue partitioned between water (30 ml) and ethyl acetate (30 ml). The phases were separated and the aqueous phase extracted with ethyl acetate (2×30 ml), then the combined extracts washed with brine (30 ml), dried ($MgSO_4$) and evaporated under reduced pressure to give the title compound (566 mg, 93%) as a yellow solid. δ ($CDCl_3$): 1.06 (3H,t), 2.43 (2H,q), 2.55 (4H,m), 3.08 (4H,m), 3.40 (6H,2xs), 3.70 (4H, 2xd), 5.60 (1H,m), 8.10 (1H,s), 8.44 (1H,s). LRMS: m/z 452.

PREPARATION 67
2-(1,3-Dimethoxyprop-2-oxy)-5-(4-ethylpiperazin-1-ylsulphonyl)pyridine-3-carboxylic Acid Ethyl Ester Obtained as a yellow solid (84%) from the title compound of Preparation 66, using the procedure of Preparation 19. δ (CDCl$_3$): 1.05 (3H,t), 1.40 (3H,t), 2.42 (2H,q), 2.55 (4H,m), 3.09 (4H,m), 3.40 (6H, 2xs), 3.70 (4H, 2xd), 4.37 (2H,q), 5.70 (1H,m), 8.40 (1H,s), 8.62 (1H,s). LRMS: m/z 446 (M+1)$^+$.

PREPARATION 68
3-Bromo-5-(4-ethylpiperazin-1-ylsulphonyl)-2-(tetrahydropyran-4-yloxy)pyridine Obtained as a clear oil (70%) from the title compound of Preparation 13 and 4-hydroxytetrahydropyran, following the procedure of Preparation 14, after purification by column chromatography on silica gel, using ethyl acetate as eluant. δ (CDCl$_3$): 1.05 (3H,t), 1.88 (2H,m), 2.08 (2H,m), 2.42 (2H,q), 2.54 (4H,m), 3.08 (4H,m), 3.66 (2H,m), 3.99 (2H,m) 5.40 (1H,m), 8.10 (1H,s), (1H,s). LRMS: m/z 434 (M)$^+$.

PREPARATION 69
5-(4-Ethylpiperazin-1-ylsulphonyl)-2-(tetrahydropyran-4-yloxy)pyridine-3-carboxylic Acid Ethyl Ester Obtained as an oil (92%) from the title compound of Preparation 68, using the procedure of Preparation 19. δ (CDCl$_3$): 1.04 (3H,t), 1.40 (3H,t), 1.88 (2H,m), 2.08 (2H,m), 2.43 (2H,q), 2.55 (4H,m), 3.09 (4H,m), 3.66 (2H,m), 4.00 (2H,m), 4.40 (2H,q), 5.50 (1H,m), 8.40 (1H,s), 8.60 (1H,s). LRMS: m/z 427 (M)$^+$.

PREPARATION 70
5-(4-Ethylpiperazin-1-ylsulphonyl)-2-(tetrahydropyran-4-yloxy)pyridine-3-carboxylic Acid Sodium Salt A mixture of the title compound of Preparation 69 (611 mg, 1.4 mmol), 1M aqueous sodium hydroxide solution (1.6 ml, 1.6 mmol) and ethanol (6 ml) was stirred at room temperature for 6 hours, then evaporated under reduced pressure. The residue was dissolved in water (16 ml), then the solution washed with ethyl acetate (2×10 ml) and evaporated under reduced pressure to provide the title compound (520 mg, 93%) as a tan-coloured solid. δ (DMSOd$_6$): 1.19 (3H,t), 1.70 (2H,m), 2.00 (2H,m), 2.80–3.88 (14H,m), 8.32 (1H,s), 8.73 (1H,s), 10.93 (1H,s). LRMS: m/z 400 (M+1)$^+$.

PREPARATION 71
2-11 3-Dimethoxyprop-2-oxy)-5-(4-ethylpiperazin-1-ylsulphonyl)pyridine-3-carboxylic Acid Sodium Salt Obtained as a solid (92%) from the title compound of Preparation 67, using the procedure of Preparation 70. LRMS: m/z 418 (M+1)$^+$.

PREPARATION 72
4-[2-(1,3-Dimethoxyprop2-oxy)-5-(4-ethylpiperazin-1-ylsulphonyl)pyridine-3-ylcarboxamido]-3-n-propyl-2-(pyridin-2-yl)methylpyrazole-5-carboxamide A mixture of the title compounds of Preparation 71 (418 mg, 0.95 mmol) and Preparation 41 (250 mg, 1.0 mmol), 1-hydroxybenzotrazole hydrate (270 mg, 2.0 mmol), 1-(3-dimethylaminopropyl)-3-ethylcarbodiimide hydrochloride (380 mg, 2.0 mmol), triethylamine (280 μl, 2.0 mmol) and tetrahydrofuran (10 ml) was stirred at room temperature for 36 hours, then evaporated under reduced pressure. The residue was partitioned between dichloromethane (10 ml) and brine (10 ml), the phases separated, the aqueous phase extracted with dichloromethane (2×10 ml) and the combined organic solutions dried (MgSO$_4$) and evaporated under reduced pressure. The residual yellow oil was purified by column chromatography on silica gel, using an elution gradient of dichloromethane: methanol (98:2 to 96:4) to furnish the title compound (350 mg, 56%) as an off-white solid. δ (CDCl$_3$): 0.81 (3H,t), 1.03 (3H,t), 1.44 (2H,m), 2.40 (2H,q), 2.52 (4H,m), 2.80 (2H,t), 3.10 (4H,m), 3.38 (6H,s), 3.78 (2H,dd), 3.92 (2H,dd), 5.31 (1H,s), 5.47 (2H,s), 5.93 (1H,m), 6.70 (1H,s), 6.92 (1H,d), 7.23 (1H,m), 7.65 (1H,m), 8.58 (1H,d), 8.65 (1H,d), 8.80 (1H,s), 10.26 (1H,s). LRMS: m/z 660 (M+2)$^+$.

PREPARATION 73
3-Bromo-5-(4-ethylpiperazin-1-ylsulphonyl)-2-(tetrahydrofuran-3(R)-yloxy)pyridine Obtained as an oil (89%) from the title compound of Preparation 13 and (R)-(−)-3-hydroxytetrahydrofuran, using the procedure of Preparation 17. δ (CDCl$_3$): 1.05 (3H,t), 2.20 (1H,m), 2.30 (1H,m), 2.42 (2H,q), 2.54 (4H,m), 3.07 (4H,m), 3.94 (2H,m), 4.02 (1H,m), 4.10 (1H,m), 5.63 (1H,m), 8.11 (1H,s), 8.43 (1H,s). LRMS: m/z 421 (M+1)$^+$.

PREPARATION 74
5-(4-Ethylpiperazin-1-ylsulphonyl)-2-(tetrahydrofuran-3(R)-yloxy)pyridine-3-carboxylic Acid Ethyl Ester Obtained as an oil (84%), from the title compound of Preparation 73, using the procedure of Preparation 19. δ (CDCl$_3$): 1.03 (3H,t), 1.40 (3H,t), 2.26 (2H,m), 2.42 (2H,q), 2.55 (4H,m), 3.10 (4H,m), 3.98 (3H,m), 4.12 (1H,m), 4.38 (2H,q), 5.70 (1H,m), 8.42 (1H,s), 8.62 (1H,s). LRMS: m/z 414 (M+1)$^+$.

PREPARATION 75
3-Ethyl-4-[5-(4-ethylpiperazin-1-ylsulphonyl)-2-(tetrahydrofuran-3(R)-yloxy)pyridin-3-ylcarboxamido]-2-(pyridin-2-yl)methylpyrazole-5-carboxamide Obtained as a foam (78%) from the title compounds of Preparation 74 and Preparation 40, using the procedure of Preparation 56. δ (CDCl$_3$): 1.04 (6H,m), 2.40 (3H,m), 2.52 (5H,m), 2.84 (2H,q), 3.10 (4H,m), 3.94 (1H,m), 4.15 (3H,m), 5.28 (1H,s), 5.48 (2H,s), 5.90 (1H,m), 6.68 (1H,s), 6.92 (1H,d), 7.22 (1H,m), 7.67 (1H,m), 8.60 (1H,d), 8.64 (1H,s), 8.86 (1H,s), 10.28 (1H,s). LRMS: m/z 613 (M+1)$^+$.

PREPARATION 76
4-[5-(4-Ethylpiperazin-1-ylsulphonyl)-2-(tetrahydropyran-4-yloxy)pyridin-3-ylcarboxamido]-3-n-propyl-2-(pyridin-2-yl)methylpyrazole-5-carboxamide A mixture of the title compounds of Preparation 70 (520 mg, 1.3 mmol) and Preparation 41 (285 mg, 1.1 mmol), 1-(3-dimethylaminopropyl)-3-ethylcarbodiimide hydrochloride (250 mg, 1.3 mmol), 1-hydroxybenzotriazole hydrate (199 mg, 1.3 mmol), N-ethyldiisopropylamine (226 μl, 1.3 mmol) and tetrahydrofuran (20 ml) was stirred for 1 week at room temperature. Ethyl acetate (150 ml) was then added and the resulting mixture washed with brine (2×50 ml), dried (MgSO$_4$) and evaporated under reduced pressure. The residue was purified by column chromatography on silica gel, using an elution gradient aof ethyl acetate: dichloromethane:methanol (32:64:4 to 0:95:5), to afford the title compound (603 mg, 86%) as a white foam. δ (DMSOd$_6$): 0.74 (3H,t), 0.91 (3H,t), 1.39 (2H,m), 1.90 (2H,m), 2.05 (2H,m), 2.30 (2H,q), 2.42 (4H,m), 2.74 (2H,t), 2.95 (4H,m), 3.50 (2H,m), 3.85 (2H,m), 5.48 (2H,s), 5.52 (1H,m), 7.09 (1H,d), 7.35 (3H,m), 7.48 (1H,m), 8.39 (1H,s), 8.54 (1H,d), 8.65 (1H,s), 10.18 (1H,s). LRMS: m/z 641 (M+1)$^+$.

PREPARATION 77
4-[2-Ethoxy-5-(4-ethylpiperazin-1-ylsulphonyl)pyridin-3-ylcarboxamido]-3-n-propyl-2-(pyridin-2-yl)methylpyrazole-5-carboxamide A stirred mixture of the title compounds of Preparation 28 (3.07 g, 7.71 mmol) and Preparation 41 (2.0 g, 7.71 mmol)

in pyridine (50 ml) was heated at 50° C. for 48 hours, then allowed to cool and evaporated under reduced pressure. The residue was partitioned between dichloromethane (100 ml) and water (20 ml), then the organic phase separated, dried ($MgSO_4$) and evaporated under reduced pressure. The residual brown foam was purified by column chromatography on silica gel, using an elution gradient of ethyl acetate: methanol (100:0 to 90:10), to give the title compound (3.19 g, 71%) as a white foam. Found: C, 54.66; H. 6.17; N, 18.38. $C_{27}H_{36}N_8O_5S$: 0.40 $H_2O$ requires C, 54.79;H, 6.27; N, 18.93%. δ ($CDCl_3$): 0.82 (3H,t), 1.03 (3H,t), 1.45 (2H,m), 1.58 (3H,t), 2.40 (2H,q), 2.52 (4H,m), 2.86 (2H,t), 3.10 (4H,m), 4.79 (2H,q), 5.29 (1H,s), 5.46 (2H,s), 6.70 (1H,s), 6.93 (1H,d), 7.21 (1H,m), 7.64 (1H,m), 8.59 (1H,d), 8.64 (1H,s), 8.81 (1H,s), 10.56 (1H,s). LRMS: m/z 585 $(M+1)^+$.

PREPARATION 78
5-(4-Ethylpiperazin-1-ylsulphonyl)-2-proipoxypyridine-3-carboxylic Acid Methyl Ester Obtained as an oil (53%) from the title compound of Preparation 49 and 1-ethylpiperazine, using the procedure of Preparation 18. δ ($CDCl_3$): 1.05 (6H,m), 1.86 (2H,m), 2.41 (2H,q), 2.54 (4H,m), 3.08 (4H,m), 3.92 (3H,s), 4.46 (2H,t), 8.40 (1H,s), 8.62 (1H,s). LRMS: m/z 372 $(M+1)^+$.

PREPARATION 79
5-(4-Ethylpiperazin-1-ylsulphonyl)-2-n-propoxypyridine-3-carboxylic Acid A mixture of the title compound of Preparation 78 (370 mg, 1.0 mmol), 2M aqueous sodium hydroxide solution (1 ml, 2 mmol) and methanol (10 ml) was stirred at room temperature for 2 hours. The resulting mixture was treated with solid carbon dioxide in order to adjust its pH to 7 and then evaporated under reduced pressure. The residue was triturated with dichloromethane (3×50 ml) and the combined organic solutions evaporated under reduced pressure to yield the title compound (340 mg, 95%) as a white solid. LRMS: m/z 357 $(M)^+$.

PREPARATION 80
4-[5-(4-Ethylpiperazin-1-ylsulphonyl)-2-n-propoxypyridin-3-ylcarboxamido]-3-n-propyl-2-(pyridin-2-yl)methylpyrazole-5-carboxamide Oxalyl chloride (122 μl, 5.6 mmol) was added dropwise to a stirred solution of the title compound of Preparation 79 (478 mg, 1.4 mmol) and dimethylformamide (3 drops) in dichloromethane (10 ml) and the reaction mixture stirred at room temperature for 18 hours, then evaporated under reduced pressure. The residue was azeotroped with dichloromethane (3×10 ml), then added to a stirred, ice-cooled solution of the title compound of Preparation 41 (360 mg, 1.4 mmol) in pyridine (10 ml) and the reaction mixture stirred at room temperature for 18 hours, then evaporated under reduced pressure. The residue was partitioned between water (50 ml) and dichloromethane (50 ml), the phases separated and the aqueous phase extracted with dichloromethane (2×50 ml). The combined organic solutions were dried ($Na_2SO_4$) and evaporated under reduced pressure, then the crude product purified by column chromatography on silica gel, using ethyl acetate:methanol (80:20) as eluant, to provide the title compound (500 mg, 37%) as a colourless glass. δ ($CDCl_3$): 0.81 (3H,t), 1.04 (3H,t), 1.27 (3H,t), 1.46 (2H,m), 2.00 (2H,m), 2.40 (2H,q), 2.53 (4H,m), 2.86 (2H,t), 3.09 (4H,m), 4.66 (2H,t), 5.27 (1H,s), 5.47 (2H,s), 6.68 (1H,s), 6.93 (1H,d), 7.21 (1H,m), 7.66 (1H,m), 8.59 (1H,d), 8.64 (1H,s), 8.80 (1H,s), 10.47 (1H,s). LRMS: m/z 599 $(M+1)^+$.

PREPARATION 81
2-(2-Benzyloxyethoxy)-3-bromo-5-(4-ethylpiperazin-1-ylsulphonyl)pyrdine A mixture of a 2M solution of sodium bis(trimethylsilyl)amide in tetrahydrofuran (4.1 ml, 8.2 mmol), 2-benzyloxyethanol (1.16 ml, 8.2 mmol) and tetrahydrofuran (5 ml) was stirred at about 0° C. for 1 hour. The title compound of Preparation 13 (2.0 g, 5.43 mmol) was added and the reaction mixture stirred at room temperature for 5 hours, then evaporated under reduced pressure. The residue was suspended in ethyl acetate (10 ml) and the suspension extracted with 2M hydrochloric acid (3×10 ml). The combined extracts were basified with aqueous sodium bicarbonate solution and extracted with ethyl acetate (3×15 ml). These combined extracts were dried ($MgSO_4$) and evaporated under reduced pressure, then the crude product purified by column chromatography on silica gel, using an elution gradient of dichloromethane: methanol (100:0 to 95:5), to furnish the title compound (1.95 g, 74%) as an oil. δ ($CDCl_3$): 1.02 (3H,t), 2.40 (2H,q), 2.52 (4H,m), 3.07 (4H, m), 3.88 (2H,t), 4.62 (4H,m), 7.26 (1H,m), 7.34 (4H,m), 8.09 (1H,s), 8.42 (1H,s). LRMS: m/z 486 $(M+2)^+$.

PREPARATION 82
2-(2-Benzyloxyethoxy)-5-(4-ethylpiperazin-1-ylsulphonyl)pyridine-3-carboxylic Acid Ethyl Ester Obtained as an oil (42%) from the title compound of Preparation 81, using the procedure of Preparation 21. δ ($CDCl_3$): 1.04 (3H,t), 1.38 (3H,t), 2.42 (2H,q), 2.54 (4H,m), 3.08 (4H,m), 3.90 (2H,t), 4.38 (2H,q), 4.67 (4H,m), 7.28 (1H,m), 7.35 (4H,m), 8.41 (1H,s), 8.62 (1H,s). LRMS: m/z 478 $(M+1)^+$.

PREPARATION 83
2-(2-Benzyloxyethoxy)-5-(4-ethylpiperazin-1-ylsulphonyl)pyridine-3-carboxylic Acid Hydrochloride Obtained as a pale yellow solid (88%) from the title compound of Preparation 82, using the procedure of Preparation 26. δ ($CDCl_3$): 1.45 (3H,t), 2.82 (2H,m), 3.09 (2H,q), 3.26 (2H,m), 3.64 (2H,m), 3.90 (4H,m), 4.64 (2H,s), 4.78 (2H,t), 7.33 (1H,m), 7.37 (4H,m), 8.58 (1H,s), 8.64 (1H,s), 12.17 (1H,s). LRMS: m/z 450 $(M+1)^+$.

PREPARATION 84
4-[2-(2-Benzyloxyethoxy)-5-(4-ethylpiperazin-1-ylsulphonyl)pyridin-3-ylcarboxamido]-3-n-propyl-2-(pyridin-2-yl)methylpyrazole-5-carboxamide Obtained as an orange solid (80%) from the title compounds of Preparation 83 and Preparation 41, using the procedure of Preparation 52. δ ($CDCl_3$): 0.80 (3H,t), 1.02 (3H,t), 1.42 (2H,m), 2.40 (2H,q), 2.64 (4H,m), 2.81 (2H,t), 3.10 (4H,m), 4.06 (2H,t), 4.57 (2H,s), 4.86 (2H,t), 5.26 (1H,s), 5.45 (2H,s), 6.68 (1H,s), 6.90 (1H,d), 7.17–7.27 (5H,m), 7.34 (1H,m), 7.63 (1H,m), 8.59 (1H,d), 8.62 (1H,s), 8.82 (1H,s), 10.50 (1H,s). LRMS: m/z 692 $(M+2)^+$.

PREPARATION 85
2-Benzyl-3-ethyl-4-nitropyrazole-5-carboxamide

Caesium carbonate (2.9 g, 9.0 mmol) was added to a stirred, ice-cooled solution of the title compound of Preparation 35 (1.7 g, 8.8 mmol) in dimethylformamide (20 ml) and the suspension stirred for 30 minutes. Benzyl bromide (10.6 ml, 9.0 mmol) was added and the reaction mixture stirred at room temperature for 18 hours, then evaporated under reduced pressure. The residue was partitioned between ethyl acetate (125 ml) and brine (100 ml), the phases separated and the organic phase dried ($MgSO_4$) and evaporated under reduced pressure. The residue was purified by column chromatography on silica gel, using ethyl acetate as eluant, to afford the title compound (1.13 g, 47%) as a white solid. δ ($DMSOd_6$): 0.97 (3H,t), 2.96 (2H,q), 5.44

(2H,s), 7.24 (2H,m), 7.33 (3H,m), 7.68 (1H,s), 7.95 (1H,s). LRMS: m/z 274 (M+1)$^+$.

PREPARATION 86
4-Amino-2-benzyl-3-ethylryrazole-5-carboxamide

Obtained as a pale pink solid (90%) from the title compound of Preparation 85, using the procedure of Preparation 40. δ (DMSOd$_6$): 0.87 (3H,t), 2.49 (2H,q), 4.46 (2H,s), 5.22 (2H,s), 6.85 (1H,s), 7.09 (3H,m), 7.25 (1H,m), 7.31 (2H,m). LRMS: m/z 245 (M+1)$^+$.

PREPARATION 87
2-Benzyl-4-[2-ethoxy-5-(4-Ethylpiperazin-1-ylsulphonyl) pyridin-3-ylcarboxamido]-3-ethylpyrazole-5-carboxamide Obtained as a white crystalline foam (46%) from the title compounds of Preparation 18 and Preparation 86, using the procedure of Preparation 56. δ (DMSOd$_6$): 0.92 (6H,m), 1.44 (3H,t), 2.30 (2H,q), 2.41 (4H,1m), 2.74 (2H,q), 2.95 (4H,m), 4.62 (2H,q), 5.40 (2H,s), 7.17 (2H,m), 7.31 (4H,m), 7.50 (1H,s), 8.39 (1H,s), 8.65 (1H,s), 10.38 (1H,s). LRMS: m/z 571 (M+2)$^+$.

PREPARATION 88a
3-Ethyl-1-(1-methylimidazol-2-yl)methyl-4-nitropyrazole-5-carboxamide
and

PREPARATION 88b
3-Ethyl-2-(1-methylimidazol-2-yl)methyl-4-nitronyrazole-5-carboxamide A mixture of the title compound of Preparation 35 (2.2 g, 11.95 mmol), 2-chloromethyl-1-methylimidazole hydrochloride (J. Chem. Soc., 1957, 3305; 2.0 g, 11.95 mmol), caesium carbonate (8.5 g, 26.3 mmol) and dimethylformamide (100 ml) was stirred at room temperature for 6 hours, then evaporated under reduced pressure. The residue was partitioned between water (150 ml) and dichloromethane (150 ml), the phases separated and the aqueous phase extracted with dichloromethane (2×150 ml). The combined extracts were dried (MgSO$_4$) and evaporated under reduced pressure, then the residue triturated with dichloromethane: methanol (90:10) and the resulting solid collected and dried under suction to give the first title compound (1-isomer; 305 mg, 9%) as a cream solid. δ (DMSOd6): 1.16 (3H,t), 2.82 (2H,q), 3.69 (3H,s), 5.40 (2H,s), 6.81 (1H,s), 7.13 (1H,s), 8.20 (1H,s), 8.50 (1H,s). LRMS: m/z 279 (M+1)$^+$.

The filtrate was evaporated under reduced pressure and the residue purified by column chromatography on silica gel, using dichloromethane:methanol:0.88 aqueous ammonia (90:10:1) as eluant, to yield the second title compound (2-isomer; 480 mg, 14%) as a solid. δ (CDCl$_3$): 1.16 (3H,t), 3.20 (2H,q), 3.77 (3H,s), 5.48 (2H,s), 6.22 (1H,s), 6.68 (1H,s), 7.00 (1H,s), 7.25 (1H,s). LRMS: m/z279 (M+1)$^+$.

PREPARATION 89
4-Amino-3-ethyl-2-(1-methylimidazol-2-yl) methylpyrazole-5-carboxamide Obtained as a pink solid (92%) from the title compound of Preparation 88b, using the procedure of Preparation 40. δ (CDCl$_3$): 1.00 (3H,t), 2.68 (2H,q), 3.60 (3H,s), 5.34 (2H,s), 5.40 (1H,s), 6.55 (1H,s), 6.82 (1H,s), 6.98 (1H,s). LRMS: m/z 249 (M+1)$^+$.

PREPARATION 90
3-Ethyl-4-[5-(4-ethylpiperazin-1-ylsulphonyl)-2-(2-methoxyethoxy)pyridin-3-ylcarboxamido]-2-(1-methylimidazol-2-yl)methylpyrazole-5-carboxamide Obtained as a solid (48%) from the title compounds of Preparation 29 and Preparation 89, using the procedure of Preparation 45A. δ (CDCl$_3$): 1.01 (3H,t), 1.10 (3H,t), 2.40 (2H,q), 2.52 (4H,m), 2.98 (2H,q), 3.08 (4H,m), 3.36 (3H,s), 3.66 (3H,s), 3.92 (2H,t), 4.82 (2H,t), 5.35 (1H,s), 5.42 (2H,s), 6.61 (1H,s), 6.86 (1H,s), 7.00 (1H,s), 8.64 (1H,s), 8.81 (1H,s), 10.33 (1H,s). LRMS: m/z 604 (M+1)$^+$.

PREPARATION 91a
1-(1-Methylimidazol-2-yl)methyl-4-nitro-3-n-propylpyrazole-5-carboxamide
and

PREPARATION 91 b
2-(1 1-Methylimidazol-2-yl)methyl-4-nitro-3-n-propylpyrazole-5-carboxamide A stirred mixture of the title compound of Preparation 34 (5.0 g, 25.3 mmol), 2-chloromethyl-1-methylimidazole hydrochloride (J. Chem. Soc., 1957, 3305; 4.6 g, 27.7 mmol), caesium carbonate (18.1 g, 55.6 mmol) and acetonitrile (100 ml) was heated at 50° C. for 5 hours, then allowed to cool. Ethyl acetate (300 ml) was added and the mixture washed with water (2×400 ml), dried (MgSO$_4$) and concentrated under reduced pressure to a volume of about 200 ml. The resulting precipitate was collected and combined with the material produced by crystallisation from ethyl acetate of the residue obtained by evaporation under reduced pressure of the filtrate, to provide, after drying, the first title compound (1-isomer; 1.0 g, 13%) as white crystals. δ (DMSOd$_6$): 0.89 (3H,t), 1.60 (2H,m), 2.76 (2H,t), 3.66 (3H,s), 5.39 (2H,s), 6.80 (1H,s), 7.12 (1H,s), 8.20 (1H,s), 8.48 (1H,s). LRMS: m/z293 (M+1)$^+$.

The crystallisation mother liquor was evaporated under reduced pressure and the residue recrystallised from ethyl acetate to furnish the second title compound (2-isomer; 700 mg, 9%) as a solid. δ (DMSOd$_6$): 0.92 (3H,t), 1.52 (2H,m), 3.04 (2H,t), 3.68 (3H,s), 5.49 (2H,s), 6.82 (1H,s), 7.14 (1H,s), 7.66 (1H,s), 7.93 (1H,s). LRMS: m/z 293 (M+1)$^+$.

PREPARATION 92
4-Amino-2-(1-methylimidazol-2-yl)methyl-3-n-propylpyrazole-5-carboxamide A stirred mixture of the title compound of Preparation 91b (500 mg, 1.71 mmol), 10% palladium on charcoal (150 mg) and ethanol (20 ml) was hydrogenated for 4 hours at 345 kPa (50 psi), then filtered. The filtrate was combined with a dichloromethane: methanol (80:20) wash (50 ml) of the filter pad, evaporated under reduced pressure and the residue crystallised from ethyl acetate to afford the title compound (320 mg, 71%) as a pale pink solid. δ (CDCl$_3$): 0.90 (3H,t), 1.40 (2H,m), 2.60 (2H,t), 3.58 (3H,s), 3.94 (2H,s), 5.32 (3H,m), 6.54 (1H,s), 6.82 (1H,s), 6.98 (1H,s).

PREPARATION 93
3-(2-Phenylethenyl)pyridazine

Zinc chloride (820 mg, 6 mmol) was added to a stirred mixture of benzaldehyde (6.11 ml, 60 mmol) and 3-methylpyridazine (2.83 g, 30 mmol) and the resulting mixture heated for 20 hours at 150° C. The cool reaction mixture was partitioned between dichloromethane (40 ml) and 2M aqueous sodium hydroxide solution (20 ml), then the organic phase separated, combined with a dichloromethane extract (80 ml) of the aqueous phase, dried (Na$_2$SO$_4$) and evaporated under reduced pressure. The residue was purified by column chromatography on silica gel, using dichloromethane: methanol (99:1) as eluant, to give the title compound (59%) as a solid. δ (CDCL$_3$): 7.12 (1H,d), 7.34 (3H,m), 7.56 (2H,d), 7.72 (1H,d), 8.37 (1H,s), 8.50 (1H,s), 8.60 (1H,s). LRMS: m/z 183 (M+1)$^+$.

PREPARATION 94

3-Hydroxymethylpyridazine

Ozone was bubbled through a stirred solution of the title compound of Preparation 93 (3.60 g, 0.02 mol) in methanol (150 ml) at −10° C. After 30 minutes the mixture was purged with nitrogen, sodium borohydride (750 mg, 0.02 mol) added portionwise and the resulting solution stirred for 2 hours at room temperature. The reaction mixture was acidified with 2M hydrochloric acid, then basified with 0.880 aqueous ammonia solution and evaporated under reduced pressure. Purification of the residue by column chromatography on silica gel, using an elution gradient of dichloromethane: methanol (98:2 to 96:4). provided the title compound (76%) as a solid. $\delta$ ($CDCl_3$): 3.66 (1H,s), 4.92 (2H,s), 7.48 (2H,m), 9.06 (1H,d).

PREPARATION 95

3-Chloromethylpyridazine Hydrochloride

Thionyl chloride (3.05 ml, 42 mmol) was added to an ice-cooled flask containing the title compound of Preparation 94 (920 mg, 8 mmol) and the reaction mixture stirred for 45 minutes at room temperature, then evaporated under reduced pressure. The residue was azeotroped with toluene (40 ml) to furnish the crude title compound (1.4 g) as a brown solid. $\delta$ ($DMSOd_6$): 4.98 (2H,s), 7.80 (1H,m), 7.90 (1H,d), 8.19 (1H,s), 9.22 (1H,d).

PREPARATION 96

4-Nitro-3-n-propyl-2-(pyridazin-3-yl)methylpyrazole-5-carboxamide

A mixture of the title compounds of Preparation 95 (700 mg, 4.24 mmol) and Preparation 34 (840 mg, 4.24 mmol), caesium carbonate (3.45 g, 10.6 mmol) and acetonitrile (30 ml) was stirred at 80° C. for 2 hours, then allowed to cool. Brine (30 ml) was added, the mixture extracted with dichloromethane (2×80 ml) and the combined extracts dried ($Na_2SO_4$) and evaporated under reduced pressure. The residual brown oil was purified by column chromatography on silica gel, using an elution gradient of dichloromethane: methanol (100:0 to 90:10) to afford the title compound (480 mg, 39%) as a yellow solid. $\delta$ ($CDCl_3$): 1.02 (3H,t), 1.60 (2H,m), 3.06 (2H,t), 5.72 (2H,s), 5.87 (1H,s), 7.25 (1H,s), 7.54 (2H,m), 9.20 (1H,s).

PREPARATION 97

4-Amino-3-n-propyl-2-(pryidazin-3-yl)methylpyrazole-5-carboxamide

Obtained as a pink gum (97%) from the title compound of Preparation 96, using the procedure of Preparation 40. $\delta$ ($CDCl_3$): 0.90 (3H,t), 1.47 (2H,m), 2.51 (2H,t), 5.25 (1H,s), 5.58 (2H,s), 6.58 (1H,s), 7.09 (1H,d), 7.43 (1H,m), 9.14 (1H,d). LRMS: m/z 261 (M+1)$^+$.

PREPARATION 98

4-[2-Ethoxy-5-(4-ethylpriperazin-1-ylsulphonyl)pyridin-3-ylcarboxamido]-3-n-propyl-2-(pyridazin-3-yl)methylpyrazole-5-carboxamide Obtained as an orange gum (42%) from the title compounds of Preparation 28 and Preparation 97, using the procedure of Preparation 45A. $\delta$ ($CDCl_3$): 0.81 (3H,t), 1.01 (3H,t), 1.47 (2H,m), 1.55 (3H,t), 2.39 (2H,q), 2.50 (4H,m), 2.87 (2H,t), 3.07 (4H,m), 4.77 (2H,q), 5.58 (1H,s), 5.69 (2H,s), 6.71 (1H,s), 7.18 (1H,d), 7.45 (1H,m), 8.63 (1H,s), 8.79 (1H,s), 9.15 (1H,s), 10.52 (1H,s). LRMS: m/z 586 (M+1)$^+$.

PREPARATION 99

2-Methylpyrimidine-1-oxide

A freshly prepared solution of sodium metal (11.5 g, 0.50 mol) in ethanol (170 ml) was added dropwise over 1 hour to a stirred suspension of hydroxylamine hydrochloride (34.75 g, 0.50 mol) and phenolphthalein (50 mg) in ethanol (200 ml) so as to maintain a colourless solution and the mixture stirred at room temperature for 3 hours. Acetonitrile (26 ml, 0.50 mol) was added and this mixture stirred for a further 2 hours at room temperature, then at 45° C. for 48 hours. The resulting mixture was filtered and the filtrate concentrated under reduced pressure to a volume of ca. 100 ml, then cooled to 0° C. The resulting precipitate was collected and dried under suction to give the intermediate acetamidoxime (9.9 g, 27%) as white crystals.

Boron trifluoride diethyl ether complex (9.5 ml, 75 mmol), followed by 1,1,3,3-tetramethoxypropane (11.5 ml, 70 mmol), were added to a stirred mixture of dimethylformamide (100 ml) and toluene (100 ml). The aceta7+idoxime (5.0 g, 67.5 mmol) was then added and the reaction mixture heated under reflux for 45 minutes, then allowed to cool. The resulting mixture was evaporated under reduced pressure and the residual brown oil partitioned between dichloromethane: methanol (80:20) (100 ml) and aqueous sodium carbonate solution (100 ml). The phases were separated, the aqueous phase extracted with dichloromethane: methanol (80:20) (10×50 ml) and the combined organic solutions dried ($MgSO_4$) and evaporated under reduced pressure. The residue was purified by column chromatography on silica gel, using dichloromethane: methanol (98:2) as eluant, to yield the title compound (2.5 g, 34%) as an orange solid. $\delta$ ($CDCl_3$): 2.74 (3H,s), 7.19 (1H,m), 8.16 (1H,d), 8.39 (1H,d).

PREPARATION 100

2-Chloromethylpyrimidine

A stirred mixture of the title compound of Preparation 99 (2.5 g, 22.7 mmol) and phosphorous oxychloride (18 ml, 193 mmol) was heated under reflux for 2 hours, then allowed to cool. The resulting mixture was poured onto stirred ice and neutralised using solid sodium carbonate over 3 hours. The aqueous solution thus obtained was extracted with dichioromethane (3×100 ml), then the combined extracts dried ($MgSO_4$) and evaporated under reduced pressure. The residual brown oil was purified by column chromatography on silica gel, using an elution gradient of dichloromethane: methanol (100:0 to 97:3), to provide the title compound (510 mg, 17%). $\delta$ ($CDCl_3$): 4.72 (2H,s), 7.22 (1H,m), 8.75 (2H,d). LRMS: m/z 129 (M+1)$^+$.

PREPARATION 101a

4-Amino-3-n-propyl-1-(pyrimidin-2-yl)methylpyrazole-5-carboxamide
and

PREPARATION 101b

4-Amino-3-n-propyl-2-(pyrimidin-2-yl)methylpyrazole-5-carboxamide

Potassium hydroxide (393 mg, 7 mmol) was added to a stirred, ice-cooled solution of the title compound of Preparation 36 (1.2 g, 6 mmol) in dimethylformamide (10 ml) and the mixture stirred for 1 hour at room temperature. The title compound of Preparation 100 (900 mg, 7 mmol) was then added and the reaction mixture stirred at room temperature for 18 hours, then evaporated under reduced pressure. The residue was partitioned between water (10 ml) and dichloromethane (15 ml), the phases separated and the aqueous phase extracted with dichloromethane (2×15 ml). The combined organic solutions were dried ($MgSO_4$) and evaporated under reduced pressure, then the residue purified by column chromatography on silica gel, using dichloromethane: methanol (95:5) as eluant, to furnish a mixture of the title compounds (not separated) (1.06 g, 67%) as a pale pink solid. Analysis of the $^1$H nmr spectrum indicated a N1:N2 ratio (i.e. 1-isomer:2-isomer) of 22:78. δ (DMSOd$_6$): 0.81 (3H,t), 0.88 (3H,t), 1.38 (2H,m), 1.52 (2H,m), 2.48 (2H,t), 4.10 (2H,s), 4.44 (2H, s), 5.41 (2H,s), 5.73 (2H,s), 6.90 (1H,s), 7.06 (1H,s), 7.35 (1H,m), 7.42 (1H,m), 7.50 (2H,s), 8.68 (2H,d), 8.77 (2H,d). LRMS: m/z 261 (M+1)$^+$.

PREPARATION 102a
4-[5-(4-Ethylpiperazin-1-ylsulphonyl)-2-(2-methoxyethoxy)pyridin-3-ylcarboxamido]-3-n-propyl-1-(pyrimidin-2-yl)methylpyrazole-5-carboxamide
and PREPARATION 102b
4-[5-(4-Ethylpiperazin-1-ylsulphonyl)-2-(2-methoxyethoxy)pyridin-3-ylcarboxamido]-3-n-propyl-2-(pyrimidin-2-yl)methylpyrazole-5-carboxamide Triethylamine (1.12 ml, 8.0 mmol) was added to a stirred, ice-cooled suspension of the title compounds of Preparation 29 (680 mg, 1.6 mmol) and Preparations 101a/101b (417 mg, 1.6 mmol) in dichloromethane (20 ml), then the reaction mixture stirred at room temperature for 18 hours, washed with water (10 ml), dried (MgSO$_4$) and evaporated under reduced pressure. The residual brown foam was purified by column chromatography on silica gel, using an elution gradient of dichloromethane: methanol (98:2 to 95:5), to afford the first title compound (1-isomer; 56 mg, 6%) as an orange gum. δ (CDCl$_3$): 0.96 (3H,t), 1.04 (3H,t), 1.76 (2H,m), 2.42 (2H,q), 2.54 (4H,m), 3.38 (3H,s), 3.86 (2H,t), 4.76 (2H,t), 6.13 (2H,s), 7.11 (1H,m), 8.44 (1H,s), 8.62 (2H,d), 8.78 (1H,s), 10.52 (1H,s). LRMS: m/z 616 (M+1)$^+$; followed by the second title compound (2-isomer; 460 mg, 47%) as an orange foam. δ (CDCl$_3$): 0.84 (3H,t), 1.03 (3H,t), 1.50 (2H,m), 2.40 (2H,q), 2.53 (4H,m), 2.88 (2H,t), 3.11 (4H,m), 3,39 (3H,s), 3.96 (2H,t), 4.85 (2H,q), 5.23 (1H,s), 5.58 (2H,s), 6.70 (1H,s), 7.25 (1H,m), 8.63 (1H,s), 8.74 (2H,d), 8.84 (1H,s), 10.52 (1H,s). LRMS: m/z 616 (M+1)$^+$.

PREPARATION 103a
4-[2-Ethoxy-5-(4-ethylpiperazin-1-ylsulphonyl)pyridin-3-ylcarboxamido]-3-n-propyl-1-(pyrimidin-2-yl) methylpyrazole-5-carboxamide
and PREPARATION 103b
4-[2-Ethoxy-5-(4-ethylpiperazin-1-ylsulphonyl)pyridin-3-ylcarboxamido]-3-n-propyl-2-(pyrimidin-2-yl) methylpyrazole-5-carboxamide Obtained as a mixture of isomers (88%) from the title compounds of Preparation 28 and Preparations 101 a/101b using the procedure of Preparation 45A. LRMS: m/z 586 (M+1)$^+$.

PREPARATION 104
4-Amino-3-n-propyl-1-(pyridin-2-yl)methylpyrazole-5-carboxamide

Obtained as a solid (92%) from the title compound of Preparation 39a, using the procedure of Preparation 41. δ (DMSOd$_6$): 0.88 (3H,t), 1.55 (2H,m), 2.43 (2H,t), 4.18 (2H,s), 5.59 (2H,s), 6.73 (1H,d), 7.22 (1H,m), 7.57 (2H,s), 7.69 (1H,m), 8.47 (1H,d). LRMS: m/z 260 (M+1)$^+$.

PREPARATION 105
4-[2-Ethoxy-5-(4-ethylpiperazin-1-ylsulphonyl)pyridin-3-ylcarboxamido]-3-n-propyl-1-(pyridin-2-yl) methylpyrazole-5-carboxamide Obtained as a brown foam (74%) from the title compounds of Preparation 28 and Preparation 104, using the procedure of Preparation 45A. δ (CDCl$_3$): 0.94 (3H,t), 1.02 (3H,t), 1.62 (5H,m), 2.40 (2H,q), 2.52 (4H,m), 2.64 (2H,t), 3.09 (4H,m), 4.77 (2H,q), 5.58 (2H,s), 5.71 (1H,s), 7.26 (1H,m), 7.40 (1H,d), 7.74 (1H,m), 8.52 (1H,d), 8.67 (1H,s), 8.82 (1H,s), 9.60 (1H,s), 9.96 (1H,s). LRMS: m/z 585 (M+1)$^+$.

PREPARATION 106
4-Amino-3-ethyl-1-(1-methylimidazol-2-yl) methylpyrazole-5-carboxamide Obtained as a pink foam (95%) from the title compound of Preparation 88a, using the procedure of Preparation 40. δ (DMSOd$_6$): 1.09 (3H,t), 2.43 (2H,q), 3.72 (3H,s), 4.37 (2H,s), 5.44 (2H,s), 6.79 (1H,s), 7.08 (1H,s). LRMS: m/z 249 (M+1)$^+$.

PREPARATION 107
4-[2-Ethoxy-5-(4-ethylpiperazin-1-ylsulphonyl)pyridin-3-ylcarboxamido]-3-ethyl-1-(1-methylimidazol-2-yl) methylpyrazole-5-carboxamide Obtained as a solid (78%) from the title compounds of Preparation 28 and Preparation 106, using the procedure of Preparation 45A. δ (CDCl$_3$): 1.01 (3H,t), 1.21 (3H,t), 1.60 (3H,t), 2.40 (2H,q), 2.53 (4H,m), 2.72 (2H,q), 3.08 (4H,m), 3.94 (3H,s), 4.76 (2H,q), 5.54 (2H,s), 5.93 (1H,s), 6.83 (1H,s), 6.92 (1H,s), 8.65 (1H,s), 8.82 (1H,s), 9.95 (1H,s), 10.27 (1H,s). LRMS: m/z 575 (M+2)$^+$.

PREPARATION 108
4-Amino1-(1-methylimidazol-2-yl)methyl-3-n-propylpyrazole-5-carboxamide Obtained as a cream solid (78%) from the title compound of Preparation 91 a, using the procedure of Preparation 40. δ (DMSOd$_6$): 0.87 (3H,t), 1.52 (2H,m), 2.38 (2H,t), 3.70 (3H,s), 4.35 (2H,s), 5.44 (2H,s), 6.78 (1H,s), 7.08 (1H,s). LRMS: m/z 263 (M+1)$^+$.

PREPARATION 109
4-[5-(4-Ethylpiperazin-1-ylsulphonyl)-2-(2-methoxyethoxy)pyridin-3-ylcarboxamido]-1-(1-methylimidazol-2-yl)methyl-3-n-propylpyrazole-5-carboxamide Obtained (67%) from the title compounds of Preparation 25 and Preparation 108, using the procedure of Preparation 52. δ (CDCl$_3$): 0.95 (3H,t), 1.02 (3H,t), 1.66 (2H,m), 2.40 (2H,q), 2.51 (4H,m), 2.63 (2H,t), 3.09 (4H,m), 3.39 (3H,s), 3.88 (3H,s), 3.93 (2H,t), 4.80 (2H,t), 5.56 (2H,s), 5.81 (1H,s), 6.83 (1H,s), 6.92 (1H,s), 8.65 (1H,s), 8.82 (1H,s), 9.60 (1H,s), 10.08 (1 H,s).

PREPARATION 110
3-Bromo-5-(4-ethylpiperazin-1-ylsulphonyl)-2-(1-methylpiperidine-4-yloxy)pyridine A mixture of 4-hydroxy-1-methylpiperidine (560 mg, 4.89 mmol), 60% sodium hydride dispersion in mineral oil (200 mg, 4.89 mmol) and tetrahydrofuran (30 ml) was stirred at about 0° C. for 30 minutes. The title compound of Preparation 13 (600 mg, 1.63 mmol) was added and the reaction mixture heated under reflux for 90 minutes, then allowed to cool. The resulting mixture was evaporated under reduced pressure, the residue suspended in ethyl acetate (50 ml) and the suspension washed consecutively with 2M aqueous sodium hydroxide solution (2×20 ml), water (20 ml) and brine (20 ml). The resulting solution was dried (MgSO$_4$) and evaporated under reduced pressure to give the title compound (660 mg, 70%) as a yellow oil. δ (CDCl$_3$): 1.05 (3H,t), 1.92 (2H,m), 2.04 (2H,m), 2.33 (3H,s), 2.42 (4H,m), 2.55 (4H,m), 2.66 (2H,m), 3.08 (4H,m), 5.24 (1H, m), 8.09 (1H,s), 8.42 (1H,s). LRMS: m/z 447 (M)$^+$.

PREPARATION 111
5-(4-Ethylpiperazin-1-ylsulphonyl)-2-(1-methylpiperidine-4-yloxy)pyridine-3-carboxylic Acid Ethyl Ester Triethylamine (2 ml, 1.43 mmol) and tetrakis (triphenylphosphine)-palladium(0) (200 mg, 0.173 mmol) were added to a stirred solution of the title compound of Preparation 110 (640 mg, 1.43 mmol) in ethanol (20 ml) and the reaction mixture heated under carbon monoxide at 100° C. and 1034 kPa (150 psi) in a sealed vessel for 18 hours, then allowed to cool. The resulting mixture was evaporated under reduced pressure and the residue purified by column chromatography on silica gel, using dichloromethane: methanol (96.5:3.5) as eluant, to yield the title compound (550 mg, 87%) as an orange solid. δ (CDCl$_3$): 1.02 (3H,t), 1.40 (3H,t), 2.16 (2H,m), 2.41 (2H,q), 2.56 (6H,m), 2.72 (3H,s), 3.08 (4H,m), 3.19 (4H,m), 4.38 (2H,q), 5.60 (1H,m), 8.42 (1H,s), 8.62 (1H,s). LRMS: m/z 441 (M+1)$^+$.

PREPARATION 112
5-(4-Ethylpiperazin-1-ylsulphonyl)-2-(1-methylpiperidine-4-yloxy)pyridine-3-carboxylic Acid Sodium Salt A mixture of the title compound of Preparation 111 (550 mg, 1.25 mmol), 1M aqueous sodium hydroxide solution (2.4 ml, 2.40 mmol) and ethanol (5 ml) was stirred at room temperature for 18 hours, then evaporated under reduced pressure. The residue was partitioned between water (15 ml) and ethyl acetate (15 ml), the phases separated and the aqueous phase evaporated under reduced pressure to provide the title compound (510 mg, 94%) as a white solid. δ (DMSOd$_6$): 0.93 (3H,t), 1.94 (2H,m), 2.10 (2H,m), 2.16 (3H,s), 2.29 (2H,q), 2.40 (4H,m), 2.68 (4H,m), 2.88 (4H,m), 5.08 (1H,m), 7.75 (1H,s), 8.28 (1H,s),

PREPARATION 113a
4-Amino-1-(2-morpholin-4-yl)ethyl-3-n-propylpyrazole-5-carboxamide
and

PREPARATION 113b
4-Amino-2-(2-morpholin-4-yl)ethyl-3-n-propylpyrazole-5-carboxamide 4-(2-Chloroethyl)morpholine (obtained by basification of the hydrochloride salt (2.67 g, 1 4.35 mmol)) was added to a stirred solution of the title compound of Preparation 36 (2.0 g, 11.96 mmol) and potassium hydroxide (800 mg, 14.35 mmol) in dimethylformamide (20 ml) and the reaction mixture heated under reflux for 18 hours, then allowed to cool. The resulting mixture was evaporated under reduced pressure and the residue purified by column chromatography on silica gel, using dichloromethane: methanol: glacial acetic acid (95:5:1) as eluant, to furnish the second title compound (2:isomer; 480 mg, 14%). δ (CDCl$_3$): 0.98 (3H,t), 1.60 (2H,m), 2.48 (4H,m), 2.55 (2H,t), 2.76 (2H,t), 3.69 (4H,m), 3.94 (2H,s), 4.08 (2H,t), 5.19 (1H,s), 6.55 (1H,s). LRMS: m/z 282 (M+1)$^+$; followed by the first title compound (1-isomer;350 mg, 10%). δ (CDCl$_3$): 0.97 (3H,t), 1.64 (2H,m), 2.50 (6H,m), 2.81 (2H,t), 3.48 (2H,s), 3.64 (4H,m), 4.50 (2H,t).

PREPARATION 114
3-t-Butyl-1H-pyrazole-5-carboxylic Acid Hydrochloride

Hydrazine hydrate (1.7 ml, 35 mmol) was added dropwise to a stirred solution of 5,5-dimethyl-2,4-dioxohexanoic acid ethylester (J. Org. Chem., 1997, 62, 5908; 6.1 g, 30.5 mmol) in ethanol (20 ml) and the reaction mixture stirred at room temperature for 4 hours, then evaporated under reduced pressure. The residue was partitioned between dichloromethane (20 ml) and water (20 ml), the phases separated and the aqueous phase extracted with dichloromethane (2×20 ml). The combined organic solutions were dried (MgSO$_4$) and evaporated under reduced pressure to give the crude ester as a yellow solid.

A mixture of this product, 1,4-dioxan (100 ml) and 2M aqueous sodium hydroxide solution (25.5 ml, 51 mmol) was stirred at room temperature for 72 hours, then the pH of the reaction mixture adjusted to 2 with hydrochloric acid. The resulting mixture was evaporated under reduced pressure and the residue triturated with hot ethanol. This mixture was filtered and the filtrate evaporated under reduced pressure to afford the title compound (5.06 g, 81%) as an orange solid. δ (DMSOd$_6$): 1.26 (9H,s), 6.46 (1H,s).

PREPARATION 115
3-t-Butyl-4-nitro1H-pyrazole-5-carboxylic Acid

The title compound of Preparation 114 (1.5 g, 7.3 mmol) was added portionwise to stirred, ice-cooled concentrated sulphuric acid (7.5 ml), the mixture warmed to 40° C. and fuming nitric acid (1.13 ml) then added dropwise, so as to maintain the internal temperature below 50° C. The reaction mixture was stirred at 50° C. for 7 hours, allowed to cool and poured carefully onto ice/water (100 g). The resulting suspension was stirred for 2 hours and filtered, then the collected solid washed with water and dried under suction to give the title compound (975 mg, 63%) as a white solid. δ (DMSOd$_6$): 1.33 (9H,s). LRMS: m/z 231 (M+18)$^+$.

PREPARATION 116
3-t-Butyl-4-nitro-1H-pyrazole-5-carboxamide

Oxalyl chloride (1.59 ml, 18.2 mmol) was added dropwise to a stirred, ice-cooled solution of the title compound of Preparation 115 (970 mg, 4.55 mmol) and dimethylformamide (1 drop) in dichloromethane (20 ml) and the reaction mixture stirred at room temperature for 3 hours, then evaporated under reduced pressure. The residue was azeotroped firstly with dichloromethane and then with 0.88 aqueous ammonia solution. The resulting material was triturated with hot ethanol, then acetonitrile, the mixture filtered and the filtrate evaporated under reduced pressure to yield the title compound (955 mg, 99%) as a white solid. δ (DMSOd$_6$): 1.36 (9H,s), 7.60 (1H,s), 7.88 (1H,s). LRMS: m/z 230 (M+18)$^+$.

PREPARATION 117
3-t-Butyl-4-nitro-1-(pyridin-2-yl)methylpyrazole-5-carboxamide A mixture of the title compound of Preparation 116 (960 mg, 4.55 mmol), caesium carbonate (3.7 g, 11.36 mmol) and 2-(chloromethyl)pyridine hydrochloride (821 mg, 5.00 mmol) in acetonitrile (20 ml) was stirred at 70° C. for 20 hours, then allowed to cool and filtered. The filtrate was evaporated under reduced pressure, then the residue purified by column chromatography on silica gel, using an elution gradient of ethyl acetate: methanol (100:0 to 95:5), to provide the title compound (300 mg, 22%) as a yellow solid. δ (DMSOd$_6$): 1.35 (9H,s), 5.40 (2H,s), 7.18 (1H,d), 7.32 (1H,m), 7.80 (1H,m), 8.10 (1H,s), 8.46 (1H,s), 8.51 (1H,d). LRMS: m/z 304 (M+1)$^+$.

PREPARATION 118
4-Amino-3-t-butyl-1-(pyridin-2-yl)methylpyrazole-5-carboxamide A stirred mixture of the title compound of Preparation 117 (290 mg, 0.96 mmol) and 10% palladium on charcoal (29 mg) in ethanol (20 ml) was hydrogenated at 345 kPa (50 psi) and room temperature for 7 hours, then filtered. The filter pad was washed with ethanol and the combined washings and filtrate evaporated under reduced pressure. The residue was purified by column chromatography on silica gel, using an elution gradient of ethyl acetate: methanol (100:0 to 95:5), to furnish the title compound (220 mg, 84%) as an orange solid. δ (CDCl$_3$): 1.36 (9H,s), 4.00 (2H,s), 5.50 (2H,s), 7.23 (1H,m), 7.38 (1H,d), 7.71 (1H,m), 8.50 (1H,d). LRMS: m/z 274 (M+1)$^+$.

PREPARATION 119
4-[5-(4-Ethylpiperazin-1-ylsulphonyl)-2-(1-methylpiperidine-4-yloxy)pyridin-3-ylcarboxamido]-3-n-propyl-2-(pyridin-2-yl)methylpyrazole-5-carboxamide 1-(3-Dimethylaminopropyl)-3-ethylcarbodiimide hydrochloride (350 mg, 1.8 mmol) was added to a stirred solution of 1-hydroxybenzotriazole hydrate (250 mg, 1.8 mmol), triethylamine (350 μl, 2.5 mmol) and the title compounds of Preparation 112 (510 mg, 1.18 mmol) and Preparation 41 (330 mg, 1.25 mmol) in tetrahydrofuran (20 ml) and the reaction mixture stirred at room temperature for 72 hours, then evaporated under reduced pressure. The residue was triturated several times with ethyl acetate to afford the title compound (175 mg, 21%) as a white solid. δ (CDCl$_3$): 0.81 (3H,t), 1.04 (3H,t), 1.47 (2H,m), 2.17 (4H,m), 2.32 (5H,m), 2.40 (2H,q), 2.53 (4H,m), 2.76 (2H,m), 2.84 (2H,t), 3.10 (4H,m), 5.49 (3H,m), 5.64 (1H,s), 6.90 (2H,m), 7.22 (1H, m), 7.68 (1H,m), 8.60 (1H,d), 8.64 (1H,s), 8.82 (1H,s), 10.35 (1H,s). LRMS: m/z 654 (M+1)$^+$.

PREPARATION 120
4-[2-Ethoxy-5-(4-ethylpiperazin-1-ylsulphonyl)pyridin-3-ylcarboxamido]-2-(2-morpholin4-yl)ethyl-3-n-propylpyrazole-5-carboxamide 1-(3-Dimethylaminopropyl)-3-ethylcarbodiimide hydrochloride (280 mg, 1.5 mmol) was added to a stirred solution of 1-hydroxybenzotriazole hydrate (200 mg, 1.5 mmol), triethylamine (278 μl, 2.0 mmol) and the title compounds of Preparation 23 (371 mg, 1.0 mmol) and Preparation 113b (250 mg, 0.9 mmol) in dichloromethane (20 ml) and the reaction mixture stirred at room temperature for 18 hours. The resulting mixture was washed with water (10 ml), dried (MgSO$_4$) and evaporated under reduced pressure, then the residue purified by column chromatography on silica gel, using an elution gradient of dichloromethane: methanol (97:3 to 95:5), to give the title compound (430 mg, 68%) as a white solid. δ (CDCl$_3$): 0.93 (3H,t), 1.02 (3H,t), 1.58 (5H,m), 2.40 (2H,q), 2.52 (8H,m), 2.82 (2H,t), 2.90 (2H,t), 3.12 (4H,m), 3.72 (4H,m), 4.20 (2H,t), 4.79 (2H,q), 5.28 (1H,s), 6.63 (1H,s), 8.64 (1H,s), 8.82 (1H,s), 10.50 (1H,s).

PREPARATION 121
3-t-Butyl-4-[2-ethoxy-5-(4-ethylpiperazin-1-ylsulphonyl)pyridin-3-ylcarboxamido]-1-(pyridin-2-yl)methylpyrazole-5-carboxamide The title compound of Preparation 28 (384 mg, 0.967 mmol) was added dropwise to a stirred, ice-cooled solution of the title compound of Preparation 118 220 mg, 0.805 mmol) and triethylamine (330 μl, 2.42 mmol) in dichloromethane (10 ml) and the reaction mixture stirred at room temperature for 14 hours. The resulting mixture was washed with aqueous sodium bicarbonate solution (5 ml) and brine (5 ml), dried (Na$_2$SO$_4$) and evaporated under reduced pressure. The residue was purified by two column chromatography operations on silica gel, using an elution gradient of ethyl acetate: methanol (100:0 to 90:10) and then of dichloromethane: methanol (100:0 to 95:5), to yield the title compound (156 mg, 32%) as a white solid. δ (CDCl$_3$): 1.02 (3H,t), 1.36 (9H,s), 1.55 (3H,t), 2.42 (2H,q), 2.55 (4H,m), 3.10 (4H,m) 4.77 (2H,q), 5.68 (3H,m), 7.02 (1H,d), 7.19 (1H,m), 7.65 (1H,m), 7.98 (1H,s), 8.56 (1H,d), 8.70 (1H,s), 8.87 (1H,s), 9.35 (1H,s). LRMS: m/z 599 (M+1)$^+$.

PREPARATION 122
4-[2-Ethoxy-5-(4-ethylpiperazin-1-ylsulphonyl)pyridin-3-ylcarboxamido]-1-(2-morpholin-4-yl)ethyl-3-n-propylpyrazole-5-carboxamide 1-(3-Dimethylaminopropyl)-3-ethylcarbodiimide hydrochloride (1.34 g, 7.0 mmol) was added to a stirred solution of 1-hydroxybenzotriazole hydrate (945 mg. 7.0 mmol), N-ethyldiisopropylamine (1.22 ml, 7.0 mmol) and the title compounds of Preparation 113a (1.82 g, 6.5 mmol) and Preparation 23 (428 mg, 1.25 mmol) in tetrahydrofuran (120 ml) and the reaction mixture stirred at room temperature for 72 hours. The resulting mixture was evaporated under reduced pressure and the residue partitioned between aqueous sodium carbonate solution (50 ml) and dichloromethane (10 ml). The phases were separated, the aqueous phase extracted with dichloromethane (2×100 ml) and the combined organic solutions washed with brine (3×50 ml), dried (Na$_2$SO$_4$) and evaporated under reduced pressure. The residue was triturated with ether, then crystallised from ethyl acetate-methanol, to provide the title compound (310 mg, 42%) as a white solid. δ (CDCl$_3$): 0.92 (3H,t), 1.01 (3H,t), 1.54 (3H,t), 1.62 (2H,m). 2.36–2.60 (12H,m), 2.80 (2H,t), 3.08 (4H,m), 3.64 (4H,m), 4.49 (2H,t), 4.72 (2H,q), 5.78 (1H,s), 8.30 (1H,s), 8.66 (1H,s), 8.80 (1H,s), 9.49 (1H,s). LRMS: m/z 607 (M+1)$^+$.

PREPARATION 123
3-Ethyl-1-methyl-4-nitropyrazole-5-carboxamide and

PREPARATION 124
3-Ethyl-2-methyl-4-nitropyrazole-5-carboxamide

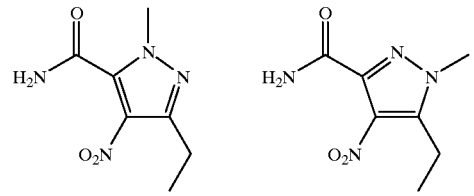

A mixture of the title compound of Preparation 35 (100 g, 0.54 mol), and caesium carbonate (194 g, 0.60 mol) in N,N-dimethylformamide (1000 ml) was stirred at room temperature for 45 minutes, then cooled in an ice-bath. Methyl iodide (37.2 ml, 0.60 mol) was added dropwise and once the addition was complete, the reaction was stirred at room temperature for 18 hours. The mixture was concentrated under reduced pressure and the residue partitioned between ethyl acetate (500 ml) and water (300 ml). The layers were separated, the aqueous phase extracted with ethyl acetate (4×500 ml) and the combined organic solutions dried (MgSO$_4$) and evaporated under reduced pressure. The crude product was recrystallised from dichloromethane/ethyl acetate to give some of the N1 isomer (17.0 g, 16%).

The filtrate was evaporated under reduced pressure and the residue was purified by column chromatography on silica gel, using ethyl acetate: pentane (80:20) as eluant to afford the title compound of Preparation 123 (25.0 g, 23%) as a white solid. δ (CDCl₃): 1.27 (3H, t), 2.94 (2H, q), 4.06 (3H, s), 6.00 (1H, br s), 7.56 (1H, br s). LRMS: m/z 216 (M+18)⁺ and the title compound of Preparation 124 (28.4 g, 27%) as a white solid. δ (CDCl₃): 1.29 (3H, t), 3.00 (2H, q), 3.92 (3H, s), 5.98 (1H, s), 7.32 (1H, s).

PREPARATION 125
2-Methyl-3-n-propyl-pyrazole-5-carboxylic Acid Ethyl Ester

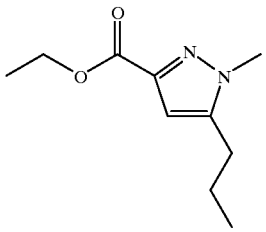

A solution of diethyloxalate (27.2 ml, 0.2 mol) in 2-pentanone (21.2 ml, 0.2 mol) was added dropwise to a solution of sodium (4.83 g, 0.21 mol) in ethanol (200 ml), and the reaction stirred at 60° C. for 5 hours, then cooled in an ice-bath. The solution was neutralised using acetic acid (11.5 ml, 0.2 mol) and N-methyl hydrazine (10.6 ml, 0.2 mol) then added dropwise. The mixture was stirred for a further 4 hours at room temperature and concentrated under reduced pressure. The residue was partitioned between dichloromethane (300 ml) and water (200 ml), and the phases separated. The aqueous layer was extracted with dichloromethane (3×100 ml), the combined organic solutions were dried (MgSO₄) and evaporated under reduced pressure. The crude is product was purified by column chromatography on silica gel, using ethyl acetate: hexane (25:75) as eluant to give ethyl 1-methyl-3-n-propyl-pyrazole-5-carboxylate (6.1 g) and the title compound (22.1 g, 56%). δ (CDCl₃): 1.00 (3H, t), 1.40 (3H, t), 1.70 (2H, m), 2.60 (2H, t), 3.87 (3H, s), 4.40 (2H, q), 6.60 (1H, s).

PREPARATION 126
2-Methyl-3-n-propylpyrazole-5-carboxylic Acid

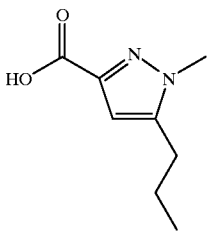

A mixture of the title compound of Preparation 125 (21.5 g, 0.11 mol) in aqueous sodium hydroxide solution (50 ml, 6 N, 0.3 mol) was heated under reflux for 3 hours. The cooled mixture was diluted with water (50 ml) and acidified using concentrated hydrochloric acid (25 ml) and the resulting precipitate was filtered and dried to give the title compound (17.3 g, 94%) as a pale yellow solid. A portion (1 g) of this solid, was recrystallised from water/ethanol. m.p. 120–122° C. δ (DMSOd₆): 0.95 (3H, t), 1.59 (2H, m), 2.60 (2H, t), 3.78 (3H, s), 6.48 (1H, s), 12.45 (1H, s).

PREPARATION 127
2-Methyl-4-nitro-3-n-propylpyrazole-5-carboxylic Acid

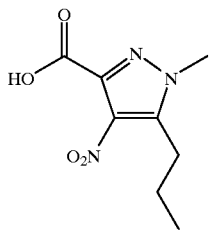

Obtained as a solid (89%) from the title compound of Preparation 126, using a similar procedure to that described in Preparation 32. δ (DMSOd₆): 0.95 (3H, t), 1.60 (2H, m), 2.96 (2H, t), 3.88 (3H, s), 13.75 (1H, s).

PREPARATION 128
2-Methyl-4-nitro-3-n-propylpyrazole-5-carboxamide

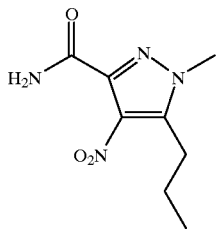

A mixture of the title compound of Preparation 127 (18.6 g, 87.3 mmol) in thionyl chloride (75 ml), was heated under reflux for 2 hours. The cooled reaction mixture was concentrated under reduced pressure and the residue poured into an ice/ammonium hydroxide mixture. This was extracted with dichloromethane (4×100 ml) and the combined organic extracts dried (MgSO₄) and evaporated under reduced pressure. The crude product was purified by column chromatography on silica gel, using dichloromethane:methanol:0.88 ammonia (95:5:1) as eluant to afford the title compound (6.8 g, 37%) as a solid. δ (CDCl₃): 1.07 (3H, t), 1.72 (2H, m), 3.00 (2H, t), 3.97 (3H, s), 6.14 (1H, s), 7.40 (1H, s).

PREPARATION 129
2,3-Diethyl-4-nitro-pyrazole-5-carboxamide

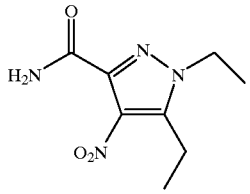

Ethyl iodide (7.2 ml, 90.0 mmol) was added to a suspension of the title compound of Preparation 35 (15.0 g, 81.0 mmol), and cesium carbonate (29.3 g, 90.0 mmol) in N,N-dimethylformamide (100 ml) and the reaction stirred at room temperature for 18 hours. The mixture was concentrated under reduced pressure and the residue triturated with water (100 ml), and the resulting solid filtered and dried. A suspension of this solid in ether (250 ml) was heated at 35° C. for an hour, and the precipitate filtered and dried. This was recrystallised from ethyl acetate to afford the title compound as a crystalline solid (5.8 g, 34%). δ (CDCl₃): 1.30 (3H, t), 1.54 (3H, t), 3.00 (2H, q), 4.20 (2H, q), 5.92 (1H,s), 7.27 (1H,s). LRMS: m/z 212 (M)⁺

PREPARATION 130
3-Ethyl-4-nitro-2-(pyridazin-3-yl)methyl-pyrazole-5-carboxamide

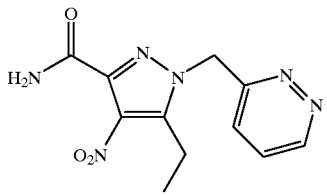

A mixture of the title compounds of Preparation 35 (2.66 g, 14.5 mmol), and 95 (2.65 g, 16.1 mmol) and caesium carbonate (13.1 g, 40.2 mmol) in acetonitrile (100 ml) was stirred under reflux for 18 hours. The cooled reaction was concentrated under reduced pressure, the residue suspended in water and extracted with dichloromethane (5×100 ml). The combined organic extracts were dried (Na₂SO₄), adsorbed onto silica gel and the product isolated by column chromatography on silica gel, using an elution gradient of methanol: dichloromethane (5:95 to 10:90) to give 3-ethyl-4-nitro-1-(pyridazin-3-yl)methylpyrazole-5-carboxamide (1.31 g), and the title compound (1.81 g, 45%) as a pale yellow solid. δ (CDCl₃): 1.20 (3H, t), 3.11 (2H, q), 5.72 (2H, s), 5.89 (1H, s), 7.29 (1H, s), 7.55 (2H, m), 9.20 (1H, d). LRMS: m/z 277 (M+1)⁺

PREPARATION 131
3-Ethyl-4-nitro-2-[1-(pyridin-2yl)ethyl]-pyrazole-5-carboxamide

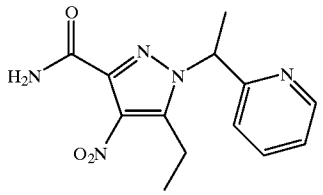

A mixture of 2-ethylpyridine (20.0 g, 187 mmol), N-bromosuccinimide (38.0 g, 213 mmol), and benzoyl peroxide (1.0 g, 75% in water) in 1,1,1-trichloroethane (200 ml), was heated under reflux for 3 hours. The cooled mixture was filtered, and the filtrate washed with water (2×100 ml), aqueous sodium thiosulphate solution (100 ml), and brine (100 ml). The solution was dried (MgSO₄), filtered through charcoal, and then hydrobromic acid (25 ml, 62%) added. This solution was concentrated under reduced pressure and azeotroped with toluene to give 2-(1-bromoethyl)pyridine hydrochloride as a dark oil (66.0 g). A mixture of the title compound of Preparation 35 (8.0 g, 43.4 mmol), caesium carbonate (35.0 g, 107.4 mmol) and the crude 2-(1-bromoethyl)pyridine hydrochloride (13.6 g, 52.0 mmol) in N,N-dimethylformamide (80 ml) was stirred at room temperature for 20 hours. The mixture was concentrated under reduced pressure and the residue partitioned between ethyl acetate (150 ml) and water (50 ml). The layers were separated and the organic phase washed with more water (3×50 ml), brine (50 ml), then dried (MgSO₄) and evaporated under reduced pressure. The residual oil was purified by column chromatography on silica gel, using an elution gradient of pentane: ethyl acetate: methanol (90:10:0 to 0:100:0 to 0:90:10) to afford the N1 isomer (4.3 g), and the title compound (5.7 g, 45%). δ (CDCl₃): 1.14 (3H, t), 2.01 (3H, d), 3.00 (2H, q), 5.66 (2H, q 5.88 (1H, s), 6.98 (1H, s), 7.18 (1H, d), 7.25 (1H, m), 7.68 (1H, m), 8.56 (1H, d). LRMS: m/z 290 (M+1)⁺

PREPARATION 132
3-Ethyl-2-(6-methylpyridin-2-yl)methyl-4-nitropyrazole-5-carboxamide

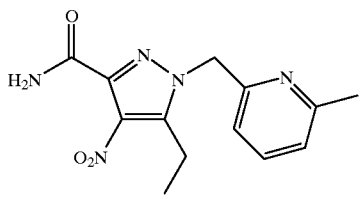

A mixture of the title compound of Preparation 35 (4.32 g, 23.5 mmol) and 6-methyl-2-picolyl chloride hydrochloride (5.0 g, 23.4 mmol) in N,N-dimethylformamide (50 ml) was stirred at room temperature for 20 hours. The reaction mixture was concentrated under reduced pressure and the residue partitioned between water (50 ml) and dichloromethane (50 ml). The layers were separated and the aqueous phase extracted with dichloromethane (3×50 ml), the combined organic solutions washed with brine (50 ml), dried (MgSO₄) and evaporated under reduced pressure. The residue was purified by column chromatography on silica gel, twice, using dichloromethane: methanol (95:5) as eluant and repeated using an elution gradient of pentane: ethyl acetate (50:50 to 0:100) to give the N1 isomer (1.0 g) and the title compound (2.47 g, 36%) as a white solid. δ (CDCl₃): 1.18 (3H, t), 2.53 (3H, s), 3.06 (2H, q), 5.42 (2H, s), 5.97 (1H,s), 6.90 (1H, d), 7.12 (1H, d), 7.22 (1H, s), 7.58 (1H, m). LRMS: m/z 312 (M+23)⁺

PREPARATION 133
2-Methoxy-6-methylpyridine

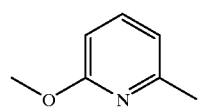

Trimethyloxonium tetrafluoroborate (10.0 g, 67.6 mmol) was added portionwise to a suspension of 6-methylpyridin-2-one (7.3 g, 67.0 mmol) in dichloromethane (100 ml), and once addition was complete, the reaction was stirred at room temperature for 24 hours. Dichloromethane (50 ml) and aqueous sodium hydroxide solution (50 ml, 2N) were added and the layers separated. The aqueous phase was extracted with dichloromethane (2×50 ml), the combined organic solutions washed with brine (50 ml), dried (MgSO₄) and evaporated under reduced pressure. The crude product was purified by column chromatography on silica gel, using an elution gradient of pentane: dichloromethane (66:34 to 0:100) to afford the title compound (2.25 g, 27%) as a colourless oil. δ (CDCl₃): 2.49 (3H, s), 3.90 (3H, s), 6.38–6.73 (2H, m), 7.23–7.40 (1 H, br d).

PREPARATION 134

6-Bromomethyl-2-methoxypyridine

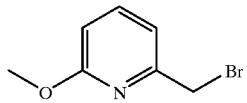

A mixture of the title compound of Preparation 133 (2.5 g, 20.3 mmol), N-bromosuccinamide (3.7 g, 20.8 mmol) and benzoyl peroxide (100 mg, 0.41 mmol) in 1,1,1-trichloroethane (50 ml) was stirred under reflux for 3 hours, and a further 16 hours at room temperature. The reaction was washed with water (2×25 ml), aqueous sodium thiosulphate solution (25 ml), brine (25 ml) and dried (MgSO$_4$) and evaporated under reduced pressure. The residue was shaken well with hydrobromic acid (62%, 2.4 ml), and the suspension concentrated under reduced pressure, and azeotroped twice with toluene, to give the title compound as a yellow solid. δ (CDCl$_3$): 3.95 (3H, s), 4.46 (2H, s), 6.63 (1H, d), 6.98 (1H, d), 7.53 (1H, m). LRMS: m/z 202/204 (M+1)$^+$

PREPARATION 135

3-Ethyl-2-(6-methoxypyridin-2-yl)methyl-4-nitro-pyrazole-5-carboxamide

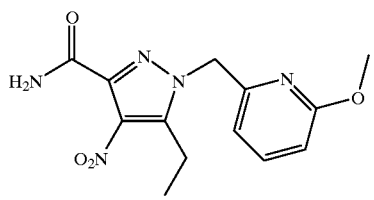

A mixture of the title compound of Preparation 134 (5.2 g, 18.4 mmol), caesium carbonate (6.58 g, 32.5 mmol) and the title compound of Preparation 35 (3.4 g, 18.4 mmol) in N,N-dimethylformamide (30 ml) was stirred at room temperature for 18 hours. The reaction was concentrated under reduced pressure, the residue partitioned between ether (100 ml) and water (50 ml), and the phases separated. The organic layer was washed with brine (20 ml), dried (MgSO$_4$) and evaporated under reduced pressure. The residual gum was triturated with ether, to give the title compound (640 mg, 11%) as a white solid. The filtrate was evaporated under reduced pressure and the residue purified by column chromatography on silica gel, using pentane: ethyl acetate (66:34) as eluant to give a further (280 mg, 5%) of the title compound. δ (DMSOd$_6$): 1.18 (3H, t), 2.84 (2H, q), 3.68 (3H, s), 5.34 (2H, s), 6.73 (2H, m), 7.66 (1H, m), 8.17 (1H, s), 8.39 (1H, s). LRMS: m/z 306 (M+1)$^+$

PREPARATION 136

4-Amino2-methyl-3-n-propylpyrazole-5-carboxamide

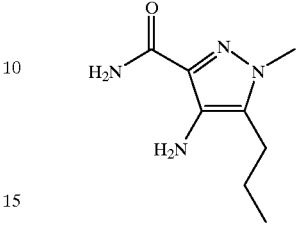

A mixture of the title compound of Preparation 128 (6.17 g, 29.0 mmol) and tin (II) chloride dihydrate (32.8 g, 145 mmol) in industrial methylated spirits (IMS) (100 ml) was heated under reflux for 2 hours. The cooled mixture was concentrated under reduced pressure to approximately half it's volume, basified to pH 9 using aqueous 2N sodium hydroxide solution, and extracted with dichloromethane (3×300 ml). The combined organic extracts were dried (MgSO$_4$) and evaporated under reduced pressure and the crude product recrystallised from ethyl acetate/methanol to afford the title compound (4.86 g, 92%). m.p.170–174° C. δ (DMSOd6): 0.90 (3H, t), 1.47 (2H, m), 2.50 (2H, t), 3.68 (3H, s), 4.43 (2H,s), 6.92 (1H, s), 7.04 (1H, s).

PREPARATION 137

4-Amino-2.3-diethyl-pyrazole-5carboxamide

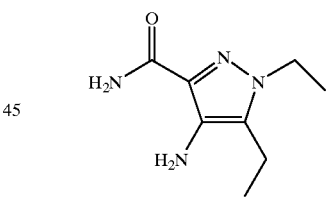

A mixture of the title compound of Preparation 129 (5.7 g, 26.9 mmol) and tin (II) chloride dihydrate (29.0 g, 128 mmol) in ethanol (200 ml) was heated under reflux for 45 minutes. The cooled reaction mixture was evaporated under reduced pressure and re-dissolved in ethyl acetate (200 ml). This solution was poured into a 10% aqueous solution of sodium carbonate (400 ml), and the mixture stirred vigorously for an hour. The layers were separated and the aqueous phase was extracted with ethyl acetate (2×100 ml). The combined organic solutions were dried (Na$_2$SO$_4$) and concentrated under reduced pressure to a volume of 50 ml, and the resulting crystals filtered off and dried, to afford the title compound (3.3 g, 67%). δ (CDCl$_3$): 1.19 (3H, t), 1.40 (3H, t), 2.59 (2H, q), 3.94 (2H, q), 4.02 (2h, q), 5.20 (1H, s), 6.57 (1H, s). LRMS: m/z 183 (M+1)$^+$

PREPARATION 138

4-Amino-3-ethyl-2-methylpyrazole-5-carboxamide

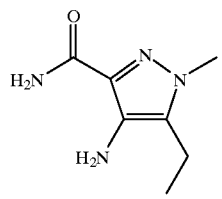

A mixture of the title compound of Preparation 124 (5.8 g, 29.3 mmol) and 10% palladium on charcoal (650 mg) in ethanol (100 ml) was hydrogenated at 60 psi and room temperature for 20 hours. The reaction was filtered through Arbocel® and the filter pad washed well with hot ethanol (200 ml). The combined filtrate was evaporated under reduced pressure to afford the title compound as a solid (4.7 g, 95%). δ (CDCl$_3$): 1.20 (3H, t), 2.59 (2H, q), 3.77 (3H, s), 3.95 (2H, s), 5.21 (1H,s), 6.54 (1H, s).

PREPARATIONS 139 TO 142

The compounds of the following tabulated Preparations of general formula:

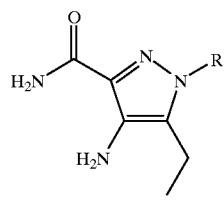

were prepared from the corresponding nitropyrazoles, using a similar procedure to that described in Preparation 138.

PREPARATION 143

4-Amino-3-ethyl-1-methyl-pyrazole-5-carboxamide

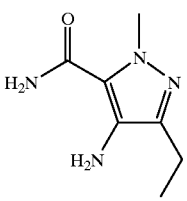

A mixture of the title compound of Preparation 123 (940 mg, 4.75 mmol), and 10% palladium on charcoal (200 mg) in ethanol (100 ml) was hydrogenated at 50 ° C. and 50 psi for 18 hours. The cooled mixture was filtered through Arbocei®, and the filtrate evaporated under reduced pressure to afford the title compound (786 mg, 98%) as a clear oil. δ (CDCl$_3$): 1.23 (3H, t), 2.59 (2H, q), 2.82 (2H, s), 4.12 (3H, s). LRMS: m/z 169 (M+1)$^+$

PREPARATION 144

3-Bromo-2-chloro-5-(4-methylpiperazin-1-ylsulphonyl) pyridine

| Preparation | R | LRMS: m/z | $^1$H nmr |
|---|---|---|---|
| 139 | | | δ (CDCl$_3$): 0.98 (3H, t), 1.93 (3H, d), 2.50 (2H, q), 3.98 (2H, s), 5.23 (1H, s), 5.50 (1H, q), 6.68 (4H, s), 6.80 (1H, d), 7.17 (1H, m), 7.59 (1H, m), 8.54 (1H, d). |
| 140 | | 282 (M + 23)$^+$ | δ (CDCl$_3$): 1.04 (3H, t), 2.55 (5H, m), 4.00 (2H, s), 5.19 (1H, s), 5.30 (2H, s), 6.52 (1H, d), 6.60 (1H, s), 7.03 (1H, d), 7.48 (1H, m). |
| 141[1] | | 298 (M + 23)$^+$ | δ (CDCl$_3$): 1.22 (3H, t), 2.57 (2H, q), 3.78 (2H, s), 3.84 (3H, s), 5.45 (2H, s), 6.68 (1H, d), 6.90 (1H, d), 7.58 (1H, m). |
| 142 | | 247 (M + 1)$^+$ | δ (CDCl$_3$): 1.05 (3H, t), 2.58 (2H, q), 4.01 (2H, s), 5.28 (1H, br s), 5.59 (2H, s), 6.60 (1H, br s), 7.11 (1H, d), 7.42 (1H, m), 9.15 (1H, d). |

[1] = purified by column chromatography using ethyl acetate as eluant

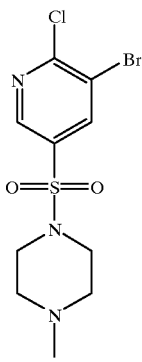

N-Methylpiperazine (7.65 ml, 69.0 mmol) was added dropwise to a solution of the title compound of Preparation 12 (10.0 g, 34.5 mmol) in ethanol (200 ml), and the reaction stirred at room temperature for 3 hours. The mixture was concentrated under reduced pressure and the residue partitioned between dichloromethane (200 ml) and water (100 ml) and the layers separated. The organic phase was dried (Na$_2$SO$_4$), and evaporated under reduced pressure to afford the title compound (10.53 g, 87%) as a yellow solid. δ (CDCl$_3$): 2.28 (3H, s), 2.51 (4H, m), 3.14 (4H, m), 8.24 (1H, s), 8.67 (1H, s).

PREPARATION 145

3-Bromo-2-ethoxy-5-(4-methylpiperazin-1-ylsulphonyl)pyridine

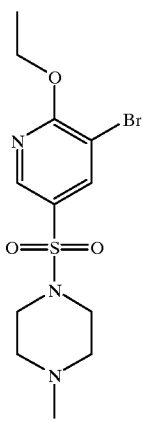

A mixture of the title compound of Preparation 144 (10.0 g, 39.1 mmol), potassium bis(trimethylsilyl)amide (5.92 g, 29.7 mmol) and ethanol (3.5 ml) in tetrahydrofuran (150 ml) was stirred at room temperature for 24 hours. The reaction mixture was concentrated under reduced pressure and the residue partitioned between ethyl acetate (150 ml) and brine (50 ml). The layers were separated, and the organic phase dried (Na$_2$SO$_4$), filtered and evaporated under reduced pressure, to afford the title compound, (9.1 g, 88%). δ (CDCl$_3$): 1.44 (3H, t), 2.29 (3H, s), 2.51 (4H, m), 3.08 (4H, m), 4.54 (2h, q), 8.10 (1H, s), 8.44 (1H, s). LRMS: m/z 365 (M+1)$^+$

PREPARATION 146

3-Bromo-5-(4-ethylpiperazin-1-ylsulphonyl)-2-n-propylaminopyridine

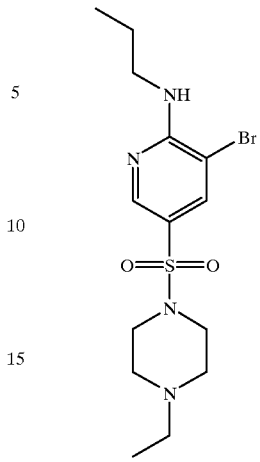

A mixture of the title compound of Preparation 13 (1.11 g, 3.0 mmol) and n-propylamine (590 mg, 10.0 mmol) in toluene (20 ml) was stirred under reflux for 90 minutes. The cooled mixture was partitioned between ethyl acetate (50 ml) and water (20 ml), and the layers separated. The organic phase was washed with brine (20 ml), dried (Na$_2$SO$_4$) and evaporated under reduced pressure. The residue was purified by column chromatography on silica gel, using an elution gradient of dichloromethane: methanol (100:0 to 96:4) to afford the title compound (1.15 g, 98%) as a yellow crystalline solid. δ (CDCl$_3$): 1.02 (6H, m), 1.68 (2H, m), 2.41 (2H, q), 2.54 (4H, m), 3.06 (4H,m), 3.47 (2H, q), 5.57 (1H, m), 7.86 (1H, s), 8.40 (1H, s). LRMS: m/z 393 (M+2)$^+$

PREPARATION 147

2-Ethoxy-5-(4-methylpiperazin-1-ylsulphonyl)pyridine-3-carboxylic Acid Ethyl Ester

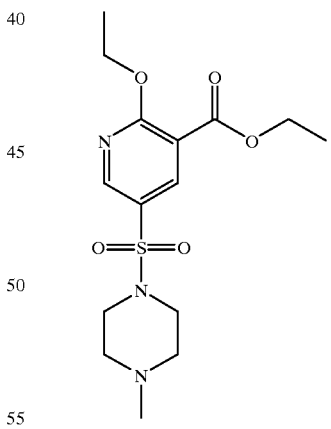

Obtained (85%) as an orange solid, from the title compound of Preparation 145 using a similar procedure to that described in Preparation 21. δ (CDCl$_3$): 1.40 (3H, t), 1.46 (3H, t), 2.28 (3H, s), 2.50 (4H, m), 3.09 (4H, m), 4.40 (2H, q), 4.57 (2H, q), 8.40 (1H, s), 8.63 (1H, s). LRMS m/z 358 (M+1)$^+$

PREPARATION 148

5-(4-Ethylpiperazin-1-ylsulphonyl)-2-n-propylaminotyridine-3-carboxylic Acid Ethyl Ester

121

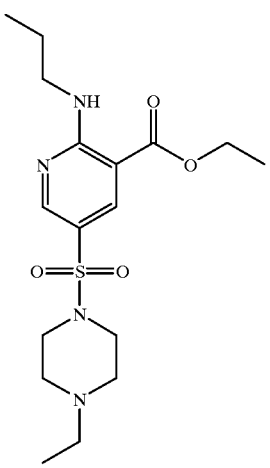

A mixture of the title compound of Preparation 146 (1.10 g, 2.81 mmol), triethylamine (5 ml), and tetrakis(triphenylphosphine)palladium (0) (250 mg, 0.216 mmol) in ethanol (25 ml) was stirred under an atmosphere of carbon monoxide at 100° C. and 100 psi for 16 hours. The cooled solution was evaporated under reduced pressure and the residue purified by column chromatography on silica gel, using an elution gradient of dichloromethane: methanol (100:0 to 96:4) to afford the title compound (1.07 g, 99%) as a yellow oil. δ (CDCl$_3$): 1.02 (6H, t), 1.40 (3H, t), 1.69 (2H, m), 2.40 (2H, q), 2.55 (4H, m), 3.05 (4H, m), 3.54 (2H, q), 4.37 (2H, q), 8.37 (1H, s), 8.57 (2H, m). LRMS: m/z 385 (M+1)$^+$

PREPARATION 149
2-Ethoxy-5-(4-methylpiperazin-1-ylsulphonyl)pyridine-3-carboxylic Acid Hydrochloride

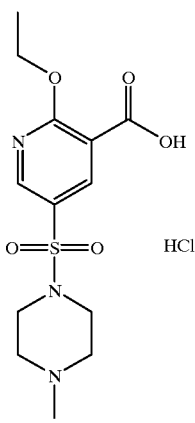

Sodium hydroxide solution (21 ml, 2M, 42.0 mmol) was added to a solution of the title compound of Preparation 147 (7.57 g, 21.0 mmol) in dioxan (150 ml) and is the reaction stirred at room temperature for 18 hours. The mixture was neutralised using hydrochloric acid, the dioxan removed under reduced pressure and the remaining aqueous solution acidified to pH 2, using hydrochloric acid. The solution was evaporated under reduced pressure, the residue re-suspended in hot ethanol, filtered, and the filtrate re-evaporated to afford the title compound (5.46 g, 71%). δ (DMSOd$_6$): 1.37 (3H, t), 2.50 (4H, m), 2.72 (3H, s), 3.13–3.39 (4H, m), 4.53 (2H, q), 8.30 (1H, s), 8.75 (1H, s). LRMS: m/z 330 (M+1)$^+$

PREPARATION 150
5-(4-Ethylpiperazin-1-ylsulphonyl)-2-n-propylaminopyridine-3-carboxylic Acid Sodium Salt

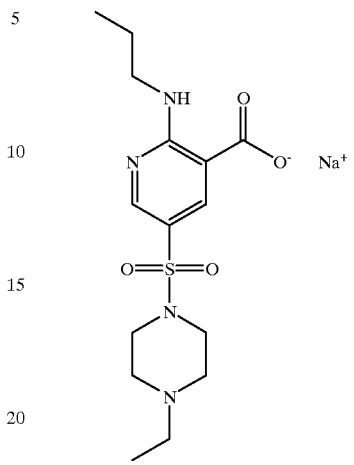

A mixture of the title compound of Preparation 148 (1.06 g, 2.76 mmol) in sodium hydroxide solution (1.5 ml, 2N, 3.0 mmol) and ethanol (10 ml) was stirred at room temperature for 4 hours. The reaction was evaporated under reduced pressure, the solid triturated with ether, and the suspension filtered and dried to afford the title compound (950 mg). δ (DMSOd$_6$): 0.87 (6H, t), 1.50 (2H, m), 2.43 (2H, q), 2.56 (4H, m), 2.78 (4H, m), 3.34 (2H, t), 8.08 (1H, s), 8.16 (1H, s).

PREPARATION 151
4-[2-Ethoxy-5-(4-methylpiperazin-1-ylsulphonyl)pyridin-3-ylcarboxamido]-2-methyl-3-n-propylpyrazole-5-carboxamide

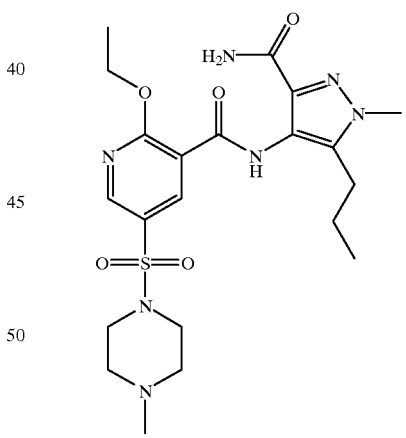

The title compound of Preparation 136 (525 mg, 2.88 mmol) was added to a mixture of the title compound of Preparation 149 (1.04 g, 3.2 mmol), 1-hydroxybenzotriazole hydrate (470 mg, 3.5 mmol), 1-(3-dimethylaminopropyl)-3-ethylcarbodiimide hydrochloride (670 mg, 3.5 mmol) and N-ethyldiisopropylamine (2.4 ml, 14.0 mmol) in tetrahydrofuran (50 ml), and the reaction stirred at room temperature for 36 hours. The reaction mixture was concentrated under reduced pressure and the residue suspended in sodium carbonate solution (20 ml) and extracted with dichloromethane (3×20 ml). The combined organic extracts were washed with brine (3×20 ml), dried (Na$_2$SO$_4$) and evaporated under reduced pressure. The crude product was triturated with ether to give a yellow solid which was then purified by column chromatography on silica gel, using an elution gradient of dichloromethane:methanol (100:0 to 96:4) to give the title compound (720 mg, 51%) as a white solid.

A sample (50 mg) of this product was recrystallised from ethyl acetate to give colourless crystals (32 mg) of the title compound. m.p. 242–244° C. δ (CDCl$_3$): 0.95 (3H, t), 1.59 (5H, m), 2.27 (3H, s), 2.48 (4H, m), 2.89 (2H, t), 3.10 (4H, m), 3.86 (3H, s), 4.79 (2H, q), 5.27 (1H, s), 6.63 (1H, s), 8.65 (1H, s), 8.84 (1H, s), 10.53 (1H, s). LRMS: m/z 494 (M+1)$^+$

PREPARATION 152

4-[2-Ethoxy-5-(4-ethylpiperazin-1-ylsulphonyl)pyridin-3-ylcarboxamido]-3-ethyl-2-methylpyrazole-5-carboxamide

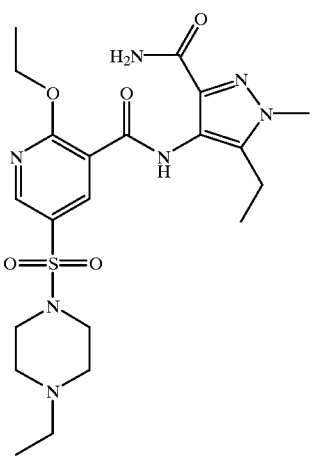

Obtained as a solid (65%) from the title compounds of Preparations 23 and 138, following the procedure described in Preparation 151. δ (CDCl$_3$): 1.02 (3H, t), 1.21 (3H, t), 1.58 (3H, t), 2.39 (2H, q), 2.54 (4H, m), 2.90 (2H, q), 3.10 (4H, m), 3.84 (3H, s), 4.78 (2H, q), 5.30 (1H, s), 6.63 (1H, s), 8.64 (1H, s), 8.83 (1H, s), 10.54 (1H, s). LRMS: m/z 494 (M+1)$_+$

PREPARATION 153

4-[2-Ethoxy-5-(4-ethylpiperazin-1-ylsulphonyl)pyridin-3-ylcarboxamido]-2-methyl-3-n-propylpyrazole-5-carboxamide

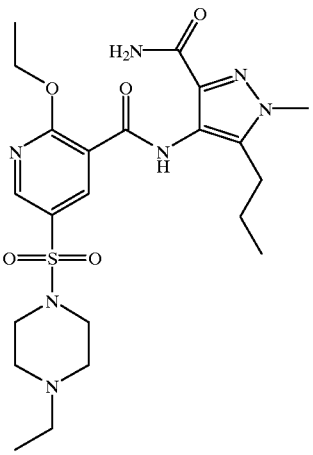

Obtained as a solid (64%) from the title compounds of Preparations 23 and 136, following a similar procedure to that described in Preparation 151, except an elution gradient of methanol: ethyl acetate (7:93 to 10:90) was used as the chromatographic eluant. δ (CDCl$_3$): 0.94 (3H, t), 1.02 (3H, t), 1.60 (5H, m), 2.40 (2H, q), 2.54 (4H, m), 2.89 (2H, t), 3.10 (4H, m), 3.84 (3H, s), 4.78 (2H, q), 5.25 (1H, s), 6.63 (1H, s), 8.65 (1H, s), 8.83 (1H, s), 10.52 (1H, s). LRMS: m/z 508 (M+1)$^+$

PREPARATION 154

4-[2-Ethoxy-5-(4-ethylpiperazin-1-ylsulphonyl)pyridin-3-ylcarboxamido]-2,3-diethylpyrazole-5-carboxamide

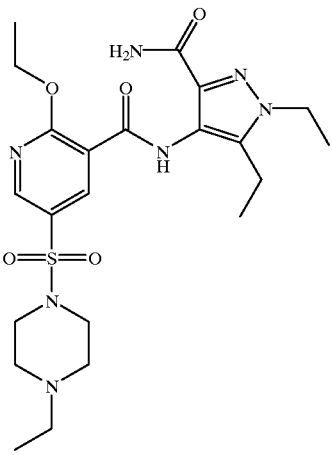

The title compound of Preparation 137 (3.3 g, 16.8 mmol) and triethylamine (7.5 ml, 54.0 mmol) were added to an ice-cooled solution of the title compound of Preparation 28 (6.51 g, 18.0 mmol) in dichloromethane (100 ml), and the reaction was stirred at room temperature for 18 hours. The mixture was washed consecutively with brine (50 ml), aqueous sodium bicarbonate solution (2×50 ml), then dried (Na$_2$SO$_4$) and evaporated under reduced pressure. The residue was purified by column chromatography on silica gel, using an elution gradient of dichloromethane:methanol (100:0 to 90:10) to afford the title compound as a solid. δ (CDCl$_3$): 1.04 (3H, t), 1.22 (3H, t), 1.50 (3H, t), 1.59 (3H, t), 2.40 (2H, q), 2.54 (4H, m), 2.91 (2H, q), 3.10 (4H, m), 4.16 (2H, q), 4.78 (2H, q), 5.30 (1H, s) 6.68 (1H, s), 8.65 (1H, s), 8.84 (1H, s), 10.55 (1H, s). LRMS: m/z 508 (M+1)$^+$

PREPARATIONS 155 TO 157

The compounds of the following tabulated Preparations of the general formula:

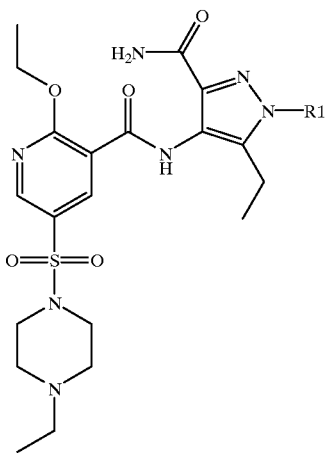

were prepared, from the title compound of Preparation 28 and the appropriate amines, following similar procedures to that described in Preparation 154.

PREPARATION 158

4-[2-Ethoxy-5-(4-ethylpiperazin-1-ylsulphonyl)pyridin-3-ylcarboxamido]-3-ethyl-1-methylpyrazole-5-carboxamide

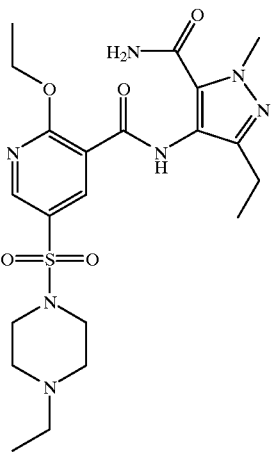

Obtained (51%) as a white solid from the title compounds of Preparations 23 and 143, using a similar procedure to that described in Preparation 151. δ (CDCl$_3$): 1.03 (3H, t), 1.25 (3H, t), 1.57 (3H, t), 2.42 (2H, q), 2.58 (6H, m), 3.10 (4H, m), 4.06 (3H, s), 4.76 (2H, q), 5.57 (1H, br s), 7.55 (1H, br s), 8.70 (1H, s), 8.83 (1H, s) 9.24 (1H, s). LRMS: m/z 494 (M+1)$^+$

PREPARATION 159

4-[2-Ethoxy-5-(4-ethylpiperazin-1-ylsulphonyl)pyridin-3-ylcarboxamido]-1-methyl-3-n-propylpyrazole-5-carboxamide

| Prep. | R1 | Data |
|---|---|---|
| 155[1] | *-CH(CH$_3$)-(2-pyridyl) | δ (CDCl$_3$): 1.02 (6H, m), 1.59 (3H, t), 1.98 (3H, d), 2.40 (2H, q), 2.54 (4H, m), 2.86 (2H, q), 3.09 (4H, m), 4.79 (2H, q), 5.32 (1H, s), 5.67 (1H, q), 6.77 (1H, s), 6.94 (1H, d), 7.20 (1H, m), 7.63 (1H, m), 8.58 (1H, d), 8.65 (1H, s), 8.82 (1H, s), 10.55 (1H, s). LRMS: m/z 585 (M + 1)$^+$ |
| 156[2] | *-CH$_2$-(6-methyl-2-pyridyl) | δ (CDCl$_3$): 1.04 (6H, m), 1.59 (3H, t), 2.40 (2H, q), 2.52 (4H, m), 2.59 (3H, s), 2.89 (2H, q), 3.09 (4H, m), 4.80 (2H, q), 5.30 (1H, s), 5.42 (2H, s), 6.62 (1H, d), 6.70 (1H, s), 7.08 (1H, d), 7.54 (1H, m), 8.64 (1H, s), 8.82 (1H, s), 10.61 (1H, s). |
| 157[2] | *-CH$_2$-(6-methoxy-2-pyridyl) | δ (CDCl$_3$): 1.04 (3H, t), 1.23 (3H, t), 1.59 (3H, t), 2.41 (2H, q), 2.54 (4H, m), 2.70 (2H, q), 3.10 (4H, m), 3.86 (3H, s), 4.78 (2H, q), 5.52 (2H, s), 5.66 (1H, s), 6.70 (1H, d), 6.93 (1H, d), 7.59 (1H, m), 8.68 (1H, s), 8.83 (1H, s), 9.02 (1H, s), 9.90 (1H, s). LRMS: m/z 601 (M + 1)$^+$ |

[1] = the title compound was isolated by trituration with ether.
[2] = ethyl acetate: methanol (94:6) was used as the chromatographic eluant.

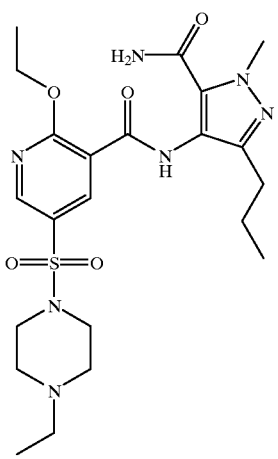

A mixture of the title compounds of Preparation 24 (2.0 g, 5.48 mmol), the hydrochloride salt of 4-amino-1-methyl-3-n-propylpyrazole-5-carboxamide, EP-A-0463756; (1.08 g, 4.94 mmol), 1-hydroxybenzotriazole hydrate (920 mg, 6.87 mmol), 1-(3-dimethylaminopropyl)-3-ethylcarbodiimide hydrochloride (1.15 g, 6.0 mmol) and N-ethyldiisopropylamine (2.86 ml, 16.5 mmol) in tetrahydrofuran (20 ml) was stirred at room temperature for 18 hours. The reaction mixture was concentrated under reduced pressure and the residue partitioned between ethyl acetate (100 ml) and water (50 ml). The layers were separated and the organic phase was dried (MgSO$_4$) and evaporated under reduced pressure. The residue was purified by column chromatography on silica gel, using dichloromethane:methanol (95:5) as eluant to afford the title compound (940 mg, 38%), as a white solid. δ (CDCl$_3$): 0.95 (3H, t), 1.02 (3H, t), 1.52 (3H, t), 1.63 (2H, m), 2.40 (2H, q), 2.54 (6H, m), 3.09 (4H, m), 4.05 (3H, s), 4.75 (2H, q), 5.81 (1H, s), 7.58 (1H, s), 8.67 (1H, s), 8.80 (1H, s), 9.25 (1H, s). LRMS: m/z 509 (M+2)$^+$

PREPARATION 160
3-Ethyl-4-[5-(4-ethylpiperazin-1-ysulphonyl)-2-n-propylaminopyridin-3-ylcarboxamido]-2-(pyridin-2-yl)methylpyrazole-5-carboxamide

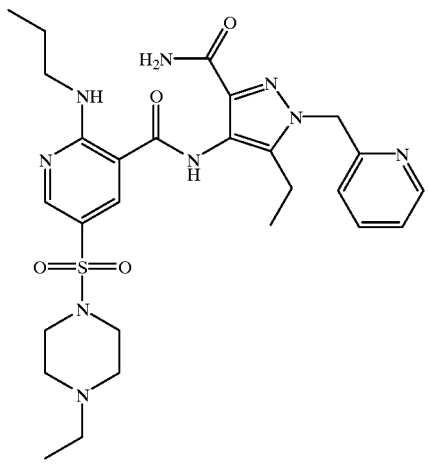

1-(3-Dimethylaminopropyl)-3-ethylcarbodiimide hydrochloride (250 mg, 1.3 mmol) was added to a solution of the title compounds of Preparations 40 (245 mg, 1.0 mmol) and 150 (456 mg, 1.2 mmol), N-ethyldiisopropylamine (194 mg, 1.5 mmol) and 1-hydroxybenzotriazole hydrate (203 mg, 1.5 mmol) in dichloromethane (10 ml), and the reaction stirred at room temperature for 16 hours. The reaction was poured into ethyl acetate (30 ml), washed with water (10 ml) and brine (10 ml), dried (MgSO$_4$) and evaporated under reduced pressure. The residue was purified by column chromatography on silica gel using an elution gradient of dichloromethane:methanol (100:0 to 94:6), and triturated with ether, to afford the title compound (242 mg, 41%) as a white solid. δ (CDCl$_3$): 0.95 (3H, t), 1.01 (6H, m), 1.62 (2H, m), 2.39 (2H, q), 2.52 (4H, m), 2.86 (2H, q), 3.09 (4H, m), 3.46 (2H, q), 5.39 (1H, s), 5.43 (2H, s), 6.64 (1H, s), 6.87 (1H, d), 7.20 (1H, m), 7.63 (1H, m), 8.17 (1H, s), 8.53 (1H, s), 8.58 (1H, d), 8.64 (1H, m), 9.58 (1H, s). LRMS: m/z 584 (M+1)$^+$

PREPARATION 161
4-(2-Ethoxy-5-nitropyridin-3-ylcarboxamido)-3-ethyl-2-methylpyrazole-5-carboxamide

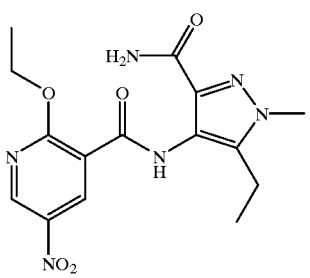

Oxalyl chloride (2.6 ml, 30.2 mmol) was added dropwise to an ice-cooled solution of the title compound of Preparation 8 (1.6 g, 7.55 mmol) and N,N-dimethylformamide (1 drop) in dichloromethane (40 ml), and the reaction stirred at room temperature for 3 hours. The mixture was concentrated under reduced pressure and azeotroped with dichloromethane several times.

This intermediate acid chloride was added to an ice-cooled solution of the title compound of Preparation 138 (960 mg, 5.74 mmol) and triethylamine (2.6 ml, 18.7 mmol) in dichloromethane (40 ml), and the reaction stirred at room temperature for 2 hours. The mixture was washed with water (20 ml), brine (20 ml), dried (Na$_2$SO$_4$) and evaporated under reduced pressure. The residue was purified by column chromatography on silica gel, using an elution gradient of dichloromethane:methanol (100:0 to 90:10) to afford the title compound (2.06 g, 99%). δ (CDCl$_3$): 1.24 (3H, t), 1.61 (3H, t), 2.92 (2H, q), 3.88 (3H, s), 4.84 (2H, q), 5.27 (1H, s), 6.66 (1H, s), 9.17 (1H, s), 9.33 (1H, s), 10.57 (1H, s). LRMS: m/z 363 (M+1)$^+$

PREPARATION 162
4-(5-Amino-2-ethoxypyridin-3-ylcarboxamido)-3-ethyl-2-methylpyrazole-5-carboxamide

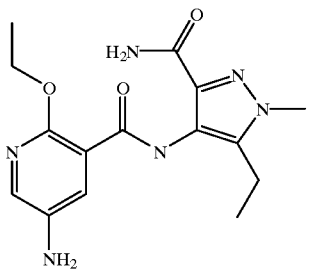

A mixture of the title compound of Preparation 161 (2.06 g, 5.7 mmol) and 10% palladium on charcoal (200 mg) in ethanol (70 ml) was hydrogenated at room temperature and 50 psi, for 6 hours. The reaction mixture was filtered through Arbocel®, the filter pad washed with further ethanol, and the combined filtrates evaporated under reduced pressure. The residue was purified by column chromatography on silica gel, using an elution gradient of dichloromethane:methanol (100:0 to 95:5) to afford the title compound (760 mg, 40%) as a solid. δ (CDCl$_3$): 1.23 (3H, t), 1.54 (3H, t), 2.87 (2H, q), 3.50 (2H, s), 3.87 (3H, s), 4.60 (2H, q), 5.24 (1H, s), 6.62 (1H, s), 7.78 (1H, s), 7.96 (1H, s), 10.54 (1H, s). LRMS: m/z 333 (M+1)$^+$

PREPARATION 163

5-(5-Amino-2-ethoxypyridin-3-yl)-3-ethyl-2-methylpyrazole-2,6-dihydro-7H-pyrazolo[4,3-d]pyrimidin-7-one

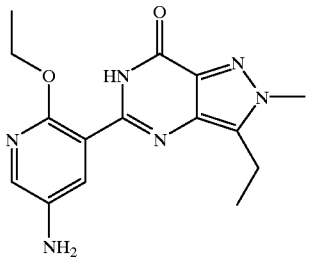

A mixture of the title compound of Preparation 162 (760 mg, 2.29 mmol) and potassium bis(trimethylsilyl)amide (685 mg, 3.43 mmol) in ethanol (50 ml) was heated at 100° C. in a sealed vessel for 20 hours. The cooled mixture was evaporated under reduced pressure. The residue was purified by column chromatography on silica gel, using an elution gradient of dichloromethane:methanol (100:0 to 95:5) to afford the title compound (550 mg, 76%) as a solid. δ (CDCl$_3$): 1.41 (3H, t), 1.53 (3H, t), 3.03 (2H, q), 3.58 (2H, s), 4.09 (3H, s), 4.58 (2H, q), 4.78 (1H, s), 8.20 (1H, s), 11.17 (1H, s). LRMS: m/z 315 (M+1)$^+$

PREPARATION 164

5-(5-Chlorosulphonyl-2-ethoxypyridin-3-yl)-3-ethyl-2-methylpyrazole-2,6-dihydro-7H-pyrazolo[4,3-d]pyrimidin-7-one

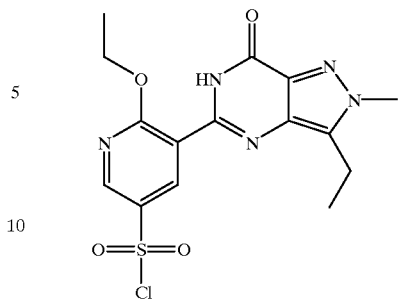

Obtained (72%) from the title compound of Preparation 163 following a similar procedure to that described in Preparation 63. δ (CDCl$_3$): 1.42 (3H, t), 1.60 (3H, t), 3.07 (2H, q), 4.14 (3H, s), 4.82 (2H, q), 8.92 (1H, s), 9.36 (1H, s), 10.58 (1H, s).

PREPARATION 165

(R)-1-Methoxy-2-propanol

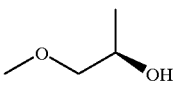

Sodium methoxide (54 g, 1.0 mol) was added portionwise to ice-cooled methanol (1000 ml), and the resulting solution stirred for 20 minutes in an ice-bath. (R)-Propylene oxide (58 g, 1 mol) was added dropwise over 30 minutes, and once addition was complete, the reaction was stirred at room temperature for 18 hours. The mixture was concentrated under reduced pressure, and acidified, with ice-cooling, using (1M) ethereal hydrochloric acid, and the resulting mixture stirred for an hour, then filtered. The filtrate was dried (K$_2$CO$_3$), filtered and evaporated under reduced pressure. The residue was heated to 70° C. over dried calcium oxide for 30 minutes, then distilled at atmospheric pressure to afford the title compound (25.4 g, 28%) as an oil. b.p. 118–120° C. δ (CDCl$_3$): 1.16 (3H, d), 2.28 (1H, d), 3.20 (1H, m), 3.36 (1H, m), 3.40 (3H, s), 13.97 (1H, m). [α]$_D$–20.83° (c=1.02, dichloromethane)

PREPARATION 166

4-Methoxy-2-butanol

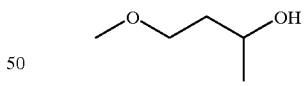

Lithium aluminium hydride (220 ml, 1.0M solution in tetrahydrofuran, 220 mmol) was added dropwise over 15 minutes, to an ice-cooled solution of 4-methoxybut-3-en-2-one (20.0 g, 200 mmol) in tetrahydrofuran (200 ml), and the reaction stirred at room temperature for 16 hours. The solution was re-cooled in an ice-bath, water (8 ml) was added dropwise, followed by 15% aqueous sodium hydroxide solution (8 ml), and after a further 10 minutes, additional water (24 ml). The mixture was stirred for 20 minutes, filtered, and the filtrate concentrated under reduced pressure to a volume of 100 ml. 10% Palladium on charcoal (500 mg) was added and the mixture hydrogenated at 60 psi for 16 hours. The reaction was filtered through Arbocel®, and the filtrate evaporated under reduced pressure. The residue was purified by column chromatography on silica gel using an elution gradient of dichloromethane:ether (99:1 to 50:50) to afford the title compound (4.0 g, 19%). δ (CDCl₃): 1.20 (3H, d), 1.67–1.78 (2H, m), 2.80 (1H, s), 3.38 (3H, s), 3.55–3.65 (2H, m), 4.00 (1H, m).

PREPARATION 167

N-Methylcyclopropylcarboxamide

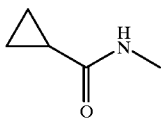

Cyclopropane carboxylic acid (15.83 ml, 200 mmol) was added dropwise to a warm (40° C.) solution of thionyl chloride (16.71 ml, 213 mmol) in toluene (80 ml), and once addition was complete, the reaction was stirred at 80° C. for 2 hours. The mixture was cooled in an ice-bath, a solution of methylamine in tetrahydrofuran (300 ml, 2M, 600 mmol) was added, the mixture allowed to warm to room temperature and concentrated under reduced pressure. The residue was suspended in dichloromethane (200 ml), washed with saturated aqueous sodium bicarbonate solution (200 ml), brine (200 ml), dried (MgSO₄) and evaporated under reduced pressure. The residual white solid was recrystallised from hexane/ether, to afford the title compound (11.3 g, 57%) as a white crystalline solid. Found: C, 58.73; H, 9.30; N, 13.70. C₅H₉NO:0.2H₂O requires C, 58.46; H, 9.22; N, 13.63% δ (CDCl₃): 0.70 (2H, m), 0.95 (2H, m), 1.32 (1H, m), 2.81 (3H, d), 5.73 (1H, s). LRMS: m/z 199 (M+1)⁺

PREPARATION 168

N-Cyclopropylmethyl-N-methylamine Hydrochloride

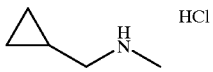

A solution of the title compound of Preparation 167 (7.90 g, 79.7 mmol) in ether (75 ml) was added dropwise over 5 minutes to a suspension of lithium aluminium hydride (3.03 g, 96.0 mmol) in ether (100 ml), and the reaction stirred under reflux for 4 hours. The cooled mixture was quenched by the consecutive addition of water (3 ml), 10% aqueous sodium hydroxide solution (9 ml) and water (3 ml). The resulting suspension was stirred for 5 minutes, filtered and the solids washed well with ether (100 ml). The combined filtrate was dried (MgSO₄), cooled in an ice-bath, and saturated with hydrochloric acid. This solution was evaporated under reduced pressure to afford the title compound (8.7 g, 90%) as a gum. δ (CDCl₃): 0.45 (2H, m), 0.72 (2H, m), 1.24 (1H, m), 2.70 (3H, t), 2.88 (3H, t), 2.88 (2H, m), 9.48 (2H, br s).

PREPARATION 169

4-[2-Ethoxy-5-(4-ethylpiperazin-1-ylsulphonyl)pyridin-3-ylcarboxamido]-3-ethyl-2-(1-methylimidazol-2-yl)methylpyrazole-5-carboxamide

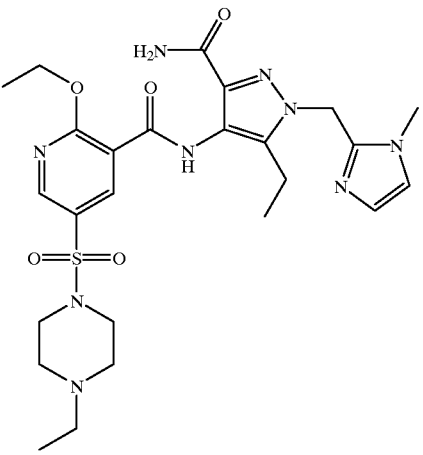

1-(3-Dimethylaminopropyl)-3-ethylcarbodiimide hydrochloride (1.2 g, 6.25 mmol) was added to a solution of the preparations of 23 (1.6 g, 4.66 mmol) and 89 (1.2 g, 4.84 mmol), hydroxybenzotriazole hydrate (960 mg, 6.2 mmol) and N-ethyldiisopropylamine (2.5 ml, 14.5 mmol) in tetrahydrofuran (15 ml), and N,N-dimethylformamide (3 ml), and the reaction stirred at room temperature for 18 hours. The mixture was diluted with water (100 ml), and extracted with dichloromethane (3×150 ml). The combined organic extracts were dried (Na₂SO₄) and evaporated under reduced pressure. The residue was purified by column chromatography on silica gel using dichloromethane:methanol (95:5) as eluant to afford the title compound (1.42 g, 2.55 mmol). δ (CDCl₃): 0.98–1.16 (6H, m), 1.52–1.70 (6H, m), 2.40 (2H, q), 2.55 (4H, m), 2.99–3.16 (6H, m), 3.72 (3H, s), 4.78 (2H, q), 5.30 (1H, br s), 5.44 (2H, s) 6.60 (1H, br s), 6.86 (1H, s), 7.00 (1H, s), 8.65 (1H, s), 8.82 (1H, s), 10.48 (1H, s). LRMS: m/z 574 (M+18)⁺

PREPARATION 170

5-[2-Ethoxy-5-(4-ethylpiperazin-1-ylsulphonyl)pyridin-3-yl]-3-ethyl-2-(1-methylimidazol-2-yl)methyl-2,6-dihydro-7H-pyrazolo[4,3-d]pyrimidin-7-one

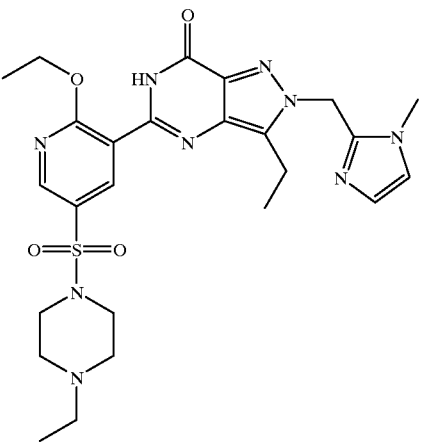

Obtained as a cream foam (62%) from the title compound of Preparation 169 following a similar procedure to that described in Example 78. δ (CDCl₃): 1.00 (3H, t), 1.30 (3H, t), 1.57 (3H, t), 2.40 (2H, q), 2.54 (4H, m), 3.06–3.20 (6H, m), 3.78 (3H, s), 4.75 (2H, q), 5.64 (2H, s), 6.84 (1H, s), 6.99 (1H,s), 8.61 (1H, s), 8.99 (1H, s), 10.66 (1H, s). LRMS: m/z 556 (M+1)⁺

Biological Activity

The following Table illustrates the in vitro activities for a range of the compounds of the invention as inhibitors of cGMP PDE5.

TABLE

| EXAMPLE | IC$_{50}$ (nm) |
|---|---|
| 10 | 10.1 |
| 11 | 10.0 |
| 18 | 8.9 |
| 43b | 3.6 |
| 46 | 8.1 |
| 48 | 6.9 |
| 98 | 7.0 |
| 99 | 5.7 |
| 127 | 7.3 |
| 153 | 7.2 |

Safety Profile

Several compounds of the invention have been tested at doses of up to 3 mg/kg i.v. in mouse and at 0.5 mg/kg p.o. in dog, with no untoward effects being observed.

What is claimed is:

1. A compound of the formula (IA) or (IB):

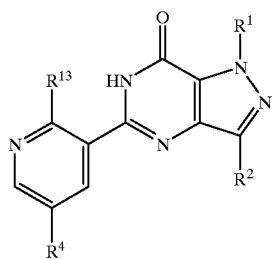
(IA)

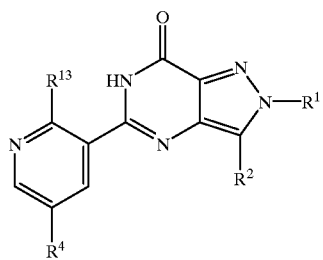
(IB)

or a pharmaceutically or veterinarily acceptable salt thereof, or a pharmaceutically or veterinarily acceptable solvate of either entity, wherein $R^1$ is $C_1$ to $C_3$ alkyl optionally substituted with phenyl, Het or a N-linked heterocyclic group selected from piperidinyl and morpholinyl; wherein said phenyl group is optionally substituted by one or more substitutents selected from $C_1$ to $C_4$ alkoxy; halo; CN; $CF_3$; $OCF_3$ or $C_1$ to $C_4$ alkyl wherein said $C_1$ to $C_4$ alkyl group is optionally substituted by $C_1$ to $C_4$ haloalkyl or haloalkoxy either of which is substituted by one or more halo atoms;

$R^2$ is $C_1$ to $C_6$ alkyl;

$R^{13}$ is $OR^3$ or $NR^5R^6$;

$R^3$ is $C_1$ to $C_6$ alkyl optionally substituted with one or two substituents selected from $C_3$ to $C_5$ cycloalkyl, OH, $C_1$ to $C_4$ alkoxy, benzyloxy, $NR^5R^6$, phenyl, furanyl and pyridinyl; $C_3$ to $C_6$ cycloalkyl; 1-($C_1$ to $C_4$ alkyl) piperidinyl; tetrahydrofuranyl or tetrahydropyranyl; and wherein said $C_1$ to $C_5$ alkyl or said $C_1$ to $C_4$ alkoxy groups are optionally terminated by haloalkyl;

$R^4$ is $SO_2NR^7R^8$;

$R^5$ and $R^6$ are each independently selected from H and $C_1$ to $C_4$ alkyl optionally substituted with $C_3$ to $C_5$ cycloalkyl or $C_1$ to $C_4$ alkoxy, or, together with the nitrogen atom to which they are attached, form an azetidinyl, pyrrolidinyl, piperidinyl or morpholinyl group;

$R^7$ and $R^8$, together with the nitrogen atom to which they are attached, form a 4-$R^{10}$-piperazinyl group optionally substituted with one or two $C_1$ to $C_4$ alkyl groups and optionally in the form of its 4-N-oxide;

$R^{10}$ is H; $C_1$ to $C_4$ alkyl optionally substituted with one or two substituents selected from OH, $NR^5R^6$, $CONR^5R^6$, phenyl optionally substituted with $C_1$ to $C_4$ alkoxy, benzodioxolyl and benzodioxanyl; $C_3$ to $C_6$ alkenyl; pyridinyl or pyrimidinyl; and Het is a C-linked 6-membered heterocyclic group containing one or two nitrogen atoms, optionally in the form of its mono-N-oxide, or a C-linked 5-membered heterocyclic group containing two or three nitrogen atoms, wherein either of said heterocyclic groups is optionally substituted with $C_1$ to $C_4$ alkyl, $C_1$ to $C_4$ alkoxy or $NHR^{15}$ wherein $R^{15}$ is H, $C_1$ to $C_4$ alkyl or $C_1$ to $C_4$ alkanoyl and halo is Br, Cl, F or I.

2. A compound according to claim 1 wherein $R^1$ is $C_1$ to $C_2$ alkyl optionally substituted with Het: 2-(morpholin-4-yl)ethyl or benzyl; $R^2$ is $C_2$ to $C_4$ alkyl; $R^{13}$ is $OR^3$ or $NR^5R^6$; $R^3$ is $C_1$ to $C_4$ alkyl optionally substituted with one or two substituents selected from cyclopropyl, cyclobutyl, OH, methoxy, ethoxy, benzyloxy, $NR^5R^6$, phenyl, furan-3-yl, pyridin-2-yl and pyridin-3-yl; cyclobutyl; 1-methylpiperidin-4-yl; tetrahydrofuran-3-yl or tetrahydropyran-4-yl; $R^5$ and $R^6$ are each independently selected from H and $C_1$ to $C_2$ alkyl optionally substituted with cyclopropyl or methoxy, or, together with the nitrogen atom to which they are attached, form a azetidinyl, pyrrolidinyl or morpholinyl group; $R^7$ and $R^8$, together with the nitrogen atom to which they are attached, form a 4-$R^{10}$-piperazinyl group optionally substituted with one or two methyl groups and optionally in the form of its 4-N-oxide; $R^{10}$ is H, $C_1$ to $C_3$ alkyl optionally substituted with one or two substituents selected from OH, $NR^5R^6$, $CONR^5R^6$, phenyl optionally substituted with methoxy, benzodioxol-5-yl and benzodioxan-2-yl; allyl; pyridin-2-yl; pyridin-4-yl or pyrimidin-2-yl; and Het is selected from pyridin-2-yl; 1-oxidopyridin-2-yl; 6-methylpyridin-2-yl; 6-methoxypyridin-2-yl; pyridazin-3-yl; pyrimidin-2-yl and 1-methylimidazol-2-yl.

3. A compound according to claim 2 wherein $R^1$ is $C_1$ to $C_2$ alkyl optionally substituted with Het; 2-(morpholin-4-yl)ethyl or benzyl; $R^2$ is $C_2$ to $C_4$ alkyl; $R^{13}$ is $OR^3$; $R^3$ is $C_1$ to $C_4$ alkyl optionally monosubstituted with cyclopropyl, cyclobutyl, OH, methoxy, ethoxy, phenyl, furan-3-yl or pyridin-2-yl: cyclobutyl; tetrahydrofuran-3-yl or tetrahydropyran-4-yl; $R^7$ and $R^8$, together with the nitrogen atom to which they are attached, form a 4-$R^{10}$-piperazinyl group optionally in the form of its 4-N-oxide; $R^{10}$ is $C_1$ to $C_3$ alkyl optionally monosubstituted with OH; and Het is selected from pyridin-2-yl; 1-oxidopyridin-2-yl; 6-methylpyridin-2-yl; 6-methoxypyridin-2-yl; pyridazin-3-yl; pyrimidin-2-yl and 1-methylimidazol-2-yl.

4. A compound according to any of claims 1 to 3 selected from:

3-ethyl-5-[2-(2-methoxyethoxy)-5-(4-methylpiperazin-1-ylsulphonyl)pyridin-3-yl]-2-(pyridin-2-yl)methyl-2,6-dihydro-7H-pyrazolo[4,3-d]pyrimidin-7-one;

3-ethyl-5-[5-(4-ethylpiperazin-1-ylsulphonyl)-2-(2-methoxyethoxy)pyridin-3-yl]-2-(pyridin-2-yl)methyl-2, 6-dihydro-7H-pyrazolo[4,3-d]pyrimidin-7-one;

3-ethyl-5-[5-(4-ethyl-4-oxidopiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one;
5-[2-(2-methoxyethoxy)-5-(4-methylpiperazin-1-ylsulphonyl)pyridin-3-yl]-3-n-propyl-2-(pyridin-2-yl)methyl-2,6-dihydro7H-pyrazolo[4,3-d]pyrimidin-7-one;
5-[5-(4-ethylpiperazin-1-ylsulphonyl)-2-(2-methoxyethoxy)pyridin-3-yl]-3-n-propyl-2-(pyridin-2-yl)methyl-2,6-dihydro-7H-pyrazolo[4,3-d]pyrimidin-7-one;
(+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one;
3-ethyl-5-[5-(4-ethylpiperazin-1-ylsulphonyl)-2-(2-methoxy-1(R)-methylethoxy)pyridin-3-yl]-2-(6-methylpyridin-2-yl)methyl-2,6-dihydro-7H-pyrazolo[4,3-d]pyrimidin-7-one;
5-[2-ethoxy-5-(4-ethylpiperazin-1-ylsulphonyl)pyridin-3-yl]-3-ethyl-2-(6-methoxypyridin-2-yl)methyl-2,6-dihydro-7H-pyrazolo[4,3-d]pyrimidin-7-one;
5-[2-i-butoxy-5-(4-ethylpiperazin-1-ylsulphonyl)pyridin-3-yl]-2,3-diethyl-2,6-dihydro-7H-pyrazolo[4,3-d]pyrimidin-7-one; and
5-[2-ethoxy-5-(4-ethylpiperazin-1-ylsulphonyl)pyridin-3-yl]-3-ethyl-2-[1(pyridin-2-yl)ethyl]-2,6dihydro-7H-pyrazolo[4,3-d]pyrimidin-7-one.

5. A pharmaceutical composition comprising a compound of formula (IA) or (IB), or a pharmaceutically acceptable salt thereof, or a pharmaceutically acceptable solvate of either entity, together with a pharmaceutically acceptable diluent or carrier.

6. A veterinary formulation comprising a compound of formula (IA) or (IB), or a veterinarily acceptable salt thereof, or a veterinarily acceptable solvate of either entity, together with a veterinarily acceptable diluent or carrier.

7. A method of treating male erectile dysfunction (MED), female sexual dysfunction (FSD), premature labour, dysmenorrhoea, benign prostatic hyperplasia (BPH), bladder outlet obstruction, incontinence, stable, unstable and variant (Prinzmetal) angina, hypertension, pulmonary hypertension, congestive heart failure, atherosclerosis, stroke, peripheral vascular disease, conditions of reduced blood vessel patency, chronic asthma, bronchitis, allergic asthma, allergic rhinitis, glaucoma or diseases characterised by disorders of gut motility in a mammal (including a human being), which comprises administering to said mammal a therapeutically effective amount of a compound of formula (IA) or (IB), or a pharmaceutically or veterinarily acceptable salt thereof, or a pharmaceutically or veterinarily acceptable solvate of either entity, or a pharmaceutical composition or veterinary formulation containing any of the foregoing.

8. A compound of formula (IIA) or (IIB):

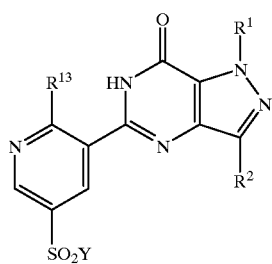

(IIA)

-continued

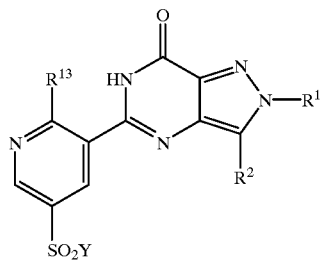

(IIB)

wherein Y is halo, and $R^1$, $R^2$ and $R^{13}$ are as defined in claim 1.

9. A compound according to claim 8 wherein Y is chloro.

10. A compound of formula (IVA) or (IVB):

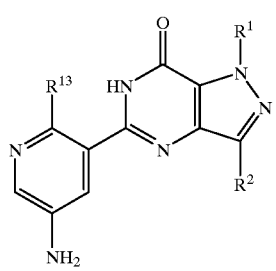

(IVA)

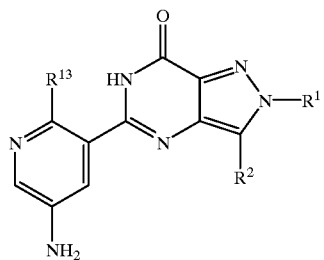

(IVB)

wherein $R^1$, $R^2$ and $R^{13}$ are as defined in claim 1.

11. A process for the preparation of a compound of formula (IA) or (IB):

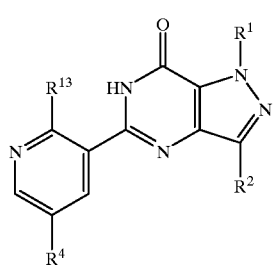

(IA)

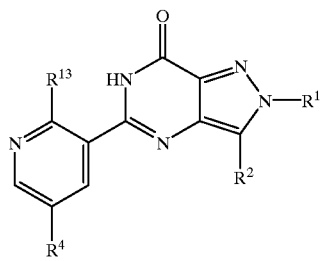

(IB)

wherein R¹ is $C_1$ to $C_3$ alkyl optionally substituted with phenyl, Het or a N-linked heterocyclic group selected from piperidinyl and morpholinyl;
   wherein said phenyl group is optionally substituted by one or more substitutents selected from $C_1$ to $C_4$ alkoxy; halo; CN; $CF_3$; $OCF_3$ or $C_1$ to $C_4$ alkyl wherein said $C_1$ to $C_4$ alkyl group is optionally substituted by $C_1$ to $C_4$ haloalkyl or haloalkoxy either of which is substituted by one or more halo atoms;
R² is $C_1$ to $C_6$ alkyl;
R¹³ is $OR^3$ or $NR^5R^6$;
R³ is $C_1$ to $C_6$ alkyl optionally substituted with one or two substituents selected from $C_3$ to $C_5$ cycloalkyl, OH, $C_1$ to $C_4$ alkoxy, benzyloxy, $NR^5R^6$, phenyl, furanyl and pyridinyl; $C_3$ to $C_6$ cycloalkyl; 1-($C_1$ to $C_4$ alkyl) piperidinyl; tetrahydrofuranyl or tetrahydropyranyl; and wherein said $C_1$ to $C_6$ alkyl or said $C_1$ to $C_4$ alkoxy groups are optionally terminated by haloalkyl;
R⁴ is $SO_2NR^7R^8$;
R⁵ and R⁶ are each independently selected from H and $C_1$ to $C_4$ alkyl optionally substituted with $C_3$ to $C_5$ cycloalkyl or $C_1$ to $C_4$ alkoxy, or, together with the nitrogen atom to which they are attached, form an azetidinyl, pyrrolidinyl, piperidinyl or morpholinyl group;
R⁷ and R⁸, together with the nitrogen atom to which they are attached, form a 4-$R^{10}$-piperazinyl group optionally substituted with one or two $C_1$ to $C_4$ alkyl groups and optionally in the form of its 4-N-oxide; $R^{10}$ is H; $C_1$ to $C_4$ alkyl optionally substituted with one or two substituents selected from OH, $NR^5R^6$, $CONR^5R^6$, phenyl optionally substituted with $C_1$ to $C_4$ alkoxy, benzodioxolyl and benzodioxanyl; $C_3$ to $C_6$ alkenyl; pyridinyl or pyrimidinyl; and Het is a C-linked 6-membered heterocyclic group containing one or two nitrogen atoms, optionally in the form of its mono-N-oxide, or a C-linked 5-membered heterocyclic group containing two or three nitrogen atoms, wherein either of said heterocyclic groups is optionally substituted with $C_1$ to $C_4$ alkyl, $C_1$ to $C_4$ alkoxy or $NHR^{15}$ wherein $R^{15}$ is H, $C_1$ to $C_4$ alkyl or $C_1$ to $C_4$ alkanoyl and halo is Br, Cl, F or I, which process comprises reacting a compound of formula (IIA) or (IIB), respectively:

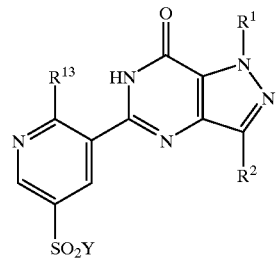

(IIA)

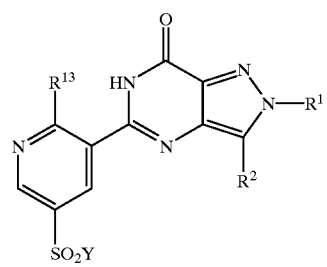

(IIB)

wherein Y is halo, and $R^1$, $R^2$ and $R^{13}$ are as previously defined in this claim, with a compound of formula (III):

$R^7R^8NH$          (III)

wherein $R^7$ and $R^8$ are as previously defined in this claim, optionally followed by formation of a pharmaceutically or veterinarily acceptable salt of the required product or a pharmaceutically or veterinarily acceptable solvate of either entity.

* * * * *